US012653887B2

(12) United States Patent
van Buuren et al.

(10) Patent No.: US 12,653,887 B2
(45) Date of Patent: Jun. 16, 2026

(54) T CELL MANUFACTURING COMPOSITIONS AND METHODS

(71) Applicants: BIONTECH US INC., Cambridge, MA (US); STICHTING HET NEDERLANDS KANKER INSTITUUT ANTONI VAN LEEUWENHOEK ZIEKENHUIS, Amsterdam (NL)

(72) Inventors: Marit M. van Buuren, Belmont, MA (US); Divya Reddy Lenkala, Watertown, MA (US); Jessica Kohler, Boston, MA (US); Flavian Duvalle Brown, Boston, MA (US); Christina Murphy Kuksin, Cambridge, MA (US); Joost Huibert van den Berg, Amsterdam (NL); Renate de Boer, Diemen (NL); Noor Bakker, Haarlem (NL); Ton Schumacher, Aloemehomal (NL); John Haanen, Amsterdam (NL)

(73) Assignees: BIONTECH US INC.; STICHTING HET NEDERLANDS KANKER INSTITUUT ANTONI VAN LEEUWENHOEK ZIEKENHUIS, Amsterdam (NL)

( * ) Notice: Subject to any disclaimer, the term of this patent is extended or adjusted under 35 U.S.C. 154(b) by 1186 days.

(21) Appl. No.: 17/609,705

(22) PCT Filed: May 7, 2020

(86) PCT No.: PCT/US2020/031898
§ 371 (c)(1),
(2) Date: Nov. 8, 2021

(87) PCT Pub. No.: WO2020/227546
PCT Pub. Date: Nov. 12, 2020

(65) Prior Publication Data
US 2022/0280621 A1 Sep. 8, 2022

Related U.S. Application Data

(60) Provisional application No. 62/845,251, filed on May 8, 2019.

(51) Int. Cl.
*A61K 40/13* (2025.01)
*A61K 40/11* (2025.01)
*A61K 40/42* (2025.01)
*C12N 5/00* (2006.01)
*C12N 5/0783* (2010.01)

(52) U.S. Cl.
CPC .............. *A61K 40/13* (2025.01); *A61K 40/11* (2025.01); *A61K 40/4201* (2025.01); *A61K 40/4271* (2025.01); *C12N 5/0081* (2013.01); *C12N 5/0636* (2013.01); *C12N 5/0638* (2013.01); *A61K 2239/31* (2023.05); *A61K 2239/38* (2023.05); *A61K 2239/57* (2023.05); *A61K 2239/59* (2023.05)

(58) Field of Classification Search
CPC .... A61K 40/13; A61K 40/11; A61K 40/4201; A61K 40/4271; A61K 2239/31; A61K 2239/38; A61K 2239/57; A61K 2239/59; A61K 2039/876; A61K 2121/00; A61K 40/32; C12N 5/0081; C12N 5/0636; C12N 5/0638; C12N 5/0087; A61P 35/00; A61P 35/02; A61P 35/04
See application file for complete search history.

(56) References Cited

U.S. PATENT DOCUMENTS

| | | | |
|---|---|---|---|
| 5,391,377 A | 2/1995 | Barnwell |
| 5,849,589 A | 12/1998 | Tedder et al. |
| 5,994,126 A | 11/1999 | Steinman et al. |
| 6,406,705 B1 | 6/2002 | Davis et al. |
| 7,276,478 B2 | 10/2007 | Sivakumar et al. |
| 9,115,402 B2 | 8/2015 | Hacohen et al. |
| 9,476,055 B2 | 10/2016 | Sahin et al. |
| 9,809,797 B2 | 11/2017 | Yee et al. |
| 10,426,824 B1 | 10/2019 | Hacohen et al. |
| 11,162,072 B2 | 11/2021 | Van Buuren et al. |
| 11,183,272 B2 | 11/2021 | Rooney et al. |

(Continued)

FOREIGN PATENT DOCUMENTS

| | | |
|---|---|---|
| CN | 103923880 A | 7/2014 |
| CN | 109476722 A | 3/2019 |

(Continued)

OTHER PUBLICATIONS

Shin, H., Park, S.-J., Yim, Y., Kim, J., Choi, C., Won, C. and Min, D.-H. (2018), Recent Advances in RNA Therapeutics and RNA Delivery Systems Based on Nanoparticles. Adv. Therap., 1: 1800065. (Year: 2018).*

(Continued)

*Primary Examiner* — Julie Wu
*Assistant Examiner* — Amber K Faust
(74) *Attorney, Agent, or Firm* — Wilson Sonsini Goodrich & Rosati

(57) ABSTRACT

The generation of antigen specific T cells by controlled ex vivo induction or expansion can provide highly specific and beneficial T cell therapies. The present disclosure provides T cell manufacturing methods and therapeutic T cell compositions which can be used for treating subjects with cancer and other conditions, diseases and disorders personal antigen specific T cell therapy.

18 Claims, 89 Drawing Sheets
Specification includes a Sequence Listing.

(56) References Cited

U.S. PATENT DOCUMENTS

| | | | |
|---|---|---|---|
| 12,258,581 | B2 | 3/2025 | Van Buuren et al. |
| 2004/0101519 | A1 | 5/2004 | June et al. |
| 2006/0034810 | A1 | 2/2006 | Riley et al. |
| 2009/0285843 | A1 | 11/2009 | Simard et al. |
| 2010/0330056 | A1 | 12/2010 | Yee et al. |
| 2011/0274723 | A1 | 11/2011 | Bot et al. |
| 2011/0293637 | A1 | 12/2011 | Hacohen et al. |
| 2015/0104441 | A1 | 4/2015 | Olweus et al. |
| 2016/0215262 | A1 | 7/2016 | Powell, Jr. |
| 2017/0037370 | A1 | 2/2017 | Kaiser et al. |
| 2017/0224800 | A1 | 8/2017 | Tran et al. |
| 2018/0043003 | A1 | 2/2018 | Schneck et al. |
| 2018/0052176 | A1 | 2/2018 | Holt et al. |
| 2018/0133296 | A1 | 5/2018 | Barrett et al. |
| 2018/0141998 | A1 | 5/2018 | Nguyen et al. |
| 2018/0273602 | A1 | 9/2018 | Alten et al. |
| 2019/0024050 | A1 | 1/2019 | Yee et al. |
| 2019/0119639 | A1 | 4/2019 | Oelke et al. |
| 2020/0165567 | A1* | 5/2020 | Van Buuren ............ A61P 35/00 |
| 2022/0177840 | A1 | 6/2022 | Van Buuren et al. |
| 2022/0282217 | A1 | 9/2022 | Ang et al. |
| 2023/0374455 | A1 | 11/2023 | Juneja et al. |
| 2023/0398218 | A1 | 12/2023 | Juneja |

FOREIGN PATENT DOCUMENTS

| | | | |
|---|---|---|---|
| EP | 2749639 | A1 | 7/2014 |
| EP | 3023788 | A1 | 5/2016 |
| EP | 3335725 | A1 | 6/2018 |
| EP | 3699266 | A1 | 8/2020 |
| RU | 2447900 | C2 | 4/2012 |
| RU | 2793344 | C2 | 3/2023 |
| TW | 201738378 | A | 11/2017 |
| WO | WO-9403205 | A1 | 2/1994 |
| WO | WO-9420127 | A1 | 9/1994 |
| WO | WO-2006015497 | A1 | 2/2006 |
| WO | WO-2006110582 | A1 | 10/2006 |
| WO | WO-2007036366 | A2 | 4/2007 |
| WO | WO-2009045308 | A2 | 4/2009 |
| WO | WO-2009106073 | A2 | 9/2009 |
| WO | WO-2011143656 | A2 | 11/2011 |
| WO | WO-2012159643 | A1 | 11/2012 |
| WO | WO-2013118899 | A1 | 8/2013 |
| WO | WO-2015095811 | A2 | 6/2015 |
| WO | WO-2015164675 | A1 | 10/2015 |
| WO | WO-2016201394 | A1 | 12/2016 |
| WO | WO-2017015427 | A1 | 1/2017 |
| WO | WO-2017026389 | A1* | 2/2017 ............ A61K 45/00 |
| WO | WO-2017044661 | A1 | 3/2017 |
| WO | WO-2017044859 | A1 | 3/2017 |
| WO | WO-2017173321 | A1 | 10/2017 |
| WO | WO-2017177337 | A1 | 10/2017 |
| WO | WO-2017184590 | A1 | 10/2017 |
| WO | WO-2018005556 | A1 | 1/2018 |
| WO | WO-2018026914 | A1 | 2/2018 |
| WO | WO-2018148671 | A1 | 8/2018 |
| WO | WO-2019094642 | A1 | 5/2019 |
| WO | WO-2020047449 | A2 | 3/2020 |
| WO | WO-2020132586 | A1 | 6/2020 |
| WO | WO-2020205778 | A1 | 10/2020 |
| WO | WO-2020227546 | A1 | 11/2020 |
| WO | WO-2022036137 | A1 | 2/2022 |
| WO | WO-2023064930 | A1 | 4/2023 |
| WO | WO-2024124222 | A1 | 6/2024 |

OTHER PUBLICATIONS

Sheng, Kuo-Ching, Day, Stephanie, Wright, Mark D., Stojanovska, Lily, Apostolopoulos, Vasso, Enhanced Dendritic Cell-Mediated Antigen-Specific CD4+ T Cell Responses: IFN-Gamma Aids TLR Stimulation, Journal of Drug Delivery, 2013, 516749, 9 pages, 2013. (Year: 2013).*

Pletinckx K, Lutz MB. Dendritic cells generated with Flt3L and exposed to apoptotic cells lack induction of T cell anergy and Foxp3+ regulatory T cell conversion in vitro. Immunobiology. Mar. 2014;219(3):230-40. (Year: 2014).*

Nezafat N, Ghasemi Y, Javadi G, Khoshnoud MJ, Omidinia E. A novel multi-epitope peptide vaccine against cancer: an in silico approach. J Theor Biol. May 21, 2014;349:121-34. (Year: 2014).*

Peng W, Lizée G, Hwu P. Blockade of the PD-1 pathway enhances the efficacy of adoptive cell therapy against cancer. Oncoimmunology. Feb. 1, 2013;2(2):e22691. (Year: 2013).*

Verdegaal, E.M.E., Visser, M., Ramwadhdoebé, T.H. et al. Successful treatment of metastatic melanoma by adoptive transfer of blood-derived polyclonal tumor-specific CD4+ and CD8+ T cells in combination with low-dose interferon-alpha. Cancer Immunol Immunother 60, 953-963 (2011). (Year: 2011).*

Varga et al. Active MAC-1 (CD11b/CD18) on DCs inhibits full T-cell activation. Blood. Jan. 15, 2007;109(2):661-9. (Year: 2007).*

Gjertsen et al. Intradermal ras peptide vaccination with granulocyte-macrophage colony-stimulating factor as adjuvant: Clinical and immunological responses in patients with pancreatic adenocarcinoma. Int J Cancer. May 1, 2001;92(3):441-50. (Year: 2001).*

Lawrence, M., Stojanov, P., Mermel, C. et al. Discovery and saturation analysis of cancer genes across 21 tumour types. Nature 505, 495-501 (2014). (Year: 2014).*

"Ali, et al., "Induction of neoantigen-reactive T cells from healthy donors" , Nature Protocols (2019)".

Allison, "The Mode of Action of Immunological Adjuvants," Dev Biol Stand, 92: 3-11 (1998).

Bernhard et al., Generation of Immunostimulatory Dendritic Cells From Human CD34+ Hematopoietic Progenitor Cells of the Bone Marrow and Peripheral Blood, Cancer Res. 55:1099-104 (1995).

Bishop, MR, et al., High-dose therapy and peripheral blood progenitor cell transplantation: effects of recombinant human granulocyte-macrophage colony-stimulating factor on the autograft, Blood, vol. 83, No. 2, pp. 610-616 (1994).

Bollard, et al., "Sustained complete Responses in Patients With Lymphoma Receiving Autologous Cytotoxic T Lymphocytes Targeting Epstein-Barr Virus Latent Membrane Proteins" Journal of Clinical Oncology, vol. 32, No. 8 (2014).

Busch et al., Degenerate binding of immunogenic peptides to HLA-DR proteins on B cell surfaces, Int. Immunol. 2:443 (1990).

"Carreno, et al., "IL-12p70-producing patient DC vaccine elicits Tc1-polarized immunity" J. Clin Invest (2013) 123(8):3383-3394, Vole 123, No. 8".

Ceppellini et al., Binding of labelled influenza matrix peptide to HLA DR in living B lymphoid cells, Nature 339:392 (1989).

Cerundolo et al., The binding affinity and dissociated rates of peptides for class I major histocompatibility complex molecules, Eur. Immunol., 21:2069-75 (1991).

Christnick et al., Peptide binding to class 1MHC on living cells and quantitation of complexes required for CTL lysis, Nature 352:67 (1991).

Del Guercio, M.F., et al., Binding of a peptide antigen to multiple HLA alleles allows definition of an A2-like supertype, J. Immunol. 154:685-693 (1995).

Dupuis, M., et al., Dendritic Cells Internalize Vaccine Adjuvant after Intramuscular Injection, Cell Immunol. 1998; 186(1):18-27.

"Erdmann, et al., "Automated closed-system manufacturing of human monocyte-derived dendritic cells for cancer immunotherapy" Journal of Immunological Methods (463 (2018) 89-96".

Exam Report and Translation issued in Russian Patent Application No. 2021106561/10 on Dec. 29, 2021.

Exam Report and Translation issued in Russian Patent Application No. 2021106561/10 on May 26, 2022.

Extended European Search Report issued in European Patent Application No. 19849341.3 on Apr. 8, 2022.

Fix. Oral controlled release technology for peptides: status and future prospects. Pharm Res. 13(12):1760-1764 (1996).

Freudenthal, et al. The distinct surface of human blood dendritic cells, as observed after an improved isolation method. Proc Natl Acad Sci U S A. Oct. 1990;87(19):7698-702.

"Fritsch, et al., "HLA-binding properties of tumor neoepitopes in humans", Cancer Immunol Res (2014) p. 1-27".

(56)          References Cited

OTHER PUBLICATIONS

Gabrilovich, et al., "IL-12 and Mutant P53 Peptide-Pulsed Dendritic Cells for the Specific Immunotherapy of Cancer," J Immunother Emphasis Tumor Immunol, 19(6): 414-418 (1997).

Gamvrellis, A. et al., Vaccines that facilitate antigen entry into dendritic cells, Immunol & Cell Biol. 2004; 82: 506-516.

"Gattinoni, et al., "A human memory T-cell subset with stem cell-like properties" Nat Med; 17(10): 1290-1297 (2012)".

"Gilboa, Eli, "The Making of a Tumor Rejection Antigen" Immunity. vol. 11, p. 263-270 (1999)".

Gjertsen et al., Cytotoxic CD4+ and CD8+ T lymphocytes, generated by mutant p21-ras (12Val) peptide vaccination of a patient, recognize 12Val-dependent nested epitopes present within the vaccine peptide and kill autologous tumour cells carrying this mutation. Int J Cancer. Sep. 4, 1997;72(5):784-90. doi: 10.1002/(sici)1097-0215(19970904)72:5784::aid-ijc143.0.co;2-9. PMID: 9311595.

Hammer, J. et al., Precise prediction of major histocompatibility complex class II-peptide interaction based on peptide side chain scanning, J. Exp. Med. 180:2353 (1994).

Hill et al., Conformational and structural characteristics of peptides binding to HLA-DR molecules, J. Immunol. 147:189 (1991).

Hill et al., Exploration of requirements for peptide binding to HLA DRB10101 and DRBI*0401, J. Immunol. 152, 2890 (1994).

International Search Report and Written Opinion dated Mar. 4, 2019, for PCT/US2018/59896.

"International Search Report and Written Opinion for corresponding PCT Application No. PCT/US2019/046876 issued Jan. 21, 2020".

Khilko, Sergi N. et al., Direct Detection of Major Histocompatibility Complex Class I Binding to Antigenic Peptides Using Surface Plasmon Resonance, J. Biol. Chem. 268:15425 (1993).

"Klebanoff, et al., "Sortying through subsets: Which T cell poulations mediate highly effective adoptive immunotherapy?", J. Immunother. (2012) 35(9): p. 651-660".

"Koski, et al., "CD14+ Monocytes as Dendritic Cell Precursors: Diverse Maturation-Inducing Pathways Lead to Common Activation of NF-kB/RelB", Critical Reviews in Immunology, 21:179-189 (2001)".

Krieg, Arthur M., Therapeutic potential of Toll-like receptor 9 activation, Nature Reviews, Drug Discovery, 5, Jun. 2006, 471-484).

"Leen, et al., "Cytotoxic T lymphocyte therapy with donor T cells prevents and treats adenovirus and Epstein-Barr virus infections after haploidentical and matched unrelated stem cell transplantation", Blood (2009) vol. 114, No. 19, p. 4283-4292".

Li et al., TCRβ repertoire of CD4+ and CD8+ T cells is distinct in richness, distribution, and CDR3 amino acid composition. J Leukoc Biol. Mar. 2016;99(3):505-13. doi: 10.1189/jlb.6A0215-071RR. Epub Sep. 22, 2015. PMID: 26394815; PMCID: PMC5338248.

"Linnemann, et al., "High-throughput epitope discovery reveals frequent recognition of neo-antigens by CD4+ T cells in human melanoma" Nature Medicine (2015) vol. 21, No. 1, p. 81-87".

"Lissina, et al., "Priming of Qualitatively Superior Human Effector CD8+ T Cells Using TLR8 Ligand Combined with FLT3 Ligand" J. Immunol (2016) 196:256-263".

Ljunggren et al., Empty MHC class I molecules come out in the cold, Nature 346:476 (1990).

"Maraskovsky, et al., "In vivo generation of human dendritic cell subsets by Flt3 lignad" (2000) Blood, vol. 96, No. 3, pp. 878-884".

Markowicz, et al. Granulocyte-macrophage colony-stimulating factor promotes differentiation and survival of human peripheral blood dendritic cells in vitro. J Clin Invest. Mar. 1990;85(3):955-61.

Mosca, Paul J. et al., Dendritic cell vaccines, Frontiers in Bioscience, (2007) 12:4050-4060).

"Nair, et al., "Isolation and Generation of Human Dendritic Cells" Curr Protoc Immunol (2012)".

O'Doherty, et al. Dendritic cells freshly isolated from human blood express CD4 and mature into typical immunostimulatory dendritic cells after culture in monocyte-conditioned medium. J Exp Med. Sep. 1, 1993;178(3):1067-76.

Parker et al., The beta 2-microglobulin dissociation rate is an accurate measure of the stability of MHC Class I heterotrimers and depends on which peptide is bound, J. Immunol. 149:1896 (1992).

Reay, Phillip A. et al., (1992), pH dependence and exchange of high and low responder peptides binding to a class II MHC molecule, EMBO J. 11:2829-39.

Samanen et al. Chemical approaches to improve the oral bioavailability of peptidergic molecules. J. Pharm. Pharmacol. 48:119-135 (1996).

Schumacher, Ton N.M., et al., (1990), Direct binding of peptide to empty MHC class I molecules on intact cells and in vitro, Cell 62:563 (1990).

Sette, et al., (1994) Peptide binding to the most frequent HLA-A class I alleles measured by quantitative molecular bindings assays, Mol. Immunol. 31:813.

Sidney, John et al., Measurement of MHC/Peptide Interactions by Gel Filtration Curr Prot Immunol, 31(1):18.3.1-18.3.19 (1999).

Townsend, A., et al., Assembly of MCH Class I molecules analyzed in vitro, Cell 62:285, Jul. 27, 1990.

"Stronen, et al., "Dendritic Cells Engineered to Express Defined Allo-HLA Peptide Complexes Induce Antigen-specific Cytotoxic T Cells Efficiently Killing Tumour Cells", Scandinavian Journal of Immunology (2009) 69, pp. 319-328".

"Van Buuren, et al., "High sensitivity of cancer exome-based CD8 T cell neo-antigen identification" OncoImmunology 3, (2014)".

Wang et al. Identification of T-cell Receptors Targeting KRAS-Mutated Human Tumors. Cancer Immunol Res. Mar. 2016;4(3):204-14. doi: 10.1158/2326-6066.CIR-15-0188. Epub Dec. 23, 2015. PMID: 26701267; PMCID: PMC4775432.

Young, et al. Dendritic cells stimulate primary human cytolytic lymphocyte responses in the absence of CD4+ helper T cells. J Exp Med. Apr. 1, 1990;171(4):1315-32.

Sakaguchi, et al., "Regulatory T Cells and Immune Tolerance" Cell 133, May 30, 2008, p. 775-787.

Kurd, et al., "T cell selection in the thymus: a spatial and temporal perspective" Immunol Rev (2016): 271(1): p. 114-126.

Andersen, et al., "Dissection of T-cell Antigen Specificity in Human Melanoma" Cancer Res; 72(7) Apr. 1, 2012, p. 1642-1650.

Abdelhakim: The activation marker CD137 identifies a highly active subset of donor lymphocytes agaiast acute myeloid leukemia future. Biol. Blood Marrow Transplant. 25(3):290-442 (2019) Abstract.

Al-Kadhimi, Zaid. et al. The Use of Clinical Grade Magnetic Beads to Deplete Immune Suppressive Elements from Autologous Peripheral Blood Hematopoietic Stem Cell Grafts Enhances T Cell Immune Responses. Blood 112(11):2311, 1-3 (2008).

Boon, Thierry, et al., Human T Cell Responses Against Melanoma. Annual Review of Immunology 24:175-208 (2006).

Borgers et al: Personalized, autologous neoantigen-specific T cell therapy in metastatic melanoma: a phase 1 trial. Nat Med 31:881-893 (2025).

Borish, Larry. et al. Cytokines and chemokines. J Allergy Clin Immunol 111(2 Suppl):S460-475 (2003).

Chae, Young Kwang. et al. Current landscape and future of dual anti-CTLA4 and PD-1/PD-L1 blockade immunotherapy in cancer; lessons learned from clinical trials with melanoma and non- small cell lung cancer (NSCLC). J Immunother Cancer 6(1):39, 1-27 (2018).

Dengjel, Jorn, et al., Glycan Side Chains on Naturally Presented MHC Class IL Ligands. Journal of Mass Spectrometry 40(1):100-104 (2005).

Dermer, Gerald B, et al., Another Anniversary for the War on Cancer. Biotechnology 12:320 (1994).

Di Stasi, Antonio, et al., Inducible Apoptosis as a Safety Switch for Adoptive Cell Therapy. The New England Journal of Medicine 365(18):1673-1683 (2011).

Ding, Li, et al., Genome Remodelling in a Basal-like Breast Cancer Metastasis and Xenograft. Nature 464:999-1005 (2010).

Ding, Li, et al., Somatic Mutations Affect Key Pathways in Lung Adenocarcinoma. Nature 455:1069-1075 (2008).

Dong et al.: Flt-3 Ligand: A Potent Dendritic Cell Stimulator and Novel Antitumor. Cancer Biology & Therapy. 1(5):486-489 (2002).

(56)　　　　　References Cited

OTHER PUBLICATIONS

Efremova, et al.: Neoantigens Generated By Individual Mutations And Their Role in Cancer Immunitya nd Immunotherapy. Frontiers in Immunology (2017) vol. 8, pp. 1-8.

Eisenhauer, E A. et al. New Response Evaluation Criteria In Solid Tumours: Revised RECIST Guideline (Version 1.1). European Journal of Cancer 45(2):228-247 (2009).

EP11781409.5 Extended European Search Report dated Apr. 16, 2014.

EP15198284.0 Extended European Search Report dated Apr. 11, 2016.

EP20801696.4 Extended European Search Report dated May 22, 2023.

EP21856741.0 European Search Report dated Jul. 22, 2024.

Erlich, Rachel L, et al., Next-Generation Sequencing for HLA Typing of Class I Loci. BMC Genomics 12(1):42, 39pages (2011).

Hacohen, Nir, et al., Getting Personal with Neoantigen-Based Therapeutic Cancer Vaccines. Cancer immunology research 1(1):11-15 (2013).

Hadrup, Sine Reker. et al. Parallel Detection of Antigen-Specific T-CellResponses by Multidimensional Encoding of MHC Multimers. Nature Methods 6(7):520-526 (2009).

Halabi, Susan. et al. Prognostic model for predicting survival in men with hormone-refractory metastatic prostate cancer. Journal of Clinical Oncology 21(7):1232-1237 (2003).

Hall, Neil. Advanced Sequencing Technologies and Their Wider Impact in Microbiology. Journal of Experimental Biology 210(9):1518-1525 (2007).

Hamanishi, Junzo. et al. PD-1/PD-L1 blockade in cancer treatment: perspectives and issues. Int J Clin Oncol 21(3):462-473 (2016).

Han, Arnold, et al., Linking T-Cell Receptor Sequence to Functional Phenotype at the Single-Cell Level. Nature Biotechnology 32(7):684-692 (2014).

Hanahan, Douglas, et al., Hallmarks of Cancer: The Next Generation. Cell 144(5): 646-674 (2011).

Hansen, Kasper Daniel, et al. Increased Methylation Variation in Epigenetic Domains Across Cancer Types. Nature Genetics 43(8):768-775 (2011).

Hanzelmann, Sonja, et al., GSVA: Gene Set Variation Analysis for Microarray and RNA-seq Data. BMC Bioinformatics, 14:7,15 Pages (2013).

Harndahl, Mikkel, et al., Peptide-MHC Class I Stability is a Better Predictor than Peptide Affinity of CTL Immunogenicity. European Journal of Immunology 42(6):1405-1416 (2012).

Harndahl, Mikkel et al. Real-time, High-Throughput Measurements of Peptide-MHC-I Dissociation Using a Scintillation Proximity Assay. Journal of Immunological Methods vol. 374, 1-2: pp. 5-12 (2011).

Harris, R Alan, et al., Comparison of Sequencing-based Methods to Profile DNA Methylation and Identification of Monoallelic Epigenetic Modifications. Nature Biotechnology 28(10):1097-1105 (2010).

Harris, Reuben S, et al., RNA Editing Enzyme APOBECI and some of its Homologs can Act as DNA Mutators. Molecular Cell 10(5):1247-1253 (2002).

Hartley et al.: Pancreatic cancer, treatment options, and GI-4000. Human Vaccines & Immunotherapeutics 11(4):931-937 (2015).

He et al., RAS gene mutations in Chinese leukaemia patients and members of a family with high incidence of leukaemia. Leuk Res. Nov.-Dec. 1996;20(11-12):901-3. doi: 10.1016/s0145-2126(96)00044-6. PMID: 9009246.

Heemskerk, Bianca. et al. The Cancer Antigenome. EMBO Journal 32(2):194-203 (2013).

Hel, Zdenek. et al. Potentiation of simian immunodeficiency virus (SIV)-specific CD4(+) and CD8(+) T cell responses by a DNA-SIV and NYVAC-SIV prime/boost regimen. Journal of immunology 167(12):7180-7191 (2001).

Herbeuval, Jean-Philippe, et al., HAART Reduces Death Ligand but not Death Receptors in Lymphoid Tissue of HIV-Infected Patients and Simian Immunodeficiency Virus-Infected Macaques. AIDS 23(1):35-40 (2009).

Herbst, Roy S, et al., Predictive Correlates of Response to the Anti-PD-L1 Antibody MPDL3280A in Cancer Patients. Nature 515(7528):563-567 (2014).

Herman, J, et al., Differences in the Recognition by CTL of Peptides Presented by the HLA-B* 4402 and the HLA-B*4403 Molecules Which Differ by a Single Amino Acid. Tissue Antigens 53(2):111-121 (1999).

Herman, S E M, et al., Ibrutinib-Induced Lymphocytosis in Patients With Chronic Lymphocytic Leukemia: Correlative Analyses From a Phase II Study. Leukemia 28(11):2188-2196 (2014).

Hersey, Peter, et al., Phase I/II Study of Treatment with Dendritic cell Vaccines in Patient with Disseminated Melanoma. Cancer Immunol Immunother 53(2):125-134 (2004).

Hickman, Heather, et al., Toward a Definition of Self: Proteomic Evaluation of the Class I Peptide Repertoire. Journal of Immunology 172(5):2944-2952 (2004).

Hinrichs, Christian S, et al., Exploiting the Curative Potential of Adoptive T-cell Therapy for Cancer. Immunological Reviews 257(1):56-71 (2014).

Hocker, Thomas, et al., Ultraviolet Radiation and Melanoma: A Systematic Review and Analysis of Reported Sequence Variants. Human mutation 28(6):578-588 (2007).

Hodi, F Stephen, et al., Biologic Activity of Cytotoxic T Lymphocyte-Associated Antigen 4 Antibody Blockade in Previously Vaccinated Metastatic Melanoma and Ovarian Carcinoma Patients. Proceedings of the National Academy of Sciences of the United States of America 100(8):4712-4717 (2003).

Hodi, F Stephen, et al., Immunologic and Clinical Effects of Antibody Blockade of Cytotoxic T Lymphocyte-Associated Antigen 4 in Previously Vaccinated Cancer Patients. Proceedings of the National Academy of Sciences of the United States of America 105(8):3005-3010 (2008).

Hodi, F Stephen, et al., Improved Survival With Ipilimumab in Patients With Metastatic Melanoma. The New England Journal of Medicine 363(8):711-723 (2010).

Hombrink, Pleun. et al. High-Throughput Identification of Potential Minor Histocompatibility Antigens by MHC Tetramer-Based Screening: Feasibility and Limitations. PLoS One 6(8): e22523, 1-11 (2011).

Hombrink, Pleun, et al., Identification of Biological Relevant Minor Histocompatibility Antigens within the B-lymphocyte-Derived HLA-Ligandome Using a Reverse Immunology Approach. Clinical Cancer Research 21(9):2177-2186 (2015).

Honigberg, Lee A, et al., The Bruton Tyrosine Kinase Inhibitor PCI-32765 Blocks B-cell Activation and is Efficacious in Models of Autoimmune Disease and B-cell Malignancy. Proceedings of the National Academy of Sciences of the United States of America 107(29):13075--13080 (2010).

Horig, Heidi. et al. Phase 1 Clinical Trial of a Recombinant Canarypoxvirus (ALVAC) Vaccine Expressing Human Carcinoembryonic Antigen and the B7.1 Co-stimulatory Molecule. Cancer Immunology Immunotherapy 49(9):504-514 (2000).

Illumina, Immunotherapy, the Next Generation of Cancer Treatment, NGS-guided assessment of interactions between tumors and the immune system leads to new discoveries in immuno-oncology. 1-10 (2016).

Inokuchi, Koiti, et al., DCC Protein Expression in Hematopoietic Cell Populations and Its Relation to Leukemogenesis. The Journal of Clinical Investigation 97(3):852-857 (1996).

International Search Report and Written Opinion in corresponding PCT Application No. PCT/US2019/038019 dated Dec. 4, 2019.

International Search Report and Written Opinion issued in PCT/US2020/025796 on Jun. 23, 2020.

Ishihama, Yasushi, et al., Exponentially Modified Protein Abundance Index (emPAI) for Estimation of Absolute Protein Amount in Proteomics by the Number of Sequenced Peptides Per Protein. Molecular & Cellular Proteomics 4(9):1265-1272 (2005).

Izeradjene, Kamel, et al., Casein Kinase II (CK2) Enhances Death-inducing Signaling Complex (DISC) Activity in TRAIL-induced Apoptosis in Human Colon Carcinoma Cell Lines. Oncogene 24(12):2050-2058 (2005).

Jaatinen, Taina, et al., Global Gene Expression Profile of Human Cord Blood-derived CD133+ Cells. Stem Cells 24(3):631-641 (2006).

(56) References Cited

OTHER PUBLICATIONS

Jarmalavicius, Saulius, et al., High Immunogenicity of the Human Leukocyte Antigen Peptidomes of Melanoma Tumor Cells. The Journal of Biological Chemistry 287(40):33401-33411 (2012).

Jayasinghe, Reyka G, et al., Systematic Analysis of Splice-site-creating Mutations in Cancer. Cell Reports 23(1):270-281 (2018).

Jeffery, K J, et al., The Influence of HLA Class I Alleles and Heterozygosity on the Outcome of Human T Cell Lymphotropic Virus Type I Infection. Journal of Immunology 165(12):7278-7284 (2000).

Jema, Ahmedin, et al., Cancer statistics, 2007. CA Cancer Journal for Clinicians 57(1):43-66 (2007).

Jennewein, Carla, et al., Sumoylation of Peroxisome Proliferator-activated Receptor Gamma by Apoptotic Cells Prevents Lipopolysaccharide-induced NCoR Removal From KappaB Binding Sites Mediating Transrepression of Proinflammatory Cytokines. Journal of Immunology 181(8):5646-5652 (2008).

Johnson, Barbara J, et al., Single-cell Perforin and Granzyme Expression Reveals the Anatomical Localization of Effector CD8+ T Cells in Influenza Virus-infected Mice. Proceedings of the National Academy of Sciences of the United States of America 100(5):2657-2662 (2003).

Johnson, Kenneth, et al., Discovery of Naturally Processed and HLA-Presented Class I Peptides from Vaccinia Virus Infection using Mass Spectrometry for Vaccine Development. Vaccine 28(1):38-47 (2009).

Jones, Peter A, et al., The Epigenomics of Cancer. Cell 128(4):683-692 (2007).

Jones, Peter A. Functions of DNA Methylation: Islands, Start Sites, Gene Bodies and Beyond. Nature Reviews Genetics 13(7):484-492 (2012).

Jones, Philip, et al., InterProScan 5: Genome-Scale Protein Function Classification. Bioinformatics 30(9):1236-1240 (2014).

Kalaora, Shelly, et al., Use of HLA Peptidomics and Whole Exome Sequencing to Identify Human Immunogenic Neo-Antigens. Oncotarget 7(5):5110-5117 (2016).

Kandoth, Cyriac, et al., Mutational Landscape and Significance Across 12 Major Cancer Types. Nature 502(7471):333-339 (2013).

Kannan, S. et al., Vaccination Strategies in Follicular Lymphoma. Current Hematologic Malignancy Reports 4(4):189-195 (2009).

Karnani, Neerja, et al., Pan-S Replication Patterns and Chromosomal Domains Defined by Genome-Tiling Arrays of ENCODE Genomic Areas. Genome Research 17(6):865-876 (2007).

Karolchik, Donna, et al., The UCSC Table Browser Data Retrieval Tool. Nucleic Acids Research 32:D493-D496 (2004).

Kawai, Taro, et al., TLR Signaling. Seminars in Immunology 19(1):24-32 (2007).

Keskin, Derin B, et al., Neoantigen Vaccine Generates Intratumoral T Cell Responses in Phase Ib Glioblastoma Trial. Nature 565(7738):234-239 (2019).

Khong, Hung T, et al., Natural Selection of Tumor Variants in the Generation of "tumor escape" Phenotypes. Nature Immunology 3(11):999-1005 (2002).

Kim, Daehwan et al. TopHat2: Accurate Alignment of Transcriptomes in the Presence of Insertions, Deletions and Gene Fusions. Genome Biology 14:R36, 1-13 (2013).

Kim, Eun Ju, et al., mTOR Inhibitors Radiosensitize PTEN-Deficient Non-Small-Cell Lung Cancer Cells Harboring an EGFR Activating Mutation by Inducing Autophagy. Journal of Cellular Biochemistry 114(6):1248-1256 (2013).

Kim, Jonghwan, et al., A Myc Network Accounts for Similarities Between Embryonic Stem and Cancer Cell Transcription Programs. Cell 143(2):313-324 (2010).

Kim, Yohan, et al., Positional Bias of MHC Class I Restricted T-Cell Epitopes in Viral Antigens Is Likely due to a Bias in Conservation. PLoS Computational Biology 9(1):e1002884,8 Pages (2013).

Kirkwood, John M, et al., High- and Low-Dose Interferon Alpha-2b in High-risk Melanoma: First Analysis of Intergroup Trial E1690/S9111/C9190. Journal of Clinical Oncology 18(12):2444-2458 (2000).

Kirkwood, John M, et al., Interferon alfa-2b Adjuvant Therapy of High-risk Resected Cutaneous Melanoma: The Eastern Cooperative Oncology Group Trial EST 1684. Journal of Clinical Oncology 14(1):7-17 (1996).

Klebanoff, Christopher A, et al., Therapeutic Cancer Vaccines: are we there yet?. Immunological Reviews 239(1):27-44 (2011).

Klein, Allon M, et al., Droplet Barcoding for Single-cell Transcriptomics Applied to Embryonic Stem Cells. Cell 161(5):1187-1201 (2015).

Kloor, Matthias, et al., Immune Evasion of Microsatellite Unstable Colorectal Cancers. International Journal of Cancer 127(5):1001-1010 (2010).

Klug, Felix, et al., Characterization of MHC Ligands for Peptide Based Tumor Vaccination. Current Pharmaceutical Design 15(28):3221-3236 (2009).

Koch, Hauke., Combining Morphology and DNA Barcoding Resolves the Taxonomy of Western Malagasy Liotrigona Moure, 1961. African Invertebrates 51(2):413-421 (2010).

Kreso, Antonija, et al., Variable Clonal Repopulation Dynamics Influence Chemotherapy Response in Colorectal Cancer. Science 339(6119):543-548 (2013).

Kress, W. John, et al., DNA Barcodes: Genes, Genomics, and Bioinformatics. Proceedings of the National Academy of Sciences of the United States of America 105(8):2761-2762 (2008).

Kress, W. John, et al., Use of DNA Barcodes to Identify Flowering Plants. Proceedings of the National Academy of Sciences of the United States of America 102(23):8369-8374 (2005).

Kulis, Marta, et al., Epigenomic Analysis Detects Widespread Gene-Body DNA Hypomethylation in Chronic Lymphocytic Leukemia. Nature Genetics 44(11):1236-1242 (2012).

Lahaye, Renaud, et al., DNA Barcoding the Floras of Biodiversity Hotspots. Proceedings of the National Academy of Sciences of the United States of America 105(8):2923-2928 (2008).

Landan, Gilad, et al., Epigenetic Polymorphism and the Stochastic Formation of Differentially Methylated Regions in Normal and Cancerous Tissues. Nature Genetics 44(11):1207-1214 (2012).

Landau, Dan A, et al., Clonal Evolution in Hematological Malignancies and Therapeutic Implications. Leukemia 28(1):34-43 (2014).

Leffers, Ninke, et al., Immunization with a P53 Synthetic Long Peptide Vaccine Induces P53-Specific Immune Responses in Ovarian Cancer Patients, a Phase II Trial. International Journal of Cancer 125(9):2104-2113 (2009).

Leffers, Ninke, et al., Long-term Clinical and Immunological Effects of p53-SLP® Vaccine in Patients with Ovarian Cancer. International Journal of Cancer 130(1):105-112 (2012).

Lemay, Serge, et al., Dok-3, A Novel Adapter Molecule Involved in the Negative Regulation of Immunoreceptor Signaling. Molecular and Cellular Biology 20:2743-2754 (2000).

Lewintre, Eloisa, et al., Analysis of Chronic Lymphotic Leukemia Transcriptomic Profile: Differences Between Molecular Subgroups. Leukemia & Lymphoma 50:68-79 (2009).

Li, Bo, et al., RSEM: Accurate Transcript Quantification from RNA-Seq Data With or Without a Reference Genome. BMC Bioinformatics 12:323, 1-16 (2011).

Li, Heng, et al., Fast and Accurate Long-Read Alignment with Burrows-Wheeler Transform. Bioinformatics 26(5):589-595 (2010).

Li, Heng, et al., Fast and Accurate Short Read Alignment with Burrows-Wheeler Transform. Bioinformatics 25(14):1754-1760 (2009).

Li, Heng. et al. Mapping Short DNA Sequencing Reads and Calling Variants Using Mapping Quality Scores. Genome Research 18(11):1851-1858 (2008).

Li, Meng, et al., Inactivating Mutations of the Chromatin Remodeling Gene ARID2 in Hepatocellular Carcinoma. Nature Genetics 43:828-829 (2011).

Liggins, Amanda, et al., MORC4, A Novel Member of the MORC Family, is Highly Expressed in a Subset of Diffuse Large B-Cell Lymphomas. British Journal of Haematology 138:479-486 (2007).

Lim, Elgene, et al., Transcriptome Analyses of Mouse and Human Mammary Cell Subpopulations Reveal Multiple Conserved Genes and Pathways. Breast Cancer Research 12:R21, 1-14 (2010).

Lin, Katherine, et al., Relevance of the Immunoglobulin VH Somatic Mutation Status in Patients with Chronic Lymphocytic Leukemia

(56)         References Cited

OTHER PUBLICATIONS

Treated with Fludarabine, Cyclophosphamide, and Rituximab (FCR) or Related Chemoimmunotherapy Regimens. Blood 113:3168-3171 (2009).

Linardou, Helena, et al., Assessment of Somatic k-RAS Mutations as a Mechanism Associated with Resistance to EGFR-targeted Agents: A Systematic Review and Meta-Analysis of Studies in Advanced Non-Small-Cell Lung Cancer and Metastatic Colorectal Cancer. The Lancet Oncology 9(10):962-972 (2008).

Linardou, Helena, et al., Somatic EGFR Mutations and Efficacy of Tyrosine Kinase Inhibitors in NSCLC. Nature Reviews Clinical Oncology 6(6):352-366 (2009).

Link et al., Electric control of droplets in microfluidic devices, Angew Chem Int Ed Engl, 45(16):2556-2560 (2006).

Liu, Su-Yang, et al., Systematic Identification of Type I and Type II Interferon-Induced Antiviral Factors. Proceedings of the National Academy of Sciences of the United States of America 109(11):4239-4244 (2012).

Livak, Kenneth J, et al., Methods for qPCR Gene Expression Profiling Applied to 1440 Lymphoblastoid Single Cells. Methods 59(1):71-79 (2013).

Llobet, D, et al., CK2 Controls Trail and Fas Sensitivity by Regulating FLIP Levels in Endometrial Carcinoma Cells. Oncogene 27:2513-2524 (2008).

Lohr, Jens, et al., Discovery and Prioritization of Somatic Mutations in Diffuse Large B-cell Lymphoma (DLBCL) by Whole-Exome Sequencing. Proceedings of the National Academy of Sciences of the United States of America 109(10):3879-3884 (2012).

Lorente, Elena, et al., Diversity of Natural Self-Derived Ligands Presented by Different HLA Class I Molecules in Transporter Antigen Processing-deficient Cells. PLoS One 8:10 pages (2013).

Lozzio et al.: Human chronic myelogenous leukemia cell-line with positive Philadelphia chromosome. Blood 45(3):321-334 (1975).

Lu, Yong-Chen, et al., Mutated 1PPP1R3B is Recognized by T Cells Used to Treat a Melanoma Patient Who Experienced a Durable Complete Tumor Regression. Journal of Immunology 190(12):6034-6042 (2013).

Lucas, S, et al., About Human Tumor Antigens to be used in Immunotherapy. Seminars in Immunology 20(5):301-307 (2008).

Lund, Jennifer, et al., Coordination of Early Protective Immunity to Viral Infection by Regulatory T Cells. Science 320(5880):1220-1224 (2008).

Luo, Heng, et al., Machine Learning Methods for Predicting HLA-Peptide Binding Activity. Bioinformatics and Biology Insights 9(S3):21-29 (2015).

Ma, Bin., Novor: Real-Time Peptide De Novo Sequencing Software. Journal of the American Society for Mass Spectrometry 26:1885-1894 (2015).

Maegawa, Shinji, et al., Age-Related Epigenetic Drift in the Pathogenesis of MDS and AML. Genome Research 24:580-591 (2014).

Mair, Barbara, et al., Gain- and Loss-of-function Mutations in the Breast Cancer Gene GATA3 Result in Differential Drug Sensitivity. Public Library of Science Genetics 12(9):e1006279, 1-26 (2016).

Marshall, K W, et al., Role of the Polymorphic Residues in HLA-DR Molecules in Allele-specific Binding of Peptide Ligands. Journal of Immunology 152(10):4946-4957 (1994).

Matsumura, Noriomi. et al. Immunostimulatory effect of FMS-like tyrosine kinase 3 ligand on peripheral monocyte-derived dendritic cells and natural killer cells: utilization for ovarian cancer treatment. Oncology Reports 19(2):505-515 (2008).

Mayer, Jens, et al., A Revised Nomenclature for Transcribed Human Endogenous Retroviral Loci. Mobile DNA 2:7, 8 Pages (2011).

McCleskey et al., GATA3 expression in advanced breast cancer: prognostic value and organ-specific relapse. Am J Clin Pathol. Nov. 2015;144(5):756-63. doi: 10.1309/AJCP5MMR1FJVVTPK. PMID: 26486740.

McMurtrey, Curtis, et al., Toxoplasma Gondii Peptide Ligands Open the Gate of the HLA Class I Binding Groove. eLife 5:e12556,19 Pages (2016).

Medema, Jan Paul, et al., Immune Escape of Tumors in Vivo by Expression of Cellular FLICE-Inhibitory Protein. The Journal of Experimental Medicine 190:1033-1038 (1999).

Meissnar, Alexander, et al., Genome-Scale DNA Methylation Maps of Pluripotent and Differentiated Cells. Nature 454:766-770 (2008).

Menkle, Aswin L, et al., Genetic Interactions Between the Wilms' Tumor 1 Gene and the P53 Gene. Cancer Research 62(22):6615-6620 (2002).

Mermel, Craig H. et al. GISTIC2. 0 facilitates sensitive and confident localization of the targets of focal somatic copy-number alteration in human cancers. Genome biology 12:R41, 1-14 (2011).

Messmer, Bradley T, et al., In Vivo Measurements Document the Dynamic Cellular Kinetics of Chronic Lymphocytic Leukemia B Cells. The Journal of Clinical Investigation 115(3):755-764 (2005).

Milner, Elena, et al., The Effect of Proteasome Inhibition on the Generation of the Human Leukocyte Antigen (HLA) Peptidome. Molecular & Cellular Proteomics 12:1853-1864 (2013).

Milner, Elena, et al., The Turnover Kinetics of Major Histocompatibility Complex Peptides of Human Cancer Cells. Molecular & Cellular Proteomics 5:357-365 (2006).

Missale, Gabriele, et al., HLA-A31- and HLA-Aw68-restricted Cytotoxic T Cell Responses to a Single Hepatitis B Virus Nucleocapsid Epitope During Acute Viral Hepatitis. The Journal of Experimental Medicine 177(3):751-762 (1993).

Mocellin, Simone, et al., Interferon Alpha Adjuvant Therapy in Patients With High-risk Melanoma: A Systematic Review and Meta-analysis. Journal of the National Cancer Institute 102(7):493-501 (2010).

Morison, Ian M, et al., A Census of Mammalian Imprinting. Trends in Genetics 21(8):457-465 (2005).

Morozov, Vladimir A, et al., The Transmembrane Protein of the Human Endogenous Retrovirus--K (HERV-K) Modulates Cytokine Release and Gene Expression. PLoS One 8(8):e70399,9 Pages (2013).

Morton, Donald L, et al., Prolonged Survival of Patients Receiving Active Immunotherapy With Canvaxin Therapeutic Polyvalent Vaccine After Complete Resection of Melanoma Metastatic to Regional Lymph Nodes. Annals of Surgery 236(4):438-448 (2002).

Mosmann, T.R, et al., TH1 and TH2 Cells: Different Patterns of Lymphokine Secretion Lead to Different Functional Properties. Annual Review of Immunology 7:145-173 (1989).

Muller et al., Spliceosomal peptide P140 for immunotherapy of systemic lupus erythematosus: results of an early phase II clinical trial. Arthritis Rheum. 58(12):3873-83 (2008).

Muntel, Jan, et al., Abundance-based Classifier for the Prediction of Mass Spectrometric Peptide Detectability Upon Enrichment (PPA). Molecular & Cellular Proteomics 14:430-440 (2015).

Ng, Julio, et al., Dereplication and De Novo Sequencing of Nonribosomal Peptides. Nature Methods 6:596--599 (2009).

Nielsen, Morten, et al., NetMHCpan, a Method for Quantitative Predictions of Peptide Binding to Any HLA-A and -B Locus Protein of Known Sequence. PLoS One 2:e796, 10 Pages (2007).

Nielsen, Morten, et al., NetMHCpan-3.0; Improved Prediction of Binding to MHC Class I Molecules Integrating Information from Multiple Receptor and Peptide Length Datasets. Genome Medicine 8:33,9 Pages (2016).

Nielsen, Morten, et al., The Role of the Proteasome in Generating Cytotoxic T-cell Epitopes: Insights Obtained from Improved Predictions of Proteasomal Cleavage. Immunogenetics 57:33-41 (2005).

Novershtern, Noa, et al., Densely Interconnected Transcriptional Circuits Control Cell States in Human Hematopoiesis. Cell 144(2):296-309 (2011).

Ohnishi, Kotaro, et al., Premature Termination of Reprogramming in Vivo Leads to Cancer Development Through Altered Epigenetic Regulation. Cell 156(4):663-677 (2014).

Okada, Hideho. et al. Induction of CD8+ T-cell responses against novel glioma-associated antigen peptides and clinical activity by vaccinations with α-type 1 polarized dendritic cells and polyinosinic-polycytidylic acid stabilized by lysine and carboxymethylcellulose in patients with recurrent malignant glioma. Journal of Clinical Oncology 29(3):330-336 (2011).

(56) References Cited

OTHER PUBLICATIONS

Oshiumi, Hiroyuki, et al., DEAD/H BOX 3 (DDX3) Helicase Binds the RIG-I Adaptor IPS-1 to Up-regulate IFN-beta-inducing Potential. European Journal of Immunology 40(4):940-948 (2010).

Ott, Patrick, et al., CTLA-4 and PD-1/PD-L1 blockade: New Immunotherapeutic Modalities With Durable Clinical Benefit in Melanoma Patients. Clinical Cancer Research 19(19):5300-5309 (2013).

Padgett, K A, et al., Creating Seamless Junctions Independent of Restriction Sites in Pcr Cloning. Gene 168(1):31-35 (1996).

Pagès, Franck, et al., Effector Memory T Cells, Early Metastasis, and Survival in Colorectal Cancer. New England Journal of Medicine 353(25):2654-2666 (2005).

Pan et al.: Immunoprevention of KRAS-driven lung adenocarcinoma by a multipeptide vaccine. Oncotarget. 8(47):82689-82699 (2017).

PCT/US2011/036665 International Preliminary Report on Patentability dated Nov. 20, 2012.

PCT/US2014/033185 International Preliminary Report on Patentability dated Oct. 22, 2015.

PCT/US2014/067146 International Preliminary Report on Patentability dated May 31, 2016.

PCT/US2014/068746 International Preliminary Report on Patentability dated Jun. 7, 2016.

PCT/US2014/068893 International Preliminary Report on Patentability dated Jun. 7, 2016.

PCT/US2014/071707 International Preliminary Report on Patentability dated Jun. 21, 2016.

PCT/US2021/045800 International Search Report and Written Opinion dated Dec. 22, 2021.

PCT/US2022/078161 International Search Report and Written Opinion dated Feb. 16, 2023.

PCT/US2023/083256 International Search Report and Written Opinion dated Mar. 26, 2024.

Pei, Lirong, et al., Genome-wide DNA Methylation Analysis Reveals Novel Epigenetic Changes in Chronic Lymphocytic Leukemia. Epigenetics 7(6):567-578 (2012).

Peng, Qisheng, et al., DOK3 Negatively Regulates LPS Responses and Endotoxin Tolerance. Public Library of Science one 7(6):e39967, 11 Pages (2012).

Perez, C A, et al., p63 Consensus DNA-binding Site: Identification, Analysis and Application Into a p63MH Algorithm. Oncogene 26(52):7363-7370 (2007).

Pieters, Jean, et al., On Guard: Coronin Proteins in Innate and Adaptive Immunity. Nature Reviews Immunology 13(7):510-518 (2013).

Pirard, Delphine, et al., Interferon Alpha as Adjuvant Postsurgical Treatment of Melanoma: A Meta-analysis. Dermatology 208(1):43-48 (2004).

Poncette, Lucia. et al. Effective NY-ESO-1-specific MHC II-restricted T cell receptors from antigen-negative hosts enhance tumor regression. J Clin Invest 129(1):324-335. (2019) Published online Dec. 10, 2018.

Powell, Maria L C, et al., NCoR1 Mediates Papillomavirus E8;E2CTranscriptional Repression. Journal of Virology 84(9):4451-4460 (2010).

Pujadas, Elisabet, et al., Regulated Noise in the Epigenetic Landscape of Development and Disease. Cell 148(6):1123-1131 (2012).

Qin, Dong, et al., Soft Lithography for Micro- and Nanoscale Patterning. Nature protocols 5(3):491-502 (2010).

Quesada, Victor, et al., Exome Sequencing Identifies Recurrent Mutations of the Splicing Factor SF3B1 Gene in Chronic Lymphocytic Leukemia. Nature genetics 44(1):47-52 (2011).

Quezada, Sergio, et al., CTLA4 Blockade and GM-CSF Combination Immunotherapy Alters the Intratumor Balance of Effector and Regulatory T Cells. Journal of Clinical Investigation 116(7):1935-1945 (2006).

Ramsköld, Daniel, et al., Full-length mRNA-Seq From Single-cell Levels of RNA and Individual Circulating Tumor Cells. Nature Biotechnology 30(8):777-782 (2012).

Rassenti, Laura, et al., Relative Value of ZAP-70, CD38, and Immunoglobulin Mutation Status in Predicting Aggressive Disease in Chronic Lymphocytic Leukemia. Blood 112(5):1923-1930 (2008).

Raval, Aparna, et al., Downregulation of Death-associated Protein Kinase 1 (DAPK1) in Chronic Lymphocytic Leukemia. Cell 129(5):879-890 (2007).

Ravi, Rajani, et al., Sensitization of Tumor Cells to Apo2 Ligand/TRAIL-Induced Apoptosis by Inhibition of Casein Kinase II. Cancer Research 62(15):4180-4185 (2002).

Richter, Wolfgang F, et al., Mechanistic Determinants of Biotherapeutics Absorption Following SC Administration. American Association of Pharmaceutical Scientists Journal 14(3):559-570 (2012).

Rini, Brian I, et al., Biology and Treatment of Advanced Renal Cell Carcinoma: a Global Perspective. Seminars in oncology 40(4):419-420 (2013).

Robbins, Paul F, et al., Mining Exomic Sequencing Data to Identify Mutated Antigens Recognized by Adoptively Transferred Tumor-reactive T Cells. Nature Medicine 19(6):747-752 (2013).

Robinson, James T, et al., Integrative Genomics Viewer. Nature Biotechnology 29(1):24-26 (2011).

Robinson, Mark D, et al., edgeR: a Bioconductor Package for Differential Expression Analysis of Digital Gene Expression Data. Bioinformatics 26(1):139-140 (2010).

Robinson, R A, et al., A Phase I-II Trial of Multiple-dose Polyriboinosic-polyribocytidylic Acid in Patients With Leukemia or Solid Tumors. Journal of the National Cancer Institute 57(3):599-602 (1976).

Rosenberg, Steven A., Raising the Bar: the Curative Potential of Human Cancer Immunotherapy. Science Translational Medicine 4(127):127ps8, 5 pages (2012).

Rossi, Davide, et al., Integrated Mutational and Cytogenetic Analysis Identifies New Prognostic Subgroups in Chronic Lymphocytic Leukemia. Blood 121(8):1403-1412 (2013).

Rubin, Alan F, et al., Mutation Patterns in Cancer Genomes. Proceedings of the National Academy of Sciences of the United States of America 106(51):21766-21770 (2009).

Rubio-Moscardo, Fanny, et al., Characterization of 8p21.3 Chromosomal Deletions in B-cell Lymphoma: TRAIL-R1 and TRAIL-R2 as Candidate Dosage-dependent Tumor Suppressor Genes. Blood 106(9):3214-3222 (2005).

Rutledge, Caleb W, et al., Tumor-infiltrating Lymphocytes in Glioblastoma Are Associated With Specific Genomic Alterations and Related to Transcriptional Class. Clinical Cancer Research 19(18):4951-4960 (2013).

Saint-Jean, Melanie. et al. Adoptive Cell Therapy with Tumor-Infiltrating Lymphocytes in Advanced Melanoma Patients. J Immunol Res 2018:3530148, 1-10 (2018).

Salem, Mohamed L, et al., Defining the Antigen-specific T-cell Response to Vaccination and Poly(I:C)/TLR3 Signaling: Evidence of Enhanced Primary and Memory CD8 T-cell Responses and Antitumor Immunity. Journal of Immunotherapy 28(3):220-228 (2005).

Samuels, Yardena, et al., Oncogenic PI3K and its Role in Cancer. Current Opinion in Oncology 18(1):77-82 (2006).

Sato, Norihiro, et al., Discovery of Novel Targets for Aberrant Methylation in Pancreatic Carcinoma Using High-throughput Microarrays. Cancer Research 63(13):3735-3742 (2003).

Saturno, Grazia, et al., Combining Trail With PI3 Kinase or HSP90 Inhibitors Enhances Apoptosis in Colorectal Cancer Cells via Suppression of Survival Signaling. Oncotarget 4(8):1185-1198 (2013).

Schmitt, Katja, et al., Transcriptional Profiling of Human Endogenous Retrovirus Group HERV-K(HML-2) Loci in Melanoma. Genome Biology and Evolution 5(2):307-328 (2013).

Schreiber, Robert D, et al., Cancer Immunoediting: Integrating Immunity's Roles in Cancer Suppression and Promotion. Science 331(6024):1565-1570 (2011).

Schumacher, K, et al., Prognostic Significance of Activated CD8(+) T Cell Infiltrations Within Esophageal Carcinomas. Cancer research 61(10):3932-3936 (2001).

Schuster, Stephen J, et al., Vaccination With Patient-specific Tumor-derived Antigen in First Remission Improves Disease-free Survival in Follicular Lymphoma. Journal of Clinical Oncology 29(20):2787-2794 (2011).

(56)         References Cited

OTHER PUBLICATIONS

Secchiero, Paola, et al., Aberrant Expression of TRAIL in B Chronic Lymphocytic Leukemia (B-CLL) Cells. Journal of Cellular Physiology 205(2):246-252 (2005).

Selezneva et al.: Complex Approach to the Study of Pharmacological Agents In Vitro, Ex Vivo, In Vivo. International Research Journal. 6(37):1-13 (2015).

Sensi, Marialuisa, et al., Unique Tumor Antigens: Evidence for Immune Control of Genome Integrity and Immunogenic Targets for T Cell-mediated Patient-specific Immunotherapy. Clinical Cancer Research 12(17):5023-5032 (2006).

Serafini, Paolo. et al. Phosphodiesterase-5 inhibition augments endogenous antitumor immunity by reducing myeloid-derived suppressor cell function. J Exp Med 203(12):2691-2702 (2006).

Shah, Neil P, et al., Multiple BCR-ABL Kinase Domain Mutations Confer Polyclonal Resistance to the Tyrosine Kinase Inhibitor Imatinib (STI571) in Chronic Phase and Blast Crisis Chronic Myeloid Leukemia. Cancer cell 2(2):117-125 (2002).

Shannon, C E, et al., A Mathematical Theory of Communication. The Bell System Technical Journal 27(3):379-423 (1948).

Shao, Haipeng, et al., Clonally Related Histiocytic/dendritic Cell Sarcoma and Chronic Lymphocytic Leukemia/small Lymphocytic Lymphoma: a Study of Seven Cases. Modern Pathology 24(11):1421-1432 (2011).

Shendure, Jay, and Hanlee Ji. Next-generation DNA sequencing. Nature biotechnology 26(10):1135-1145 (2008).

Sidney, John, et al., HLA Class I Supertypes: a Revised and Updated Classification. BioMed Central Immunology 9:1, 15 Pages (2008).

Sidney, John. et al. Several HLA Alleles Share Overlapping Peptide Specificities. The Journal of Immunology 154(1):247-259 (1995).

Siegel, Rebecca, et al., Cancer Statistics, 2013. Cancer Journal for Clinicians 63(1):11-30 (2013).

Simmons, Andrew D, et al., Local Secretion of Anti-CTLA-4 Enhances the Therapeutic Efficacy of a Cancer Immunotherapy With Reduced Evidence of Systemic Autoimmunity. Cancer Immunology and Immunotherapy 57(8):1263-1270 (2008).

Simpson, Andrew J G, et al., Cancer/testis Antigens, Gametogenesis and Cancer. Nature Reviews Cancer 5(8):615-625 (2005).

Simpson, Tyler R, et al., Fc-dependent Depletion of Tumor-infiltrating Regulatory T Cells Co-defines the Efficacy of Anti-CTLA-4 Therapy Against Melanoma. Journal of Experimental Medicine 210(9):1695-1710 (2013).

Slingluff, Craig L, et al., Randomized Multicenter Trial of the Effects of Melanoma-associated Helper Peptides and Cyclophosphamide on the Immunogenicity of a Multipeptide Melanoma Vaccine. Journal of Clinical Oncology 29(21):2924-2932 (2011).

Soares, Helena, et al., A Subset of Dendritic Cells Induces Cd4+ T Cells to Produce IFN-gamma by an IL-12-independent but CD70-dependent Mechanism in Vivo. The Journal of Experimental Medicine 2215(11):1095-1106 (2007).

Soininen, Eeva M, et al., Analysing Diet of Small Herbivores: the Efficiency of DNA Barcoding Coupled With High-throughput Pyrosequencing for Deciphering the Composition of Complex Plant Mixtures. Frontiers in Zoology 6:1-9 (2009).

Song, Jae J, et al., c-Cbl Acts as a Mediator of Src-Induced Activation of the PI3K-Akt Signal Transduction Pathway During TRAIL Treatment. Cellular Signalling 22(3):377-385 (2010).

Sosman, Jeffrey A, et al., A Phase 2 Trial of Complete Resection for Stage IV Melanoma: results of Southwest Oncology Group Clinical Trial S9430. Cancer 117(20):4740-4746 (2011).

Speetjens, Frank M, et al., Induction of P53-specific Immunity by a P53 Synthetic Long Peptide Vaccine in Patients Treated for Metastatic Colorectal Cancer. Clinical Cancer Research : an Official Journal of the American Association for Cancer Research 15(3):1086-1095 (2009).

Spencer, Sabrina L, et al., Non-genetic Origins of Cell-to-cell Variability in Trail-Induced Apoptosis. Nature 459:428-432 (2009).

Spranger, Stefani. et al. Up-regulation of PD-L1, IDO, and T(regs) in the melanoma tumor microenvironment is driven by CD8(+) T cells. Sci Transl Med 5(200):200ra116, 1-10 (2013).

Srivastava, Nisheeth, et al., Modeling the Repertoire of True Tumor-specific Mhc I Epitopes in a Human Tumor. PloS One 4(7):e6094, 5pages (2009).

Srivastava, Pramod K., Therapeutic Cancer Vaccines, Current Opinion in Immunology 18:201-205 (2006).

Stransky, Nicolas. et al. The Mutational Landscape of Head and Neck Squamous Cell Carcinoma. Science 333(6046):1157-1160 (2011).

Stranzl, Thomas, et al., NetCTLpan: Pan-Specific MHC Class I Pathway Epitope Predictions. Immunogenetics 62(6):357-368 (2010).

Su, Zhenqiang, et al., Next-generation Sequencing and its Applications in Molecular Diagnostics. Expert Review of Molecular Diagnostics 11(3):333-343 (2011).

Suzuki, kichiya, et al., A Novel Glycosylphosphatidyl Inositol-anchored Protein on Human Leukocytes: a Possible Role for Regulation of Neutrophil Adherence and Migration. Journal of Immunology 162(7):4277-4284 (1999).

Sykulev, Yuri, et al., Evidence That a Single Peptide-MHC Complex on a Target Cell Can Elicit a Cytolytic T Cell Response. Immunity 4:565-571 (1996).

Takaku, Motoki, et al., GATA3 in Breast Cancer: Tumor Suppressor or Oncogene?. Gene Expression 16(4):163-168 (2015).

Takaku, Motoki, et al., GATA3 Zinc Finger 2 Mutations Reprogram the Breast Cancer Transcriptional Network. Nature Communications 9(1):1059, 14 Pages (2018).

Tan, et al., "Induction of CTLs by DCs pulsed with K-ras mutant peptide on the surface of nanoparticles in the treatment of pancreatic cancer" Oncology Reports (2011) 26: 215-221.

Tang, Ka-Wei, et al., The Landscape of Viral Expression and Host Gene Fusion and Adaptation in Human Cancer. Nature Communications 4:2513, 9pages (2013).

Tang, Shaojun, et al., NeoantigenR: An Annotation Based Pipeline for Tumor Neoantigen Identification from Sequencing Data. BioRxiv preprint :19pages (2017).

Ten Bosch, John R, et al., Keeping Up With the Next Generation: Massively Parallel Sequencing in Clinical Diagnostics. The Journal of Molecular Diagnostics 10(6):484-492 (2008).

Testori, Alessandro, et al., Phase III Comparison of Vitespen, an Autologous Tumor-derived Heat Shock Protein gp96 Peptide Complex Vaccine, With Physician's Choice of Treatment for Stage IV Melanoma: the C-100-21 Study Group. Journal of clinical oncology : official journal of the American Society of Clinical Oncology 26(6):955-962 (2008).

Textor, Sonja, et al., Human NK Cells Are Alerted to Induction of P53 in Cancer Cells by Upregulation of the NKG2D Ligands ULBP1 and ULBP2. Cancer Research 71:5998-6009 (2011).

The Cancer Genome Atlas Network, Comprehensive Molecular Portraits of Human Breast Tumours. Nature 490(7418):61-70 (2012).

Thillier, Yann. et al. Synthesis of 5' cap-0 and cap-1 RNAs using solid-phase chemistry coupled with enzymatic methylation by human (guanine-$N^7$)-methyl transferase. RNA 18(4):856-868 (2012).

Timp, Winston, et al., Cancer as a Dysregulated Epigenome Allowing Cellular Growth Advantage at the Expense of the Host. Nature Reviews.Cancer 13:497-510 (2013).

Tough, David F, et al., Induction of Bystander T Cell Proliferation by Viruses and Type I Interferon in Vivo. Science 272(5270):1947-1950 (1996).

Tran, Eric et al., Cancer Immunotherapy Based on Mutation-Specific CD4+ T Cells in a Patient with Epithelial Cancer. Science 344(6184):641-645 (2014).

Tran, et al., "T-Cell Transfer Therapy Targeting Mutant KRAS in Cancer" N Engl J Med Dec. 8, 2016; 375(23): 2255-2262.

Trolle, Thomas, et al., Automated Benchmarking of Peptide-MHC Class I Binding Predictions. Bioinformatics 31(13):2174-2181 (2015).

Trumpfheller, Christine, et al., Intensified and Protective CD4+ T Cell Immunity in Mice With Anti-dendritic Cell HIV gag Fusion Antibody Vaccine. The Journal of Experimental Medicine 203(3):607-617 (2006).

Trumpfheller, Christine, et al., The Microbial Mimic Poly IC Induces Durable and Protective CD4+ T Cell Immunity Together With a Dendritic Cell Targeted Vaccine. Proceedings of the National Academy of Sciences of the United States of America 105(7):2574-2579 (2008).

(56)        References Cited

OTHER PUBLICATIONS

Tucker, Tracy. et al. Massively Parallel Sequencing:The Next Big Thing in Genetic Medicine. American Journal of Human Genetics 85(2):142-154 (2009).
Turchaninova, Maria A, et al., Pairing of T-cell Receptor Chains via Emulsion PCR. European Journal of Immunology 43:2507-2515 (2013).
Uderhardt, Stefan, et al., 12/15-Lipoxygenase Orchestrates the Clearance of Apoptotic Cells and Maintains Immunologic Tolerance. Immunity 36(5):834-846 (2012).
U.S. Appl. No. 13/108,610 Office Action dated Aug. 15, 2013.
U.S. Appl. No. 13/108,610 Office Action dated Dec. 3, 2014.
U.S. Appl. No. 14/794,449 Office Action dated Dec. 29, 2016.
U.S. Appl. No. 14/794,449 Office Action dated Jul. 24, 2018.
U.S. Appl. No. 14/877,125 Office Action dated Mar. 27, 2017.
U.S. Appl. No. 14/877,125Office Action dated Nov. 2, 2018.
U.S. Appl. No. 15/038,504 Office Action dated Sep. 6, 2017.
U.S. Appl. No. 15/102,129 Office Action dated Dec. 17, 2018.
U.S. Appl. No. 15/102,129 Office Action dated Jul. 28, 2017.
U.S. Appl. No. 15/102,129 Office Action dated Mar. 7, 2018.
U.S. Appl. No. 15/105,961 Office Action dated Jan. 8, 2019.
U.S. Appl. No. 15/105,961 Office Action dated Nov. 20, 2017.
U.S. Appl. No. 15/187,174 Office Action dated Dec. 5, 2016.
U.S. Appl. No. 15/187,174 Office Action dated Jan. 22, 2018.
U.S. Appl. No. 15/187,174, Office Action dated Oct. 12, 2018.
U.S. Appl. No. 15/513,127 Office Action dated Nov. 26, 2018.
U.S. Appl. No. 15/537,785 Office Action dated Dec. 21, 2018.
U.S. Appl. No. 16/181,098 Office Action dated Jan. 31, 2019.
U.S. Appl. No. 17/494,633 Office Action dated Apr. 4, 2024.
U.S. Appl. No. 17/494,633 Office Action dated Jul. 11, 2024.
U.S. Appl. No. 13/108,610 Office Action dated Mar. 7, 2013.
U.S. Appl. No. 14/794,449 Office Action dated Oct. 26, 2016.
U.S. Appl. No. 14/877,125 Office Action dated Nov. 18, 2016.
U.S. Appl. No. 15/038,504 Office Action dated Jun. 22, 2017.
U.S. Appl. No. 15/102,129 Office Action dated May 8, 2017.
U.S. Appl. No. 15/105,961 Office Action dated Jul. 13, 2017.
U.S. Appl. No. 15/187,174 Office Action dated Sep. 9, 2016.
U.S. Appl. No. 15/513,127 Office Action dated Aug. 13, 2018.
U.S. Appl. No. 15/537,785 Office Action dated Mar. 22, 2018.
U.S. Appl. No. 15/575,328 Office Action dated Feb. 7, 2019.
Usary, Jerry, et al., Mutation of GATA3 in Human Breast Tumors. Oncogene 23(46):7669-7678 (2004).
Ushijima, Toshikazu, et al., Fidelity of the Methylation Pattern and Its Variation in the Genome. Genome Research 13:868-874 (2005).
Uyttenhove, Catherine, et al., Evidence for a Tumoral Immune Resistance Mechanism Based on Tryptophan Degradation by Indoleamine 2,3-di Oxygenase. Nature Medicine 9:1269-1274 (2003).
Vaishampayan et al., Active immunotherapy of metastatic melanoma with allogeneic melanoma lysates and interferon alpha, Clin Cancer Res, 8(12):3696-3701 (2002).
Van Elsas, Andrea, et al., Combination Immunotherapy of B16 Melanoma Using Anti-cytotoxic T Lymphocyte-associated Antigen 4 (CTLA-4) and Granulocyte/Macrophage Colony-stimulating Factor (GM-CSF)-producing Vaccines Induces Rejection of Subcutaneous and Metastatic Tumors Accompanied by Autoimmune Depigmentation. Journal of Experimental Medicine 190(3):355-366,12pages (1999).
Van Poelgeest, Mariette I E, et al., HPV16 Synthetic Long Peptide (HPV16-SLP) Vaccination Therapy of Patients With Advanced or Recurrent HPV16-Induced Gynecological Carcinoma, A Phase II Trial. Journal of Translational Medicine 11:88, 14pages (2013).
Verdegaal, Els. E.M. Adoptive cell therapy: a highly successful individualized therapy for melanoma with great potential for other malignancies. Curr Opin Immunol 39:90-95 (2016).
Vermeji, Renee et al., Potentiation of a P53-SLP Vaccine by Cyclophosphamide in Ovarian Cancer: A Single-Arm Phase II Study. International Journal of Cancer 131(5):e670-680 (2012).

Vogel, Roland, et al., Mass Spectrometry Reveals Changes in MHC I Antigen Presentation After Lentivector Expression of a Gene Regulation System. Molecular Therapy-Nucleic Acids 2:e75,8pages (2013).
Wahl, Geoffrey M. et al. Molecular Hybridization of Immobilized Nucleic Acids: Theoretical Concepts and Practical Considerations. Methods in Enzymology 152:399-407 (1987).
Wang et al.: Identification of T-cell Receptors Targeting KRAS-Mutated Human Tumors. Cancer Immunol Res. 4(3):204-214 (2016).
Wang, et al., "Identification of T-Cell Receptors Targeting KRAS-Mutated Human Tumors" Cancer Immunology Research (2016) vol. 4, No. 3, pp. 204-214.
Wang, Guixia, et al., Role of Protein Kinase CK2 in the Regulation of Tumor Necrosis Factor-related Apoptosis Inducing Ligand-induced Apoptosis in Prostate Cancer Cells. Cancer Research 66:2242-2249 (2006).
Wang, Hao, et al., Widespread Plasticity in CTCF Occupancy Linked to DNA Methylation. Genome Research 22:1680-1688 (2012).
Wang, Lili, et al., SF3B1 and Other Novel Cancer Genes in Chronic Lymphocytic Leukemia. The New England Journal of Medicine 365:2497-2506 (2011).
Welters, Marij J P, et al., Induction of Tumor-Specific CD4+ and CD8+ T-Cell Immunity in Cervical Cancer Patients by a Human Papillomavirus Type 16 E6 and E7 Long Peptides Vaccine. Clinical cancer research : an official journal of the American Association for Cancer Research 14(1):178-187 (2008).
Welters, Marij J P, et al., Success or Failure of Vaccination for HPV16-Positive Vulvar Lesions Correlates With Kinetics and Phenotype of Induced T-cell Responses. Proceedings of the National Academy of Sciences of the United States of America 107(26):11895-11899 (2010).
Wheatley, Keith, et al., Does Adjuvant Interferon-alpha for High-risk Melanoma Provide a Worthwhile Benefit? A Meta-analysis of the Randomised Trials. Cancer Treatment Reviews 29(4):241-252 (2003).
Widschwendter, Martin, et al., Epigenetic Stem Cell Signature in Cancer. Nature Genetics 39(2):157-158 (2007).
Wierda, William G, et al., Multivariable Model for Time to First Treatment in Patients With Chronic Lymphocytic Leukemia. Journal of Clinical Oncology 29(31):4088-4095 (2011).
Wilde, Susanne. et al. Dendritic cells pulsed with RNA encoding allogeneic MHC and antigen induce T cells with superior antitumor activity and higher TCR functional avidity. Blood 114(10):2131-2139 (2009).
Winzeler, E A, et al., Functional Characterization of the S. Cerevisiae Genome by Gene Deletion and Parallel Analysis. Science 285(5429):901-906 (1999).
Wolchok, Jedd D, et al., Nivolumab Plus Ipilimumab in Advanced Melanoma. The New England Journal of Medicine 369(2):122-133 (2013).
Wong, David J, et al., Module Map of Stem Cell Genes Guides Creation of Epithelial Cancer stem cells. Cell Stem Cell 2:333-344 (2008).
Woodfine, Kathryn, et al., Quantitative Analysis of DNA Methylation at All Human Imprinted Regions Reveals Preservation of Epigenetic Stability in Adult Somatic Tissue. Epigenetics & Chromatin 4(1):1-13 (2011).
Woyach, Jennifer A, et al., Resistance Mechanisms for the Bruton's Tyrosine Kinase Inhibitor Ibrutinib. The New England Journal of Medicine 370:2286-2294 (2014).
Wraith, David C., The Future of Immunotherapy: A 20-Year Perspective, Frontiers in Immunology 8:1668, 6pages (2017).
Xi, Yuanxin, et al., BSMAP: Whole Genome Bisulfite Sequence MAPping Program. BMC Bioinformatics 10:232, 9pages (2009).
Xie, Huafeng, et al., Stepwise Reprogramming of B Cells Into Macrophages. Cell 117(5):663-676 (2004).
Xu, Qikai et al. Design of 240,000 Orthogonal 25mer DNA Barcode Probes. Proceedings of the National Academy of Sciences vol. 106,7: pp. 2289-2294 (2009).
Felgner, Philip L. et al. Lipofection: a highly efficient, lipid-mediated DNA-transfection procedure. Proceedings of the National Academy of Sciences 84(21):7413-7417 (1987).

(56) References Cited

OTHER PUBLICATIONS

Friedberg, Jonathan W, et al., Inhibition of Syk With Fostamatinib Disodium Has Significant Clinical Activity in Non-Hodgkin Lymphoma and Chronic Lymphocytic Leukemia. Blood 115(13):2578-2585 (2010).

Fujii et al., Clinical significance of KRAS gene mutation and epidermal growth factor receptor expression in Japanese patients with squamous cell carcinoma of the larynx, oropharynx and hypopharynx. Int J Clin Oncol. Jun. 2013;18(3):454-63. doi: 10.1007/s10147-012-0402-z. Epub Mar. 24, 2012. PMID: 22441881.

Gennaro, Alfonso R. et al. Remington's Pharmaceutical Sciences, 18th Edition. Mack Publishing Company (1990).

Gevaert, Kris. et al. Protein Identification Methods in Proteomics. Electrophoresis 21(6):1145-1154 (2000).

Gjertsen, et al., "Intradermal RAS Peptide vaccination with granulocyte-macrophage colony-stimulating factor as adjuvant: clinical and immunological responses in patients with pancreatic adenocarcinoma" Int. J. Cancer: (2001) 92, 441-450.

Greenman et al., Patterns of somatic mutation in human cancer genomes, Nature, 446:153-158 (2007).

Gururangan, Sridharan. et al. Total tumor RNA pulsed dendritic cells plus adoptive transfer of ex-vivo enriched autologous T-lymphocytes in the treatment of children with primary brain tumors. Neuroimmunology and Neuroinflammation 5(10):45, 1-15 (2018).

Landau, Dan A, et al., Evolution and Impact of Subclonal Mutations in Chronic Lymphocytic Leukemia. Cell 152(4):714-726 (2013).

Langmead, Ben, et al., Fast Gapped-Read Alignment with Bowtie 2. Nature Methods 9(4):357-359 (2012).

Langmead, Ben, et al., Ultrafast and Memory-Efficient Alignment of Short DNA Sequences to the Human Genome. Genome Biology 10(3):R25, 10 Pages (2009).

Lata, Sneh, et al., MHCBN 4.0: A Database of MHC/TAP Binding Peptides and T-cell Epitopes. BMC Research Notes 2:61,6 Pages (2009).

Lauss, Martin. et al. Mutational and putative neoantigen load predict clinical benefit of adoptive T cell therapy in melanoma. Nat Commun 8(1):1738, 1-11 (2017).

Lawrence, Michael S, et al., Discovery and Saturation Analysis of Cancer Genes Across 21 Tumour Types. Nature 505(7484):495-501 (2014).

Lawrence, Michael S, et al., Mutational Heterogeneity in Cancer and the Search for New Cancer-Associated Genes. Nature 499(7457):214-218 (2013).

Le, Dung T, et al., Evaluation of Ipilimumab in Combination with Allogeneic Pancreatic Tumor Cells Transfected with a GM-CSF Gene in Previously Treated Pancreatic Cancer. Journal of Immunotherapy 36(7):382-389 (2013).

Lee, Jae H, et al., Sequential Amplification of Cloned DNA as Tandem Multimers using Class-IIS Restriction Enzymes. Genetic Analysis: Biomolecular Engineering 13(6):139-145 (1996).

Yan, Zhijian, et al., PBAF Chromatin-Remodeling Complex Requires a Novel Specificity subunit, BAF200, to Regulate Expression of Selective Interferon-Responsive Genes. Genes & Development 19(14):1662-1667 (2005).

Yang, Aram, et al., HDR Syndrome With a Novel Mutation in GATA3 Mimicking a Congenital X-linked Stapes Gusher: a Case Report. BioMed Central Medical Genetics Medical Genetics 18(1):121, 6 Pages (2017).

Yang, Wanling, et al., Meta-analysis followed by Replication Identifies loci in or near CDKN1B, TET3, CD80, DRAM1, and ARID5B as Associated with systemic Lupus Erythematosus in Asians, American Journal of Human Genetics, 92:41-51 (2013).

Yarchoan, Mark. et al. Targeting neoantigens to augment antitumour immunity. Nat Rev Cancer 17(4):209-222 (2017).

Ye, Kai, et al., Systematic Discovery of Complex Insertions and Deletions in Human Cancers. Nature Medicine 22(1):97-104 (2016).

Yoshihara, Kosuke, et al., Inferring Tumour Purity and Stromal and Immune Cell Admixture from Expression Data. Nature Communications 4:2612, 11 Pages (2013).

Zhu, Xinmei, et al., Toll Like Receptor-3 Ligand Poly-ICLC Promotes the Efficacy of Peripheral Vaccinations With Tumor Antigen-derived Peptide Epitopes in Murine CNS Tumor Models. Journal of Translational Medicine 5:10, 15 Pages (2007).

Zou et al.: Cytokines in the generation and maturation of dendritic cells: recent advances. European cytokine network. 13(2):186-199 (2002).

* cited by examiner

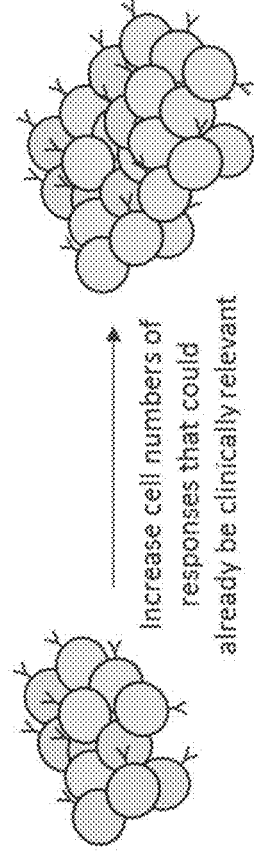
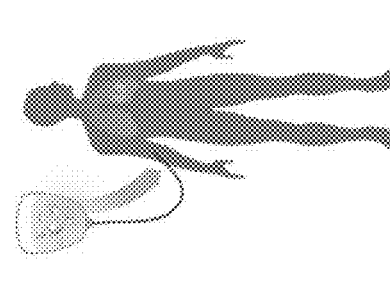
Increase cell numbers of responses that could already be clinically relevant
Broaden the Tc repertoire that can potentially target the tumor
Steer towards favorable phenotype and function
1. Expand out pre-existing memory responses
2. Induce T cell responses from the naïve repertoire
3. Generate a T cell product with clinical efficacy
FIG. 24

1. Perform induction

2. Recall on peptide loaded fresh DCs

3. Assess specificity, phenotype and/or function of T cells

Specificity/sensitivity assay (e.g., by flow cytometry), cell killing assay, and/or cytokine release assay first time period second time period PBMC+DC (no peptide)

PBMC+DC (+ peptides)

PBMC+DC (no peptide)

PBMC+DC (+ peptides)

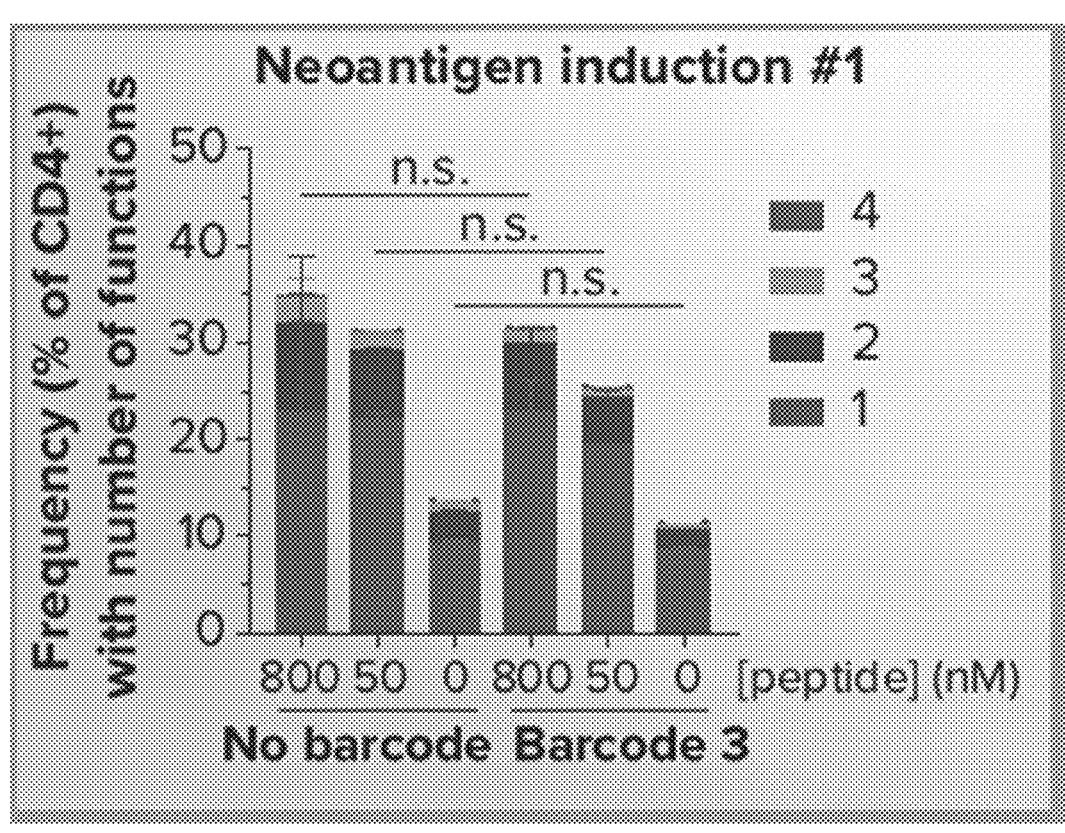
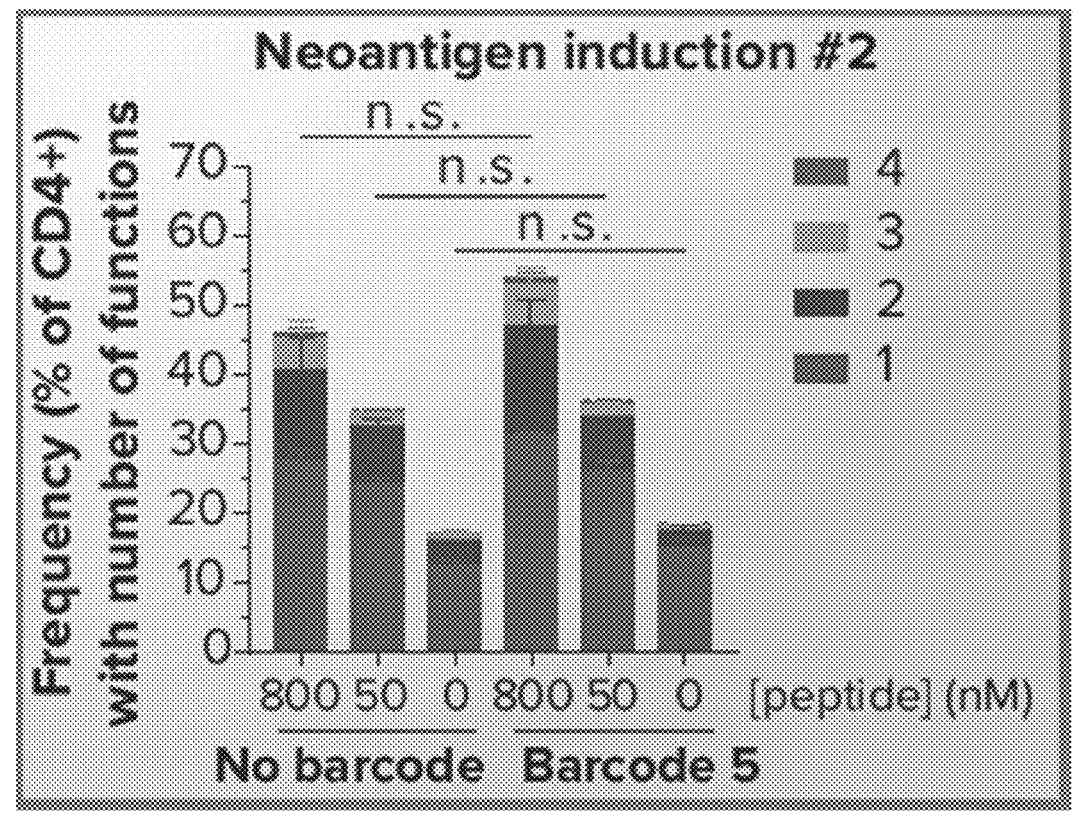
FIG. 28B

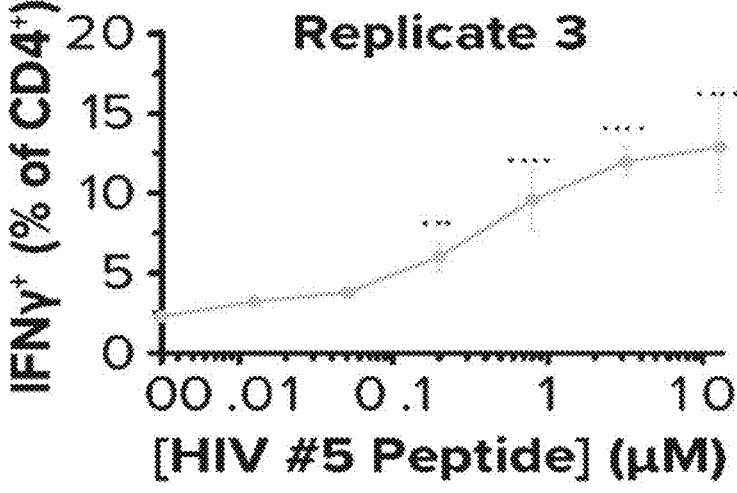
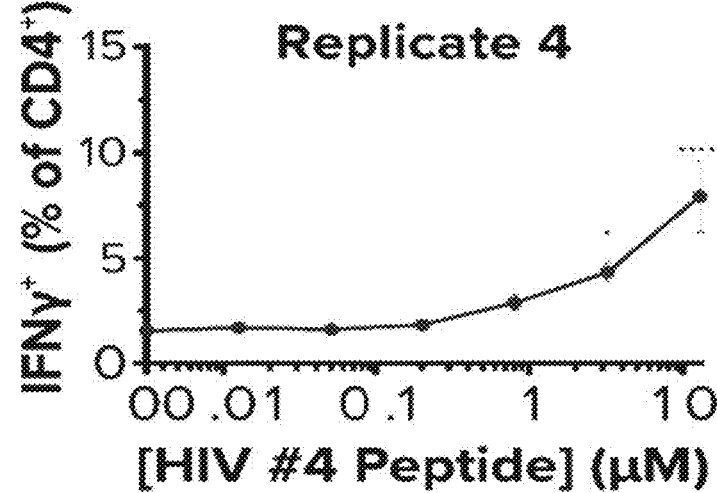
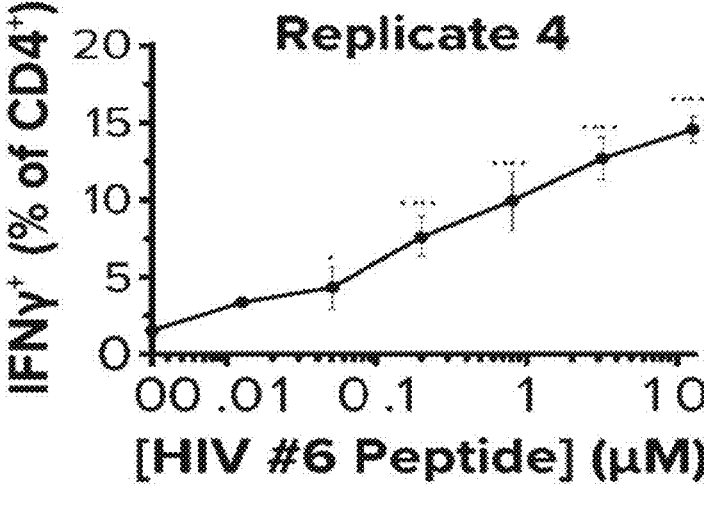
FIG. 30C

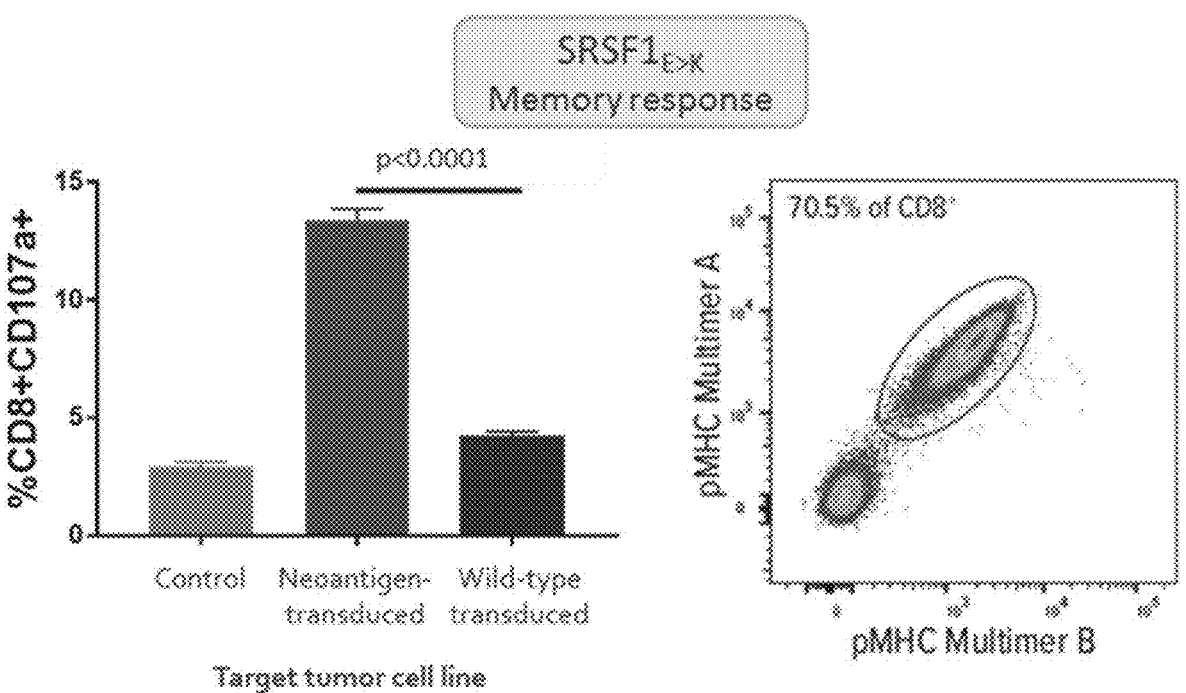
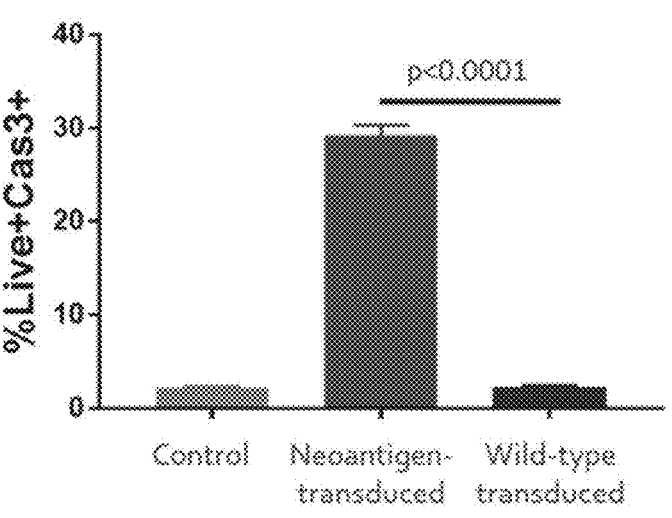
FIG. 37B

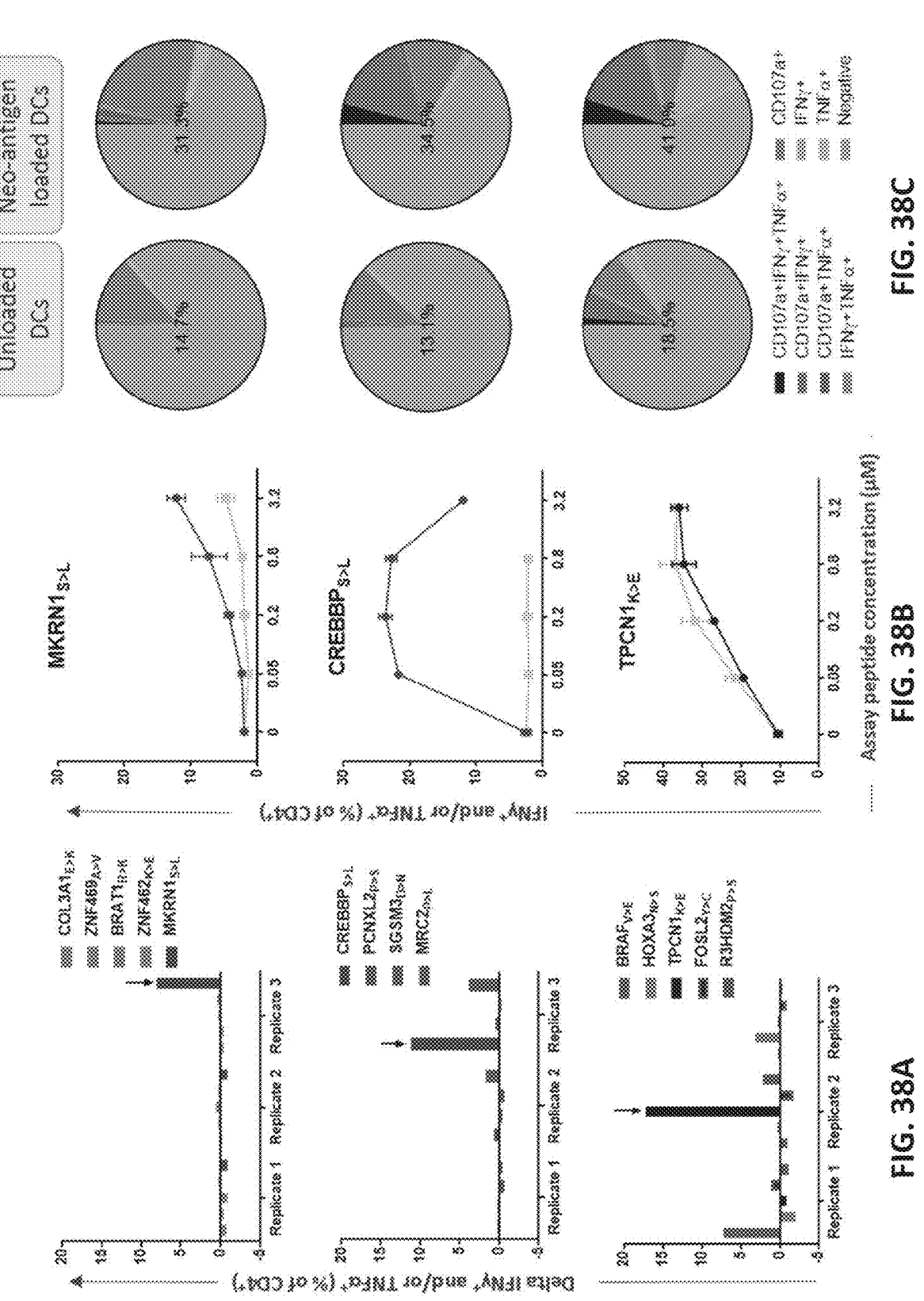

| | FLT3L ctrl | CD11b- | 11b-/19- |
|---|---|---|---|
| Peptide A | 1/6 | | 1/6 |
| Peptide B | | 1/6 | 1/6 |
| ACTN4 | 1/6 | | |
| HIV3 | | | |
| CSNK1A1 | | | 1/6 |
| | | HD69 | |

| | FLT3L ctrl | CD11b- | 11b-/19- |
|---|---|---|---|
| Peptide A | 5/6 | 5/6 | 5/6 |
| Peptide B | 4/6 | 5/6 | 6/6 |
| ACTN4 | | | |
| HIV3 | 2/6 | 2/6 | 2/6 |
| CSNK1A1 | 1/6 | | |
| | | HD67 | |

| | FLT3L ctrl | CD11b- | 11b-/19- |
|---|---|---|---|
| Peptide A | 3/6 | | 1/6 |
| Peptide B | 1/6 | 2/6 | 5/6 |
| ACTN4 | | 1/6 | |
| HIV3 | | | 2/6 |
| CSNK1A1 | | | |
| | | HD66 | |

Naïve CD8 T cell priming
(high and low immunogenic peptides)

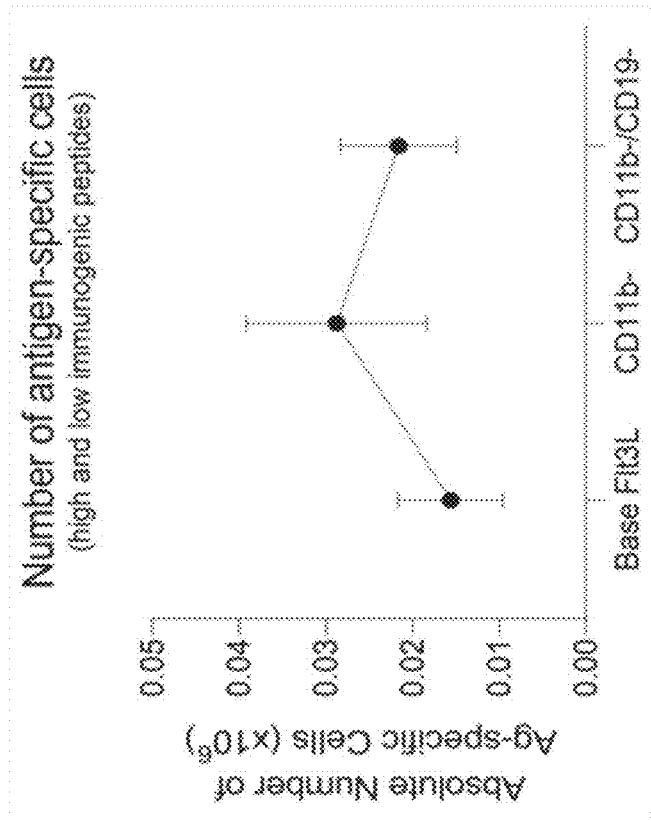
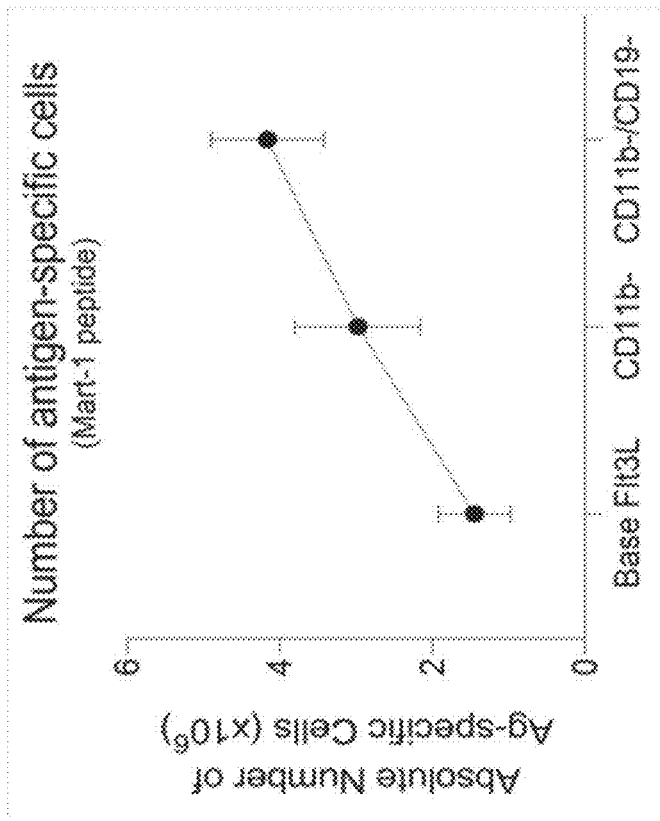
FIG. 50

HD114

| | Base | CD11b- CD19- | APC |
|---|---|---|---|
| Peptide A | | 1/6 | 3/6 |
| Peptide B | 1/6 | 2/6 | 3/6 |
| ACTN4 | | | 2/6 |
| HIV3 | | | |
| CSNK1A1 | 2/6 | 1/6 | 1/6 |

HD113

| | Base | CD11b- CD19- | APC |
|---|---|---|---|
| Peptide A | | 3/6 | 3/6 |
| Peptide B | | 3/6 | 4/6 |
| ACTN4 | | | 1/6 |
| HIV3 | | 1/6 | |
| CSNK1A1 | 1/6 | 3/6 | 1/6 |

HD101

| | Base | CD11b- CD19- | APC |
|---|---|---|---|
| Peptide A | | 5/6 | 4/6 |
| Peptide B | | 4/6 | 3/6 |
| ACTN4 | | 2/6 | 2/6 |
| HIV3 | | | |
| CSNK1A1 | | 1/6 | 3/6 |

Naive CD8 T cell priming
(high and low immunogenic peptides)

HD101
HD113
HD114

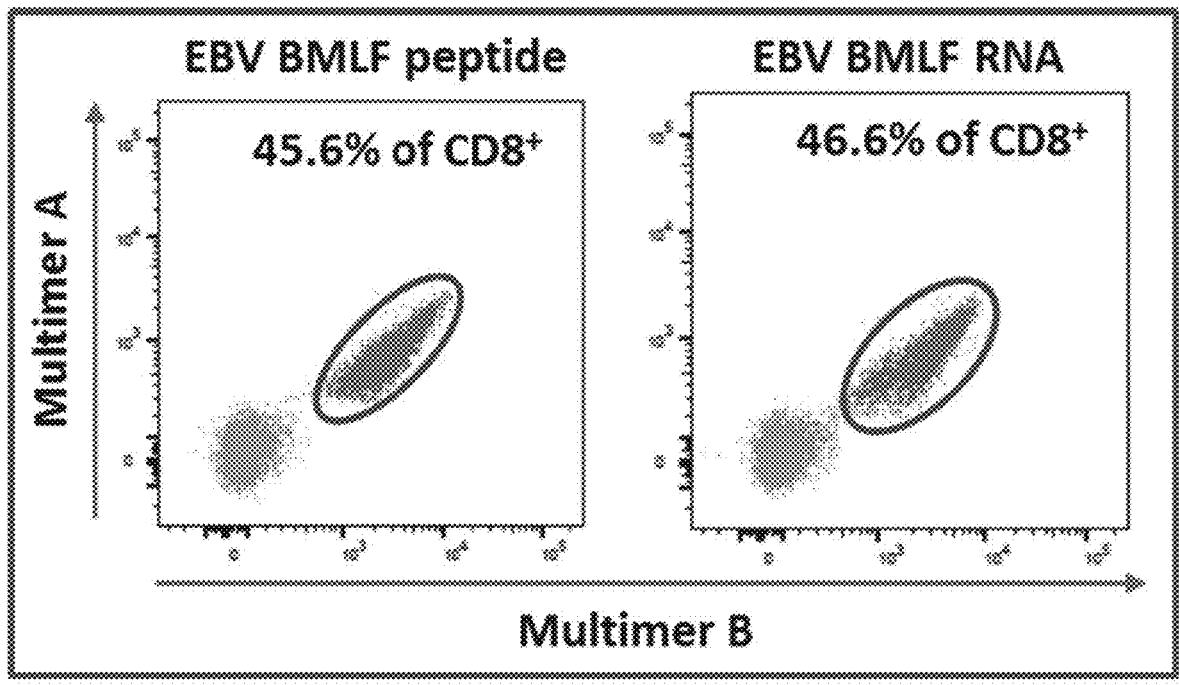
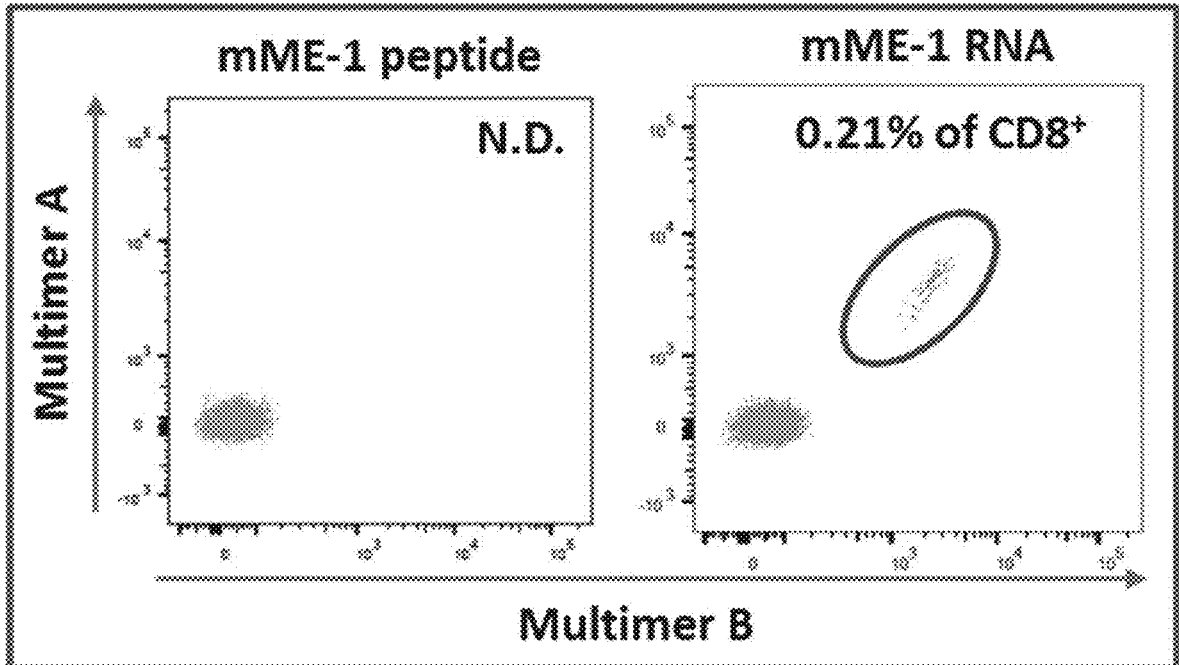
FIG. 55

5' – ACTCACTATAGGNNNNN – 3'    (SEQ ID NO:8)
5' – ACTCACTATAAGGNNNN – 3'    (SEQ ID NO:9)
FIG. 58A
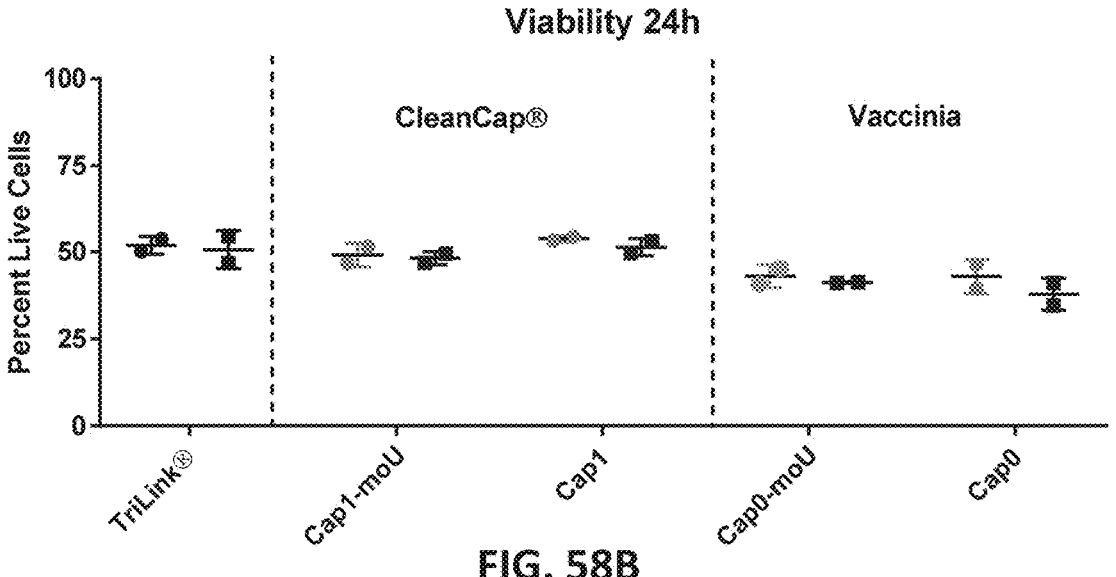
FIG. 58B
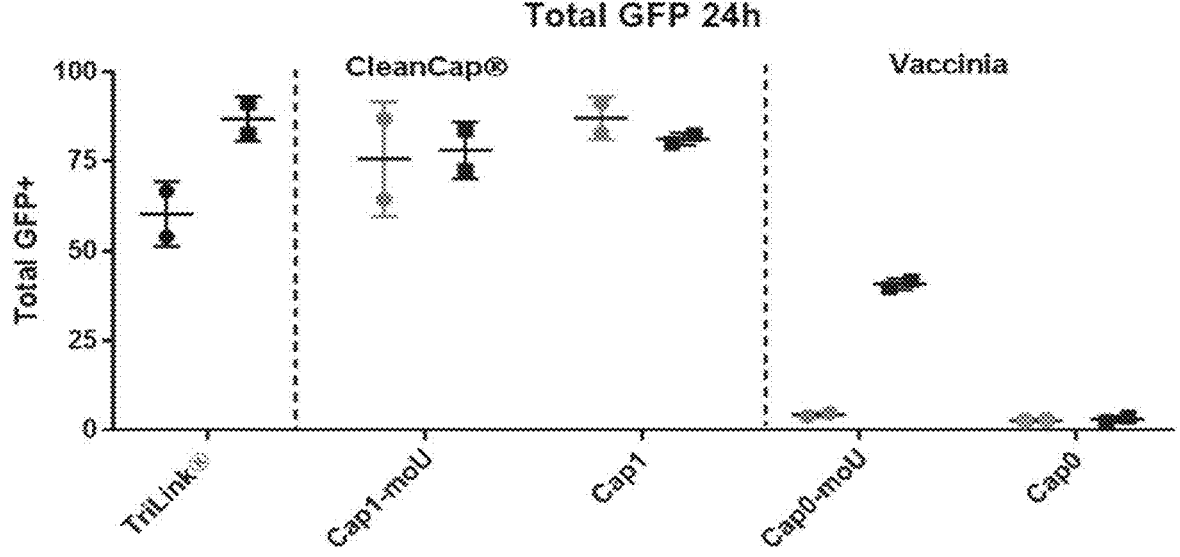
FIG. 58C

Absolute multimer+ cells

Cumulative fold expansion

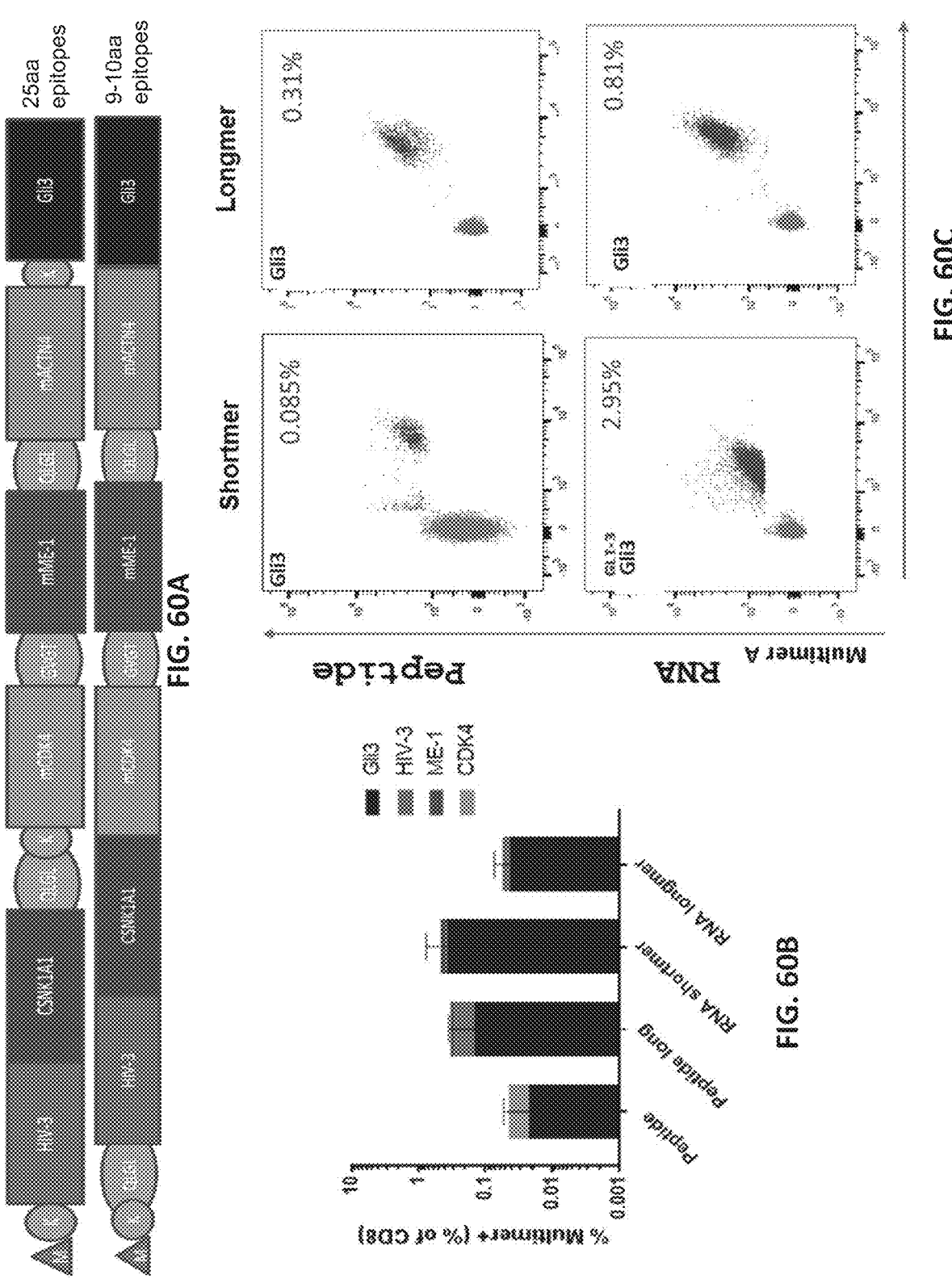

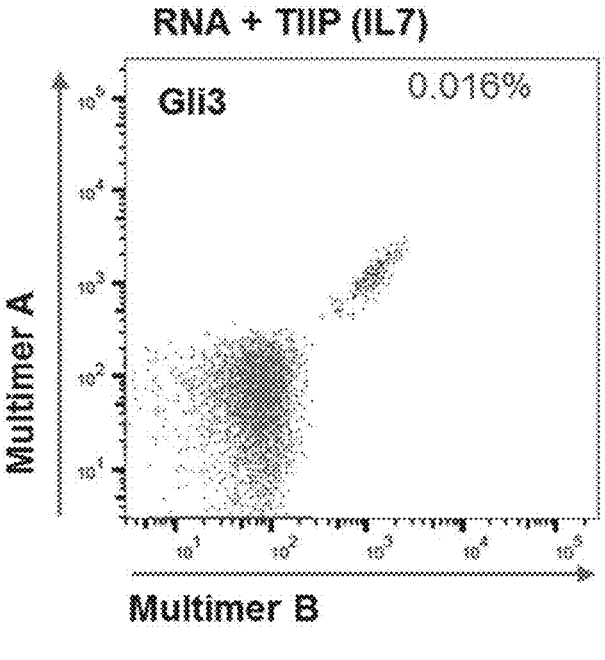
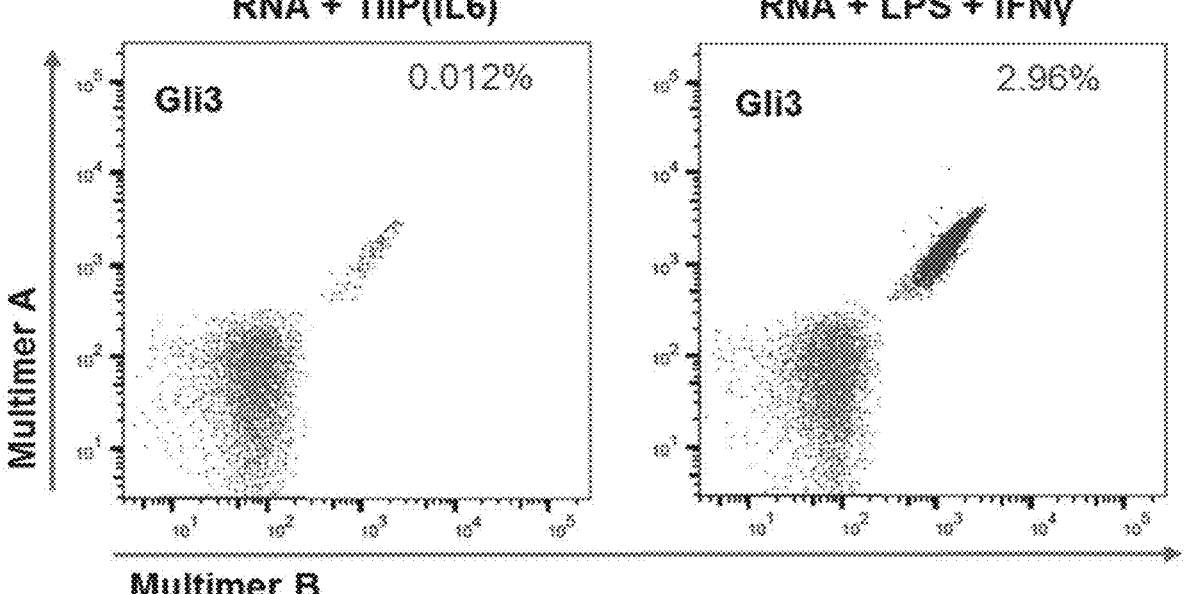
FIG. 62D

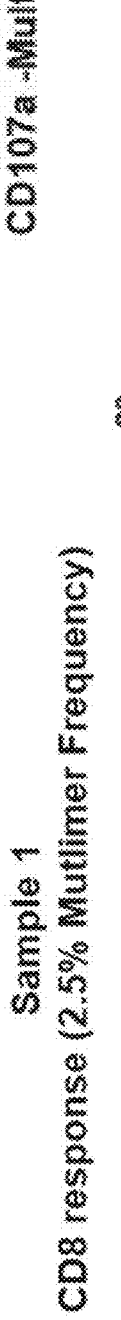
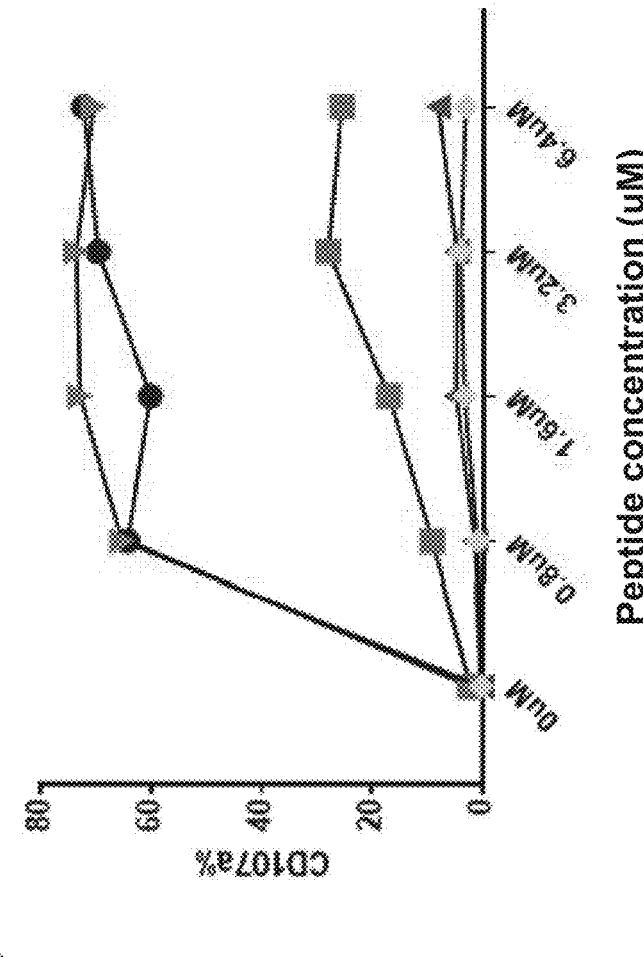
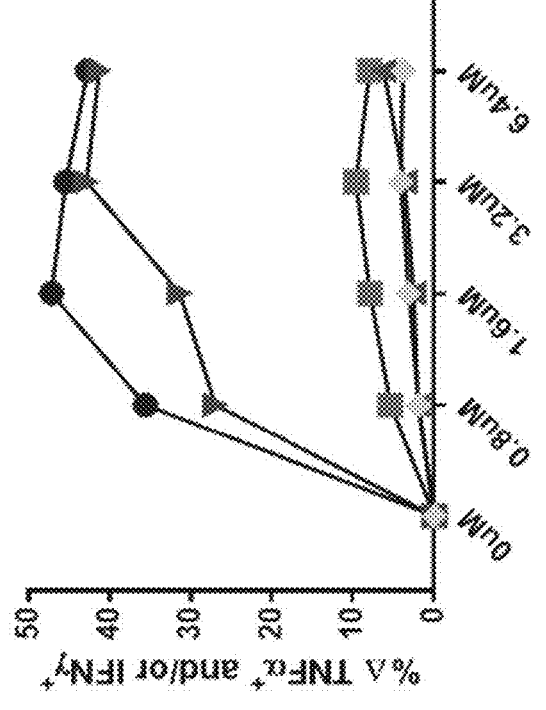
FIG. 64A

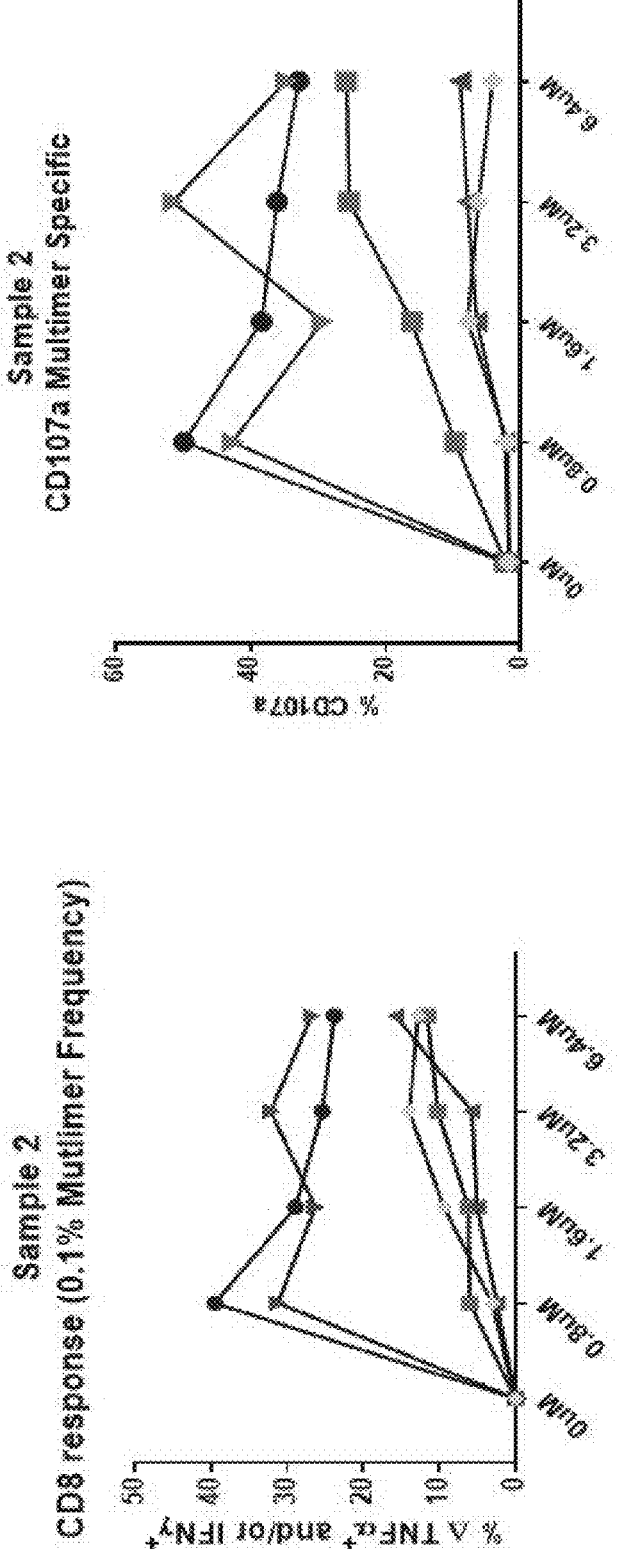
FIG. 64B

FIG. 65

1. Multiple, tumor-specific targets
   - Reduce risk of antigen escape
   - Reduce risk of off-target toxicity 2. Optimal T cell phenotype to drive persistence and tumor cell killing 3. Broad clinical opportunity across solid tumors 4. A non-engineered product, limited toxicity expected

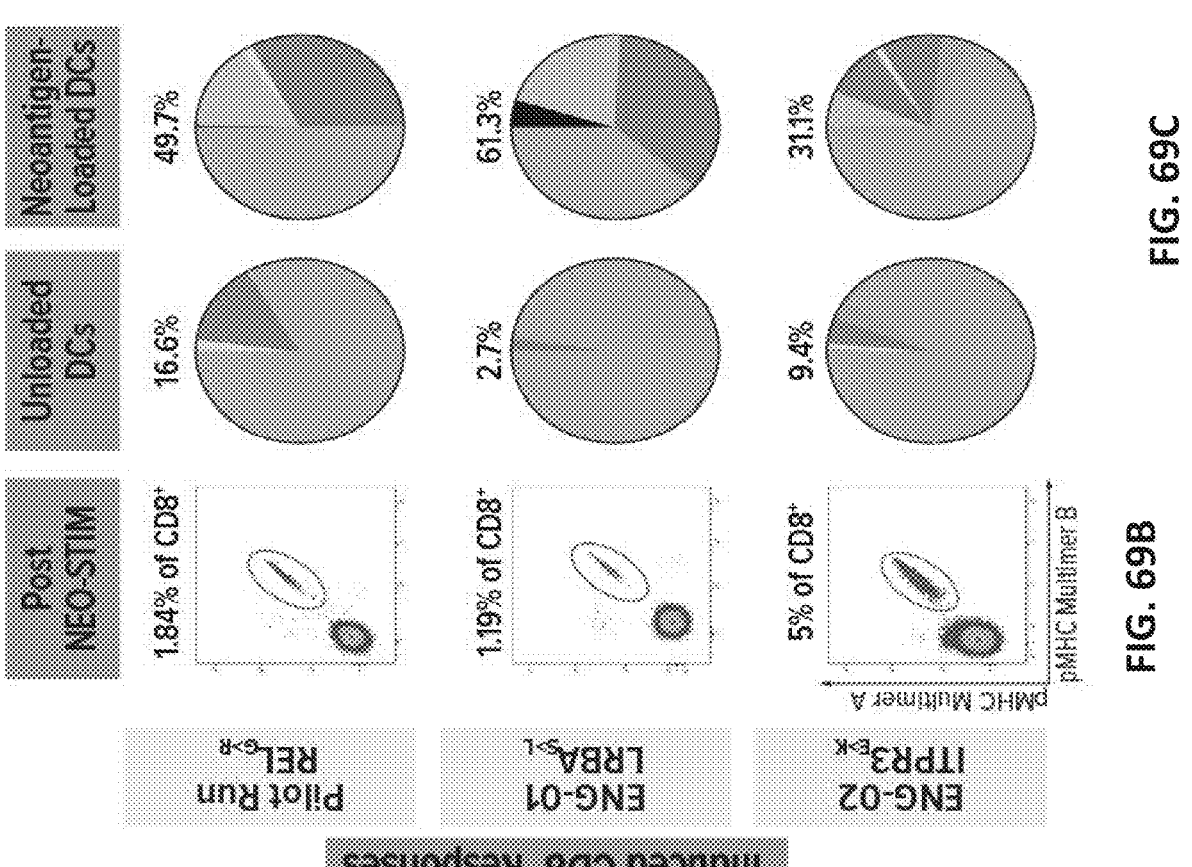
FIG. 69C
FIG. 69B
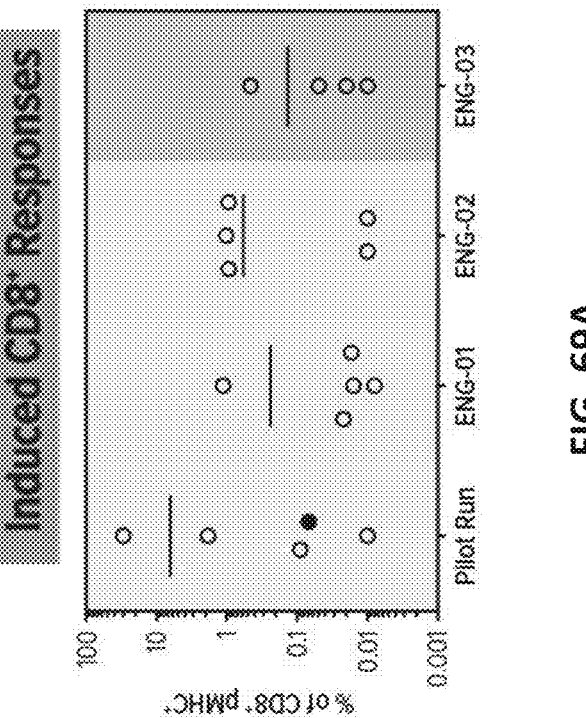
FIG. 69A

FIG. 75

SEQUENCE LISTING

```
<160> NUMBER OF SEQ ID NOS: 29

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggcggcagcg gcggcggcgg cagcggcggc                                       30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggcggcagcc tgggcggcgg cggcagcggc                                       30

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggcgtcggca cc                                                          12

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cagctgggcc tg                                                          12

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 5
caactgggat tg                                                            12

<210> SEQ ID NO 6
<211> LENGTH: 200
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(200)
<223> OTHER INFORMATION: This sequence may encompass 100-200 nucleotides

<400> SEQUENCE: 6
aaaaaaaaaa aaaaaaaaaa aaaaaaaaaa aaaaaaaaaa aaaaaaaaaa aaaaaaaaaa        60
aaaaaaaaaa aaaaaaaaaa aaaaaaaaaa aaaaaaaaaa aaaaaaaaaa aaaaaaaaaa        120
aaaaaaaaaa aaaaaaaaaa aaaaaaaaaa aaaaaaaaaa aaaaaaaaaa aaaaaaaaaa        180
aaaaaaaaaa aaaaaaaaaa                                                    200

<210> SEQ ID NO 7
<211> LENGTH: 250
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(250)
<223> OTHER INFORMATION: This sequence may encompass 100-250 nucleotides

<400> SEQUENCE: 7
aaaaaaaaaa aaaaaaaaaa aaaaaaaaaa aaaaaaaaaa aaaaaaaaaa aaaaaaaaaa        60
aaaaaaaaaa aaaaaaaaaa aaaaaaaaaa aaaaaaaaaa aaaaaaaaaa aaaaaaaaaa        120
aaaaaaaaaa aaaaaaaaaa aaaaaaaaaa aaaaaaaaaa aaaaaaaaaa aaaaaaaaaa        180
aaaaaaaaaa aaaaaaaaaa aaaaaaaaaa aaaaaaaaaa aaaaaaaaaa aaaaaaaaaa        240
aaaaaaaaaa                                                               250

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(17)
<223> OTHER INFORMATION: a, c, t, g, unknown or other

<400> SEQUENCE: 8
actcactata ggnnnnn                                                       17

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (14)..(17)
<223> OTHER INFORMATION: a, c, t, g, unknown or other

<400> SEQUENCE: 9
actcactata aggnnnn                                                  17

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Leu Ile Pro Gly Ile Pro Thr Val
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Leu Ile Pro Gly Ile Thr Val
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Leu Tyr Asn Thr Val Ala Thr Leu
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Phe Ile Ala Ser Asn Gly Val Lys Leu Val
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Cys Asp Pro His Ser Gly His Phe Val
1               5                   10

<210> SEQ ID NO 15
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Leu Asp Glu Phe Met Glu Gly Val
1               5

<210> SEQ ID NO 16
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Ile His Pro Ala Pro Thr Phe Pro Thr Gln Arg Leu Ile Pro Gly
1               5                   10                  15

Ile Pro Thr Val Leu Asn Pro Val Gln
            20                  25

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Leu Ile Pro Gly Ile Pro Thr Val Leu
1               5                   10

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Pro Ala Pro Thr Phe Pro Thr Gln Arg Leu Ile Pro Gly Ile Pro Thr
1               5                   10                  15

Val

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Leu Ile Pro Gly Ile Pro Thr Val Leu Asn Pro Val Gln
1               5                   10

<210> SEQ ID NO 20
<211> LENGTH: 130
<212> TYPE: RNA
<213> ORGANISM: Artificial Sequence
<220> FEATURE:
```

-continued

```
<223> OTHER INFORMATION: Description of Artificial Sequence: Synthetic
      polynucleotide
<220> FEATURE:
<221> NAME/KEY: misc_feature
<222> LOCATION: (1)..(130)
<223> OTHER INFORMATION: This sequence may encompass 120-130 nucleotides

<400> SEQUENCE: 20
aaaaaaaaaa aaaaaaaaaa aaaaaaaaaa aaaaaaaaaa aaaaaaaaaa aaaaaaaaaa        60
aaaaaaaaaa aaaaaaaaaa aaaaaaaaaa aaaaaaaaaa aaaaaaaaaa aaaaaaaaaa       120
aaaaaaaaaa                                                              130

<210> SEQ ID NO 21
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 21
aaaaaaaaaa aaaaaaaaaa aaaaaaaaaa aaaaaaaaaa aaaaaaaaaa aaaaaaaaaa        60
aaaaaaaaaa aaaaaaaaaa aaaaaaaaaa aaaaaaaaaa aaaaaaaaaa aaaaaaaaaa       120

<210> SEQ ID NO 22
<211> LENGTH: 121
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 22
aaaaaaaaaa aaaaaaaaaa aaaaaaaaaa aaaaaaaaaa aaaaaaaaaa aaaaaaaaaa        60
aaaaaaaaaa aaaaaaaaaa aaaaaaaaaa aaaaaaaaaa aaaaaaaaaa aaaaaaaaaa       120
a                                                                      121

<210> SEQ ID NO 23
<211> LENGTH: 122
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 23
aaaaaaaaaa aaaaaaaaaa aaaaaaaaaa aaaaaaaaaa aaaaaaaaaa aaaaaaaaaa        60
aaaaaaaaaa aaaaaaaaaa aaaaaaaaaa aaaaaaaaaa aaaaaaaaaa aaaaaaaaaa       120
aa                                                                     122

<210> SEQ ID NO 24
<211> LENGTH: 123
<212> TYPE: RNA
<213> ORGANISM: Artificial Sequence
<220> FEATURE:
<223> OTHER INFORMATION: Description of Artificial Sequence: Synthetic
      polynucleotide
```

-continued

```
<400> SEQUENCE: 24
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaa                                                                  123

<210> SEQ ID NO 25
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 25
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaa                                                                 124

<210> SEQ ID NO 26
<211> LENGTH: 125
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 26
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaa                                                                125

<210> SEQ ID NO 27
<211> LENGTH: 129
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 27
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaa                                                            129

<210> SEQ ID NO 28
<211> LENGTH: 135
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(135)
<223> OTHER INFORMATION: This sequence may encompass 120-135 nucleotides
```

-continued

```
<400> SEQUENCE: 28
aaaaaaaaaa aaaaaaaaaa aaaaaaaaaa aaaaaaaaaa aaaaaaaaaa aaaaaaaaaa        60
aaaaaaaaaa aaaaaaaaaa aaaaaaaaaa aaaaaaaaaa aaaaaaaaaa aaaaaaaaaa       120
aaaaaaaaaa aaaaa                                                        135

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Leu Gly Leu
1
```

T CELL MANUFACTURING COMPOSITIONS AND METHODS

CROSS REFERENCE

This application claims the benefit of U.S. Provisional Application No. 62/845,251, filed on May 8, 2019, which is incorporated herein by reference in its entirety.

SEQUENCE LISTING

The instant application contains a Sequence Listing which has been submitted electronically in ASCII format and is hereby incorporated by reference in its entirety. Said ASCII copy, created on May 13, 2025, is named 50401-745_831_SL.txt and is 9,767 bytes in size.

BACKGROUND

Tumor vaccines are typically composed of tumor antigens and immunostimulatory molecules (e.g., adjuvants, cytokines or TLR ligands) that work together to induce antigen-specific cytotoxic T cells (CTLs) that recognize and lyse tumor cells. Such vaccines contain either shared tissue restricted tumor antigens or a mixture of shared and patient-specific antigens in the form of whole tumor cell preparations. The shared tissue restricted tumor antigens are ideally immunogenic proteins with selective expression in tumors across many individuals and are commonly delivered to patients as synthetic peptides or recombinant proteins. In contrast, whole tumor cell preparations are delivered to patients as autologous irradiated cells, cell lysates, cell fusions, heat-shock protein preparations or total mRNA. Since whole tumor cells are isolated from the autologous patient, the cells may include patient-specific tumor antigens as well as shared tumor antigens. Finally, there is a third class of tumor antigens, neoantigens, that has rarely been used in vaccines, which consists of proteins with tumor-specific mutations (which can be patient-specific or shared) that result in altered amino acid sequences. Such mutated proteins are: (a) unique to the tumor cell as the mutation and its corresponding protein are present only in the tumor; (b) avoid central tolerance and are therefore more likely to be immunogenic; (c) provide an excellent target for immune recognition including by both humoral and cellular immunity.

Adoptive immunotherapy or adoptive cellular therapy (ACT) is the transfer of lymphocytes to a subject for the therapy of disease. Adoptive immunotherapy has yet to realize its potential for treating a wide variety of diseases including cancer, infectious disease, autoimmune disease, inflammatory disease, and immunodeficiency. However, most, if not all adoptive immunotherapy strategies require T cell activation and expansion steps to generate a clinically effective, therapeutic dose of T cells. Due to the inherent complexity of live cell culture and patient to patient variability, current technologies for generating therapeutic doses of T cells, including engineered T cells, remain limited by cumbersome T cell manufacturing processes. Existing T cell manufacturing processes are not easily scalable, repeatable, reliable, or efficient and often produce an inferior T cell product that may be prone to exhaustion and loss of effector immune cell function. To date, engineered T cell adoptive immunotherapies have met with only limited success and routinely show variable clinical activity. Therefore, such therapies are not suitable for widespread clinical use. Accordingly, there remains a need for developing compositions and methods for expansion and induction of antigen specific T cells with a favorable phenotype and function.

SUMMARY

This disclosure provides novel and improved T cell therapeutics for clinical development and use. Although autologous T cell therapeutic is safe to use, several drastic improvements are necessary to meet therapeutic standards and development in the field has been both rapid and fraught with difficulties. Applicant's previously disclosed application provides hallmark developments in the composition and methods for T cell therapy in cancer, (WO2019/094642). The instant application results from a surprising discovery that depletion of certain cells expressing specific markers at different stages of the ex vivo immune cell preparation provides highly immunogenic cell composition. The present disclosure is derived also in part from the discovery of new and improved methods for antigenic stimulation thereby resulting in improved cell composition for the therapeutics development. Provided herein are new methods and compositions wherein, at least in part, selective depletion of certain immune cells from the ex vivo stimulation and cell expansion milieu provides new therapeutic compositions and improved methods.

Provided herein is an improved ex vivo method for preparing tumor antigen-specific T cells, the method comprising: depleting CD14+ cells and/or CD25+ cells from a population of immune cells comprising antigen presenting cells (APCs) and T cells, thereby forming a CD14 and/or CD25 depleted population of immune cells comprising a first population of APCs and T cells, wherein the population of immune cells is from a biological sample from a human subject; and incubating the CD14 and/or CD25 depleted population of immune cells comprising a first population of APCs and T cells for a first time period in the presence of: FMS-like tyrosine kinase 3 receptor ligand (FLT3L), and (A) a polypeptide comprising at least one tumor antigen epitope sequence expressed by cancer cells of a human subject with cancer, or (B) a polynucleotide encoding the polypeptide; thereby forming a population of cells comprising stimulated T cells; expanding the population of cells comprising stimulated T cells, thereby forming an expanded population of cells comprising tumor antigen-specific T cells, wherein the tumor antigen-specific T cells comprise T cells that are specific to a complex comprising (i) the at least one tumor antigen epitope sequence and (ii) an MHC protein expressed by the cancer cells or APCs of the human subject of (b)(ii); and administering the expanded population of cells comprising tumor antigen-specific T cells to the human subject, wherein the expanded population of cells comprising tumor antigen-specific T cells comprises from $1\times10^8$ to $1\times10^{11}$ total cells.

Provided herein is an improved ex vivo method for preparing tumor antigen-specific T cells, the method comprising: depleting CD14+ cells and/or CD25+ cells from a population of immune cells comprising antigen presenting cells (APCs) and T cells, thereby forming a CD14 and/or CD25 depleted population of immune cells comprising a first population of APCs and T cells, wherein the population of immune cells is from a biological sample from a human subject; and incubating the CD14 and/or CD25 depleted population of immune cells comprising a first population of APCs and T cells for a first time period in the presence of: FMS-like tyrosine kinase 3 receptor ligand (FLT3L), and (A) a polypeptide comprising at least one tumor antigen epitope sequence expressed by cancer cells of a human subject with cancer, or (B) a polynucleotide encoding the polypeptide; thereby forming a population of cells comprising stimulated T cells; expanding the population of cells comprising stimulated T cells, thereby forming an expanded population of cells comprising tumor antigen-specific T cells, wherein the tumor antigen-specific T cells comprise T cells that are specific to a complex comprising (i) the at least one tumor antigen epitope sequence and (ii) an MHC protein expressed by the cancer cells or APCs of the human subject of (b)(ii); and administering the expanded population of cells comprising tumor antigen-specific T cells to the human subject, wherein the human subject: has unresectable melanoma, has previously received a PD-1 inhibitor or PD-L1 inhibitor and a CTLA-4 inhibitor containing regimen and has disease progression, or has received or is currently receiving a PD-1 inhibitor or PD-L1 inhibitor for at least 3 months and has stable disease asymptomatic progressive disease.

Provided herein is an improved ex vivo method for preparing tumor antigen-specific T cells, the method comprising: depleting CD14+ cells and/or CD25+ cells from a population of immune cells comprising antigen presenting cells (APCs) and T cells, thereby forming a CD14 and/or CD25 depleted population of immune cells comprising a first population of APCs and T cells, wherein the population of immune cells is from a biological sample from a human subject; and incubating the CD14 and/or CD25 depleted population of immune cells comprising a first population of APCs and T cells for a first time period in the presence of: FMS-like tyrosine kinase 3 receptor ligand (FLT3L), and an mRNA encoding a polypeptide comprising at least two different tumor antigen epitope sequences expressed by cancer cells of a human subject with cancer; thereby forming a population of cells comprising stimulated T cells; and expanding the population of cells comprising stimulated T cells, thereby forming an expanded population of cells comprising tumor antigen-specific T cells, wherein the tumor antigen-specific T cells comprise T cells that are specific to a complex comprising (i) the at least one tumor antigen epitope sequence and (ii) an MHC protein expressed by the cancer cells or APCs of the human subject of (b)(ii).

Provided herein is an improved ex vivo method for preparing tumor antigen-specific T cells, the method comprising: depleting CD14+ cells and/or CD25+ cells: (i) directly from a washed and/or cryopreserved peripheral blood mononuclear cell (PBMC) sample from a human subject, (ii) from a PBMC sample from a human subject containing about the same percentage of immature dendritic cells (DCs) as the percentage of immature DCs in the peripheral blood of the human subject, (iii) from a PBMC sample from a human subject containing about the same percentage of mature DCs as the percentage of mature DCs in the peripheral blood of the human subject, (iv) from a PBMC sample from a human subject containing about the same ratio of immature DCs to mature DCs as the ratio of immature DCs to mature DCs in the peripheral blood of the human subject, (v) from a PBMC sample from a human subject that has not been subject to a step of maturing immature DCs into mature DCs (vi) from a PBMC sample from a human subject containing about the same percentage of APCs of the total cell population as the percentage of APCs of the total cell population in the peripheral blood of the human subject (vii) from a PBMC sample from a human subject containing about the same percentage of DCs of the total cell population as the percentage of DCs of the total cell population in the peripheral blood of the human subject, (viii) from a PBMC sample from a human subject containing about the same percentage of CD303+ cells of the total cell population as the percentage of CD303+ of the total cell population in the peripheral blood of the human subject, (ix) from a PBMC sample from a human subject containing about the same percentage of CD141+ cells of the total cell population as the percentage of CD141+ of the total cell population in the peripheral blood of the human subject, (x) from a PBMC sample from a human subject containing about the same percentage of macrophages of the total cell population as the percentage of macrophages of the total cell population in the peripheral blood of the human subject, or (xi) from a PBMC sample from a human subject containing about the same percentage of CD19+ of the total cell population as the percentage of CD19+ of the total cell population in the peripheral blood of the human subject; thereby forming a CD14 and/or CD25 depleted population of PBMCs comprising a first population of APCs and T cells; and (b) incubating the CD14 and/or CD25 depleted population of immune cells comprising a first population of APCs and T cells for a first time period in the presence of: FMS-like tyrosine kinase 3 receptor ligand (FLT3L), and (A) a polypeptide comprising at least one tumor antigen epitope sequence expressed by cancer cells of a human subject with cancer, or (B) a polynucleotide encoding the polypeptide; thereby forming a population of cells comprising stimulated T cells; and expanding the population of cells comprising stimulated T cells, thereby forming an expanded population of cells comprising tumor antigen-specific T cells, wherein the tumor antigen-specific T cells comprise T cells that are specific to a complex comprising (i) the at least one tumor antigen epitope sequence and (ii) an MHC protein expressed by the cancer cells or APCs of the human subject of (b)(ii).

In some embodiments, the method further comprises administering the expanded population of cells comprising tumor antigen-specific T cells to the human subject.

In some embodiments, incubating comprises incubating the CD14 and/or CD25 depleted population of immune cells comprising a first population of APCs and T cells for a first time period in the presence of (i) FMS-like tyrosine kinase 3 receptor ligand (FLT3L), and (ii) an mRNA encoding a polypeptide comprising at least two different tumor antigen epitope sequences expressed by cancer cells of a human subject with cancer.

In some embodiments, introducing comprises electroporating or nucleofecting. In some embodiments, the electroporating or nucleofecting is carried out without separating the T cells from the APCs of the first population of APCs and T cells from step (a).

In some embodiments, the method further comprises administering the expanded population of cells comprising tumor antigen-specific T cells to the human subject. In some embodiments, incubating comprises incubating the CD14 and/or CD25 depleted population of immune cells comprising a first population of APCs and T cells for a first time period in the presence of (i) FMS-like tyrosine kinase 3 receptor ligand (FLT3L), and (ii) an mRNA encoding a polypeptide comprising at least two different tumor antigen epitope sequences expressed by cancer cells of a human subject with cancer.

In some embodiments, the mRNA comprises a 5' CAP. In some embodiments, the 5' CAP is CAP-1. In some embodiments, the mRNA comprises a 3' polyA tail. In some embodiments, the polyA tail is from 120 to 135 nucleotides in length (SEQ ID NO: 28). In some embodiments, a first tumor antigen epitope sequence of the at least two different tumor antigen epitope sequences is connected to a second tumor antigen epitope sequence of the at least two different tumor antigen epitope sequences via a linker sequence. In some embodiments, the 5' CAP is operably linked to a sequence encoding the at least two different tumor antigen epitope sequences via a linker sequence. In some embodiments, the at least two different tumor antigen epitope sequences are expressed as a single polypeptide chain. In some embodiments, incubating comprises incubating the CD14 and/or CD25 depleted population of immune cells comprising a first population of APCs and T cells in the presence of LPS and IFNγ.

In some embodiments, the at least two different tumor antigen epitope sequences are each 8 to 12 amino acids in length. In some embodiments, the at least two different tumor antigen epitope sequences are each 15 to 25 amino acids in length. In some embodiments, the polypeptide comprises at least 3, 4, 5, 6, 7, 8, 9, 10 or more different tumor antigen epitope sequences expressed by cancer cells of a human subject with cancer.

In some embodiments, the expanded population of cells comprising tumor antigen-specific T cells comprises from $1 \times 10^8$ to $1 \times 10^{11}$ total cells. In some embodiments, the expanded population of cells comprising tumor antigen-specific T cells comprises from $1 \times 10^8$ to $1 \times 10^{11}$ CD3+ cells.

In some embodiments, the human subject has unresectable melanoma. Unlike resectable melanoma, tumor infiltrating lymphocytes (TILs) cannot be obtained from an unresectable melanoma; thus, TILs cannot be used for treatment of unresectable melanoma. One advantage of the methods and compositions provided herein is that they can be used to treat unresectable melanoma.

In some embodiments, the human subject previously received a PD-1 inhibitor or PD-L1 inhibitor and a CTLA-4 inhibitor containing regimen and has disease progression.

In some embodiments, the human subject has received or is currently receiving a PD-1 inhibitor or PD-L1 inhibitor for at least 3 months and has stable disease asymptomatic progressive disease.

In some embodiments, the percentage of CD3+ cells in the expanded population of cells comprising tumor antigen-specific T cells is at least 40% or 50% or 60% of the total cell population.

In some embodiments, the percentage of CD107a+ cells in the expanded population of cells comprising tumor antigen-specific T cells is at least 10% of the tumor antigen-specific T cell population.

In some embodiments, the percentage of TNFα+ cells in the expanded population of cells comprising tumor antigen-specific T cells is at least 5% of the tumor antigen-specific T cell population.

In some embodiments, the percentage of IFNγ+ cells in the expanded population of cells comprising tumor antigen-specific T cells is at least 15% of the tumor antigen-specific T cell population.

In some embodiments, the percentage of TNFα+ and IFNγ+ cells in the expanded population of cells comprising tumor antigen-specific T cells is at least 2% of the tumor antigen-specific T cell population.

In some embodiments, the percentage of TNFα+ and CD107a+ cells in the expanded population of cells comprising tumor antigen-specific T cells is at least 0.5% of the tumor antigen-specific T cell population.

In some embodiments, the percentage of IFNγ+ and CD107a+ cells in the expanded population of cells comprising tumor antigen-specific T cells is at least 5% of the tumor antigen-specific T cell population.

In some embodiments, the percentage of TNFα+ and IFNγ+ and CD107a+ cells in the expanded population of cells comprising tumor antigen-specific T cells is at least 0.1% of the tumor antigen-specific T cell population.

In some embodiments, the percentage of CD4+ T cells in the expanded population of cells comprising tumor antigen-specific T cells that are naive T cells (CD62L+ and CD45RA+) is at most 15%.

In some embodiments, the percentage of CD4+ T cells in the expanded population of cells comprising tumor antigen-specific T cells that are effector memory T cells (CD62L− and CD45RA−) is at least 60%.

In some embodiments, the percentage of CD4+ T cells in the expanded population of cells comprising tumor antigen-specific T cells that are effector T cells (CD62L− and CD45RA+) is at most 5%.

In some embodiments, the percentage of CD4+ T cells in the expanded population of cells comprising tumor antigen-specific T cells that are central memory T cells (CD62L+ and CD45RA−) is at least 10%.

In some embodiments, the percentage of CD8+ T cells in the expanded population of cells comprising tumor antigen-specific T cells that are naive T cells (CD62L+CD45RA+) is at most 25%.

In some embodiments, the percentage of CD8+ T cells in the expanded population of cells comprising tumor antigen-specific T cells that are effector memory T cells (CD62L− CD45RA−) is at least 60%.

In some embodiments, the percentage of CD8+ T cells in the expanded population of cells comprising tumor antigen-specific T cells that are effector T cells (CD62L− CD45RA+) is at most 10%.

In some embodiments, the percentage of CD8+ T cells in the expanded population of cells comprising tumor antigen-specific T cells that are central memory T cells (CD62L+ CD45RA−) is at least 15%.

In some embodiments, the expanded population of cells comprising tumor antigen-specific T cells produces cytokines and cause degranulation upon recognition of target cells.

In some embodiments, the human subject is refractory to an anti-checkpoint inhibitor therapy.

In some embodiments, the human subject is age 18 to 75 years old.

In some embodiments, the human subject has a mutation in a BRAF gene and has previously received a B-raf inhibitor or a B-raf/MEK combination therapy.

In some embodiments, depleting comprises depleting CD14+ cells and CD25+ cells from a peripheral blood mononuclear cell (PBMC) sample from a human subject that has not been subject to a step of monocyte maturation into mature dendritic cells (DCs).

In some embodiments, depleting further comprises depleting CD11b+ cells from the peripheral blood mononuclear cell (PBMC) sample from the human subject that has not been subject to a step of monocyte maturation into mature dendritic cells (DCs).

In some embodiments, steps (b) and (c) are performed in less than 28 days.

In some embodiments, the fraction of CD8+ tumor antigen-specific T cells of the total number of CD8+ T cells in the expanded population of cells comprising tumor antigen specific T cells is at least two-fold higher than the fraction of CD8+ tumor antigen-specific T cells of the total number of CD8+ T cells in the biological sample.

In some embodiments, the fraction of CD4+ tumor antigen-specific T cells of the total number of CD4+ T cells in the expanded population of cells comprising tumor antigen specific T cells is at least two-fold higher than the fraction of CD4+ tumor antigen-specific T cells of the total number of CD4+ T cells in the biological sample.

In some embodiments, at least 0.1% of the CD8+ T cells in the expanded population of cells comprising tumor antigen specific T cells are CD8+ tumor antigen-specific T cells derived from naïve CD8+ T cells.

In some embodiments, at least 0.1% of the CD4+ T cells in the expanded population of cells comprising tumor antigen specific T cells are CD4+ tumor antigen-specific T cells derived from naïve CD4+ T cells.

In some embodiments, expanding comprises (A) contacting the population of cells comprising stimulated T cells with a second population of mature APCs, wherein the second population of mature APCs (i) have been incubated with FLT3L and (ii) present the at least one tumor antigen epitope sequence; and (B) expanding the population of cells comprising stimulated T cells for a second time period, thereby forming an expanded population of T cells.

In some embodiments, the second population of mature APCs have been incubated with FLT3L for at least 1 day prior to contacting the population of cells comprising stimulated T cells with the second population of mature APCs.

In some embodiments, the biological sample is a peripheral blood sample, a leukapheresis sample or an apheresis sample.

In some embodiments, the method further comprises harvesting the expanded population of cells comprising tumor antigen-specific T cells, cryopreserving the expanded population of cells comprising tumor antigen-specific T cells or preparing a pharmaceutical composition containing the expanded population of cells comprising tumor antigen-specific T cells.

In some embodiments, incubating comprises incubating the CD14/CD25 depleted population of immune cells comprising a first population of APCs and T cells for a first time period in the presence of FLT3L and an RNA encoding the polypeptide.

In some embodiments, the human subject with cancer is the human subject from which the biological sample was obtained.

In some embodiments, the polypeptide is from 8 to 50 amino acids in length.

In some embodiments, the polypeptide comprises at least two tumor antigen epitope sequences, each expressed by cancer cells of a human subject with cancer.

In some embodiments, depleting CD14+ cells and/or CD25+ cells from the population of immune cells comprising a first population of APCs and T cells comprises contacting the population of immune cells comprising a first population of APCs and T cells with a CD14 binding agent and/or a CD25 binding agent.

In some embodiments, depleting further comprising depleting CD19+ cells from the population of immune cells comprising a first population of APCs and T cells.

Provided herein is an ex vivo method for preparing tumor antigen-specific T cells, the method comprising: depleting CD11b+ cells from a population of immune cells comprising antigen presenting cells (APCs) and T cells, thereby forming a CD11b depleted population of immune cells comprising a first population of APCs and T cells, wherein the population of immune cells is from a biological sample from a human subject; and incubating the CD11b depleted population of immune cells comprising a first population of APCs and T cells for a first time period in the presence of: FMS-like tyrosine kinase 3 receptor ligand (FLT3L), and (A) a polypeptide comprising at least one tumor antigen epitope sequence expressed by cancer cells of a human subject with cancer, or (B) a polynucleotide encoding the polypeptide; thereby forming a population of cells comprising stimulated T cells; and expanding the population of cells comprising stimulated T cells, thereby forming an expanded population of cells comprising tumor antigen-specific T cells, wherein the tumor antigen-specific T cells comprise T cells that are specific to a complex comprising (i) the at least one tumor antigen epitope sequence and (ii) an MHC protein expressed by the cancer cells or APCs of the human subject of (b)(ii).

Provided herein is a pharmaceutical composition comprising the expanded population of cells comprising tumor antigen-specific T cells produced by a method described herein; and a pharmaceutically acceptable carrier.

Provided herein is a pharmaceutical composition comprising: (a) a population of immune cells from a biological sample, wherein the population of immune cells comprises antigen presenting cell (APC)-stimulated T cells comprising a T cell receptor (TCR) specific to an epitope of a polypeptide, wherein (i) an amount of immune cells expressing CD11b in the population of immune cells is proportionally less than an amount of immune cells expressing CD11b in the biological sample, and/or (ii) an amount of immune cells expressing CD11c in the population of immune cells is proportionally more than an amount of immune cells expressing CD11c in the biological sample; and (b) a pharmaceutically acceptable excipient.

Provided herein is a pharmaceutical composition comprising: (a) a population of immune cells from a biological sample, wherein the population of immune cells comprises antigen presenting cell (APC)-stimulated T cells comprising a T cell receptor (TCR) specific to an epitope of a polypeptide, wherein the APC-stimulated T cells have been incubated with a cytokine; (b) the cytokine; and (c) a pharmaceutically acceptable excipient.

Provided herein is a pharmaceutical composition comprising: (a) a population of immune cells from a biological sample from a subject that has been administered fins-like tyrosine kinase 3 ligand (FLT3L), wherein the population of immune cells comprises antigen presenting cell (APC)-stimulated T cells comprising a T cell receptor (TCR) specific to an epitope of a polypeptide; and (b) a pharmaceutically acceptable excipient.

In some embodiments, the population of immune cells is from a biological sample from a subject.

In some embodiments, the population of immune cells is from a biological sample from a subject that has been administered fins-like tyrosine kinase 3 ligand (FLT3L).

In some embodiments, the APC-stimulated T cells have been incubated with a cytokine and wherein the pharmaceutical composition further comprises the cytokine.

In some embodiments, an amount of immune cells expressing CD11b in the population of immune cells is proportionally less than an amount of immune cells expressing CD11b in the biological sample.

In some embodiments, an amount of immune cells expressing CD11c in the population of immune cells is proportionally more than an amount of immune cells expressing CD11c in the biological sample.

In some embodiments, an amount of immune cells expressing CD14 in the population is proportionally less than an amount of immune cells expressing CD14 in the biological sample.

In some embodiments, an amount of immune cells expressing CD25 in the population is proportionally less than an amount of immune cells expressing CD25 in the biological sample.

In some embodiments, an amount of immune cells expressing CD19 in the population is proportionally less than an amount of immune cells expressing CD19 in the biological sample.

In some embodiments, the APC is a FMS-like tyrosine kinase 3 receptor ligand (FLT3L)-stimulated APC.

In some embodiments, the APC-stimulated T cells are T cells stimulated with FLT3L-stimulated APCs.

In some embodiments, the cytokine is IL-7 or IL-15 or IL-21.

In some embodiments, the APC-stimulated T cells comprise T cells stimulated by antigen loaded APCs presenting the epitope on a MHC class I or an MHC class II molecule.

In some embodiments, the antigen loaded APCs comprise plasmacytoid dendritic cells (pDCs), CD11c+ DCs, CD1c+ DCs, or CD141+ DCs.

In some embodiments, the CD11b cells comprise CD16+ mononuclear cells.

In some embodiments, the pharmaceutical composition further comprises an agent promoting cell growth and maintenance ex vivo comprises a growth factor, a cytokine, an amino acid, a supplement or a combination thereof.

In some embodiments, an amount of immune cells expressing CD1c in the population of immune cells is proportionally more than an amount of immune cells expressing CD1c in the biological sample.

In some embodiments, an amount of immune cells or APCs expressing CD141 in the population of immune cells is proportionally more than an amount of immune cells or APCs expressing CD141 in the biological sample.

In some embodiments, the cell population comprising the antigen loaded APCs comprises greater than 20%, greater than 25%, greater than 30% greater than 35%, greater than 40%, greater than 45%, greater than 50%, greater than 60% or greater than 70% CD11c+ cells.

In some embodiments, the APC-stimulated T cells comprise T cells stimulated by a cell population containing less than 20%, less than 15%, less than 10%, less than 9%, less than 8%, less than 7%, less than 6%, or less than 5%, CD11b+ cells.

In some embodiments, the APC-stimulated T cells comprise T cells stimulated by a cell population containing greater than 90% CD11c+ cells.

In some embodiments, the pharmaceutical composition described herein comprises T cells stimulated by a cell population containing greater than 70% neoantigenic peptide expressing cells that are CD11c+, CD1c+, or CD141+ cells.

In some embodiments, the pharmaceutical composition comprises at least 60% of the T cells in the pharmaceutical composition are specific to the epitope.

In some embodiments, the pharmaceutical composition described herein comprises a greater proportion of naive T cells induced or converted to neoantigen primed T cells compared to a cellular composition obtained by contacting isolated T cells with antigen loaded APCs without the reduction or the depletion of CD11b+ and/or CD19+ cells.

In some embodiments, the pharmaceutical composition described herein comprises greater than 35% naive T cells which are induced or converted to antigen-specific activated T cells that are specific to the epitope.

In some embodiments, the pharmaceutical composition described herein comprises greater proportion of cancer neoantigen specific CD8+ T cells compared to a cellular composition obtained by contacting isolated T cells with antigen loaded APCs without the reduction or the depletion of CD11b+ cells and/or CD19+ cells.

In some embodiments, the pharmaceutical composition described herein comprises at least 30% CD8+ T cells.

In some embodiments, the pharmaceutical composition described herein comprises greater proportion of memory T cell compared to a cellular composition obtained by contacting isolated T cells with antigen loaded APCs without the reduction or the depletion of CD11b+ cells and/or CD19+.

Provided herein is a method of treating cancer in a subject in need thereof, comprising administering a pharmaceutical composition described herein to the subject.

Provided herein is a method of preparing T cells comprising a T cell receptor (TCR) specific to an epitope of a polypeptide, the method comprising (a) depleting cells expressing CD11b from a population of immune cells comprising antigen presenting cells and T cells, thereby forming a CD11b-depleted population of immune cells comprising T cells; and (b) incubating or expanding the CD11b-depleted population of immune cells comprising T cells; wherein memory T cells comprising a TCR specific to the epitope are expanded, or naïve T cells comprising a TCR specific to the epitope are induced.

Provided herein is a method of preparing T cells comprising a T cell receptor (TCR) specific to an epitope, the method comprising (a) enriching a population of immune cells comprising APCs and T cells for cells expressing CD11c, thereby forming a CD11c-enriched population of immune cells comprising T cells; and (b) incubating or expanding the CD11c-enriched population of immune cells comprising T cells; wherein memory T cells comprising a TCR specific to the epitope are expanded, or naïve T cells comprising a TCR specific to the epitope are induced. In some embodiments, the method for the APC preparation comprises FMS-like tyrosine kinase 3 receptor ligand (FLT3L)-stimulated APCs.

In some embodiments, the method further comprises preparing the APC preparation.

In some embodiments, the method for preparing the APC preparation comprises incubating APCs with FLT3L.

In some embodiments, the method for preparing the APC preparation comprises incubating APCs with the polypeptide or a polynucleotide encoding the polypeptide.

Provided herein is a method of treating cancer in a subject in need thereof comprising administering a population of immune cells from a biological sample to the subject, wherein the population of immune cells comprises antigen presenting cell (APC)-stimulated T cells comprising a T cell receptor (TCR) specific to an antigen peptide sequence, and wherein the subject that has been administered fins-like tyrosine kinase 3 ligand (FLT3L).

Provided herein is a method of treating cancer in a subject in need thereof comprising: (a) administering a FMS-like tyrosine kinase 3 receptor ligand (FLT3L) to the subject; and (b) administering a population of immune cells from a biological sample to the subject, wherein the population of immune cells comprises antigen presenting cell (APC)-stimulated T cells comprising a T cell receptor (TCR) specific to an antigen peptide sequence.

Provided herein is a method of treating cancer in a subject in need thereof comprising: (a) administering a population of immune cells from a biological sample to the subject, wherein the population of immune cells comprises antigen presenting cell (APC)-stimulated T cells comprising a T cell receptor (TCR) specific to an antigen peptide sequence; and (b) administering a polypeptide comprising the antigen peptide sequence or a polynucleotide encoding the antigen peptide sequence to the subject.

In some embodiments, the method further comprises administering a FMS-like tyrosine kinase 3 receptor ligand (FLT3L) to the subject prior to administration of the population of immune cells.

BRIEF DESCRIPTION OF THE DRAWINGS

FIG. 24 depicts schematics of examples of methods for generating a therapeutic T cell composition including expansion of memory T cells and induction of naïve T cells.

FIG. 28B depicts example bar graphs of the percent of CD4$^+$ T cells with number of functions incubated with DCs loaded with the indicated concentration of peptide in a recall response assay. Samples of two induced cultures containing de novo CD4$^+$ T cell responses were analyzed either alone without barcoding or mixed with irrelevant samples. Barcoding did not alter detectable functionality. The number of functions and magnitude of response elicited from the cells was not significantly changed with sample barcoding.

FIG. 30C depicts an example result of sensitivity determination by detection and functional characterization of de novo induced CD4$^+$ responses with multiple specificities in the same culture. Similar magnitude was observed for each response in the pool deconvolution assay. The responses to HIV #5, HIV #6 and HIV #4 demonstrated an EC$_{50}$ of 0.45 μM, 0.43 μM and 9.1 μM, respectively.

FIG. 37B depicts another example of the cytotoxicity profile of a memory response induced in a patient with melanoma as quantified by the frequency of CD8$^+$CD107a$^+$ T cells. It also depicts target cell killing by these T cell responses as quantified by the frequency of aCAS3+ tumor cells. The cytotoxic capacity of the induced CD8+ T cell responses was assessed by re-challenging with mutant or wildtype neoantigen transduced tumor cells. Un-transduced tumor cells (parental A375 line) or tumor cells transduced with a 200aa construct were used. The construct either contained the mutant or wildtype sequence, mutation in the center. Upregulation of CD107a on CD8+ T cells and active Caspase3 on tumor cells were measured upon co-culture. Red circles highlight the pMHC+ fractions. Effector:Target ratio: 5:1 (SRSF1$_{E>K}$). Statistical analysis: unpaired T test, P values ≤0.01, **≤0.0001.

FIG. 38A depicts the identification of neoantigen specific CD4+ T cell responses in a melanoma patient. Responses are identified based on the production of IFN-γ & TNFα (Y axis) when re-challenged with mutant neoantigen peptide loaded DCs (0.8 μM). MKRN1$_{S>L}$, CREBBP$_{S>L}$, and TPCN1$_{K>E}$ were identified as positive responses.

FIG. 38B depicts the specificity of the CD4+ T cell responses depicted in FIG. 38A towards the indicated mutated and wildtype peptides. In a confirmatory study the CD4 T cell responses shown in FIG. 38A were challenged with different concentrations (X axis—0 μM, 0.05 μM, 0.2 μM, 0.8 μM and 3.2 μM) of mutant and wildtype neoantigen peptides and measured IFNγ+ and/or TNFα+ of total CD4+ (Y axis) in the samples. Two of the CD4+ T cell responses (MKRN1$_{S>L}$ and CREEBP$_{S>L}$) show significant difference to 0 μM concentration and not responsive to wild type neoantigen peptide but TPCN1$_{K>E}$ response was reactive to both mutant and wildtype neoantigen peptide. Statistical analysis: FDR for adjusted p value, P value<0.05);

FIG. 38C depicts the polyfunctionality profile of these CD4+ T cell responses, as shown by a combination of 1, 2, 3, or 4 functions (e.g., the one or more functions are production of one or more factors selected from IFNγ, TNFα, CD107a and 4-1BB). The poly-functionality of identified CD4+ T cell responses was assessed by re-challenge with mutant neoantigen peptide loaded DCs (0.8 μm). Percentages in the pie charts represent percentage functional CD4+ T cells (1, 2 and/or 3 functions). Representative data depicted, generated from post-stimulation CD4+ T cell responses induced in a patient.

FIG. 50 depicts exemplary graphical representations of the number of antigen specific cells in a population of cells activated by highly immunogenic and low immunogenic antigens that T cells are responsive to after performing three antigen presenting cell enrichment and antigen loading protocols using PBMCs derived from healthy donors. The treatments are: Base Flt3L, FLT3L treatment alone; CD11b, FLT3L treatment and depletion of CD11b expressing cells; CD11b–/CD19–, FLT3L treatment and depletion of CD11b expressing cells and CD19 expressing cells.

FIG. 55 depicts exemplary flow cytometric analyses showing antigen specific CD8+ memory responses using viral peptide or RNA encoding the peptide and naïve responses using neoantigen encoding peptide or RNA in a short term induction protocol.

FIG. 57A depicts a schematic of an exemplary RNA concantemer construct encoding a string of neoantigens.

FIG. 57B depicts a schematic of an exemplary arrangement of the neoantigen string in 5'-3' orientation within the construct shown in FIG. 57A.

FIG. 58A depicts a schematic of an exemplary mRNA sequence for incorporating 5'-CAP structures in mRNA encoding concatenated neoantigen strings for expression in PBMCs. Addition of an "A" nucleotide in the mRNA string was used for compatibility with CleanCap® Technology. Figure discloses SEQ ID NOS 8-9, respectively, in order of appearance.

FIG. 58B depicts an exemplary graphical representation of the percentage of live cells 24 hours after expressing mRNAs encoding concatenated neoantigen strings with different 5'-CAP structures in PBMCs.

FIG. 58C depicts an exemplary graphical representation of the total number of GFP positive cells 24 hours after expressing mRNAs encoding concatenated neoantigen strings with different 5'-CAP structures in PBMCs.

FIG. 60A depicts exemplary schematics of mRNA constructs using shortmers (9-10 amino acids, top) and longmers (25 amino acids, bottom) used for expression in cells.

FIG. 60B depicts an exemplary graph of multimer specific CD8+ cells as the percentage of total CD8+ cells. The antigens used for the multimer assay are shown.

FIG. 60C depicts exemplary flow cytometry analyses of detection of multimer positive CD8+ T cells, comparing shortmer (9-10 amino acids) and longmer (25 amino acids) peptide stimulated APCs and APCs containing encoding the same shortmer (9-10 amino acids) and longmer (25 amino acids) peptides.

FIG. 62D depicts exemplary flow cytometry data showing detection Gli3 multimer positive T cells that were grown in the presence of the indicated maturation mixes.

FIG. 64A depicts exemplary graphical representations from a recall assay of the percentage change in TNFα and/or IFNγ production (left) or percentage of CD107a positive cells (right) from neoantigen specific-CD8 T cells challenged with increasing concentrations of the indicated peptides used to load APCs. Figure discloses SEQ ID NOS 10 and 16-19, respectively, in order of appearance.

FIG. 64B depicts exemplary graphical representations from a multimer assay of the percentage change in TNFα and/or IFNγ production (left) or percentage of CD107a positive cells (right) from neoantigen specific-CD8 T cells challenged with increasing concentrations of the indicated peptides used to load APCs. Figure discloses SEQ ID NOS 10 and 16-19, respectively, in order of appearance.

FIG. 65 depicts an exemplary Venn diagram of criteria considered for generating an optimum product personal T cell therapeutic, using mRNA as an immunogen.

FIG. 69A depicts an exemplary graphical representation of data showing characterization of a patient specific T cell product prepared by multiple engineering runs. The percentage of multimer positive CD8 positive cells is shown.

FIG. 69B depicts exemplary representative flow cytometry data showing characterization of a patient specific T cell product prepared by multiple engineering runs. The percentage of multimer A positive and multimer B positive CD8 cells for the indicated epitopes is shown.

FIG. 69C depicts exemplary pie charts showing the polyfunctionality of identified pMHC$^+$ CD8$^+$ T cells upon re-challenge with mutant neoantigen-loaded DCs as compared to unloaded DCs.

FIG. 75 depicts an exemplary schematic of cohorts and doses for use in a clinical study (NEO-PTC-01).

DETAILED DESCRIPTION

Figure 1A:
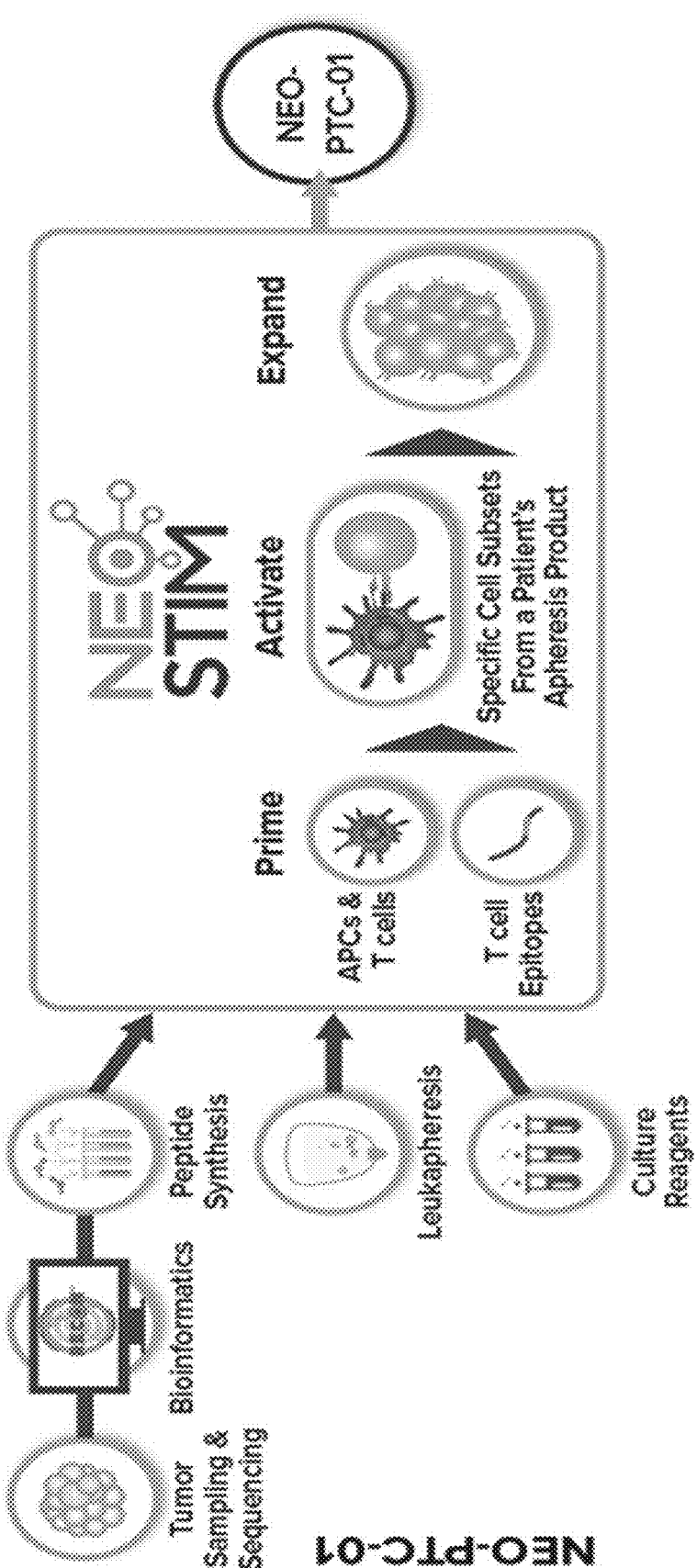
FIG. 1A depicts an example schematic of an antigen specific T cell manufacturing protocol.

A T cell therapeutic is expected to be a relatively safe and well-tolerated adoptive T cell product. However, based on an assessment of the risks associated with the product, there are 3 general classes of potential toxicities associated with a T cell therapeutic: (a) treatment related toxicity due to lymphodepletion, cell infusion, or cytokine release syndrome; (b) off-tumor, off-target toxicity due to the expansion of autoreactive clones or cross reactivity of the neoantigen specific T cells; and (c) off-tumor, on-target toxicity due to the presentation of the neoantigens on non-tumor tissue. Described herein are novel immunotherapeutic agents and uses thereof based on the discovery of neoantigens arising from mutational events unique to an individual's tumor. Accordingly, the present disclosure described herein provides methods and protocols to create antigen specific immune cells, for example T cells, for use in treating disease.

Presented herein is a composition of neoantigen responsive T cells for cancer immunotherapy. Although adoptive T cell therapy is a promising new approach for cancer therapy it requires several improvements. Generally, the T cells have to be adequately cytotoxic to cancer cells, have to spare the non-cancer cells in the body, should not lose immunogenicity in the tumor environment and should offer long term protection. Additionally, use of virally transduced cells has its own challenges. Therefore, striking the right balance to achieve therapeutically effective composition which specifically target cancer cells, sparing healthy cell, stall the progress of the disease, cause amelioration or at least substantial tumor regression and prevent relapse of the cancer, requires several improvements in almost all the steps of the complex process.

To facilitate an understanding of the present disclosure, a number of terms and phrases are defined below.

An antigen is a foreign substance to the body that induces an immune response. A "neoantigen" refers to a class of tumor antigens which arise from tumor-specific changes in proteins. Neoantigens encompass, but are not limited to, tumor antigens which arise from, for example, a substitution in a protein sequence, a frame shift mutation, a fusion polypeptide, an in-frame deletion, an insertion, and expression of an endogenous retroviral polypeptide.

A "neoepitope" refers to an epitope that is not present in a reference, such as a non-diseased cell, e.g., a non-cancerous cell or a germline cell, but is found in a diseased cell, e.g., a cancer cell. This includes situations where a corresponding epitope is found in a normal non-diseased cell or a germline cell but, due to one or more mutations in a diseased cell, e.g., a cancer cell, the sequence of the epitope is changed so as to result in the neoepitope.

A "mutation" refers to a change of or a difference in a nucleic acid sequence (e.g., a nucleotide substitution, addition or deletion) compared to a reference nucleic acid. A "somatic mutation" can occur in any of the cells of the body except the germ cells (sperm and egg) and are not passed on to children. These alterations can (but do not always) cause cancer or other diseases. In some embodiments, a mutation is a non-synonymous mutation. A "non-synonymous mutation" refers to a mutation, for (e.g., a nucleotide substitution), which does result in an amino acid change such as an amino acid substitution in the translation product. A "frameshift" occurs when a mutation disrupts the normal phase of a gene's codon periodicity (also known as "reading frame"), resulting in translation of a non-native protein sequence. It is possible for different mutations in a gene to achieve the same altered reading frame.

"Antigen processing" or "processing" refers to the degradation of a polypeptide or antigen into procession products, which are fragments of said polypeptide or antigen (e.g., the degradation of a polypeptide into peptides) and the association of one or more of these fragments (e.g., via binding) with MHC molecules for presentation by cells, for example, antigen presenting cells, to specific T cells.

An "antigen presenting cell" (APC) refers to a cell which presents peptide fragments of protein antigens in association with MHC molecules on its cell surface. The term includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

The term "affinity" refers to a measure of the strength of binding between two members of a binding pair (e.g., a human leukocyte antigen (HLA)-binding peptide and a class I or II HLA, or a peptide-HLA complex and a T cell receptor (TCR)). $K_D$ refers to the dissociation constant between two members of a binding pair and has units of molarity. $K_A$ refers to the affinity constant between two members of a binding pair is the inverse of the dissociation constant. Affinity may be determined experimentally, for example by surface plasmon resonance (SPR) using commercially available Biacore SPR units. $K_{off}$ refers to the off-rate constant of two members of a binding pair, (e.g., the off-rate constant of an HLA-binding peptide and a class I or II HLA, or a peptide-HLA complex and a TCR). $K_{on}$ refers to the on-rate constant of two members of a binding pair, (e.g., the on-rate constant of an HLA-binding peptide and a class I or II HLA, or a peptide-HLA complex and a TCR).

Throughout this disclosure, "binding data" results may be expressed in terms of an "IC$_{50}$." Affinity may also be expressed as the inhibitory concentration 50 (IC$_{50}$), or the concentration at which 50% of a first member of a binding pair (e.g., a peptide) is displaced. Likewise, ln(IC$_{50}$) refers to the natural log of the IC$_{50}$. For example, an IC$_{50}$ may be the concentration of a tested peptide in a binding assay at which 50% inhibition of binding of a labeled reference peptide is observed. Given the conditions in which the assays are run (e.g., limiting HLA protein concentrations and/or labeled reference peptide concentrations), these values can approximate $K_D$ values. Assays for determining binding are well known in the art and are described in detail, for example, in PCT publications WO 94/20127 and WO 94/03205, and other publications such Sidney et al., Current Protocols in Immunology 18.3.1 (1998); Sidney, et al., J. Immunol. 154:247 (1995); and Sette, et al., Mol. Immunol. 31:813 (1994). Alternatively, binding can be expressed relative to binding by a reference standard peptide. Binding can also be determined using other assay systems including those using: live cells (e.g., Ceppellini et al., Nature 339:392 (1989); Christnick et al., Nature 352:67 (1991); Busch et al., Int. Immunol. 2:443 (1990); Hill et al., J. Immunol. 147:189 (1991); del Guercio et al., J. Immunol. 154:685 (1995)), cell free systems using detergent lysates (e.g., Cerundolo et al., J. Immunol. 21:2069 (1991)), immobilized purified MHC (e.g., Hill et al., J. Immunol. 152, 2890 (1994); Marshall et al., J. Immunol. 152:4946 (1994)), ELISA systems (e.g., Reay et al., EMBO J. 11:2829 (1992)), surface plasmon resonance (e.g., Khilko et al., J. Biol. Chem. 268:15425 (1993)); high flux soluble phase assays (Hammer et al., J. Exp. Med. 180:2353 (1994)), and measurement of class I MHC stabilization or assembly (e.g., Ljunggren et al., Nature 346:476 (1990); Schumacher et al., Cell 62:563 (1990); Townsend et al., Cell 62:285 (1990); Parker et al., J. Immunol. 149:1896 (1992)).

The term "derived" when used to discuss an epitope is a synonym for "prepared." A derived epitope can be isolated from a natural source, or it can be synthesized according to standard protocols in the art. Synthetic epitopes can comprise artificial amino acid residues "amino acid mimetics," such as D isomers of natural occurring L amino acid residues or non-natural amino acid residues such as cyclohexylalanine. A derived or prepared epitope can be an analog of a native epitope. The term "derived from" refers to the origin or source, and may include naturally occurring, recombinant, unpurified, purified or differentiated molecules or cells. For example, an expanded or induced antigen specific T cell may be derived from a T cell. For example, an expanded or induced antigen specific T cell may be derived from an antigen specific T cell in a biological sample. For example, a matured APC (e.g., a professional APC) may be derived from a non-matured APC (e.g., an immature APC). For example, an APC may be derived from a monocyte (e.g., a CD14+ monocyte). For example, a dendritic cell may be derived from a monocyte (e.g., a CD14+ monocyte). For example, an APC may be derived from a bone marrow cell.

An "epitope" is the collective features of a molecule (e.g., a peptide's charge and primary, secondary and tertiary structure) that together form a site recognized by another molecule (e.g., an immunoglobulin, T cell receptor, HLA molecule, or chimeric antigen receptor). For example, an epitope can be a set of amino acid residues involved in recognition by a particular immunoglobulin; a Major Histocompatibility Complex (MHC) receptor; or in the context of T cells, those residues recognized by a T cell receptor protein and/or a chimeric antigen receptor. Epitopes can be prepared by isolation from a natural source, or they can be synthesized according to standard protocols in the art. Synthetic epitopes can comprise artificial amino acid residues, amino acid mimetics, (such as D isomers of naturally-occurring L amino acid residues or non-naturally-occurring amino acid residues). Throughout this disclosure, epitopes may be referred to in some cases as peptides or peptide epitopes. In certain embodiments, there is a limitation on the length of a peptide of the present disclosure. The embodiment that is length-limited occurs when the protein or peptide comprising an epitope described herein comprises a region (i.e., a contiguous series of amino acid residues)

having 100% identity with a native sequence. In order to avoid the definition of epitope from reading, e.g., on whole natural molecules, there is a limitation on the length of any region that has 100% identity with a native peptide sequence. Thus, for a peptide comprising an epitope described herein and a region with 100% identity with a native peptide sequence, the region with 100% identity to a native sequence generally has a length of: less than or equal to 600 amino acid residues, less than or equal to 500 amino acid residues, less than or equal to 400 amino acid residues, less than or equal to 250 amino acid residues, less than or equal to 100 amino acid residues, less than or equal to 85 amino acid residues, less than or equal to 75 amino acid residues, less than or equal to 65 amino acid residues, and less than or equal to 50 amino acid residues. In certain embodiments, an "epitope" described herein is comprised by a peptide having a region with less than 51 amino acid residues that has 100% identity to a native peptide sequence, in any increment down to 5 amino acid residues; for example 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2 or 1 amino acid residues.

A "T cell epitope" refers to a peptide sequence bound by an MHC molecule in the form of a peptide-MHC (pMHC) complex. A peptide-MHC complex can be recognized and bound by a TCR of a T cell (e.g., a cytotoxic T-lymphocyte or a T-helper cell).

A "T cell" includes CD4+ T cells and CD8+ T cells. The term T cell also includes both T helper 1 type T cells and T helper 2 type T cells. T cells may be generated by the method described in the application, for a clinical application. T cells or adoptive T cells referred to here, such as for a clinical application are cells isolated from a biological source, manipulated and cultured ex vivo and prepared into a drug candidate for a specific therapy such as a cancer, e.g., melanoma. When drug candidate cells pass specific qualitative and quantitative criteria for fitness for a clinical application, the drug candidate may be designated a drug product. In some cases, a drug product is selected from a number of drug candidates. In the context of this application, a drug product is a T cell, more specifically, a population of T cells, or more specifically a population of T cells with heterogeneous characteristics and subtypes. For example, a drug product, as disclosed herein may have a population of T cells comprising CD8+ T cells, CD4+ T cells, with cells at least above a certain exhibiting antigen specificity, a certain percentage of each exhibiting a memory phenotype, among others.

An "immune cell" refers to a cell that plays a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

An "immunogenic" peptide or an "immunogenic" epitope or an "immunogenic" peptide epitope is a peptide that binds to an HLA molecule and induces a cell-mediated or humoral response, for example, a cytotoxic T lymphocyte (CTL) response, a helper T lymphocyte (HTL) response and/or a B lymphocyte response. Immunogenic peptides described herein are capable of binding to an HLA molecule and thereafter induce a cell-mediated or humoral response (e.g., a CTL (cytotoxic) response, or a HTL response) to the peptide.

A "protective immune response" or "therapeutic immune response" refers to a CTL and/or an HTL response to an antigen derived from an pathogenic antigen (e.g., a tumor antigen), which in some way prevents or at least partially arrests disease symptoms, side effects or progression. The immune response can also include an antibody response which has been facilitated by the stimulation of helper T cells.

A "T cell receptor" ("TCR") refers to a molecule, whether natural or partly or wholly synthetically produced, found on the surface of T lymphocytes (T cells) that recognizes an antigen bound to a major histocompatibility complex (MHC) molecule. The ability of a T cells to recognize an antigen associated with various diseases (e.g., cancers) or infectious organisms is conferred by its TCR, which is made up of both an alpha ($\alpha$) chain and a beta ($\beta$) chain or a gamma ($\gamma$) and a delta ($\delta$) chain. The proteins which make up these chains are encoded by DNA, which employs a unique mechanism for generating the tremendous diversity of the TCR. This multi-subunit immune recognition receptor associates with the CD3 complex and binds peptides presented by the MHC class I and II proteins on the surface of antigen-presenting cells (APCs). Binding of a TCR to a peptide on an APC is a central event in T cell activation.

As used herein, a "chimeric antigen receptor" or "CAR" refers to an antigen binding protein in that includes an immunoglobulin antigen binding domain (e.g., an immunoglobulin variable domain) and a T cell receptor (TCR) constant domain. As used herein, a "constant domain" of a TCR polypeptide includes a membrane-proximal TCR constant domain, a TCR transmembrane domain and/or a TCR cytoplasmic domain, or fragments thereof. For example, in some embodiments, a CAR is a monomer that includes a polypeptide comprising an immunoglobulin heavy chain variable domain linked to a TCRβ constant domain. In some embodiments, the CAR is a dimer that includes a first polypeptide comprising an immunoglobulin heavy or light chain variable domain linked to a TCRα or TCRβ constant domain and a second polypeptide comprising an immunoglobulin heavy or light chain variable domain (e.g., a κ or λ variable domain) linked to a TCRβ or TCRα constant domain.

"Major Histocompatibility Complex" or "MHC" is a cluster of genes that plays a role in control of the cellular interactions responsible for physiologic immune responses. The terms "major histocompatibility complex" and the abbreviation "MHC" can include any class of MHC molecule, such as MHC class I and MHC class II molecules, and relate to a complex of genes which occurs in all vertebrates. In humans, the MHC complex is also known as the human leukocyte antigen (HLA) complex. Thus, a "Human Leukocyte Antigen" or "HLA" refers to a human Major Histocompatibility Complex (MHC) protein (see, e.g., Stites, et al., Immunology, 8$^{TH}$ Ed., Lange Publishing, Los Altos, Calif (1994). For a detailed description of the MHC and HLA complexes, see, Paul, Fundamental Immunology, 3$^{rd}$ Ed., Raven Press, New York (1993).

The major histocompatibility complex in the genome comprises the genetic region whose gene products expressed on the cell surface are important for binding and presenting endogenous and/or foreign antigens and thus for regulating immunological processes. MHC proteins or molecules are important for signaling between lymphocytes and antigen presenting cells or diseased cells in immune reactions. MHC proteins or molecules bind peptides and present them for recognition by T-cell receptors. The proteins encoded by the MHC can be expressed on the surface of cells, and display both self-antigens (peptide fragments from the cell itself) and non-self-antigens (e.g., fragments of invading microorganisms) to a T-cell. MHC binding peptides can result from the proteolytic cleavage of protein antigens and represent potential lymphocyte epitopes. (e.g., T cell epitope and B cell epitope). MHCs can transport the peptides to the cell surface and present them there to specific cells, such as cytotoxic T-lymphocytes, T-helper cells, or B cells. The MHC region can be divided into three subgroups, class I, class II, and class III. MHC class I proteins can contain an α-chain and β2-microglobulin (not part of the MHC encoded by chromosome 15). They can present antigen fragments to cytotoxic T-cells. MHC class II proteins can contain α- and β-chains and they can present antigen fragments to T-helper cells. MHC class III region can encode for other immune components, such as complement components and cytokines. The MHC can be both polygenic (there are several MHC class I and MHC class II genes) and polymorphic (there are multiple alleles of each gene).

A "receptor" refers to a biological molecule or a molecule grouping capable of binding a ligand. A receptor may serve, to transmit information in a cell, a cell formation or an organism. A receptor comprises at least one receptor unit, for example, where each receptor unit may consist of a protein molecule. A receptor has a structure which complements that of a ligand and may complex the ligand as a binding partner. The information is transmitted in particular by conformational changes of the receptor following complexation of the ligand on the surface of a cell. In some embodiments, a receptor is to be understood as meaning in particular proteins of MHC classes I and II capable of forming a receptor/ligand complex with a ligand, in particular a peptide or peptide fragment of suitable length. A "ligand" refers to a molecule which has a structure complementary to that of a receptor and is capable of forming a complex with this receptor. In some embodiments, a ligand is to be understood as meaning a peptide or peptide fragment which has a suitable length and suitable binding motifs in its amino acid sequence, so that the peptide or peptide fragment is capable of forming a complex with MHC proteins such as MHC class I or MHC class II proteins. In some embodiments, a "receptor/ligand complex" is also to be understood as meaning a "receptor/peptide complex" or "receptor/peptide fragment complex", including a peptide- or peptide fragment-presenting MHC molecule such as MHC class I or MHC class II molecules.

A "native" or a "wild type" sequence refers to a sequence found in nature. The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

The terms "peptide" and "peptide epitope" are used interchangeably with "oligopeptide" in the present specification to designate a series of residues connected one to the other, typically by peptide bonds between the α-amino and carboxyl groups of adjacent amino acid residues. A "synthetic peptide" refers to a peptide that is obtained from a non-natural source, e.g., is man-made. Such peptides can be produced using such methods as chemical synthesis or recombinant DNA technology. "Synthetic peptides" include "fusion proteins."

The term "motif" refers to a pattern of residues in an amino acid sequence of defined length, for example, a peptide of less than about 15 amino acid residues in length, or less than about 13 amino acid residues in length, for example, from about 8 to about 13 amino acid residues (e.g., 8, 9, 10, 11, 12, or 13) for a class I HLA motif and from about 6 to about 25 amino acid residues (e.g., 6, 7, 8, 9, 10, 11, 12, 13, 14, 15, 16, 17, 18, 19, 20, 21, 22, 23, 24, or 25) for a class II HLA motif, which is recognized by a particular HLA molecule. Motifs are typically different for each HLA protein encoded by a given human HLA allele. These motifs differ in their pattern of the primary and secondary anchor residues. In some embodiments, an MHC class I motif identifies a peptide of 7, 8 9, 10, 11, 12 or 13 amino acid residues in length. In some embodiments, an MHC class II motif identifies a peptide of 15, 16, 17, 18, 19, 20, 21, 22, 23, 24, 25 or 26 amino acid residues in length. A "cross-reactive binding" peptide refers to a peptide that binds to more than one member of a class of a binding pair members (e.g., a peptide bound by both a class I HLA molecule and a class II HLA molecule).

The term "residue" refers to an amino acid residue or amino acid mimetic residue incorporated into a peptide or protein by an amide bond or amide bond mimetic, or that is encoded by a nucleic acid (DNA or RNA). The nomenclature used to describe peptides or proteins follows the conventional practice. The amino group is presented to the left (the amino- or N-terminus) and the carboxyl group to the right (the carboxy- or C-terminus) of each amino acid residue. When amino acid residue positions are referred to in a peptide epitope they are numbered in an amino to carboxyl direction with the first position being the residue located at the amino terminal end of the epitope, or the peptide or protein of which it can be a part. In the formulae representing selected specific embodiments of the present invention, the amino- and carboxyl-terminal groups, although not specifically shown, are in the form they would assume at physiologic pH values, unless otherwise specified. In the amino acid structure formulae, each residue is generally represented by standard three letter or single letter designations. The L-form of an amino acid residue is represented by a capital single letter or a capital first letter of a three-letter symbol, and the D-form for those amino acid residues having D-forms is represented by a lower case single letter or a lower case three letter symbol. However, when three letter symbols or full names are used without capitals, they can refer to L amino acid residues. Glycine has no asymmetric carbon atom and is simply referred to as "Gly" or "G". The amino acid sequences of peptides set forth herein are generally designated using the standard single letter symbol. (A, Alanine; C, Cysteine; D, Aspartic Acid; E, Glutamic Acid; F, Phenylalanine; G, Glycine; H, Histidine; I, Isoleucine; K, Lysine; L, Leucine; M, Methionine; N, Asparagine; P, Proline; Q, Glutamine; R, Arginine; S, Serine; T, Threonine; V, Valine; W, Tryptophan; and Y, Tyrosine.)

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Methods of identifying nucleotide and amino acid conservative substitutions which do not eliminate peptide function are well-known in the art.

"Pharmaceutically acceptable" refers to a generally nontoxic, inert, and/or physiologically compatible composition or component of a composition. A "pharmaceutical excipient" or "excipient" comprises a material such as an adjuvant, a carrier, pH-adjusting and buffering agents, tonicity adjusting agents, wetting agents, preservatives, and the like. A "pharmaceutical excipient" is an excipient which is pharmaceutically acceptable.

According to the present disclosure, the term "vaccine" relates to a pharmaceutical preparation (pharmaceutical composition) or product that upon administration induces an immune response, for example, a cellular or humoral immune response, which recognizes and attacks a pathogen or a diseased cell such as a cancer cell. A vaccine may be used for the prevention or treatment of a disease. The term "individualized cancer vaccine" or "personalized cancer vaccine" "personal cancer vaccine" concerns a particular cancer patient and means that a cancer vaccine is adapted to the needs or special circumstances of an individual cancer patient.

The terms "polynucleotide" and "nucleic acid" are used interchangeably herein and refer to polymers of nucleotides of any length, and include DNA and RNA, for example, mRNA. The nucleotides can be deoxyribonucleotides, ribonucleotides, modified nucleotides or bases, and/or their analogs, or any substrate that can be incorporated into a polymer by DNA or RNA polymerase. In some embodiments, the polynucleotide and nucleic acid can be in vitro transcribed mRNA. In some embodiments, the polynucleotide that is administered using the methods of the invention is mRNA.

The terms "isolated" or "biologically pure" refer to material which is substantially or essentially free from components which normally accompany the material as it is found in its native state. Thus, isolated peptides described herein do not contain some or all of the materials normally associated with the peptides in their in situ environment. For example, an "isolated" epitope can be an epitope that does not include the whole sequence of the protein from which the epitope was derived. For example, a naturally-occurring polynucleotide or peptide present in a living animal is not isolated, but the same polynucleotide or peptide, separated from some or all of the coexisting materials in the natural system, is isolated. Such a polynucleotide could be part of a vector, and/or such a polynucleotide or peptide could be part of a composition, and still be "isolated" in that such vector or composition is not part of its natural environment. Isolated RNA molecules include in vivo or in vitro RNA transcripts of the DNA molecules described herein, and further include such molecules produced synthetically. In some embodiments, a polypeptide, antibody, polynucleotide, vector, cell, or composition which is isolated is substantially pure. The term "substantially pure" as used herein refers to material which is at least 50% pure (i.e., free from contaminants), at least 90% pure, at least 95% pure, at least 98% pure, or at least 99% pure.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software that can be used to obtain alignments of amino acid or nucleotide sequences are well-known in the art. These include, but are not limited to, BLAST, ALIGN, Megalign, BestFit, GCG Wisconsin Package, and variations thereof. In some embodiments, two nucleic acids or polypeptides described herein are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60 residues, at least about 60-80 residues in length or any integral value there between. In some embodiments, identity exists over a longer region than 60-80 residues, such as at least about 80-100 residues, and in some embodiments the sequences are substantially identical over the full length of the sequences being compared, such as an amino acid sequence of a peptide or a coding region of a nucleotide sequence.

The term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The terms "effective amount" or "therapeutically effective amount" or "therapeutic effect" refer to an amount of a therapeutic effective to "treat" a disease or disorder in a subject or mammal. The therapeutically effective amount of a drug has a therapeutic effect and as such can prevent the development of a disease or disorder; slow down the development of a disease or disorder; slow down the progression of a disease or disorder; relieve to some extent one or more of the symptoms associated with a disease or disorder; reduce morbidity and mortality; improve quality of life; or a combination of such effects.

The terms "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent or slow the development of a targeted pathologic condition or disorder. Thus, those in need of treatment include those already with the disorder; those prone to have the disorder; and those in whom the disorder is to be prevented.

The term "depleted" when used to describe a cell sample (e.g., a peripheral blood mononuclear cell (PBMC) sample) refers to a cell sample in which a subpopulation of cells has been removed or depleted. For example, an immune cell sample depleted of CD25 expressing cells refers to an immune cell sample in which CD25 expressing cells have been removed or depleted. For example, one or more binding agents can be used to remove or deplete one or more cells or cell types from a sample. For example, CD14$^+$ cells can be depleted or removed from a PBMC sample, such as by using an antibody that binds to CD14.

The "stimulation" refers to a response induced by binding of a stimulatory molecule with its cognate ligand thereby mediating a signal transduction event. For example, stimulation of a T cell can refer to binding of a TCR of a T cell to a peptide-MHC complex. For example, stimulation of a T cell can refer to a step within protocol 1 or protocol 2 in which PBMCs are cultured together with peptide loaded APCs.

The term "enriched" refers to a composition or fraction wherein an object species has been partially purified such that the concentration of the object species is substantially higher than the naturally occurring level of the species in a finished product without enrichment. The term "induced cell" refers to a cell that has been treated with an inducing compound, cell, or population of cells that affects the cell's protein expression, gene expression, differentiation status, shape, morphology, viability, and the like.

A "reference" can be used to correlate and/or compare the results obtained in the methods of the present disclosure from a diseased specimen. Typically, a "reference" may be obtained on the basis of one or more normal specimens, in particular specimens which are not affected by a disease, either obtained from an individual or one or more different individuals(e.g., healthy individuals), such as individuals of the same species. A "reference" can be determined empirically by testing a sufficiently large number of normal specimens.

As used herein, a tumor unless otherwise mentioned, is a cancerous tumor, and the terms cancer and tumor are used interchangeably throughout the document. While a tumor is a cancer of solid tissue, several of the compositions and methods described herein are in principle applicable to cancers of the blood, leukemia.

Overview of T Cell Therapies

Generating antigen specific T cells by controlled ex vivo induction or expansion of T cells (e.g., autologous T cells) can provide highly specific and beneficial T cell therapies (e.g., adoptive T cell therapies). The present disclosure provides T cell manufacturing methods and therapeutic T cell compositions which can be used for treating subjects with cancer and other conditions, diseases and disorders. The objective is to expand and induce antigen specific T cells with a favorable phenotype and function. The present disclosure provides compositions and methods for manufacturing of T cells which can be used for antigen specific T cell therapy (e.g., personal or personalized T cell therapies). The T cell compositions provided herein can be personal antigen specific T cell therapies. FIG. 1 graphically represents an overview of the process related to T cell therapy: which includes on one hand, identification of the cancer and cancer specific antigens in the subject having the cancer, leading to the production of neoantigenic peptides; and on the other hand, preparing activated, antigen specific cells for immunotherapy and administering the cellular product.

Neoantigens for T Cell-Based Therapy

Traditional antigen-targeted immunotherapies have focused on tumor associated antigens (TAAs), antigens including cancer testes antigens (typically germ line restricted gene products which are aberrantly expressed in tumors) or antigens derived from genes which show tissue specific expression. However, tumors also display protein products of mutated genes which are called neoantigens. The number and type of mutations can be readily defined using next generation sequencing approaches and include single amino acid missense mutations, fusion protein, and novel open reading frames (neoORFs) varying in length from one up to one hundred or more amino acids. Neoantigens are antigens that comprise a non-silent mutation in an epitope, and the same antigen is not expressed in a non-cancer cell within the same human body. Mutation-based antigens are particularly valuable as these have bypassed central tolerance (the process which occurs during normal thymic development of removing self-reactive T cells) and demonstrate exquisite tumor specificity. Each nonsynonymous (i.e., protein coding) mutation has the potential to generate a neoantigen that can be recognized by the patient's T cells. T cells recognizing these neoantigens can function both to kill tumor cells directly and to catalyze a broader immune response against the tumor. The methods described herein aim to induce and expand such neoantigen-reactive T cells in a patient-specific fashion and utilize these cells for adoptive cell therapy.

In some embodiments, the neoantigens used herein comprises a point mutation.

In some embodiments, the neoantigens used herein comprises a frameshift mutation.

In some embodiments, the neoantigens used herein comprises a crossover mutation.

In some embodiments, the neoantigens used herein comprises an insertion mutation, caused by the insertion of one or more than one nucleotides.

In some embodiments, the neoantigens used herein comprises a deletion mutation, caused by the deletion of one or more than one nucleotides.

In some embodiments, the neoantigens may be caused by a insertion-deletion (in-del) mutation.

In some embodiments, an antigen or neoantigen peptide binds an HLA protein (e.g., HLA class I or HLA class II). In specific embodiments, an antigen or neoantigen peptide binds an HLA protein with greater affinity than a corresponding wild-type peptide. In specific embodiments, an antigen or neoantigen peptide has an $IC_{50}$ or $K_D$ of at least less than 5000 nM, at least less than 500 nM, at least less than 100 nM, at least less than 50 nM or less.

In some embodiments, an antigen or neoantigen peptide can be from about 8 and about 50 amino acid residues in length, or from about 8 and about 30, from about 8 and about 20, from about 8 and about 18, from about 8 and about 15, or from about 8 and about 12 amino acid residues in length. In some embodiments, an antigen or neoantigen peptide can be from about 8 and about 500 amino acid residues in length, or from about 8 and about 450, from about 8 and about 400, from about 8 and about 350, from about 8 and about 300, from about 8 and about 250, from about 8 and about 200, from about 8 and about 150, from about 8 and about 100, from about 8 and about 50, or from about 8 and about 30 amino acid residues in length.

In some embodiments, an antigen or neoantigen peptide can be at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more amino acid residues in length. In some embodiments, the neoantigen peptides can be at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 70, 80, 90, 100, 150, 200, 250, 300, 350, 400, 450, 500 or more amino acid residues in length. In some embodiments, an antigen or neoantigen peptide can be at most 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or less amino acid residues in length. In some embodiments, an antigen or neoantigen peptide can be at most 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 70, 80, 90, 100, 150, 200, 250, 300, 350, 400, 450, 500, or less amino acid residues in length.

In some embodiments, an antigen or neoantigen peptide has a total length of at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 40, at least 50, at least 60, at least 70, at least 80, at least 90, at least 100, at least 150, at least 200, at least 250, at least 300, at least 350, at least 400, at least 450, or at least 500 amino acids.

In some embodiments, an antigen or neoantigen peptide has a total length of at most 8, at most 9, at most 10, at most 11, at most 12, at most 13, at most 14, at most 15, at most 16, at most 17, at most 18, at most 19, at most 20, at most 21, at most 22, at most 23, at most 24, at most 25, at most 26, at most 27, at most 28, at most 29, at most 30, at most 40, at most 50, at most 60, at most 70, at most 80, at most 90, at most 100, at most 150, at most 200, at most 250, at most 300, at most 350, at most 400, at most 450, or at most 500 amino acids.

In some embodiments, the neoantigen peptides can have a pI value of about 0.5 and about 12, about 2 and about 10, or about 4 and about 8. In some embodiments, the neoantigen peptides can have a pI value of at least 4.5, 5, 5.5, 6, 6.5, 7, 7.5, or more. In some embodiments, the neoantigen peptides can have a pI value of at most 4.5, 5, 5.5, 6, 6.5, 7, 7.5, or less.

In some embodiments, an antigen or neoantigen peptide can have an HLA binding affinity of from about 1 μM and about 1 mM, about 100 μM and about 500 μM, about 500 μM and about 10 μM, about 1 nM and about 1 μM, or about 10 nM and about 1 μM. In some embodiments, an antigen or neoantigen peptide can have an HLA binding affinity of at least 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 700, 800, 900 μM, or more. In some embodiments, an antigen or neoantigen peptide can have an HLA binding affinity of at most 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 700, 800, 900 μM.

In some embodiments, an antigen or neoantigen peptide described herein can comprise carriers such as those well known in the art, e.g., thyroglobulin, albumins such as human serum albumin, tetanus toxoid, polyamino acid residues such as poly L-lysine, poly L-glutamic acid, influenza virus proteins, hepatitis B virus core protein, and the like.

In some embodiments, an antigen or neoantigen peptide described herein can be modified by terminal-$NH_2$ acylation, e.g., by alkanoyl ($C_1$-$C_{20}$) or thioglycolyl acetylation, terminal-carboxyl amidation, e.g., ammonia, methylamine, etc. In some embodiments these modifications can provide sites for linking to a support or other molecule.

In some embodiments, an antigen or neoantigen peptide described herein can contain modifications such as but not limited to glycosylation, side chain oxidation, biotinylation, phosphorylation, addition of a surface active material, e.g. a lipid, or can be chemically modified, e.g., acetylation, etc. Moreover, bonds in the peptide can be other than peptide bonds, e.g., covalent bonds, ester or ether bonds, disulfide bonds, hydrogen bonds, ionic bonds, etc.

In some embodiments, an antigen or neoantigen peptide described herein can contain substitutions to modify a physical property (e.g., stability or solubility) of the resulting peptide. For example, an antigen or neoantigen peptide can be modified by the substitution of a cysteine (C) with α-amino butyric acid ("B"). Due to its chemical nature, cysteine has the propensity to form disulfide bridges and sufficiently alter the peptide structurally so as to reduce binding capacity. Substituting α-amino butyric acid for C not only alleviates this problem, but actually improves binding and crossbinding capability in certain instances. Substitution of cysteine with α-amino butyric acid can occur at any residue of an antigen or neoantigen peptide, e.g., at either anchor or non-anchor positions of an epitope or analog within a peptide, or at other positions of a peptide.

In some embodiments, an antigen peptide or neoantigen peptide described herein can comprise amino acid mimetics or unnatural amino acid residues, e.g. D- or L-naphtylalanine; D- or L-phenylglycine; D- or L-2-thieneylalanine; D- or L-1, 2, 3, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-ρ-fluorophenylalanine; D- or L-ρ-biphenyl-phenylalanine; D- or L-ρ-methoxybiphenylphenylalanine; D- or L-2-indole(allyl)alanines; and, D- or L-alkylalanines, where the alkyl group can be a substituted or unsubstituted methyl, ethyl, propyl, hexyl, butyl, pentyl, isopropyl, iso-butyl, sec-isotyl, iso-pentyl, or a non-acidic amino acid residues. Aromatic rings of a non-natural amino acid include, e.g., thiazolyl, thiophenyl, pyrazolyl, benzimidazolyl, naphthyl, furanyl, pyrrolyl, and pyridyl aromatic rings. Modified peptides that have various amino acid mimetics or unnatural amino acid residues are particularly useful, as they tend to manifest increased stability in vivo. Such peptides can also possess improved shelf-life or manufacturing properties.

In some embodiments, the peptides are contacted to immune cells to activate the cells and make them antigen responsive.

In some embodiments, the peptides are contacted to immune cells ex vivo.

In some embodiments, the peptides are contacted to immune cells in the living system, e.g., a human being.

In some embodiments, the immune cells are antigen presenting cells.

In some embodiments, the immune cells are T cells.

The present disclosure relates to methods for manufacturing T cells which are specific to immunogenic antigens.

The present disclosure also relates to compositions comprising antigen specific T cells stimulated with APCs. In some embodiments, one or more antigen peptides are loaded on to APCs, wherein the peptide loaded APCs are then used to stimulate T cells to produce antigen specific T cells. In some embodiments, the antigens are neoantigens. In some embodiments, the APCs used for peptide loading are dendritic cells.

In some embodiments, a peptide sequence comprises a mutation that is not present in non-cancer cells of a subject. In In some embodiments, a peptide is encoded by a gene or an expressed gene of a subject's cancer cells. In some embodiments, a peptide sequence has a length of at least 8; 9; 10; 11; 12; 13; 14; 15; 16; 17; 18; 19; 20; 21; 22; 23; 24; 25; 26; 27; 28; 29; 30; 40; 50; 60; 70; 80; 90; 100; 150; 200; 250; 300; 350; 400; 450; 500; 600; 700; 800; 900; 1,000; 1,500; 2,000; 2,500; 3,000; 4,000; 5,000; 7,500; or 10,000 or more naturally occurring amino acids.

In some embodiments, a peptide sequence binds to a protein encoded by a class I HLA allele and has a length of from 8-12 naturally occurring amino acids. In some embodiments, a peptide sequence binds to a protein encoded by a class II HLA allele and has a length of from 16-25 naturally occurring amino acids. In some embodiments, a peptide sequence comprises a plurality of antigen peptide sequences. In some embodiments, the plurality of antigen peptide sequences comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200, 250, 300, 350, 400, 450, or 500 antigen peptide sequences.

In some embodiments, the antigens described herein are neoantigens. Candidate immunogenic neoantigen sequences can be identified by any suitable method known in the art. The methods of the present disclosure can be useful, for example, to produce therapies specific to a subject's disease or to produce vaccines to a disease. Candidate immunogenic neoantigens can be neoantigens previously identified. In some embodiments, candidate immunogenic neoantigens may not be previously identified. Candidate immunogenic neoantigens for use in the methods and compositions described herein can be specific to a subject. In some embodiments, candidate neoantigens for use in the methods and compositions described herein can be specific to a plurality of subjects.

In both animals and humans, mutated epitopes can be potentially effective in inducing an immune response or activating T cells. In one embodiment, the potentially immunogenic epitopes of an infectious agent in a subject, such as a virus, can be determined. In one embodiment, the potentially immunogenic mutated epitopes of a subject with a disease, such as cancer, can be determined. In some embodiments, a potentially immunogenic antigen or neoantigen for use in the methods described herein can be a differentiation antigen expressed in a tumor and cells of the type of tissue from which they are generated. In some embodiments, a potentially immunogenic antigen or neoantigen for use in the methods described herein can be a cancer/germ line antigens not expressed in another differentiated tissue. In some embodiments, a potentially immunogenic antigen or neoantigen for use in the methods described herein can be a mutated antigen. For example, a candidate immunogenic antigen or neoantigen peptide for use in the methods described herein can comprise a missense point mutation or an antigen or neoantigen of a fusion protein generated through tumor specific translocation of a gene segment. In some embodiments, a potentially immunogenic antigen or neoantigen for use in the methods described herein can be an overexpressed antigen. In some embodiments, a potentially immunogenic antigen or neoantigen can be found in tumors. For example, a potentially immunogenic antigen or neoantigen for use in the methods described herein can include a protein whose expression is strictly regulated in cells of differentiated normal tissue.

Potentially immunogenic mutated epitopes can be determined by genomic or exomic sequencing of tumor tissue and healthy tissue from a cancer patient using next generation sequencing technologies. For example, genes selected based on their mutation frequency and ability to act as an antigen or neoantigen can be sequenced using next generation sequencing technology. In one embodiment, sequencing data can be analyzed to identify potentially immunogenic mutated peptides that can bind to HLA molecules of the subject. In one embodiment, the data can be analyzed using a computer. In another embodiment the sequence data can be analyzed for the presence of antigen or neoantigen peptides. In one embodiment, potentially immunogenic antigen or neoantigen peptides can be determined by their affinity to MHC molecules.

Potentially immunogenic antigen or neoantigen peptides can be determined by direct protein sequencing. For example, protein sequencing of enzymatic protein digests using multidimensional mass spectrometry techniques (e.g., tandem mass spectrometry (MS/MS)) can be used to identify potentially immunogenic antigen or neoantigen peptides for use in the methods described herein.

High-throughput methods for de novo sequencing of unknown proteins may be used to identify potentially immunogenic antigen or neoantigen peptides. For example, high-throughput methods for de novo sequencing of unknown proteins, such as meta-shotgun protein sequencing, may be used to analyze the proteome of a subject's tumor to identify potentially immunogenic expressed neoantigens.

Potentially immunogenic antigen or neoantigen peptides may also be identified using MHC multimers to identify antigen-specific T cell responses. For example, high-throughput analysis of antigen-specific T cell responses in patient samples may be performed using MHC tetramer-based screening techniques. Tetramer-based screening techniques may be used for the initial identification of potentially immunogenic tumor specific antigens, or alternatively as a secondary screening protocol to assess what potentially immunogenic antigens a patient may have already been exposed to, thereby facilitating the selection of potentially immunogenic antigens for use in the methods described herein.

In some embodiments, specific neoantigens are targeted for immunotherapy. In some embodiments, neoantigenic peptides are synthesized. The neoantigenic peptides used herein are designed such that each peptide is specific for an HLA antigen and can bind to the HLA antigen with a high binding affinity and specificity. In some embodiments, the peptides used herein are designed based on a high performance HLA binding prediction model generated by the inventors, and have been described in, for example the following patent applications/publications: WO2011143656, WO2017184590, and U.S. provisional application Nos. 62/783,914 and 62/826,827; all of which are incorporated by reference herein. NetMHCIIpan may be the current prediction standard, but it may not be regarded as accurate. Of the three Class II loci (DR, DP, and DQ), data may only exist for certain common alleles of HLA-DR. Briefly, the newly generated prediction model helps identify immunogenic antigen peptides and can be used to develop drugs, such as personalized medicine drugs, and isolation and characterization of antigen-specific T cells, wherein the machine-learning HLA-peptide presentation prediction model comprises, a plurality of predictor variables identified at least based on training data wherein the training data comprises: sequence information of sequences of peptides presented by a HLA protein expressed in cells and identified by mass spectrometry; training peptide sequence information comprising amino acid position information, wherein the training peptide sequence information is associated with the HLA protein expressed in cells; and a function representing a relation between the amino acid position information received as input and the presentation likelihood generated as output based on the amino acid position information and the predictor variables. CD4+ T cell responses may have anti-tumor activity. In existing prediction methods high rate of CD4+ T cell responses may be shown without using Class II prediction (e.g., 60% of SLP epitopes in NeoVax study (49% in NT-001), and 48% of mRNA epitopes in BioNTech study). It may not be clear whether these epitopes are typically presented natively (by tumor or by phagocytic DCs). It was therefore desirable to translate high CD4+T response rates into therapeutic efficacy by improving identification of naturally presented Class II epitopes. The roles of gene expression, enzymatic cleavage, and pathway/localization bias may have not been robustly quantified. It may be unclear whether autophagy (Class II presentation by tumor cells) or phagocytosis (Class II presentation of tumor epitopes by APCs) is the more relevant pathway, although most existing MS data may be presumed to derive from autophagy. There may be different data generation approaches for learning the rules of Class II presentation, including the field standard and the proposed approach. The field standard may comprise affinity measurements, which may be the basis for the NetMHCIIpan predictor, providing low throughput and requiring radioactive reagents, and it misses the role of processing. The new approach comprises mass spectrometry, where data from cell lines/tissues/tumors may help determine processing rules for autophagy (much of this data is already published) and Mono-allelic MS may enable determination of allele-specific binding rules (multi-allelic MS data is presumed overly complex for efficient learning. The newly generated prediction method comprises training a machine-learning HLA-peptide presentation prediction model, wherein training comprises inputting amino acid position information sequences of HLA-peptides isolated from one or more HLA-peptide complexes from a cell expressing a HLA class II allele into the HLA-peptide presentation prediction model using a computer processor; the machine-learning HLA-peptide presentation prediction model comprising: a plurality of predictor variables identified at least based on training data that comprises: sequence information of sequences of peptides presented by a HLA protein expressed in cells and identified by mass spectrometry; training peptide sequence information comprising amino acid position information of training peptides, wherein the training peptide sequence information is associated with the HLA protein expressed in cells; and a function representing a relation between the amino acid position information received as input and a presentation likelihood generated as output based on the amino acid position information and the predictor variables. In some embodiments, the presentation model has a positive predictive value of at least 0.25 at a recall rate of from 0.1%-10%. In some embodiments, the presentation model has a positive predictive value of at least 0.4 at a recall rate of from 0.1%-10%. In some embodiments, the presentation model has a positive predictive value of at least 0.6 at a recall rate of from 0.1%-10%. In some embodiments, the mass spectrometry is mono-allelic mass spectrometry. In some embodiments, the peptides are presented by a HLA protein expressed in cells through autophagy. In some embodiments, the peptides are presented by a HLA protein expressed in cells through phagocytosis. In some embodiments, the quality of the training data is increased by using a plurality of quality metrics. In some embodiments, the plurality of quality metrics comprises common contaminant peptide removal, high scored peak intensity, high score, and high mass accuracy. In some embodiments, the scored peak intensity is at least 50%. In some embodiments, the scored peak intensity is at least 70%. In some embodiments, the peptides presented by a HLA protein expressed in cells are peptides presented by a single immunoprecipitated HLA protein expressed in cells. In some embodiments, the plurality of predictor variables comprises a peptide-HLA affinity predictor variable. In some embodiments, the plurality of predictor variables comprises a source protein expression level predictor variable. In some embodiments, the plurality of predictor variables comprises a peptide cleavability predictor variable. In some embodiments, the peptides presented by the HLA protein comprise peptides identified by searching a peptide database using a reversed-database search strategy. In some embodiments, the HLA protein is an HLA-DR, and HLA-DP or an HLA-DQ protein. In some embodiments, the HLA protein is an HLA-DR protein selected from the group consisting of an HLA-DR, and HLA-DP or an HLA-DQ protein. In some embodiments, the HLA protein is an HLA-DR protein selected from the group consisting of: HLA-DPB1*01:01/HLA-DPA1*01:03, HLA-DPB1*02:01/HLA-DPA1*01:03, HLA-DPB1*03:01/HLA-DPA1*01:03, HLA-DPB1*04:01/HLA-DPA1*01:03, HLA-DPB1*04:02/HLA-DPA1*01:03, HLA-DPB1*06:01/HLA-DPA1*01:03,HLA-DQB1*02:01/HLA-DQA1*05:01,HLA-DQB1*02:02/HLA-DQA1*02:01, HLA-DQB1*06:02/HLA-DQA1*01:02,HLA-DQB1*06:04/HLA-DQA1*01:02, HLA-DRB1*01:01, HLA-DRB1*01:02, HLA-DRB1*03:01, HLA-DRB1*03:02, HLA-DRB1*04:01, HLA-DRB1*04:02, HLA-DRB1*04:03, HLA-DRB1*04:04, HLA-DRB1*04:05, HLA-DRB1*04:07, HLA-DRB1*07:01, HLA-DRB1*08:01, HLA-DRB1*08:02, HLA-DRB1*08:03, HLA-DRB1*08:04, HLA-DRB1*09:01, HLA-DRB1*10:01, HLA-DRB1*11:01, HLA-DRB1*11:02, HLA-DRB1*11:04, HLA-DRB1*12:01, HLA-DRB1*12:02, HLA-DRB1*13:01, HLA-DRB1*13:02, HLA-DRB1*13:03, HLA-DRB1*14:01, HLA-DRB1*15:01, HLA-DRB1*15:02, HLA-DRB1*15:03, HLA-DRB1*16:01, HLA-DRB3*01:01, HLA-DRB3*02:02, HLA-DRB3*03:01, HLA-DRB4*01:01, and HLA-DRB5*01:01. In some embodiments, the peptides presented by the HLA protein comprise peptides identified by comparing MS/MS spectra of the HLA-peptides with MS/MS spectra of one or more HLA-peptides in a peptide database.

In some embodiments, the mutation is selected from the group consisting of a point mutation, a splice site mutation, a frameshift mutation, a read-through mutation, and a gene fusion mutation.

In some embodiments, the peptides presented by the HLA protein have a length of 15-40 amino acids. In some embodiments, the peptides presented by the HLA protein comprise peptides identified by (a) isolating one or more HLA complexes from a cell line expressing a single HLA class II allele; (b) isolating one or more HLA-peptides from the one or more isolated HLA complexes; (c) obtaining MS/MS spectra for the one or more isolated HLA-peptides; and (d) obtaining a peptide sequence that corresponds to the MS/MS spectra of the one or more isolated HLA-peptides from a peptide database; wherein one or more sequences obtained from step (d) identifies the sequence of the one or more isolated HLA-peptides.

Various antigen peptides can be used to induce or expand T cells. Various antigen peptides can be used to activate antigen presenting cells (APCs), which in turn activate the T cells by contacting the T cells with antigen loaded APCs.

In some embodiments, a peptide comprises a mutation selected from (A) a point mutation, (B) a splice-site mutation, (C) a frameshift mutation, (D) a read-through mutation, (E) a gene-fusion mutation, and combinations thereof. In some embodiments, a peptide comprises a point mutation and binds to the HLA protein of a subject with a greater affinity than a corresponding wild-type peptide.

In some embodiments, a peptide binds to the HLA protein of a subject with an $IC_{50}$ of less than 500 nM, 250 nM, 150 nM, 100 nM, 50 nM, 25 nM or 10 nM. In some embodiments, a peptide binds to the HLA protein of a subject with an $IC_{50}$ or a $K_D$ of less than 500 nM, 250 nM, 150 nM, 100 nM, 50 nM, 25 nM or 10 nM. In some embodiments, each peptide binds to a protein encoded by an HLA allele expressed by a subject. In some embodiments, a TCR of an antigen specific T cell induced or expanded binds to a peptide-HLA complex with an $IC_{50}$ or a $K_D$ of less than 500 nM, 250 nM, 150 nM, 100 nM, 50 nM, 25 nM or 10 nM. In some embodiments, the TCR binds to an peptide-HLA complex with an $IC_{50}$ or a $K_D$ of less than 500 nM, 250 nM, 150 nM, 100 nM, 50 nM, 25 nM or 10 nM. In some embodiments, each of the at least one antigen peptide sequences comprises a mutation that is not present in non-cancer cells of a subject. In some embodiments, each of the at least one antigen peptide sequences is encoded by gene or an expressed gene of a subject's cancer cells.

In some embodiments, a peptide has a length of at least 8; 9; 10; 11; 12; 13; 14; 15; 16; 17; 18; 19; 20; 21; 22; 23; 24; 25; 26; 27; 28; 29; 30; 40; 50; 60; 70; 80; 90; 100; 150; 200; 250; 300; 350; 400; 450; 500; 600; 700; 800; 900; 1,000; 1,500; 2,000; 2,500; 3,000; 4,000; 5,000; 7,500; or 10,000 or more naturally occurring amino acids. In some embodiments, a peptide binds to a protein encoded by a class I HLA allele and has a length of from 8-12 naturally occurring amino acids. In some embodiments, a peptide binds to a protein encoded by a class II HLA allele and has a length of from 16-25 naturally occurring amino acids. In some embodiments, a peptide comprises a plurality of peptides. In some embodiments, the plurality of peptides comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200, 250, 300, 350, 400, 450, or 500 or more antigen peptides.

In some aspects, the present disclosure provides peptides or polynucleotides encoding peptides identified using the methods described briefly above herein (e.g., a peptide with a tumor specific mutation, a viral peptide, or peptide associated with a non-cancerous disease).

In some embodiments, an optical method is used to select or identify immunogenic antigens. In some embodiments, a barcoded probe is used to select or identify immunogenic antigens. In some embodiments, a barcoded probe comprising a target specific region and a barcoded region is used to select or identify immunogenic antigens. In some embodiments the target specific region comprises a nucleic acid sequence that hybridizes to or has at least about 90%, 95% or 100% sequence complementarity to a nucleic acid sequence of a target polynucleotide.

Preparing Activated, Antigen-Specific T Cells

Provided herein are methods for stimulating T cells. For example, the methods provided herein can be used to stimulate antigen specific T cells. The methods provided herein can be used to induce or activate T cells. For example, the methods provided herein can be used to expand activated T cells. For example, the methods provided herein can be used to induce naïve T cells. For example, the methods provided herein can be used to expand antigen specific $CD8^+$ T cells. For example, the methods provided herein can be used to expand antigen specific $CD4^+$ T cells. For example, the methods provided herein can be used to expand antigen specific $CD8^+$ T cells having memory phenotype. For example, the therapeutic compositions can comprise antigen specific CD8+ T cells. For example, the therapeutic compositions can comprise antigen specific memory T cells.

T cells can be activated ex vivo with a composition comprising neoantigenic peptides or polynucleotides encoding the neoantigenic peptides.

T cells can be activated ex vivo with a composition comprising antigen loaded antigen presenting cells.

In some embodiments, the APCs and/or T cells are derived from a biological sample which is obtained from a subject.

In some embodiments, the APCs and/or T cells are derived from a biological sample which is peripheral blood mononuclear cells (PBMC).

In some embodiments, the subject is administered FLT3L prior to obtaining the biological sample for preparing the APCs and/or T cells.

In some embodiments, the APCs and/or T cells are derived from a biological sample which is a leukapheresis sample.

In some embodiments antigen presenting cells are first loaded with neoantigenic peptides ex vivo and used to prepare neoantigen activated T cells. In some embodiments, the compositions provided herein comprise T cells that are stimulated by APCs, such as APCs pre-loaded with antigen peptides. The compositions can comprise a population of immune cells comprising T cells from a sample (e.g., a biological sample), wherein the T cells comprise APC-stimulated T cells. In some embodiments, mRNA encoding one or more neoantigenic peptides are introduced into APCs for expression of the neoantigenic peptides. Such APCs are used for stimulating or activating T cells.

In some embodiments, the biological sample comprises a percentage of the at least one antigen specific T cell in the composition is at least about 0.00001%, 0.00002%, 0.00005%, 0.0001%, 0.0005%, 0.001%, 0.005%, 0.01%, 0.05%, 0.1%, 0.5%. In some embodiments, the biological sample comprises less than 0.0001%, 0.0005%, 0.001%, 0.005%, 0.01%, 0.05%, 0.1%, 0.5%. 1%, 2%, 3%, 4%, 5%, or less than 10% antigen activated T cells of the total cell count in the biological sample that is derived from peripheral blood or leukapheresis. In some embodiments, the biological sample comprises less than 1%, 2%, 3%, 4%, 5%, 6%, 7%, 8%, 9%, 10%, 11%, 12%, 13%, 14%, 15%, 16%, 17%, 18%, 19%, 20%, 25%, 30% antigen activated T cells of the total cell count in the biological sample that is derived from peripheral blood or leukapheresis.

In some embodiments, the biological sample comprises antigen naive T cells. In some embodiments, the biological sample comprises greater than about 0.00001%, 0.00002%, 0.00005%, 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% antigen naive cells of the total cell count in the biological sample that is derived from peripheral blood or leukapheresis.

In some embodiments, a percentage of at least one antigen specific CD8$^+$ T cell in the composition is less than about 0.00001%, 0.00002%, 0.00005%, 0.0001%, 0.0005%, 0.001%, 0.005%, 0.01%, 0.05%, 0.1%, 0.5%, 1%, 2%, 3%, 4%, 5% in the biological sample derived from peripheral blood or leukapheresis. In some embodiments, a percentage of at least one antigen specific CD4$^+$ T cell in the composition is at least about 0.00001%, 0.00002%, 0.00005%, 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, of in the biological sample derived from peripheral blood or leukapheresis.

In some embodiments, a percentage of the at least one antigen specific T cell in the biological sample is at most about 0.00001%, 0.00005%, 0.0001%, 0.0005%, 0.001%, 0.005%, 0.01%, 0.05%, 0.1% or 0.5% of the total immune cells. In some embodiments, a percentage of at least one antigen specific CD8$^+$ T cell in the biological sample is at most about 0.00001%, 0.00005%, 0.0001%, 0.0005%, 0.001%, 0.005%, 0.01%, 0.05%, 0.1% or 0.5% of the total immune cells. In some embodiments, a percentage of at least one antigen specific CD4$^+$ T cell in the biological sample is at most about 0.00001%, 0.00005%, 0.0001%, 0.0005%, 0.001%, 0.005%, 0.01%, 0.05%, 0.1% or 0.5% of the total immune cells. In some embodiments, a percentage of antigen specific T cells in the biological sample is at most about 0.5%. In some embodiments, a percentage of neoantigen specific CD8$^+$ T cells in the biological sample is at most about 0.5%. In some embodiments, a percentage of antigen specific CD4$^+$ T cells in the biological sample is at most about 0.5% in the biological sample.

Preparing Neoantigen Loaded APCs

In some embodiments, a composition comprises a population of immune cells that has been incubated with one or more cytokines, growth factors or ligands, such as a ligand that binds to a cell surface receptor of an APC or a T cell. Non-limiting examples of such cytokines, growth factors and ligands include, but are not limited to, GM-CSF, IL-4, IL-7, FLT3L, TNF-α, IL-1β, IL-15, PGE1, IL-6, IFN-α, IFN-γ, R848, LPS, ss-rna40, and polyLC. In some embodiments, a composition comprises a population of immune cells that has been incubated with one or more APCs or APC preparations. For example, a composition can comprise a population of immune cells that has been incubated with one or more cytokine, growth factor and/or ligand stimulated APCs or cytokine, growth factor and/or ligand stimulated APC preparations. For example, a composition can comprise a population of immune cells that has been incubated with one or more cytokine stimulated APCs or cytokine stimulated APC preparations. For example, a composition can comprise a population of immune cells that have been incubated with one or more growth factor stimulated APCs or growth factor stimulated APC preparations. For example, a composition can comprise a population of immune cells that has been incubated with one or more ligand stimulated APCs or ligand stimulated APC preparations.

In some embodiments, the APC is an autologous APC, an allogenic APC, or an artificial APC.

Immune cells are characterized by cell surface molecules. In some embodiments the immune cells are preferably selected based on the cell surface markers, for example, from the biological sample, by using antibodies that can bind to the cell surface receptors. In some embodiments some cells are negatively selected to enrich one or more cell types that do not express the cell surface molecule that they are negatively selected for.

In some embodiments, antigen presenting cells (APCs) are prepared from the biological sample by selecting from APCs or precursor cells that can be cultured in presence of neoantigenic peptides to generate neoantigen-loaded APCs, which are used for activating T cells. Some of the related cell surface markers for selecting and/or enriching for a set of cells is described below.

CD1 (cluster of differentiation 1) is a family of glycoproteins expressed on the surface of various human antigen-presenting cells. They are related to the class I MHC molecules, and are involved in the presentation of lipid antigens to T cells.

CD11b or Integrin alpha M (ITGAM) is one protein subunit that forms heterodimeric integrin alpha-M beta-2 ($\alpha_M \beta_2$) molecule, also known as macrophage-1 antigen (Mac-1) or complement receptor 3(CR3). ITGAM is also known as CR3A, and cluster of differentiation molecule 11b (CD11b). The second chain of $\alpha_M \beta_2$ is the common integrin $\beta_2$ subunit known as CD18, and integrin $\alpha_M \beta_2$ thus belongs to the $\beta_2$ subfamily (or leukocyte) integrins. $\alpha_M \beta_2$ is expressed on the surface of many leukocytes involved in the innate immune system, including monocytes, granulocytes, macrophages, and natural killer cells. It mediates inflammation by regulating leukocyte adhesion and migration and has been implicated in several immune processes such as phagocytosis, cell-mediated cytotoxicity, chemotaxis and cellular activation. It is involved in the complement system due to its capacity to bind inactivated complement component 3b (iC3b). The ITGAM (alpha) subunit of integrin $\alpha_M\beta_2$ is directly involved in causing the adhesion and spreading of cells but cannot mediate cellular migration without the presence of the β2 (CD18) subunit.

CD11c, also known as Integrin, alpha X (complement component 3 receptor 4 subunit) (ITGAX), is a gene that encodes for CD11c. CD11c is an integrin alpha X chain protein. Integrins are heterodimeric integral membrane proteins composed of an alpha chain and a beta chain. This protein combines with the beta 2 chain (ITGB2) to form a leukocyte-specific integrin referred to as inactivated-C3b (iC3b) receptor 4 (CR4). The alpha X beta 2 complex seems to overlap the properties of the alpha M beta 2 integrin in the adherence of neutrophils and monocytes to stimulated endothelium cells, and in the phagocytosis of complement coated particles. CD11c is a type I transmembrane protein found at high levels on most human dendritic cells, but also on monocytes, macrophages, neutrophils, and some B cells that induces cellular activation and helps trigger neutrophil respiratory burst; expressed in hairy cell leukemias, acute nonlymphocytic leukemias, and some B-cell chronic lymphocytic leukemias.

CD14 is a surface antigen that is preferentially expressed on monocytes/macrophages. It cooperates with other proteins to mediate the innate immune response to bacterial lipopolysaccharide. Alternative splicing results in multiple transcript variants encoding the same protein. CD14 exists in two forms, one anchored to the membrane by a glycosylphosphatidylinositol tail (mCD14), the other a soluble form (sCD14). Soluble CD14 either appears after shedding of mCD14 (48 kDa) or is directly secreted from intracellular vesicles (56 kDa). CD14 acts as a co-receptor (along with the Toll-like receptor TLR 4 and MD-2) for the detection of bacterial lipopolysaccharide (LPS). CD14 can bind LPS only in the presence of lipopolysaccharide-binding protein (LBP). Although LPS is considered its main ligand, CD14 also recognizes other pathogen-associated molecular patterns such as lipoteichoic acid.

CD25 is expressed by conventional T cells after stimulation, and it has been shown that in human peripheral blood, only the $CD4^+CD25^{hi}$ T cells are 'suppressors'.

In some embodiments, the APC comprises a dendritic cell (DC). In some embodiments, the APC is derived from a $CD14^+$ monocyte. In some embodiments, the APCs can be obtained from skin, spleen, bone marrow, thymus, lymph nodes, peripheral blood, or cord blood. In some embodiments, the $CD14^+$ monocyte is from a biological sample from a subject comprising PBMCs. For example, a $CD14^+$ monocyte can be isolated from, enriched from, or purified from a biological sample from a subject comprising PBMCs. In some embodiments, the $CD14^+$ monocyte is stimulated with one or more cytokines or growth factors. In some embodiments, the one or more cytokines or growth factors comprise GM-CSF, IL-4, FLT3L, TNF-α, IL-1β, PGE1, IL-6, IL-7, IL-15, IFN-γ, IFN-α, R848, LPS, ss-rna40, poly I:C, or a combination thereof. In some embodiments, the $CD14^+$ monocyte is from a second biological sample comprising PBMCs.

In some embodiments, an isolated population of APCs can be enriched or substantially enriched. In some embodiments, the isolated population of APCs is at least 30%, at least 50%, at least 75%, or at least 90% homogeneous. In some embodiments, the isolated population of APCs is at least 60%, at least 75%, or at least 90% homogeneous. APCs, such as APCs can include, for example, APCs derived in culture from monocytic dendritic precursors as well as endogenously-derived APCs present in tissues such as, for example, peripheral blood, cord blood, skin, spleen, bone marrow, thymus, and lymph nodes.

APCs and cell populations substantially enriched for APCs can be isolated by methods also provided by the present invention. The methods generally include obtaining a population of cells that includes APC precursors, differentiation of the APC precursors into immature or mature APCs, and can also include the isolation of APCs from the population of differentiated immature or mature APCs.

APC precursor cells can be obtained by methods known in the art. APC precursors can be isolated, for example, by density gradient separation, fluorescence activated cell sorting (FACS), immunological cell separation techniques such as panning, complement lysis, rosetting, magnetic cell separation techniques, nylon wool separation, and combinations of such methods. Methods for immuno-selecting APCs include, for example, using antibodies to cell surface markers associated with APC precursors, such as anti-CD34 and/or anti-CD14 antibodies coupled to a substrate.

Enriched populations of APC precursors can also be obtained. Methods for obtaining such enriched precursor populations are known in the art. For example, enriched populations of APC precursors can be isolated from a tissue source by selective removal of cells that adhere to a substrate. Using a tissue source such as, e.g., bone marrow or peripheral blood, adherent monocytes can be removed from cell preparations using a commercially-treated plastic substrate (e.g., beads or magnetic beads) to obtain a population enriched for nonadherent APC precursors.

Monocyte APC precursors can also be obtained from a tissue source by using an APC precursor-adhering substrate. For example, peripheral blood leukocytes isolated by, e.g., leukapheresis, are contacted with a monocytic APC precursor-adhering substrate having a high surface area to volume ratio and the adherent monocytic APC precursors are separated. In additional embodiments, the substrate coupled can be a particulate or fibrous substrate having a high surface-to-volume ratio, such as, for example, microbeads, microcarrier beads, pellets, granules, powder, capillary tubes, microvillous membrane, and the like. Further, the particulate or fibrous substrate can be glass, polystyrene, plastic, glass-coated polystyrene microbeads, and the like.

The APC precursors can also be cultured in vitro for differentiation and/or expansion. Methods for differentiation/expansion of APC precursors are known in the art. Generally, expansion can be achieved by culturing the precursors in the presence of at least one cytokine that induces APC (e.g., dendritic cell) differentiation/proliferation. Typically, these cytokines are granulocyte colony stimulating factor (G-CSF) or granulocyte/macrophage colony stimulating factor (GM-CSF). In addition, other agents can be used to inhibit proliferation and/or maturation of non-APC cell types in the culture, thereby further enriching the population of APC precursors. Typically, such agents include cytokines such as, e.g., IL-13, IL-4, or IL-15, and the like.

The isolated populations of APC precursors are cultured and differentiated to obtain immature or mature APCs. Suitable tissue culture media include, for example, but not limited to, AIM-V®, RPMI 1640, DMEM, X-VIVO, and the like. The tissue culture media is typically supplemented with amino acids, vitamins, divalent cations, and cytokines to promote differentiation of the precursors toward the APC phenotype. Typically, the differentiation-promoting cytokines are GM-CSF and/or IL-4.

Further, cultures of APC precursors during expansion, differentiation, and maturation to the APC phenotype can include plasma to promote the development of APCs. A typical plasma concentration is about 5%. In addition, where, for example, APC precursors are isolated by adherence to a substrate, plasma can be included in the culture media during the adherence step to promote the CD14$^+$ phenotype early in culture. A typical plasma concentration during adherence is about 1% or more.

The monocytic APC precursors can be cultured for any suitable time. In certain embodiments, suitable culture times for the differentiation of precursors to immature APCs can be about 1 to about 10 days, e.g., about 4 to about 7 days. The differentiation of immature APCs from the precursors can be monitored by methods known to those skilled in the art, such as by the presence or absence of cell surface markers (e.g., CD11c$^+$, CD83$^{low}$, CD86$^{-/low}$, HLA-DR$^+$). Immature APCs can also be cultured in appropriate tissue culture medium to maintain the immature APCs in a state for further differentiation or antigen uptake, processing and presentation. For example, immature APCs can be maintained in the presence of GM-CSF and IL-4.

In some embodiments, APC precursors may be isolated prior to differentiation. In some embodiments, the isolated population may be enriched or substantially enriched for APC precursors. In some embodiments, APC precursors are isolated with a CD14 specific probe. In one exemplary embodiment, CD14 expressing cells are detected by FACS using a CD14 specific probe either directly conjugated to a fluorescent molecule (e.g., FITC or PE) or with a unlabeled antibody specific for CD14 and a labeled second antibody specific for the first antibody. CD14$^+$ cells can also be separated from CD14$^{low}$ and CD14$^-$ cells by FACS sorting. Gating for CD14$^{high}$ positivity can be determined in reference to CD14 staining on, e.g., PBMC-derived monocytes. Typically, the CD14 specific binding agent is, for example, an anti-CD14 antibody (e.g., monoclonal or antigen binding fragments thereof). A number of anti-CD14 antibodies suitable for use in the present invention are well known to the skilled artisan and many can be purchased commercially. Differentiation into immature APCs (CD14 negative) can take place following isolation.

In another embodiment, a CD14 specific probe is coupled to a substrate and the CD14$^+$ cells are isolated by affinity selection. A population of cells that includes CD14$^+$ cells is exposed to the coupled substrate and the CD14$^+$ cells are allowed to specifically adhere. Non-adhering CD14$^-$ cells are then washed from the substrate, and the adherent cells are then eluted to obtain an isolated cell population substantially enriched in APC precursors. The CD14 specific probe can be, for example, an anti-CD14 antibody. The substrate can be, for example, commercially available tissue culture plates or beads (e.g., glass or magnetic beads). Methods for affinity isolation of cell populations using substrate-coupled antibodies specific for surface markers are generally known.

During culture, immature APCs can optionally be exposed to a predetermined antigen. Suitable predetermined antigens can include any antigen for which T-cell modulation is desired. In one embodiment, immature APCs are cultured in the presence of prostate specific membrane antigen (PSMA) for cancer immunotherapy and/or tumor growth inhibition. Other antigens can include, for example, bacterial cells, viruses, partially purified or purified bacterial or viral antigens, tumor cells, tumor specific or tumor associated antigens (e.g., tumor cell lysate, tumor cell membrane preparations, isolated antigens from tumors, fusion proteins, liposomes, and the like), recombinant cells expressing an antigen on its surface, autoantigens, and any other antigen. Any of the antigens can also be presented as a peptide or recombinantly produced protein or portion thereof. Following contact with antigen, the cells can be cultured for any suitable time to allow antigen uptake and processing, to expand the population of antigen-specific APCs, and the like.

For example, in one embodiment, the immature APCs can be cultured following antigen uptake to promote maturation of the immature APCs into mature APCs that present antigen in the context of MHC molecules. Methods for APC maturation are known. Such maturation can be performed, for example, by culture in the presence of known maturation factors, such as cytokines (e.g., TNF-$\alpha$, IL-1$\beta$, or CD40 ligand), bacterial products (e.g., LPS or BCG), and the like. The maturation of immature APCs to mature APCs can be monitored by methods known in the art, such as, for example by measuring the presence or absence of cell surface markers (e.g., upregulation of CD83, CD86, and MHC molecules) or testing for the expression of mature APC specific mRNA or proteins using, for example, an oligonucleotide array.

Optionally, the immature APCs can be cultured in an appropriate tissue culture medium to expand the cell population and/or maintain the immature APCs in state for further differentiation or antigen uptake. For example, immature APCs can be maintained and/or expanded in the presence of GM-CSF and IL-4. Also, the immature APCs can be cultured in the presence of anti-inflammatory molecules such as, for example, anti-inflammatory cytokines (e.g., IL-10 and TGF-$\beta$) to inhibit immature APC maturation.

In another aspect, the isolated population of APCs is enriched for mature APCs. The isolated population of mature APCs can be obtained by culturing a differentiated population of immature APCs in the presence of maturation factors as described above (e.g., bacterial products, and/or proinflammatory cytokines), thereby inducing maturation. Immature APCs can be isolated by removing CD14+ cells.

According to yet another aspect of the invention, APCs can be preserved, e.g., by cryopreservation either before exposure or following exposure to a suitable antigen. Cryopreservation agents which can be used include but are not limited to dimethyl sulfoxide (DMSO), glycerol, polyvinylpyrrolidone, polyethylene glycol, albumin, dextran, sucrose, ethylene glycol, i-erythritol, D-ribitol, D-mannitol, D-sorbitol, i-inositol, D-lactose, choline chloride, amino acids, methanol, acetamide, glycerol monoacetate, and inorganic salts. A controlled slow cooling rate can be critical. Different cryoprotective agents and different cell types typically have different optimal cooling rates. The heat of fusion phase where water turns to ice typically should be minimal. The cooling procedure can be carried out by use of, e.g., a programmable freezing device or a methanol bath procedure. Programmable freezing apparatuses allow determination of optimal cooling rates and facilitate standard reproducible cooling. Programmable controlled-rate freezers such as Cryomed or Planar permit tuning of the freezing regimen to the desired cooling rate curve.

After thorough freezing, APCs can be rapidly transferred to a long-term cryogenic storage vessel. In a typical embodiment, samples can be cryogenically stored in liquid nitrogen (−196° C.) or its vapor (−165° C.). Considerations and procedures for the manipulation, cryopreservation, and long term storage of hematopoietic stem cells, particularly from bone marrow or peripheral blood, is largely applicable to the APCs of the invention.

Frozen cells are preferably thawed quickly (e.g., in a water bath maintained at 37-41° C.) and chilled immediately upon thawing. It may be desirable to treat the cells in order to prevent cellular clumping upon thawing. To prevent clumping, various procedures can be used, including but not limited to the addition before and/or after freezing of DNAse, low molecular weight dextran and citrate, hydroxyethyl starch, and the like. The cryoprotective agent, if toxic in humans, should be removed prior to therapeutic use of the thawed APCs. One way in which to remove the cryoprotective agent is by dilution to an insignificant concentration. Once frozen APCs have been thawed and recovered, they can be used to activate T cells as described herein with respect to non-frozen APCs.

In one aspect, a composition for T cell activation comprises a population of immune cells that has been depleted of one or more types of immune cells. For example, a composition can comprise a population of immune cells that has been depleted of one or more types of immune cells that express one or more proteins, such as one or more cell surface receptors. In some embodiments, a composition comprises a population of immune cells from a biological sample comprising at least one antigen specific T cells comprising a T cell receptor (TCR) specific to at least one antigen peptide sequence, wherein an amount of CD14 and/or CD25 expressing immune cells in the population is proportionally different from an amount of immune cells expressing CD14 and/or CD25 in the biological sample. For example, a composition can comprise a population of immune cells from a biological sample comprising at least one antigen specific T cells comprising a T cell receptor (TCR) specific to at least one antigen peptide sequence, wherein an amount of CD14 expressing immune cells in the population is proportionally different from an amount of immune cells expressing CD14 in the biological sample. For example, a composition can comprise a population of immune cells from a biological sample comprising at least one antigen specific T cells comprising a T cell receptor (TCR) specific to at least one antigen peptide sequence, wherein an amount of CD25 expressing immune cells in the population is proportionally different from an amount of immune cells expressing CD25 in the biological sample. For example, a composition can comprise a population of immune cells from a biological sample comprising at least one antigen specific T cells comprising a T cell receptor (TCR) specific to at least one antigen peptide sequence, wherein an amount of CD14 and CD25 expressing immune cells in the population is proportionally different from an amount of immune cells expressing CD14 and CD25 in the biological sample. For example, a composition can comprise a population of immune cells from a biological sample, wherein an amount of immune cells expressing CD14 and CD25 in the population is proportionally less than an amount of immune cells expressing CD14 and CD25 in the biological sample.

Provided herein is a method for preparing a cellular composition for cancer immunotherapy, comprising: I. preparing antigen loaded antigen presenting cells (APC), comprising: (a) obtaining peripheral blood mononuclear cells (PBMC) from a subject pretreated with fms-like tyrosine kinase 3 ligand (FLT3L); (b) contacting the PBMCs ex vivo with: (i) a plurality of cancer neoantigen peptides, or one or more polynucleotides encoding the plurality of cancer neoantigen peptides, and wherein, each of the cancer neoantigen peptides or a portion thereof binds to a protein encoded by an HLA allele expressed in the subject, (ii) a stimulant for activating the cells, (iii) an agent promoting cell growth and maintenance ex vivo, thereby obtaining a cell population, and (iv) an agent for reducing or depleting CD11b+ cells from the cell population to obtain a CD11b$^{low}$ or CD11b depleted antigen loaded APC; II. contacting isolated T cells with the CD11b$^{low}$ or CD11b depleted antigen loaded APCs ex vivo; III. preparing antigen primed T cells for a cellular composition for cancer immunotherapy.

Provided herein is an improved method for preparing tumor antigen-specific T cells ex vivo, the method comprises (a) depleting CD14+ cells and/or CD25+ cells from a population of immune cells comprising antigen presenting cells (APCs) and T cells, thereby forming a CD14 and/or CD25 depleted population of immune cells comprising a first population of APCs and T cells, wherein the population of immune cells is from a biological sample from a human subject; (b) incubating the first population of APCs and T cells from step (a) for a first time period in the presence of: (i) FMS-like tyrosine kinase 3 receptor ligand (FLT3L), and (ii) (A) a polypeptide comprising at least one tumor antigen epitope sequence expressed by cancer cells of a human subject with cancer, or (B) a polynucleotide encoding the polypeptide; thereby forming a population of cells comprising stimulated T cells; (c) expanding the stimulated T cells from step (b), thereby forming an expanded population of cells comprising tumor antigen-specific T cells, wherein the tumor antigen-specific T cells comprise T cells that are specific to a complex comprising (i) the at least one tumor antigen epitope sequence from step (b)(ii), and, (ii) an MHC protein expressed by the cancer cells, or APCs of the human subject of (b)(ii). Provided herein is a method, comprising administering the expanded population of cells from (c) to the human subject, wherein the expanded population of cells from step (c) comprises from $1 \times 10^8$ to $1 \times 10^{11}$ total cells.

In some embodiments, the subject is pretreated with FLT3L at least about 1 hour, 2 hours, 3 hours, 4 hours, 5 hours, 6 hours, 12 hours, 1 day, 2 days, 3 days, 4 days, 5 days, 6 days, or 1 week before isolation of PBMC or leukapheresis. In some embodiments, the subject is pretreated with FLT3L at least about 1 week, 2 weeks, 3 weeks, 4 weeks, or 5 weeks before isolation of PBMC or leukapheresis.

In some embodiments, the cell population is enriched for CD11c+ cells. In some embodiments, the antigen loaded APC comprises dendritic cells (DCs). In some embodiments, the antigen loaded APC comprises plasmacytoid dendritic cells (pDCs). In some embodiments, the antigen loaded APC comprises CD1c+ DCs. In some embodiments, the antigen loaded APC comprises CD141+ DCs. In some embodiments, the cell population comprises macrophages. In some embodiments, the method further comprises reducing or depleting CD19+ cells from the cell population for activating or enriching neoantigen activated T cells. In some embodiments, the method further comprises reducing or depleting both CD11b+ and CD19+ cells from the cell population for activating or enriching neoantigen activated T cells.

In some embodiments, the method further comprises reducing or depleting CD14+ cells from the cell population for preparing and enriching antigen activated T cells. In some embodiments, the method further comprises reducing or depleting CD25+ cells from the cell population for preparing and enriching antigen activated T cells. In some embodiments, the method further comprises reducing or depleting one or more of CD19+, CD14+, CD25+ or CD11b+ cells from the cell population for activating or enriching neoantigen activated T cells.

In some embodiments the stimulant for activating the cells comprises FL3TL.

In some embodiments the agent promoting cell growth and maintenance ex vivo comprises a growth factor, a cytokine, an amino acid, a supplement or a combination thereof.

In some embodiments the antigen loaded APCs can stimulate T cells for 2, 3, 4, 5, 6, or 7 days.

In some embodiments, each of the plurality of cancer neoantigen peptides is 8-30 amino acids long.

In some embodiments, each of the plurality of neoantigenic peptide comprises a neoantigenic epitope. In some embodiments the plurality of cancer neoantigen peptides comprises 2, 3, 4, 5, 6, 7 or 8 neoantigenic peptides; and each of the plurality of neoantigenic peptides have the neoantigenic peptide characteristics as described in the previous section.

In some embodiments, the neoantigenic peptides used to prepare antigen loaded APCs are long peptides comprising at least 20 amino acids, or at least 30 amino acids or at least 40 amino acids or at least 50 amino acids, or any number of amino acids in between. In some embodiments, the neoantigenic peptides used to prepare antigen loaded APCs comprise the amino acids flanking on either side of the mutation that facilitate endogenous processing of the neoantigenic peptide for increased rate of presentation to a T cell.

A longer immunogenic peptide can be designed in several ways. In some embodiments, when HLA-binding peptides are predicted or known, a longer immunogenic peptide could consist of (1) individual binding peptides with extensions of 2-5 amino acids toward the N- and C-terminus of each corresponding gene product; or (2) a concatenation of some or all of the binding peptides with extended sequences for each. In other embodiments, when sequencing reveals a long (>10 residues) epitope sequence, e.g., a neoepitope present in a tumor (e.g. due to a frameshift, read-through or intron inclusion that leads to a novel peptide sequence), a longer neoantigen peptide could consist of the entire stretch of novel tumor-specific amino acids as either a single longer peptide or several overlapping longer peptides. In some embodiments, use of a longer peptide is presumed to allow for endogenous processing by patient cells and can lead to more effective antigen presentation and induction of T cell responses. In some embodiments, two or more peptides can be used, where the peptides overlap and are tiled over the long neoantigen peptide.

In some embodiments, each of the plurality of neoantigenic peptide comprises the same neoantigenic epitope. In some embodiments the plurality of neoantigenic peptide comprises more than one neoantigenic epitope.

In some embodiments the one or more polynucleotides encoding the plurality of cancer neoantigen peptides is DNA.

In some embodiments the one or more polynucleotides encoding the plurality of cancer neoantigen peptides is inserted in one or more mammalian expression vectors.

In some embodiments the one or more polynucleotides encoding the plurality of cancer neoantigen peptides is messenger RNA.

In some embodiments, the invention provides RNA, oligoribonucleotide, and polyribonucleotide molecules comprising a modified nucleoside.

In some embodiments, the invention provides gene therapy vectors comprising the RNA, oligoribonucleotide, and polyribonucleotide.

In some embodiments, the invention provides gene therapy methods and gene transcription silencing methods comprising same.

In some embodiments the polynucleotide encodes a single neoantigenic peptide.

In some embodiments the one polynucleotide encodes more than one neoantigenic peptide.

In some embodiments, the polynucleotide is messenger RNA. In some embodiments, each messenger RNA comprises coding sequence for two or more neoantigenic peptides in tandem.

In some embodiments each messenger RNA comprises a coding sequence for two, three, four, five, six, seven, eight, nine or ten or more neoantigenic peptides in tandem. Typically, an mRNA comprises a 5'-UTR, a protein coding region, and a 3'-UTR. mRNA only possesses limited half-life in cells and in vitro. In some embodiments, the mRNA is self-amplifying mRNA. In the context of the present invention, mRNA may be generated by in vitro transcription from a DNA template. The in vitro transcription methodology is known to the skilled person. For example, there is a variety of in vitro transcription kits commercially available.

The stability and translation efficiency of RNA may be modified. For example, RNA may be stabilized and its translation increased by one or more modifications having a stabilizing effects and/or increasing translation efficiency of RNA. Such modifications are described, for example, in PCT/EP2006/009448 incorporated herein by reference. In order to increase expression of the RNA used according to the present invention, it may be modified within the coding region, i.e. the sequence encoding the expressed peptide or protein, without altering the sequence of the expressed peptide or protein, so as to increase the GC-content to increase mRNA stability and to perform a codon optimization and, thus, enhance translation in cells.

In some embodiments, an mRNA can include multiple neoantigenic epitopes. In some embodiment, long polyribonucleotide sequences can be used, that can encode neo-ORFs, for example, mutated GATA3 sequences, encoding neo-ORFs. In some a mRNA of a large portion of, or even the entire coding region of a gene comprising sequences encoding neoantigenic peptides are delivered into an immune cell for endogenous processing and presentation of antigens.

In some embodiments, the coding sequence for each neoantigenic peptide is 24-120 nucleotides long.

In some embodiments, the mRNA is 50-10,000 nucleotides long. In some embodiments, the mRNA is 100-10,000 nucleotides long. In some embodiments, the mRNA is 200-10,000 nucleotides long. In some embodiments, the mRNA is 50-5,000 nucleotides long. In some embodiments, the mRNA is 100-5,000 nucleotides long. In some embodiments, the mRNA is 100-1,000 nucleotides long. In some embodiments, the mRNA is 300-800 nucleotides long. In some embodiments, the mRNA is 400-700 nucleotides long. In some embodiments, the mRNA is 450-600 nucleotides long. In some embodiments, the mRNA is at least 200 nucleotides long. In some embodiments the mRNA is greater than 250 nucleotides, greater than 300 nucleotides, greater than 350 nucleotides, greater than 400 nucleotides, greater than 450 nucleotides, greater than 500 nucleotides, greater than 550 nucleotides, greater than 600 nucleotides, greater than 650 nucleotides, greater than 700 nucleotides, greater than 750 nucleotides, greater than 800 nucleotides, greater than 850 nucleotides long, greater than 900 nucleotides long greater than 950 nucleotides long, greater than 1000 nucleotides long, greater than 2000 nucleotides long, greater than 3000 nucleotides long, greater than 4000 nucleotides long or greater than 5000 nucleotides long.

In some embodiments, mRNA encoding one or more neoantigenic peptide is modified, wherein the modification relates to the 5'-UTR. In some embodiments, the modification relates to providing an RNA with a 5-cap or 5'-cap analog in the 5'-UTR. The term "5-cap" refers to a cap structure found on the 5-end of an mRNA molecule and generally consists of a guanosine nucleotide connected to the mRNA via an unusual 5' to 5' triphosphate linkage. In some embodiments, this guanosine is methylated at the 7-position. The term "conventional 5-cap" refers to a naturally occurring RNA 5-cap, to the 7-methylguanosine cap (m G). In the context of the present invention, the term "5-cap" includes a 5-cap analog that resembles the RNA cap structure and is modified to possess the ability to stabilize RNA and/or enhance translation of RNA if attached thereto, in vivo and/or in a cell. In some embodiments, mRNA is capped cotranscriptionally.

In some embodiments, the mRNA encoding one or more neoantigenic peptides comprise a 3'-UTR comprising a poly A tail. In some embodiments, the poly A tail is 100-200 bp long (SEQ ID NO: 6). In some embodiments, the poly A tail is longer than 20 nucleotides. In some embodiments, the poly A tail is longer than 50 nucleotides. In some embodiments, the poly A tail is longer than 60 nucleotides. In some embodiments, the poly A tail is longer than 70 nucleotides. In some embodiments, the poly A tail is longer than 80 nucleotides. In some embodiments, the poly A tail is longer than 90 nucleotides. In some embodiments, the poly A tail is longer than 100 nucleotides. In some embodiments, the poly A tail is longer than 110 nucleotides. In some embodiments, the poly A tail is longer than 120 nucleotides. In some embodiments, the poly A tail is longer than 130 nucleotides. In some embodiments, the poly A tail is longer than 140 nucleotides. In some embodiments, the poly A tail is longer than 150 nucleotides. In some embodiments, the poly A tail is longer than 160 nucleotides. In some embodiments, the poly A tail is longer than 170 nucleotides. In some embodiments, the poly A tail is longer than 180 nucleotides. In some embodiments, the poly A tail is longer than 190 nucleotides. In some embodiments, the poly A tail is longer than 200 nucleotides. In some embodiments, the poly A tail is longer than 210 nucleotides. In some embodiments, the poly A tail is longer than 220 nucleotides. In some embodiments, the poly A tail is longer than 230 nucleotides. In some embodiments, the poly A tail is longer than 100 nucleotides. In some embodiments, the poly A tail is longer than 240 nucleotides. In some embodiments, the poly A tail is longer than 100 nucleotides. In some embodiments, the poly A tail is about 250 nucleotides.

In some embodiments, the poly A tail comprises 100-250 adenosine units (SEQ ID NO: 7). In some embodiments, the poly A tail comprises 120-130 adenine units (SEQ ID NO: 20). In some embodiments, the poly A tail comprises 120 adenine units (SEQ ID NO: 21). In some embodiments, the poly A tail comprises 121 adenine units (SEQ ID NO: 22). In some embodiments, the poly A tail comprises 122 adenine units (SEQ ID NO: 23). In some embodiments, the poly A tail comprises 123 adenine units (SEQ ID NO: 24). In some embodiments, the poly A tail comprises 124 adenine units (SEQ ID NO: 25). In some embodiments, the poly A tail comprises 125 adenine units (SEQ ID NO: 26). In some embodiments, the poly A tail as 129 bases (SEQ ID NO: 27).

In some embodiments, the coding sequence for two consecutive neoantigenic peptides are separated by a spacer or linker.

In some embodiments, the spacer or linker comprises up to 5000 nucleotide residues. An exemplary spacer sequence is GGCGGCAGCGGCGGCGGCGGCAGCGGCGGC (SEQ ID NO: 1). Another exemplary spacer sequence is GGCGGCAGCCTGGGCGGCGGCGGCAGCGGC (SEQ ID NO: 2). Another exemplary spacer sequence is GGCGTCGGCACC (SEQ ID NO: 3). Another exemplary spacer sequence is CAGCTGGGCCTG (SEQ ID NO: 4). Another exemplary spacer is a sequence that encodes a lysine, such as AAA or AAG. Another exemplary spacer sequence is CAACTGGGATTG (SEQ ID NO: 5).

In some embodiments, the mRNA comprises one or more additional structures to enhance antigen epitope processing and presentation by APCs.

In some embodiments, the linker or spacer region may contain cleavage sites. The cleavage sites ensure cleavage of the protein product comprising strings of epitope sequences into separate epitope sequences for presentation. The preferred cleavage sites are placed adjacent to certain epitopes in order to avoid inadvertent cleavage of the epitopes within the sequences. In some embodiments, the design of epitopes and cleavage regions on the mRNA encoding strings of epitopes are non-random.

In certain embodiments, an mRNA encoding a neoantigen peptide of the invention is administered to a subject in need thereof. In some embodiments, the mRNA to be administered comprises at least one modified nucleoside-phosphate.

In some embodiments, T cells are activated with neoantigenic peptides by artificial antigen presenting cells. In some embodiments, artificial scaffolds are used to activate a T cells with neoantigenic peptides, the artificial scaffolds are loaded with neoantigenic peptides couples with an MHC antigen to which the neoantigenic peptide can bind with high affinity.

In some embodiments, the additional structures comprise encoding specific domains from the proteins selected from a group MITD, SP1, and 10th Fibronectin Domain: 10FnIII.

In some embodiments, the cells derived from peripheral blood or from leukapheresis are contacted with the plurality of cancer neoantigen peptides, or one or more polynucleotides encoding the plurality of cancer neoantigen peptides once or more than once to prepare the antigen loaded APCs.

In some embodiments, the method comprises incubating the APC or one or more of the APC preparations with a first medium comprising at least one cytokine or growth factor for a first time period.

In some embodiments, the method comprises incubating one or more of the APC preparations with at least one peptide for a second time period.

In some embodiments, the enriched cells further comprise CD1c+ cells.

In some embodiments, the cell population is enriched for CD11c+ and CD141+ cells.

In some embodiments, the cell population comprising the antigen loaded APCs comprises greater than 1%, 2%, 3%, 4%, 5%, 6, 7%, 8%, 9%, 10%, 15%, 20%, 25%, 30% 35%, 40%, 45%, 50%, 55%, 60%, 65%, 70%, 75%, 80%, 85%, 90%, or 95% or more CD11c+ cells.

In some embodiments, the cell population comprising the antigen loaded APCs comprises less than 95%, 90%, 85%, 80%, 75%, 70%, 65%, 60%, 55%, 50%, 45%, 40%, 35%, 30%, 20%, 10%, 8%, 7%, 6%, 5%, 4% or lower CD11b+ expressing cells.

In some embodiments, the cell population comprising the antigen loaded APCs comprises greater than 1%, 2%, 3%, 4%, 5%, 6, 7%, 8%, 9%, 10%, 15%, 20%, 25%, 30% 35%, 40%, 45%, 50%, 55%, 60%, 65%, 70%, 75%, 80%, 85%, 90%, or 95% neoantigenic peptide expressing cells that are CD11c+.

In some embodiments, the cell population comprising the antigen loaded APCs comprises greater than 1%, 2%, 3%, 4%, 5%, 6, 7%, 8%, 9%, 10%, 15%, 20%, 25%, 30% 35%, 40%, 45%, 50%, 55%, 60%, 65%, 70%, 75%, 80%, 85%, 90%, or 95% neoantigenic peptide expressing cells that are CD11c+CD1c+, or CD141+ cells.

In some embodiments, the neoantigen loaded APCs comprise mature APCs.

In some embodiments, the method comprises obtaining a biological sample from a subject comprising at least one APC and at least one PBMC or at least on T cell.

In some embodiments, the method comprises depleting cells expressing CD14 and/or CD25 and/or CD19 from a biological sample, thereby obtaining a CD14 and/or CD25 and/or CD19 cell depleted sample.

In some embodiments, the method comprises incubating a CD14 and/or CD25 and/or CD19 cell depleted sample with FLT3L for a first time period.

In some embodiments, the method comprises incubating at least one peptide with a CD14 and/or CD25 and/or CD19 cell depleted sample for a second time period, thereby obtaining a first matured APC peptide loaded sample.

Preparing Neoantigen Activated T Cells Using Neoantigen Loaded APCs

In some embodiments, the neoantigen loaded APC (APC) prepared by the methods described above is incubated with T cells to obtain antigen activated T cells. The method can comprise generating at least one antigen specific T cell where the antigen is a neoantigen. In some embodiments, the generating at least one antigen specific T cell comprises generating a plurality of antigen specific T cells.

In some embodiments, the T cells are obtained from a biological sample from a subject.

In some embodiments, the T cells are obtained from a biological sample from the same subject from whom the APCs are derived. In some embodiments, the T cells are obtained from a biological sample from a different subject than the subject from whom the APCs are derived.

In some embodiments, the APCs and/or T cells are derived from a biological sample which is peripheral blood mononuclear cells (PBMC). In some embodiments, the APCs and/or T cells are derived from a biological sample which is a leukapheresis sample.

In some embodiments, the APC comprises a dendritic cell (DC).

In some embodiments, the APC is derived from a CD14+ monocyte, or is a CD14 enriched APC, or is a CD141 enriched APC.

In some embodiments, the CD14+ monocyte is enriched from a biological sample from a subject comprising peripheral blood mononuclear cells (PBMCs).

In some embodiments, the APC is PBMC. In some embodiments, the PBMC is freshly isolated PBMC. In some embodiments the PBMC is frozen PBMC. In some embodiments, the PBMC is autologous PBMC isolated from the subject or the patient.

In some embodiments, the PBMC is loaded with antigens, where the antigens may be peptides or polypeptides or polynucleotides, such as mRNA, that encode the peptides and polypeptides. PBMCs (monocytes, DCs phagocytic cells) can take up antigens by phagocytosis and process and present them on the surface for T cell activation. Peptides or polypeptides loaded on the PBMCs may be supplemented with adjuvants to increase immunogenicity. In some embodiments, the PBMC is loaded with nucleic acid antigens. Nucleic acid antigens may be in the form of mRNA, comprising sequences encoding one or more antigens. In some embodiments, mRNA antigen loading does not require adjuvant supplementation, because, for example, RNA can act as a self-adjuvant.

In some embodiments, PBMCs are directly isolated or thawed from a frozen sample, and subjected to incubating with one or more antigens, such as a neoantigen, or a composition comprising a neoantigen, or one or more nucleic acids or polynucleotides encoding the one or more antigens. In some embodiments, the PBMC sample is not further cultured for differentiation or subjected to further maturation of one or more cell components within the PBMC, (for example, maturation of antigen presenting cells, or differentiation of monocytes to dendritic cells), before exposing the PBMCs to one or more antigens or nucleic acid encoding the one or more antigens. In some embodiments one or more cell types are depleted or removed from the freshly isolated PBMC cell population or a freshly thawed PBMC population before exposing or incubating the cells to one or more antigens or nucleic acid encoding the one or more antigens. In some embodiments, CD14+ cells are depleted from the PBMC. In some embodiments, CD25+ cells are depleted from the PBMC. In some embodiments, CD11b+ cells are depleted from the PBMC. In some embodiments, the CD14+ and CD25+ cells are depleted from the PBMCs, before incubating with one or more antigens or one or more nucleic acids encoding the one or more antigens. In some embodiments, the CD11b+, and/or the CD14+ and/or CD25+ cells cells are depleted from the PBMC. In some embodiments, a method provided herein comprises preparing tumor antigen-specific T cells by depleting CD14+ cells and/or CD25+ cells from a PBMC sample from a human subject containing about the same percentage of immature dendritic cells (DCs) as the percentage of immature DCs in the peripheral blood of the human subject. In some embodiments, a method provided herein comprises preparing tumor antigen-specific T cells by depleting CD14+ cells and/or CD25+ cells from a PBMC sample from a human subject containing about the same percentage of mature DCs as the percentage of mature DCs in the peripheral blood of the human subject. In some embodiments, a method provided herein comprises preparing tumor antigen-specific T cells by depleting CD14+ cells and/or CD25+ cells from a PBMC sample from a human subject containing about the same ratio of immature DCs to mature DCs as the ratio of immature DCs to mature DCs in the peripheral blood of the human subject. In some embodiments, a method provided herein comprises preparing tumor antigen-specific T cells by depleting CD14+ cells and/or CD25+ cells from a PBMC sample from a human subject that has not been subject to a step of maturing immature DCs into mature DCs.

In some embodiments, the CD14+ monocyte is stimulated with one or more cytokines or growth factors.

In some embodiments, one or more cytokines or growth factors comprise GM-CSF, IL-4, FLT3L, TNF-α, IL-1β, PGE1, IL-6, IL-7, IL-15, IFN-γ, IFN-α, R848, LPS, ss-rna40, poly I:C, or a combination thereof.

In some embodiments, the CD14+ monocyte is from a second biological sample comprising PBMCs.

In some embodiments, the second biological sample is from the same subject.

In some embodiments, the biological sample comprises peripheral blood mononuclear cells (PBMCs).

In some embodiments, the at least one antigen-specific T cell is stimulated in a medium comprising IL-7, IL-15, an indoleamine 2,3-dioxygenase-1 (IDO) inhibitor, an anti-PD-1 antibody, IL-12, or a combination thereof.

In some embodiments, the IDO inhibitor is epacadostat, navoximod, 1-methyltryptophan, or a combination thereof.

In some embodiments, the subject is administered FLT3L prior to obtaining the biological sample for preparing the APCs and/or T cells.

In some embodiments, the T cells are obtained from a biological sample from a subject as described in the previous sections of this disclosure.

In some embodiments, the biological sample is freshly obtained from a subject or is a frozen sample.

In some embodiments, the incubating is in presence of at least one cytokine or growth factor, which comprises GM-CSF, IL-4, FLT3L, TNF-α, IL-1β, PGE1, IL-6, IL-7, IL-15, IFN-γ, IFN-α, IL-15, R848, LPS, ss-rna40, poly I:C, or any combination thereof.

In some embodiments, a method comprises stimulating T cells with IL-7, IL-15, or a combination thereof. In some embodiments, a method comprises stimulating T cells with IL-7, IL-15, or a combination thereof, in the presence of an IDO inhibitor, a PD-1 antibody or IL-12. In some embodiments, the stimulated T cell is expanded in presence of the one or more tumor antigen epitope sequence or APCs loaded with the one or more tumor antigen epitope sequence, or APCs loaded with (e.g. expressing) nucleic acid sequences (such as mRNA sequences) encoding the one or more tumor antigen epitope sequence, one or more cytokines or growth factors comprise GM-CSF, IL-4, FLT3L, TNF-α, IL-1β, PGE1, IL-6, IL-7, IL-15, IFN-γ, IFN-α, R848, LPS, ss-rna40, poly I:C, or a combination thereof, FLT3L, under suitable T cell growth conditions ex vivo. In some embodiments, the method further comprises administering the antigen specific T cells to a subject.

In some embodiments, the method comprises incubating the APC prepared as described in the previous sections with T cells in presence of a medium comprising the at least one cytokines or growth factor to generate neoantigen activated T cells.

In some embodiments, the incubating comprises incubating a first APC preparation of the APC preparations to the T cells for more than 7 days. In some embodiments, the incubated T cells are stimulated T cells that expand in vitro on presence of the APC preparation, cytokines and growth factors for more than 7 days.

In some embodiments, the incubating comprises incubating a first APC preparation of the APC preparations to the T cells for more than 7, 8, 9, 10, 11, 12, 13, 14, 15, 16, 17, 18, 19, or 20 days.

In some embodiments, the first time period of the one or more time periods is about 1, 2 3, 4, 5, 6, 7, 8, or 9 days.

In some embodiments, a total time period of the separate time periods is less than 28 days. In some embodiments, a total time period of the separate time periods is from 20-27 days. In some embodiments, a total time period of the separate time periods is 15, 16, 17, 18, 19, 20, 21, 22, 23, 24, 25, 26, 27, 28, 29, 30, 31, 32, 33, 34, 35, 36, 37, 38, or 39 days.

In some embodiments, a method comprises incubating a first APC preparation of the APC preparations with the T cells for more than 7 days. In some embodiments, a method comprises incubating a first APC preparation of the APC preparations with the T cells for more than 7, 8, 9, 10, 11, 12, 13, 14, 15, 16, 17, 18, 19, or 20 days. In some embodiments, a method comprises incubating a first APC preparation of the APC preparations with the T cells for from 7-20, 8-20, 9-20, 10-20, 11-20, or 12-20 days. In some embodiments, a method comprises incubating a first APC preparation of the APC preparations with the T cells for about 10-15 days.

In some embodiments, a method comprises incubating a second APC preparation of the APC preparations to the T cells for 5-9 days. In some embodiments, a method comprises incubating a second APC preparation of the APC preparations to the T cells for 5, 6, 7, 8, or 9 days. In some embodiments, the method further comprises removing the one or more cytokines or growth factors of the second medium after the third time period and before a start of the fourth time period.

In some embodiments, a method comprises incubating a third APC preparation of the APC preparations to the T cells for 5-9 days. In some embodiments, the method comprises incubating a third APC preparation of the APC preparations to the T cells for 5, 6, 7, 8, or 9 days.

In some embodiments, the method comprises incubating a first APC preparation of the APC preparations with the T cells for about 1, 2, 3, 4, 5, 6, 7, 8, 9, 10, 11, 12, 13, 14, 15, 16, 17, 18, 19, 20, 21, or 22 days, incubating a second APC preparation of the APC preparations to the T cells for about 1, 2, 3, 4, 5, 6, 7, 8, 9, 10, 11, 12, 13, 14, 15, 16, 17, 18, 19, 20, 21, or 22 days, and incubating a third APC preparation of the APC preparations to the T cells for about 1, 2, 3, 4, 5, 6, 7, 8, 9, 10, 11, 12, 13, 14, 15, 16, 17, 18, 19, 20, 21, or 22 days.

In some embodiments, the method is performed ex vivo. In some embodiments, the T cells are cultured in a medium containing a cytokine. In some embodiments, an example of cytokines includes IL-7. In some embodiments, an example of cytokines includes IL-15. In some embodiments, an example of cytokines includes IL-7 and IL-15. In some embodiments, the T cells are cultured in a medium comprising IL-7, and/or IL-15. In some embodiments, the cytokine in a T cell culture or a medium has a final concentration of at least 0.05 ng/mL, 0.1 ng/mL, 0.2 ng/mL, 0.3 ng/mL, 0.4 ng/mL, 0.5 ng/mL, 0.8 ng/mL, 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 12 ng/mL, 15 ng/mL, 18 ng/mL, or 20 ng/mL. In some embodiments, the IL-7 in a T cell culture or a medium has a final concentration of at least 0.05 ng/mL, 0.1 ng/mL, 0.2 ng/mL, 0.3 ng/mL, 0.4 ng/mL, 0.5 ng/mL, 0.8 ng/mL, 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 12 ng/mL, 15 ng/mL, 18 ng/mL, or 20 ng/mL. In some embodiments, the IL-15 in a T cell culture or a medium has a final concentration of at least 0.05 ng/mL, 0.1 ng/mL, 0.2 ng/mL, 0.3 ng/mL, 0.4 ng/mL, 0.5 ng/mL, 0.8 ng/mL, 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 12 ng/mL, 15 ng/mL, 18 ng/mL, or 20 ng/mL. In some embodiments, the T cells are cultured in a medium further containing FLT3L. In some embodiments, the FLT3L in a T cell culture or a medium has a final concentration of in a T cell culture or a medium has a final concentration of at least 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 12 ng/mL, 15 ng/mL, 18 ng/mL, 20 ng/mL, 30 ng/mL, 40 ng/mL, 50 ng/mL, 60 ng/mL, 70 ng/mL, 80 ng/mL, 90 ng/mL, 100 ng/mL, or 200 ng/mL. In some embodiments, the T cells are incubated, induced, or stimulated in a medium containing FLT3L for a first period time. In some embodiments, the T cells are incubated, induced, or stimulated in a medium containing additionally added FLT3L for a second period time. In some embodiments, the T cells are incubated, induced, or stimulated in a medium containing additional added FLT3L for a third period time. In some embodiments, the T cells are incubated, induced, or stimulated in a medium containing additional added FLT3L for a fourth, a fifth, or a sixth period time, with freshly added FLT3L in each time period.

In some embodiments, the T cells are cultured in presence a neoantigen, e.g. a neoantigen presented by an APC, wherein the media comprises high potassium $[K]^+$ content. In some embodiments, the T cells are cultured in presence of high $[K]^+$ content in the media for at least a period of time during the incubation with APCs or T cells. In some embodiments, the $[K]^+$ content in the media is altered for at least a period of time during the incubation with APCs or T cells. In some embodiments, the content in the media is kept constant over the period of T cell ex vivo culture. In some embodiments, the $[K]^+$ content in the T cell culture medium is ≥5 mM. In some embodiments, the $[K]^+$ content in the T cell culture medium is ≥6 mM. In some embodiments, the $[K]^+$ content in the T cell culture medium is ≥7 mM. In some embodiments, the $[K]^+$ content in the T cell culture medium is ≥8 mM. In some embodiments, the $[K]^+$ content in the T cell culture medium is ≥9 mM. In some embodiments, the $[K]^+$ content in the T cell culture medium is ≥10 mM. In some embodiments, the $[K]^+$ content in the T cell culture medium is ≥11 mM. In some embodiments, the $[K]^+$ content in the T cell culture medium is ≥12 mM. In some embodiments, the $[K]^+$ content in the T cell culture medium is ≥13 mM. In some embodiments, the $[K]^+$ content in the T cell culture medium is ≥14 mM. In some embodiments, the $[K]^+$ content in the T cell culture medium is ≥15 mM. In some embodiments, the $[K]^+$ content in the T cell culture medium is ≥16 mM. In some embodiments, the $[K]^+$ content in the T cell culture medium is ≥17 mM. In some embodiments, the $[K]^+$ content in the T cell culture medium is ≥18 mM. In some embodiments, the $[K]^+$ content in the T cell culture medium is ≥19 mM. In some embodiments, the $[K]^+$ content in the T cell culture medium is ≥20 mM. In some embodiments, the $[K]^+$ content in the T cell culture medium is ≥22 mM. In some embodiments, the $[K]^+$ content in the T cell culture medium is ≥25 mM. In some embodiments, the $[K]^+$ content in the T cell culture medium is ≥30 mM. In some embodiments, the $[K]^+$ content in the T cell culture medium is ≥35 mM. In some embodiments, the $[K]^+$ content in the T cell culture medium is ≥40 mM. In some embodiments, the $[K]^+$ content in the T cell culture medium is about 40 mM.

In some embodiments, the $[K]^+$ content in the T cell culture medium is about 40 mM for at least a period of time during the incubation of T cells with neoantigen. In some embodiments, the neoantigen may be presented by the neoantigen loaded APCs. In some embodiments, the T cells in the presence of $[K]^+$ are tested for T effector functions, CD8+ cytotoxicity, cytokine production, and for memory phenotype. In some embodiments, T cells are grown in the presence of high $[K]^+$ express effector T cell phenotype. In some embodiments, T cells grown in presence of high $[K]^+$ express memory cell marker. In some embodiments, T cells grown in presence of high $[K]^+$ do not express T cell exhaustion markers.

In some embodiments, the stimulated T cell is a population of immune cells comprising the activated T cells stimulated with APCs comprising a neoantigenic peptide-MHC complex. In some embodiments, a method can comprise incubating a population of immune cells from a biological sample with APCs comprising a peptide-MHC complex, thereby obtaining a stimulated immune cell sample; determining expression of one or more cell markers of at least one immune cell of the stimulated immune cell sample; and determining binding of the at least one immune cell of the stimulated immune cell sample to a peptide-MHC complex; wherein determining expression of certain cell surface markers or other determinant markers, such as intracellular factors, or released agents, such as cytokines etc., and determining binding to the neoantigen-MHC complex are performed simultaneously. In some embodiments, the one or more cell markers comprise TNF-α, IFN-γ, LAMP-1, 4-1BB, IL-2, IL-17A, Granzyme B, PD-1, CD25, CD69, TIM3, LAG3, CTLA-4, CD62L, CD45RA, CD45RO, FoxP3, or any combination thereof. In some embodiments, the one or more cell markers comprise a cytokine. In some embodiments, the one or more cell markers comprise a degranulation marker. In some embodiments, the one or more cell markers comprise a cell-surface marker. In some embodiments, the one or more cell markers comprise a protein. In some embodiments, determining binding of the at least one immune cell of the stimulated immune cell sample to the peptide-MHC complex comprises determining binding of the at least one immune cell of the stimulated immune cell sample to a MHC tetramer comprising the peptide and the MHC of the peptide-MHC complex. In some embodiments, the MHC is a class I MHC or a class II MHC. In some embodiments, the peptide-MHC complex comprises one or more labels.

In some embodiments, activation of T cell is verified by detecting the release of a cytokine by the activated T cell. In some embodiments, the cytokine is one or more of: TNF-α, IFN-γ, or IL-2. In some embodiments the activation of T cell is verified by its specific antigen binding and cytokine release. In some embodiments, the activation of T cells is verified by its ability to kill tumor cells in vitro. A sample of activated T cells may be used to verify the activation status of the T cells. In some embodiments, a sample from the T cells is withdrawn from the T cell culture to determine the cellular composition and activation state by flow cytometry.

In some embodiments, a percentage of the at least one antigen specific T cell in the composition is at least about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total T cells or total immune cells. In some embodiments, the percentage of the at least one antigen specific T cells in the composition is about 5%. In some embodiments, the percentage of the at least one antigen specific T cells in the composition is about 7%. In some embodiments, the percentage of the at least one antigen specific T cells in the composition is about 10%. In some embodiments, the percentage of the at least one antigen specific T cells in the composition is about 12%. In some embodiments, the percentage of the at least one antigen specific T cells in the composition is about 15%. In some embodiments, the percentage of the at least one antigen specific T cells in the composition is about 20%. In some embodiments, the percentage of the at least one antigen specific T cells in the composition is about 25%. In some embodiments, the percentage of the at least one antigen specific T cells in the composition is about 30%. In some embodiments, the percentage of the at least one antigen specific T cells in the composition is about 40%. In some embodiments, the percentage of the at least one antigen specific T cells in the composition is about 50%. In some embodiments, the percentage of the at least one antigen specific T cells in the composition is about 60%. In some embodiments, the percentage of the at least one antigen specific T cells in the composition is about 70%. In some embodiments, the percentage of the at least one antigen specific T cells in the composition is about 80%. In some embodiments, the percentage of the at least one antigen specific T cells in the composition is about 90%.

In some embodiments, a percentage of at least one antigen specific CD8+ T cell in the composition is at least about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total CD4+ T cells, total CD8+ T cells, total T cells or total immune cells. In some embodiments, the percentage of the at least one antigen specific CD8+ T cells in the composition is about 5%. In some embodiments, the percentage of the at least one antigen specific CD8+ T cells in the composition is about 7%. In some embodiments, the percentage of the at least one antigen specific CD8+ T cells in the composition is about 10%. In some embodiments, the percentage of the at least one antigen specific CD8+ T cells in the composition is about 12%. In some embodiments, the percentage of the at least one antigen specific CD8+ T cells in the composition is about 15%. In some embodiments, the percentage of the at least one antigen specific CD8+ T cells in the composition is about 20%. In some embodiments, the percentage of the at least one antigen specific CD8+ T cells in the composition is about 25%. In some embodiments, the percentage of the at least one antigen specific CD8+ T cells in the composition is about 30%. In some embodiments, the percentage of the at least one antigen specific CD8+ T cells in the composition is about 40%. In some embodiments, the percentage of the at least one antigen specific CD8+ T cells in the composition is about 50%. In some embodiments, the percentage of the at least one antigen specific CD8+ T cells in the composition is about 60%. In some embodiments, the percentage of the at least one antigen specific CD8+ T cells in the composition is about 70% of total CD4+ T cells, total CD8+ T cells, total T cells or total immune cells.

In some embodiments, a percentage of at least one antigen specific CD4+ T cell in the composition is at least about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total CD4+ T cells, total CD8+ T cells, total T cells or total immune cells.

In some embodiments, a percentage of the at least one antigen specific T cell in the biological sample is at most about 0.00001%, 0.00005%, 0.0001%, 0.0005%, 0.001%, 0.005%, 0.01%, 0.05%, 0.1% or 0.5% of total CD4+ T cells, total CD8+ T cells, total T cells or total immune cells.

In some embodiments, a percentage of at least one antigen specific CD8+ T cell in the biological sample is at most about 0.00001%, 0.00005%, 0.0001%, 0.0005%, 0.001%, 0.005%, 0.01%, 0.05%, 0.1% or 0.5% of total CD4+ T cells, total CD8+ T cells, total T cells or total immune cells.

In some embodiments, a percentage of at least one antigen specific CD4+ T cell in the biological sample is at most about 0.00001%, 0.00005%, 0.0001%, 0.0005%, 0.001%, 0.005%, 0.01%, 0.05%, 0.1% or 0.5% of total CD4+ T cells, total CD8+ T cells, total T cells or total immune cells.

In some embodiments, the antigen is a neoantigen, a tumor associated antigen, an overexpressed antigen, a viral antigen, a minor histocompatibility antigen or a combination thereof.

In some embodiments, the number of at least one antigen specific CD8+ T cell in the composition is at least about 1×10^6, 2×10^6, 5×10^6, 1×10^7, 2×10^7, 5×10^7, 1×10^8, 2×10^8, or 5×10^8, antigen specific CD8+ T cells.

In some embodiments, a number of at least one antigen specific CD4+ T cell in the composition is at least about 1×10^6, 2×10^6, 5×10^6, 1×10^7, 2×10^7, 5×10^7, 1×10^8, 2×10^8, or 5×10^8, antigen specific CD4+ T cells.

Pharmaceutical Compositions

Provided herein are compositions (e.g., pharmaceutical compositions) comprising a population of immune cells. The compositions can comprise at least one antigen specific T cells comprising a T cell receptor (TCR). The compositions can comprise at least one antigen specific T cells comprising a T cell receptor (TCR) specific to at least one antigen peptide sequence.

Pharmaceutical compositions can be formulated using one or more physiologically acceptable carriers including excipients and auxiliaries which facilitate processing of the active agents into preparations which can be used pharmaceutically. Proper formulation can be dependent upon the route of administration chosen. Any of the well-known techniques, carriers, and excipients can be used as suitable and as understood in the art.

In some cases, a pharmaceutical composition is formulated as cell based therapeutic, e.g., a T cell therapeutic. In some embodiments, the pharmaceutical composition comprises a peptide-based therapy, a nucleic acid-based therapy, an antibody based therapy, and/or a cell based therapy. In some embodiments, a pharmaceutical composition comprises a peptide-based therapeutic, or nucleic acid based therapeutic in which the nucleic acid encodes the polypeptides. In some embodiments, a pharmaceutical composition comprises a peptide-based therapeutic, or nucleic acid based therapeutic in which the nucleic acid encodes the polypeptides; wherein the peptide-based therapeutic, or nucleic acid based therapeutic are comprised in a cell, wherein the cell is a T cell. In some embodiments, a pharmaceutical composition comprises as an antibody based therapeutic. A composition can comprise T cells specific for two or more immunogenic antigen or neoantigen peptides.

In one aspect, provided herein is a pharmaceutical composition comprising (a) a population of immune cells comprising T cells from a biological sample, wherein the T cells comprise at least one antigen specific T cell that is an APC-stimulated T cell and comprises a T cell receptor (TCR) specific to at least one antigen peptide sequence, wherein the APC is a FLT3L-stimulated APC; and (b) a pharmaceutically acceptable excipient.

In one aspect, provided herein is a pharmaceutical composition comprising: (a) a population of immune cells from a biological sample comprising at least one antigen specific T cell comprising a T cell receptor (TCR) specific to at least one antigen peptide sequence, and (b) a pharmaceutically acceptable excipient; wherein an amount of immune cells expressing CD14 and/or CD25 in the population is proportionally different from an amount of immune cells expressing CD14 and/or CD25 in the biological sample. In some embodiments, the at least one antigen specific T cell comprises at least one APC-stimulated T cell. In some embodiments, the amount of immune cells expressing CD14 and/or CD25 in the population is proportionally less than the amount of immune cells expressing CD14 and/or CD25 in the biological sample. In some embodiments, the amount of immune cells expressing CD14 and/or CD25 in the population is proportionally more than the amount of immune cells expressing CD14 and/or CD25 in the biological sample. In some embodiments, the at least one antigen specific T cell comprises at least one CD4+ T cell. In some embodiments, the at least one antigen specific T cell comprises at least one CD8+ T cell. In some embodiments, the at least one antigen specific T cell comprises at least one CD4 enriched T cell. In some embodiments, the at least one antigen specific T cell comprises at least one CD8 enriched T cell. In some embodiments, the at least one antigen specific T cell comprises a memory T cell. In some embodiments, the at least one antigen specific T cell comprises a memory CD4+ T cell. In some embodiments, the at least one antigen specific T cell comprises a memory CD8+ T cell. In some embodiments, a percentage of the at least one antigen specific T cell in the composition is at least about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total T cells or total immune cells. In some embodiments, a percentage of at least one antigen specific CD8+ T cell in the composition is at least about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total CD4+ T cells, total CD8+ T cells, total T cells or total immune cells.

Pharmaceutical compositions can include, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration.

Acceptable carriers, excipients, or stabilizers are those that are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

Acceptable carriers are physiologically acceptable to the administered patient and retain the therapeutic properties of the compounds with/in which it is administered. Acceptable carriers and their formulations are generally described in, for example, Remington' pharmaceutical Sciences (18$^{th}$ ed. A. Gennaro, Mack Publishing Co., Easton, PA 1990). One example of carrier is physiological saline. A pharmaceutically acceptable carrier is a pharmaceutically acceptable material, composition or vehicle, such as a liquid or solid filler, diluent, excipient, solvent or encapsulating material, involved in carrying or transporting the subject compounds from the administration site of one organ, or portion of the body, to another organ, or portion of the body, or in an in vitro assay system. Acceptable carriers are compatible with the other ingredients of the formulation and not injurious to a subject to whom it is administered. Nor should an acceptable carrier alter the specific activity of the neoantigens.

In one aspect, provided herein are pharmaceutically acceptable or physiologically acceptable compositions including solvents (aqueous or non-aqueous), solutions, emulsions, dispersion media, coatings, isotonic and absorption promoting or delaying agents, compatible with pharmaceutical administration. Pharmaceutical compositions or pharmaceutical formulations therefore refer to a composition suitable for pharmaceutical use in a subject. Compositions can be formulated to be compatible with a particular route of administration (i.e., systemic or local). Thus, compositions include carriers, diluents, or excipients suitable for administration by various routes.

In some embodiments, a composition can further comprise an acceptable additive in order to improve the stability of immune cells in the composition. Acceptable additives may not alter the specific activity of the immune cells. Examples of acceptable additives include, but are not limited to, a sugar such as mannitol, sorbitol, glucose, xylitol, trehalose, sorbose, sucrose, galactose, dextran, dextrose, fructose, lactose and mixtures thereof. Acceptable additives can be combined with acceptable carriers and/or excipients such as dextrose. Alternatively, examples of acceptable additives include, but are not limited to, a surfactant such as polysorbate 20 or polysorbate 80 to increase stability of the peptide and decrease gelling of the solution. The surfactant can be added to the composition in an amount of 0.01% to 5% of the solution. Addition of such acceptable additives increases the stability and half-life of the composition in storage.

The pharmaceutical composition can be administered, for example, by injection. Compositions for injection include aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). The carrier can be a solvent or dispersion medium containing, for example, water, ethanol, polyol (for example, glycerol, propylene glycol, and liquid polyethylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as mannitol, sorbitol, and sodium chloride can be included in the composition. The resulting solutions can be packaged for use as is, or lyophilized; the lyophilized preparation can later be combined with a sterile solution prior to administration. For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as needed. Sterile injectable solutions can be prepared by incorporating an active ingredient in the required amount in an appropriate solvent with one or a combination of ingredients enumerated above, as required, followed by filtered sterilization. Generally, dispersions are prepared by incorporating the active ingredient into a sterile vehicle which contains a basic dispersion medium and the required other ingredients from those enumerated above. In the case of sterile powders for the preparation of sterile injectable solutions, the preferred methods of preparation can be vacuum drying and freeze drying which yields a powder of the active ingredient plus any additional desired ingredient from a previously sterile-filtered solution thereof.

Compositions can be conventionally administered intravenously, such as by injection of a unit dose, for example. For injection, an active ingredient can be in the form of a parenterally acceptable aqueous solution which is substantially pyrogen-free and has suitable pH, isotonicity and stability. One can prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required. Additionally, compositions can be administered via aerosolization.

When the compositions are considered for use in medicaments or any of the methods provided herein, it is contemplated that the composition can be substantially free of pyrogens such that the composition will not cause an inflammatory reaction or an unsafe allergic reaction when administered to a human patient. Testing compositions for pyrogens and preparing compositions substantially free of pyrogens are well understood to one or ordinary skill of the art and can be accomplished using commercially available kits.

Acceptable carriers can contain a compound that acts as a stabilizing agent, increases or delays absorption, or increases or delays clearance. Such compounds include, for example, carbohydrates, such as glucose, sucrose, or dextrans; low molecular weight proteins; compositions that reduce the clearance or hydrolysis of peptides; or excipients or other stabilizers and/or buffers. Agents that delay absorption include, for example, aluminum monostearate and gelatin. Detergents can also be used to stabilize or to increase or decrease the absorption of the pharmaceutical composition, including liposomal carriers. To protect from digestion the compound can be complexed with a composition to render it resistant to acidic and enzymatic hydrolysis, or the compound can be complexed in an appropriately resistant carrier such as a liposome. Means of protecting compounds from digestion are known in the art (e.g., Fix (1996) Pharm Res. 13:1760 1764; Samanen (1996) J. Pharm. Pharmacol. 48:119 135; and U.S. Pat. No. 5,391,377).

The compositions can be administered in a manner compatible with the dosage formulation, and in a therapeutically effective amount. The quantity to be administered depends on the subject to be treated, capacity of the subject's immune system to utilize the active ingredient, and degree of binding capacity desired. Precise amounts of active ingredient required to be administered depend on the judgment of the practitioner and are peculiar to each individual. Suitable regimes for initial administration and booster shots are also variable, but are typified by an initial administration followed by repeated doses at one or more hour intervals by a subsequent injection or other administration. Alternatively, continuous intravenous infusions sufficient to maintain concentrations in the blood are contemplated.

In some embodiments, the present invention is directed to an immunogenic composition, e.g., a pharmaceutical composition capable of raising a neoantigen-specific response (e.g., a humoral or cell-mediated immune response). In some embodiments, the immunogenic composition comprises neoantigen therapeutics (e.g., peptides, polynucleotides, TCR, CAR, cells containing TCR or CAR, dendritic cell containing polypeptide, dendritic cell containing polynucleotide, antibody, etc.) described herein corresponding to a tumor specific antigen or neoantigen.

In some embodiments, a pharmaceutical composition described herein is capable of raising a specific cytotoxic T cells response, specific helper T cell response, or a B cell response.

In some embodiments, antigen polypeptides or polynucleotides can be provided as antigen presenting cells (e.g., dendritic cells) containing such polypeptides or polynucleotides. In other embodiments, such antigen presenting cells are used to stimulate T cells for use in patients. In some embodiments, the antigen presenting cells are dendritic cells. In related embodiments, the dendritic cells are autologous dendritic cells that are pulsed with the neoantigen peptide or nucleic acid. The neoantigen peptide can be any suitable peptide that gives rise to an appropriate T cell response. In some embodiments, the T cell is a CTL. In some embodiments, the T cell is a HTL. Thus, one embodiment of the present disclosure is an immunogenic composition containing at least one antigen presenting cell (e.g., a dendritic cell) that is pulsed or loaded with one or more neoantigen polypeptides or polynucleotides described herein. In some embodiments, such APCs are autologous (e.g., autologous dendritic cells). Alternatively, peripheral blood mononuclear cells (PBMCs) isolated from a patient can be loaded with neoantigen peptides or polynucleotides ex vivo. In related embodiments, such APCs or PBMCs are injected back into the patient. The polynucleotide can be any suitable polynucleotide that is capable of transducing the dendritic cell, thus resulting in the presentation of a neoantigen peptide and induction of immunity. In some embodiments, such antigen presenting cells (APCs) (e.g., dendritic cells) or peripheral blood mononuclear cells (PBMCs) are used to stimulate a T cell (e.g., an autologous T cell). In related embodiments, the T cell is a CTL. In other related embodiments, the T cell is an HTL. In some embodiments, the T cells are CD8$^+$ T cells. In some embodiments, the T cells are CD4$^+$ T cells. Such T cells are then injected into the patient.

In some embodiments, CTL is injected into the patient. In some embodiments, HTL is injected into the patient. In some embodiments, both CTL and HTL are injected into the patient. Administration of either therapeutic can be performed simultaneously or sequentially and in any order.

In some embodiments, a pharmaceutical composition (e.g., immunogenic compositions) described herein for therapeutic treatment can be formulated for parenteral, topical, nasal, oral or local administration. In some embodiments, the pharmaceutical compositions described herein are administered parenterally, e.g., intravenously, subcutaneously, intradermally, or intramuscularly. In some embodiments, the composition can be administered intratumorally. The compositions can be administered at the site of surgical excision to induce a local immune response to the tumor. In some embodiments, described herein are compositions for parenteral administration which comprise a solution of the neoantigen peptides and immunogenic compositions are dissolved or suspended in an acceptable carrier, for example, an aqueous carrier. A variety of aqueous carriers can be used, e.g., water, buffered water, 0.9% saline, 0.3% glycine, hyaluronic acid and the like. These compositions can be sterilized by conventional, well known sterilization techniques, or can be sterile filtered. The resulting aqueous solutions can be packaged for use as is, or lyophilized, the lyophilized preparation being combined with a sterile solution prior to administration. The compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The ability of an adjuvant to increase the immune response to an antigen is typically manifested by a significant increase in immune-mediated reaction, or reduction in disease symptoms. For example, an increase in humoral immunity can be manifested by a significant increase in the titer of antibodies raised to the antigen, and an increase in T cell activity can be manifested in increased cell proliferation, or cellular cytotoxicity, or cytokine secretion. An adjuvant can also alter an immune response, for example, by changing a primarily humoral or T helper 2 response into a primarily cellular, or T helper 1 response.

Suitable adjuvants are known in the art (see, WO 2015/095811) and include, but are not limited to poly(I:C), poly-ICLC, STING agonist, 1018 ISS, aluminum salts, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, JuvImmune, Lipo-Vac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel® vector system, PLG microparticles, resiquimod, SRL172, virosomes and other virus-like particles, YF-17D, VEGF trap, R848, β-glucan, Pam3Cys, Pam3CSK4, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Several immunological adjuvants (e.g., MF59) specific for dendritic cells and their preparation have been described (Dupuis M, et al., Cell Immunol. 1998; 186(1):18-27; Allison A C; Dev Biol Stand. 1998; 92:3-11) (Mosca et al. Frontiers in Bioscience, 2007; 12:4050-4060) (Gamvrellis et al. Immunol & Cell Biol. 2004; 82: 506-516). Also, cytokines can be used. Several cytokines have been directly linked to influencing dendritic cell migration to lymphoid tissues (e.g., TNF-(α), accelerating the maturation of dendritic cells into efficient antigen-presenting cells for T-lymphocytes (e.g., GM-CSF, PGE1, PGE2, IL-1, IL-1β, IL-4, IL-6 and CD40L) (U.S. Pat. No. 5,849,589 incorporated herein by reference in its entirety) and acting as immunoadjuvants (e.g., IL-12) (Gabrilovich D I, et al., J Immunother Emphasis Tumor Immunol. 1996 (6):414-418).

CpG immunostimulatory oligonucleotides have also been reported to enhance the effects of adjuvants in a therapeutic setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell immunogenic pharmaceutical compositions, autologous cellular immunogenic pharmaceutical compositions and polysaccharide conjugates in both prophylactic and therapeutic immunogenic pharmaceutical compositions. Importantly, it enhances dendritic cell maturation and differentiation, resulting in enhanced activation of TH1 cells and strong cytotoxic T-lymphocyte (CTL) generation, even in the absence of CD4+ T cell help. The TH1 bias induced by TLR9 stimulation is maintained even in the presence of adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially useful for inducing a strong response when the antigen is relatively weak. They can also accelerate the immune response and enabled the antigen doses to be reduced with comparable antibody responses to the full-dose immunogenic pharmaceutical composition without CpG in some experiments (Arthur M. Krieg, Nature Reviews, Drug Discovery, 5, June 2006, 471-484). U.S. Pat. No. 6,406,705 describes the combined use of CpG oligonucleotides, non-nucleic acid adjuvants and an antigen to induce an antigen-specific immune response. A commercially available CpG TLR9 antagonist is dSLIM (double Stem Loop Immunomodulator) by Mologen (Berlin, DE), which is a component of the pharmaceutical composition described herein. Other TLR binding molecules such as RNA binding TLR7, TLR8 and/or TLR9 can also be used.

Other examples of useful adjuvants include, but are not limited to, chemically modified CpGs (e.g. CpR, Idera), Poly(I and/or poly C)(e.g., polyI:CI2U), non-CpG bacterial DNA or RNA, ssRNA40 for TLR8, as well as immunoactive small molecules and antibodies such as cyclophosphamide, sunitinib, bevacizumab, celebrex, NCX-4016, sildenafil, tadalafil, vardenafil, sorafinib, XL-999, CP-547632, pazopanib, ZD2171, AZD2171, ipilimumab, tremelimumab, and SC58175, which can act therapeutically and/or as an adjuvant. The amounts and concentrations of adjuvants and additives useful in the context of the present invention can readily be determined by the skilled artisan without undue experimentation. Additional adjuvants include colony-stimulating factors, such as Granulocyte Macrophage Colony Stimulating Factor (GM-CSF, sargramostim).

In some embodiments, an immunogenic composition according to the present disclosure can comprise more than one different adjuvant. Furthermore, the invention encompasses a pharmaceutical composition comprising any adjuvant substance including any of the above or combinations thereof. In some embodiments, the immunogenic composition comprises neoantigen therapeutics (e.g., peptides, polynucleotides, TCR, CAR, cells containing TCR or CAR, dendritic cell containing polypeptide, dendritic cell containing polynucleotide, antibody, etc.) and the adjuvant can be administered separately in any appropriate sequence.

Lipidation can be classified into several different types, such as N-myristoylation, palmitoylation, GPI-anchor addition, prenylation, and several additional types of modifications. N-myristoylation is the covalent attachment of myristate, a C14 saturated acid, to a glycine residue. Palmitoylation is thioester linkage of long-chain fatty acids (C16) to cysteine residues. GPI-anchor addition is glycosyl-phosphatidylinositol (GPI) linkage via amide bond. Prenylation is the thioether linkage of an isoprenoid lipid (e.g. farnesyl (C-15), geranylgeranyl (C-20)) to cysteine residues. Additional types of modifications can include attachment of S-diacylglycerol by a sulfur atom of cysteines, O-octanoyl conjugation via serine or threonine residues, S-archaeol conjugation to cysteine residues, and cholesterol attachment.

Fatty acids for generating lipidated peptides can include C2 to C30 saturated, monounsaturated, or polyunsaturated fatty acyl groups. Exemplary fatty acids can include palmitoyl, myristoyl, stearoyl and decanoyl groups. In some instances, a lipid moiety that has adjuvant property is attached to a polypeptide of interest to elicit or enhance immunogenicity in the absence of an extrinsic adjuvant. A lipidated peptide or lipopeptide can be referred to as a self-adjuvant lipopeptide. Any of the fatty acids described above and elsewhere herein can elicit or enhance immunogenicity of a polypeptide of interest. A fatty acid that can elicit or enhance immunogenicity can include palmitoyl, myristoyl, stearoyl, lauroyl, octanoyl, and decanoyl groups.

Polypeptides such as naked peptides or lipidated peptides can be incorporated into a liposome. Sometimes, lipidated peptides can be incorporated into a liposome. For example, the lipid portion of the lipidated peptide can spontaneously integrate into the lipid bilayer of a liposome. Thus, a lipopeptide can be presented on the "surface" of a liposome. Exemplary liposomes suitable for incorporation in the formulations include, and are not limited to, multilamellar vesicles (MLV), oligolamellar vesicles (OLV), unilamellar vesicles (UV), small unilamellar vesicles (SUV), medium-sized unilamellar vesicles (MUV), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubblesomes (BSV).

Depending on the method of preparation, liposomes can be unilamellar or multilamellar, and can vary in size with diameters ranging from about 0.02 μM to greater than about 10 μm. Liposomes can adsorb many types of cells and then release an incorporated agent (e.g., a peptide described herein). In some cases, the liposomes fuse with the target cell, whereby the contents of the liposome then empty into the target cell. A liposome can be endocytosed by cells that are phagocytic. Endocytosis can be followed by intralysosomal degradation of liposomal lipids and release of the encapsulated agents.

The liposomes provided herein can also comprise carrier lipids. In some embodiments the carrier lipids are phospholipids. Carrier lipids capable of forming liposomes include, but are not limited to dipalmitoylphosphatidylcholine (DPPC), phosphatidylcholine (PC; lecithin), phosphatidic acid (PA), phosphatidylglycerol (PG), phosphatidylethanolamine (PE), phosphatidylserine (PS). Other suitable phospholipids further include distearoylphosphatidylcholine (DSPC), dimyristoylphosphatidylcholine (DMPC), dipalmitoylphosphatidyglycerol (DPPG), distearoylphosphatidyglycerol (DSPG), dimyristoylphosphatidylglycerol (DMPG), dipalmitoylphosphatidic acid (DPPA); dimyristoylphosphatidic acid (DMPA), distearoylphosphatidic acid (DSPA), dipalmitoylphosphatidylserine (DPPS), dimyristoylphosphatidylserine (DMPS), distearoylphosphatidylserine (DSPS), dipalmitoylphosphatidyethanolamine (DPPE), dimyristoylphosphatidylethanolamine (DMPE), distearoylphosphatidylethanolamine (DSPE) and the like, or combinations thereof. In some embodiments, the liposomes further comprise a sterol (e.g., cholesterol) which modulates liposome formation. The carrier lipids can be any known non-phosphate polar lipids.

A pharmaceutical composition can be encapsulated within liposomes using well-known technology. Biodegradable microspheres can also be employed as carriers for the pharmaceutical compositions of this invention.

The pharmaceutical composition can be administered in liposomes or microspheres (or microparticles). Methods for preparing liposomes and microspheres for administration to a patient are well known to those of skill in the art. Essentially, material is dissolved in an aqueous solution, the appropriate phospholipids and lipids added, along with surfactants if required, and the material dialyzed or sonicated, as necessary.

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months.

Cell-based immunogenic pharmaceutical compositions can also be administered to a subject. For example, an antigen presenting cell (APC) based immunogenic pharmaceutical composition can be formulated using any of the well-known techniques, carriers, and excipients as suitable and as understood in the art. APCs include monocytes, monocyte-derived cells, macrophages, and dendritic cells. Sometimes, an APC based immunogenic pharmaceutical composition can be a dendritic cell-based immunogenic pharmaceutical composition.

A dendritic cell-based immunogenic pharmaceutical composition can be prepared by any methods well known in the art. In some cases, dendritic cell-based immunogenic pharmaceutical compositions can be prepared through an ex vivo or in vivo method. The ex vivo method can comprise the use of autologous DCs pulsed ex vivo with the polypeptides described herein, to activate or load the DCs prior to administration into the patient. The in vivo method can comprise targeting specific DC receptors using antibodies coupled with the polypeptides described herein. The DC-based immunogenic pharmaceutical composition can further comprise DC activators such as TLR3, TLR-7-8, and CD40 agonists. The DC-based immunogenic pharmaceutical composition can further comprise adjuvants, and a pharmaceutically acceptable carrier.

An adjuvant can be used to enhance the immune response (humoral and/or cellular) elicited in a patient receiving the immunogenic pharmaceutical composition. Sometimes, adjuvants can elicit a Th1-type response. Other times, adjuvants can elicit a Th2-type response. A Th1-type response can be characterized by the production of cytokines such as IFN-γ as opposed to a Th2-type response which can be characterized by the production of cytokines such as IL-4, IL-5 and IL-10.

In some aspects, lipid-based adjuvants, such as MPLA and MDP, can be used with the immunogenic pharmaceutical compositions disclosed herein. Monophosphoryl lipid A (MPLA), for example, is an adjuvant that causes increased presentation of liposomal antigen to specific T Lymphocytes. In addition, a muramyl dipeptide (MDP) can also be used as a suitable adjuvant in conjunction with the immunogenic pharmaceutical formulations described herein.

Adjuvant can also comprise stimulatory molecules such as cytokines. Non-limiting examples of cytokines include: CCL20, α-interferon (IFNα), β-interferon (IFNβ), γ-interferon (IFNγ), platelet derived growth factor (PDGF), TNFα, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, IL-28, MHC, CD80, CD86, IL-1, IL-2, IL-4, IL-5, IL-6, IL-10, IL-18, MCP-1, MIP-1a, MIP-1-, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Fit, Apo-1, p55, WSL-1, DR3, TRAMP, Apo-3, AIR, LARD, NGRF, DR4, DRS, KILLER, TRAIL-R2, TRICK2, DR6, Caspase ICE, Fos, c-jun, Sp-1, Ap-1, Ap-2, p38, p65Rel, MyD88, IRAK, TRAF6, IκB, Inactive NIK, SAP K, SAP-I, JNK, interferon response genes, NFκB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAPI, and TAP2.

Additional adjuvants include: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Fit, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IκB, Inactive NIK, SAP K, SAP-1, JNK, interferon response genes, NFκB, Bax, TRAIL, TRAILrec, TRAIL-recDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

In some aspects, an adjuvant can be a modulator of a toll like receptor. Examples of modulators of toll-like receptors include TLR9 agonists and are not limited to small molecule modulators of toll-like receptors such as Imiquimod. Sometimes, an adjuvant is selected from bacteria toxoids, poly-oxypropylene-polyoxyethylene block polymers, aluminum salts, liposomes, CpG polymers, oil-in-water emulsions, or a combination thereof. Sometimes, an adjuvant is an oil-in-water emulsion. The oil-in-water emulsion can include at least one oil and at least one surfactant, with the oil(s) and surfactant(s) being biodegradable (metabolizable) and bio-compatible. The oil droplets in the emulsion can be less than 5 μm in diameter, and can even have a sub-micron diameter, with these small sizes being achieved with a microfluidiser to provide stable emulsions. Droplets with a size less than 220 nm can be subjected to filter sterilization.

In some instances, an immunogenic pharmaceutical composition can include carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, adjuvants, or binders, other pharma-ceutically acceptable auxiliary substances as required to approximate physiological conditions, such as pH buffering agents, tonicity adjusting agents, emulsifying agents, wet-ting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In another instances, the pharmaceutical preparation is substantially free of preser-vatives. In other instances, the pharmaceutical preparation can contain at least one preservative. It will be recognized that, while any suitable carrier known to those of ordinary skill in the art can be employed to administer the pharma-ceutical compositions described herein, the type of carrier will vary depending on the mode of administration.

An immunogenic pharmaceutical composition can include preservatives such as thiomersal or 2-phenoxyethanol. In some instances, the immunogenic pharmaceutical composition is substantially free from (e.g., <10 μg/mL) mercurial material e.g. thiomersal-free. α-Tocopherol suc-cinate may be used as an alternative to mercurial com-pounds.

For controlling the tonicity, a physiological salt such as sodium salt can be included in the immunogenic pharma-ceutical composition. Other salts can include potassium chloride, potassium dihydrogen phosphate, disodium phos-phate, and/or magnesium chloride, or the like.

An immunogenic pharmaceutical composition can have an osmolality of between 200 mOsm/kg and 400 mOsm/kg, between 240-360 mOsm/kg, or within the range of 290-310 mOsm/kg.

An immunogenic pharmaceutical composition can com-prise one or more buffers, such as a Tris buffer; a borate buffer; a succinate buffer; a histidine buffer (particularly with an aluminum hydroxide adjuvant); or a citrate buffer. Buffers, in some cases, are included in the 5-20 or 10-50 mM range.

The pH of the immunogenic pharmaceutical composition can be between about 5.0 and about 8.5, between about 6.0 and about 8.0, between about 6.5 and about 7.5, or between about 7.0 and about 7.8.

An immunogenic pharmaceutical composition can be sterile. The immunogenic pharmaceutical composition can be non-pyrogenic e.g. containing <1 EU (endotoxin unit, a standard measure) per dose, and can be <0.1 EU per dose. The composition can be gluten free.

An immunogenic pharmaceutical composition can include detergent e.g. a polyoxyethylene sorbitan ester sur-factant (known as 'Tweens'), or an octoxynol (such as octoxynol-9 (Triton X-100) or t-octylphenoxypolyethoxy-ethanol). The detergent can be present only at trace amounts. The immunogenic pharmaceutical composition can include less than 1 mg/mL of each of octoxynol-10 and polysorbate 80. Other residual components in trace amounts can be antibiotics (e.g. neomycin, kanamycin, polymyxin B).

An immunogenic pharmaceutical composition can be formulated as a sterile solution or suspension, in suitable vehicles, well known in the art. The pharmaceutical com-positions can be sterilized by conventional, well-known sterilization techniques, or can be sterile filtered. The result-ing aqueous solutions can be packaged for use as is, or lyophilized, the lyophilized preparation being combined with a sterile solution prior to administration.

Pharmaceutical compositions comprising, for example, an active agent such as immune cells disclosed herein, in combination with one or more adjuvants can be formulated to comprise certain molar ratios. For example, molar ratios of about 99:1 to about 1:99 of an active agent such as an immune cell described herein, in combination with one or more adjuvants can be used. In some instances, the range of molar ratios of an active agent such as an immune cell described herein, in combination with one or more adjuvants can be selected from about 80:20 to about 20:80; about 75:25 to about 25:75, about 70:30 to about 30:70, about 66:33 to about 33:66, about 60:40 to about 40:60; about 50:50; and about 90:10 to about 10:90. The molar ratio of an active agent such as an immune cell described herein, in combination with one or more adjuvants can be about 1:9, and in some cases can be about 1:1. The active agent such as an immune cell described herein, in combination with one or more adjuvants can be formulated together, in the same dosage unit e.g., in one vial, suppository, tablet, capsule, an aerosol spray; or each agent, form, and/or compound can be formulated in separate units, e.g., two vials, suppositories, tablets, two capsules, a tablet and a vial, an aerosol spray, and the like.

In some instances, an immunogenic pharmaceutical composition can be administered with an additional agent. The choice of the additional agent can depend, at least in part, on the condition being treated. The additional agent can include, for example, a checkpoint inhibitor agent such as an anti-PD1, anti-CTLA4, anti-PD-L1, anti CD40, or anti-TIM3 agent (e.g., an anti-PD1, anti-CTLA4, anti-PD-L1, anti CD40, or anti-TIM3 antibody); or any agents having a therapeutic effect for a pathogen infection (e.g. viral infection), including, e.g., drugs used to treat inflammatory conditions such as an NSAID, e.g., ibuprofen, naproxen, acetaminophen, ketoprofen, or aspirin. For example, the checkpoint inhibitor can be a PD-1/PD-L1 antagonist selected from the group consisting of: nivolumab (ONO-4538/BMS-936558, MDX1 106, OPDIVO), pembrolizumab (MK-3475, KEYTRUDA), pidilizumab (CT-011), and MPDL328OA (ROCHE). As another example, formulations can additionally contain one or more supplements, such as vitamin C, E or other anti-oxidants.

A pharmaceutical composition comprising an active agent such as an immune cell described herein, in combination with one or more adjuvants can be formulated in conventional manner using one or more physiologically acceptable carriers, comprising excipients, diluents, and/or auxiliaries, e.g., which facilitate processing of the active agents into preparations that can be administered. Proper formulation can depend at least in part upon the route of administration chosen. The agent(s) described herein can be delivered to a patient using a number of routes or modes of administration, including oral, buccal, topical, rectal, transdermal, transmucosal, subcutaneous, intravenous, and intramuscular applications, as well as by inhalation.

The active agents can be formulated for parenteral administration (e.g., by injection, for example bolus injection or continuous infusion) and can be presented in unit dose form in ampoules, pre-filled syringes, small volume infusion or in multi-dose containers with an added preservative. The compositions can take such forms as suspensions, solutions, or emulsions in oily or aqueous vehicles, for example solutions in aqueous polyethylene glycol.

In some embodiments, the pharmaceutical composition comprises a preservative or stabilizer. In some embodiments the preservative or stabilizer is selected from a cytokine, a growth factor or an adjuvant or a chemical substance. In some embodiments, the composition comprises at least one agent that helps preserve cell viability through at least one cycle of freeze-thaw. In some embodiments, the composition comprises at least one agent that helps preserve cell viability through at least more than one cycle of freeze-thaw.

For injectable formulations, the vehicle can be chosen from those known in art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutical vehicles. The formulation can also comprise polymer compositions which are biocompatible, biodegradable, such as poly(lactic-co-glycolic)acid. These materials can be made into micro or nanospheres, loaded with drug and further coated or derivatized to provide superior sustained release performance. Vehicles suitable for periocular or intraocular injection include, for example, suspensions of therapeutic agent in injection grade water, liposomes and vehicles suitable for lipophilic substances. Other vehicles for periocular or intraocular injection are well known in the art.

In some instances, pharmaceutical composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

Method of Manufacturing:

Provided herein are methods for antigen specific T cell manufacturing. Provided herein are methods of preparing T cell compositions, such as therapeutic T cell compositions. For example, a method can comprise expanding or inducing antigen specific T cells. Preparing (e.g., inducing or expanding) T cells can also refer to manufacturing T cells, and broadly encompasses procedures to isolate, stimulate, culture, induce, and/or expand any type of T cells (e.g., $CD4^+$ T cells and $CD8^+$ T cells). In one aspect, provided herein is a method of preparing at least one antigen specific T cell comprising a T cell receptor (TCR) specific to at least one antigen peptide sequence, the method comprising incubating an APC with a population of immune cells from a biological sample depleted of cells expressing CD14 and/or CD25. In some embodiments, the method comprises preparing at least one antigen specific T cell comprising a T cell receptor (TCR) specific to at least one antigen peptide sequence, the method comprising incubating an APC with a population of immune cells from a biological sample depleted of cells expressing CD11b and/or CD19. In some embodiments, the method comprises incubating an APC with a population of immune cells from a biological sample depleted of cells expressing any CD11b and/or CD19 and/or CD14 and/or CD25 or any combination thereof.

In a second aspect, provided here is a method of preparing at least one antigen specific T cell comprising a T cell receptor (TCR) specific to at least one antigen peptide sequence, the method comprising incubating a FMS-like tyrosine kinase 3 receptor ligand (FLT3L)-stimulated APC with a population of immune cells from a biological sample.

In a third aspect, provided herein is a method of preparing a pharmaceutical composition comprising at least one antigen specific T cell comprising a T cell receptor (TCR) specific to at least one antigen peptide sequence, the method comprising: incubating FMS-like tyrosine kinase 3 receptor ligand (FLT3L) with a population of immune cells from a biological sample for a first time period; and thereafter incubating at least one T cell of the biological sample with an APC.

In a fourth aspect, provided herein is a method of preparing at least one antigen specific T cell comprising a T cell receptor (TCR) specific to at least one antigen peptide sequence, the method comprising incubating a population of immune cells from a biological sample with one or more APC preparations for one or more separate time periods of less than 28 days from incubating the population of immune cells with a first APC preparation of the one or more APC preparations, wherein at least one antigen specific memory T cell is expanded, or at least one antigen specific naïve T cell is induced.

In a fifth aspect, provided herein is a method of preparing at least one antigen specific T cell comprising a T cell receptor (TCR) specific to at least one antigen peptide sequence, the method comprising incubating a population of immune cells from a biological sample with 3 or less APC preparations for 3 or less separate time periods, wherein at least one antigen specific memory T cell is expanded or at least one antigen specific naïve T cell is induced.

In some embodiments, a method of preparing antigen specific T cells comprises a T cell receptor (TCR) specific to at least one antigen peptide sequence comprises incubating a population of immune cells from a biological sample with one or more APC preparations for one or more separate time periods, thereby stimulating T cells to become antigen specific T cells, wherein a percentage of antigen specific T cells is at least about 0.00001%, 0.00002%, 0.00005%, 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total CD4$^+$ T cells, total CD8$^+$ T cells, total T cells or total immune cells. In some embodiments, a method of preparing antigen specific T cells comprises a T cell receptor (TCR) specific to at least one antigen peptide sequence comprises incubating a population of immune cells from a biological sample with 3 or less APC preparations for 3 or less separate time periods, thereby stimulating T cells to become antigen specific T cells. In some embodiments, a method of preparing antigen specific T cells comprises a T cell receptor (TCR) specific to at least one antigen peptide sequence comprises incubating a population of immune cells from a biological sample with 2 or less APC preparations for 2 or less separate time periods, thereby stimulating T cells to become antigen specific T cells.

In some embodiments, provided herein is a method that comprises incubating a population of immune cells from a biological sample with one or more APC preparations for one or more separate time periods, thereby stimulating T cells to become antigen specific T cells, wherein the APC preparation is a PBMC cell population from which cells expressing one or more cell surface markers are depleted prior to antigen loading of the APC population. In some embodiments, CD14+ cells are depleted prior to antigen loading of an APC population. In some embodiments, CD25+ cells are depleted prior to antigen loading of an APC population. In some embodiments, CD11b+ cells are depleted prior to antigen loading of an APC population. In some embodiments, CD19+ cells are depleted prior to antigen loading of an APC population. In some embodiments, CD3+ cells are depleted prior to antigen loading of an APC population. In some embodiments, CD25+ cells and CD14+ cells are depleted prior to antigen loading of an APC population. In some embodiments, CD11b+ and CD25+ cells are depleted prior to antigen loading of an APC population. In some embodiments, CD11b+ and CD14+ cells are depleted prior to antigen loading of an APC population. In some embodiments, CD11b+, CD14+ and CD25+ cells are depleted prior to antigen loading of an APC population. In some embodiments, CD11b+, and CD19+ cells are depleted prior to antigen loading of an APC population. In some embodiments, CD11b+, CD19+ and CD25+ cells are depleted prior to antigen loading of an APC population. In some embodiments, CD11b+, CD14+, CD19+ and CD25+ cells are depleted prior to antigen loading of an APC population. In some embodiments, the method comprises adding to any of the depleted APC population described above, an APC enriched cell PBMC-derived population that are depleted of CD3+ cell. In some embodiments, the APC enriched cell PBMC-derived population is depleted of CD3+ and cells depleted of any one or more of CD11b+, CD14+, CD19+, or CD25+.

In some embodiments, a biological sample comprises peripheral blood mononuclear cells (PBMCs). In some embodiments, the method comprises adding to a PBMC sample, a composition comprising one or more antigenic peptides or nucleic acids encoding the same, thereby loading the APCs within the PBMCs with antigens for antigen presentation to T cells in the PBMC.

In some embodiments, a method comprises: (a) obtaining a biological sample from a subject comprising at least one antigen presenting cell (APC); (b) enriching cells expressing CD11c from the biological sample, thereby obtaining a CD11c$^+$ cell enriched sample; (c) incubating the CD11c$^+$ cell enriched sample with at least one cytokine or growth factor for a first time period; (d) incubating at least one peptide with the CD11c$^+$ enriched sample of (c) for a second time period, thereby obtaining an APC peptide loaded sample; (e) incubating the APC peptide loaded sample with one or more cytokines or growth factors for a third time period, thereby obtaining a matured APC sample; (f) incubating APCs of the matured APC sample with a CD11b and/or CD14 and/or CD25 depleted sample comprising PBMCs for a fourth time period; (g) incubating the PBMCs with APCs of a matured APC sample for a fifth time period; (h) incubating the PBMCs with APCs of a matured APC sample for a sixth time period; and (i) administering at least one T cell of the PBMCs to a subject in need thereof.

In some embodiments, a method comprises: (a) obtaining a biological sample from a subject comprising at least one antigen presenting cell (APC); (b) enriching cells expressing CD14 from the biological sample, thereby obtaining a CD14$^+$ cell enriched sample; (c) incubating the CD14$^+$ cell enriched sample with at least one cytokine or growth factor for a first time period; (d) incubating at least one peptide with the CD14$^+$ enriched sample of (c) for a second time period, thereby obtaining an APC peptide loaded sample; (e) incubating the APC peptide loaded sample with one or more cytokines or growth factors for a third time period, thereby obtaining a matured APC sample; (f) incubating APCs of the matured APC sample with a CD14 and/or CD25 depleted sample comprising PBMCs for a fourth time period; (g) incubating the PBMCs with APCs of a matured APC sample for a fifth time period; (h) incubating the PBMCs with APCs of a matured APC sample for a sixth time period; and (i) administering at least one T cell of the PBMCs to a subject in need thereof.

In some embodiments, a method comprises: (a) obtaining a biological sample from a subject comprising at least one APC and at least one PBMC; (b) depleting cells expressing CD11b and/or CD19 from the biological sample, thereby obtaining a CD11b and/or CD19 cell depleted sample; (c) incubating the CD11b and/or CD19 cell depleted sample with FLT3L for a first time period; (d) incubating at least one peptide with the CD11b and/or CD19 cell depleted sample of (c) for a second time period, thereby obtaining an APC peptide loaded sample; (e) incubating the APC peptide loaded sample with the at least one PBMC for a third time period, thereby obtaining a first stimulated PBMC sample;

(f) incubating a PBMC of the first stimulated PBMC sample with an APC of a matured APC sample for a fourth time period, thereby obtaining a second stimulated PBMC sample; (g) incubating a PBMC of the second stimulated PBMC sample with an APC of a matured APC sample for a fifth time period, thereby obtaining a third stimulated PBMC sample; (h) administering at least one T cell of the third stimulated PBMC sample to a subject in need thereof.

In some embodiments, a method comprises: (a) obtaining a biological sample from a subject comprising at least one APC and at least one PBMC; (b) depleting cells expressing CD11b and/or CD19 and/or CD14 and/or CD25 from the biological sample, thereby obtaining a CD11b and/or CD19 cell depleted sample; (c) incubating the CD11b and/or CD19 and/or CD14 and/or CD25 cell depleted sample with FLT3L for a first time period; (d) incubating at least one peptide with the CD11b and/or CD19 and/or CD14 and/or CD25 cell depleted sample of (c) for a second time period, thereby obtaining an APC peptide loaded sample; (e) incubating the APC peptide loaded sample with the at least one PBMC for a third time period, thereby obtaining a first stimulated PBMC sample; (f) incubating a PBMC of the first stimulated PBMC sample with an APC of a matured APC sample for a fourth time period, thereby obtaining a second stimulated PBMC sample; (g) incubating a PBMC of the second stimulated PBMC sample with an APC of a matured APC sample for a fifth time period, thereby obtaining a third stimulated PBMC sample; (h) administering at least one T cell of the third stimulated PBMC sample to a subject in need thereof.

In some embodiments, a method comprises: (a) obtaining a biological sample from a subject comprising at least one APC and at least one PBMC; (b) depleting cells expressing CD14 and/or CD25 from the biological sample, thereby obtaining a CD14 and/or CD25 cell depleted sample; (c) incubating the CD14 and/or CD25 cell depleted sample with FLT3L for a first time period; (d) incubating at least one peptide with the CD14 and/or CD25 cell depleted sample of (c) for a second time period, thereby obtaining an APC peptide loaded sample; (e) incubating the APC peptide loaded sample with the at least one PBMC for a third time period, thereby obtaining a first stimulated PBMC sample; (f) incubating a PBMC of the first stimulated PBMC sample with an APC of a matured APC sample for a fourth time period, thereby obtaining a second stimulated PBMC sample; (g) incubating a PBMC of the second stimulated PBMC sample with an APC of a matured APC sample for a fifth time period, thereby obtaining a third stimulated PBMC sample; (h) administering at least one T cell of the third stimulated PBMC sample to a subject in need thereof.

In some embodiments, a method of preparing at least one antigen specific T cell comprising a T cell receptor (TCR) specific to at least one antigen peptide sequence comprises incubating an APC with a population of immune cells from a biological sample depleted of cells expressing CD14 and/or CD25.

In some embodiments, provided herein is a method of preparing at least one antigen specific T cell comprising a T cell receptor (TCR) specific to at least one antigen peptide sequence, the method comprising incubating a population of immune cells from a biological sample with one or more APC preparations for one or more separate time periods of less than 28 days from incubating the population of immune cells with a first APC preparation of the one or more APC preparations, wherein at least one antigen specific memory T cell is expanded, or at least one antigen specific naïve T cell is induced. In some embodiments, provided herein is a method of preparing at least one antigen specific T cell comprising a T cell receptor (TCR) specific to at least one antigen peptide sequence, the method comprising incubating a population of immune cells from a biological sample with 3 or less APC preparations for 3 or less separate time periods, wherein at least one antigen specific memory T cell is expanded or at least one antigen specific naïve T cell is induced.

In some embodiments, a method of preparing antigen specific T cells comprises a T cell receptor (TCR) specific to at least one antigen peptide sequence comprises contacting a population of immune cells (e.g., PBMCs) to APCs. In some embodiments, a method of preparing antigen specific T cells comprises a T cell receptor (TCR) specific to at least one antigen peptide sequence comprises incubating a population of immune cells (e.g., PBMCs) with APCs for a time period. In some embodiments, the population of immune cells is from a biological sample. In some embodiments, the population of immune cells is from a sample (e.g., a biological sample) depleted of CD14 expressing cells. In some embodiments, the population of immune cells is from a sample (e.g., a biological sample) depleted of CD25 expressing cells. In some embodiments, the population of immune cells is from a sample (e.g., a biological sample) depleted of CD14 expressing cells and CD25 expressing cells.

In some embodiments, a method of preparing at least one antigen specific T cell comprising a T cell receptor (TCR) specific to at least one antigen peptide sequence comprises incubating a FMS-like tyrosine kinase 3 receptor ligand (FLT3L)-stimulated APC with a population of immune cells from a biological sample. In some embodiments, provided herein is a method of preparing a pharmaceutical composition comprising at least one antigen specific T cell comprising a T cell receptor (TCR) specific to at least one antigen peptide sequence, the method comprising: incubating FMS-like tyrosine kinase 3 receptor ligand (FLT3L) with a population of immune cells from a biological sample for a first time period; and thereafter incubating at least one T cell of the biological sample with an APC.

In some embodiments, a method of preparing at least one antigen specific T cell comprising a T cell receptor (TCR) specific to at least one antigen peptide sequence comprises contacting a population of immune cells from a sample (e.g., a biological sample) with FMS-like tyrosine kinase 3 receptor ligand (FLT3L). In some embodiments, a method of preparing at least one antigen specific T cells comprises a T cell receptor (TCR) specific to at least one antigen peptide sequence comprises contacting a population of immune cells from a sample (e.g., a biological sample) with FMS-like tyrosine kinase 3 receptor ligand (FLT3L)-stimulated APCs. In some embodiments, a method of preparing at least one antigen specific T cells comprises a T cell receptor (TCR) specific to at least one antigen peptide sequence comprises incubating a population of immune cells from a sample (e.g., a biological sample) with FMS-like tyrosine kinase 3 receptor ligand (FLT3L)-stimulated APCs. In some embodiments, a method of preparing a pharmaceutical composition comprising at least one antigen specific T cell comprising a T cell receptor (TCR) specific to at least one antigen peptide sequence comprises incubating FMS-like tyrosine kinase 3 receptor ligand (FLT3L) with a population of immune cells from a biological sample (e.g., for a time period); and then contacting T cells of the biological sample to APCs. In some embodiments, a method of preparing at least one antigen specific T cell comprising a T cell receptor (TCR) specific to at least one antigen peptide sequence comprises contacting a population of immune cells from a sample (e.g., a biological sample) to one or more APC preparations. In some embodiments, a method of preparing at least one antigen specific T cell comprising a T cell receptor (TCR) specific to at least one antigen peptide sequence comprises incubating a population of immune cells from a sample (e.g., a biological sample) to one or more APC preparations for one or more separate time periods. In some embodiments, a method of preparing at least one antigen specific T cell comprising a T cell receptor (TCR) specific to at least one antigen peptide sequence comprises incubating a population of immune cells from a sample (e.g., a biological sample) to one or more APC preparations for 1, 2, 3, 4, 5, 6, 7, 8, 9 or 10 separate time periods. In some embodiments, the one or more separate time periods is less than 28 days calculated from incubating the population of immune cells with a first APC preparation of the one or more APC preparations.

In some embodiments, a method of preparing antigen specific T cells comprises a T cell receptor (TCR) specific to at least one antigen peptide sequence comprises incubating a population of immune cells to APCs for a time period, wherein the population of immune cells is from a biological sample comprising PBMCs. In some embodiments, a method of preparing antigen specific T cells comprises a T cell receptor (TCR) specific to at least one antigen peptide sequence comprises incubating a population of immune cells to APCs for a time period, wherein the population of immune cells is from a biological sample depleted of CD14 and/or CD25 expressing cells.

In some embodiments, a method of preparing antigen specific T cells comprising a T cell receptor (TCR) specific to at least one antigen peptide sequence comprises incubating a population of immune cells from a biological sample with FMS-like tyrosine kinase 3 receptor ligand (FLT3L)-stimulated APCs for a time period.

In some embodiments, a method of preparing a pharmaceutical composition comprising antigen specific T cells comprising a T cell receptor (TCR) specific to at least one antigen peptide sequence comprises incubating FMS-like tyrosine kinase 3 receptor ligand (FLT3L) with a population of immune cells from a biological sample; and then contacting T cells of the biological sample with APCs.

In some embodiments, a method of preparing antigen specific T cells comprising a T cell receptor (TCR) specific to at least one antigen peptide sequence comprises incubating a population of immune cells from a biological sample with one or more APC preparations for one or more separate time periods, thereby inducing or expanding antigen specific T cells, wherein the one or more separate time periods is less than 28 days calculated from incubating the population of immune cells with a first APC preparation of the one or more APC preparations. In some embodiments, incubating a population of immune cells from a biological sample with one or more APC preparations for one or more separate time periods is performed in a medium containing IL-7, IL-15, or a combination thereof. In some embodiments, the medium further comprises an indoleamine 2,3-dioxygenase-1 (IDO) inhibitor, an anti-PD-1 antibody, IL-12, or a combination thereof. The IDO inhibitor can be epacadostat, navoximod, 1-Methyltryptophan, or a combination thereof. In some embodiments, the IDO inhibitor may increase the number of antigen-specific CD8$^+$ cells. In some embodiments, the IDO inhibitor may maintain the functional profile of memory CD8$^+$ T cell responses. The PD-1 antibody may increase the absolute number of antigen-specific memory CD8$^+$ T cell responses. The PD-1 antibody may increase proliferation rate of the cells treated with such antibody. The additional of IL-12 can result in an increase of antigen-specific cells and/or an increase in the frequency of CD8$^+$ T cells.

In some embodiments, a method of preparing antigen specific T cells comprising a T cell receptor (TCR) specific to at least one antigen peptide sequence comprises incubating a population of immune cells comprising from a biological sample with one or more APC preparations for one or more separate time periods, thereby expanding or inducing antigen specific T cells, wherein a percentage of antigen specific T cells, antigen specific CD4$^+$ T cells, or antigen specific CD8$^+$ T cells is at least about 0.00001%, 0.00002%, 0.00005%, 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total T cells, total CD4$^+$ T cells, total CD8$^+$ T cells, total immune cells, or total cells.

In some embodiments, a method of preparing antigen specific T cells comprises a T cell receptor (TCR) specific to at least one antigen peptide sequence comprises incubating a population of immune cells from a biological sample with 3 or less APC preparations for 3 or less separate time periods, thereby stimulating T cells to become antigen specific T cells.

In some embodiments, the population of immune cells is from a biological sample depleted of CD14 and/or CD25 expressing cells. In some embodiments, the APCs are FMS-like tyrosine kinase 3 receptor ligand (FLT3L)-stimulated APCs. In some embodiments, the APCs comprise one or more APC preparations. In some embodiments, the APC preparations comprise 3 or less APC preparations. In some embodiments, the APC preparations are incubated with the immune cells sequentially within one or more separate time periods.

In some embodiments, the biological sample is from a subject. In some embodiments, the subject is a human. For example, the subject can be a patient or a donor. In some embodiments, the subject has a disease or disorder. In some embodiments, the disease or disorder is cancer. In some embodiments, the antigen specific T cells comprise CD4$^+$ and/or CD8$^+$ T cells. In some embodiments, the antigen specific T cells comprise CD4 enriched T cells and/or CD8 enriched T cells. For example, a CD4$^+$ T cell or CD8$^+$ T cell can be isolated from, enriched from, or purified from a biological sample from a subject comprising PBMCs. In some embodiments, the antigen specific T cells are naïve CD4$^+$ and/or naïve CD8$^+$ T cells. In some embodiments, the antigen specific T cells are memory CD4$^+$ and/or memory CD8$^+$ T cells.

In some embodiments, the at least one antigen peptide sequence comprises a mutation selected from (A) a point mutation and the cancer antigen peptide binds to the HLA protein of the subject with an IC50 less than 500 nM and a greater affinity than a corresponding wild-type peptide, (B) a splice-site mutation, (C) a frameshift mutation, (D) a read-through mutation, (E) a gene-fusion mutation, and combinations thereof. In some embodiments, each of the at least one antigen peptide sequence binds to a protein encoded by an HLA allele expressed by the subject. In some embodiments, each of the at least one antigen peptide sequence comprises a mutation that is not present in non-cancer cells of the subject. In some embodiments, each of the at least one antigen peptide sequences is encoded by an expressed gene of the subject's cancer cells. In some embodiments, one or more of the at least one antigen peptide sequence has a length of from 8-50 naturally occurring amino acids. In some embodiments, the at least one antigen peptide sequence comprises a plurality of antigen peptide sequences. In some embodiments, the plurality of antigen peptide sequences comprises from 2-50, 3-50, 4-50, 5-5-, 6-50, 7-50, 8-50, 9-50, or 10-50 antigen peptide sequences.

In some embodiments, the APCs comprise APCs loaded with one or more antigen peptides comprising one or more of the at least one antigen peptide sequence. In some embodiments, the APCs are autologous APCs or allogenic APCs. In some embodiments, the APCs comprise dendritic cells (DCs).

In some embodiments, a method comprises depleting CD14 and/or CD25 expressing cells from the biological sample. In some embodiments, depleting CD14$^+$ cells comprises contacting a CD14 binding agent to the APCs. In some embodiments, the APCs are derived from CD14$^+$ monocytes. In some embodiments, the APCs are enriched from the biological sample. For example, an APC can be isolated from, enriched from, or purified from a biological sample from a subject comprising PBMCs.

In some embodiments, the APCs are stimulated with one or more cytokines or growth factors. In some embodiments, the one or more cytokines or growth factors comprise GM-CSF, IL-4, FLT3L, or a combination thereof. In some embodiments, the one or more cytokines or growth factors comprise IL-4, IFN-γ, LPS, GM-CSF, TNF-α, IL-1β, PGE1, IL-6, IL-7 or a combination thereof.

In some embodiments, the APCs are from a second biological sample. In some embodiments, the second biological sample is from the same subject.

In some embodiments, a percentage of antigen specific T cells in the method is at least about 1%, 2%, 3%, 4%, 5%, 6%, 7%, 8%, 9%, 10%, 11%, 12%, 13%, 14%, 15%, 16%, 17%, 18%, 19%, or 20% of total T cells or total immune cells. In some embodiments, a percentage of antigen specific T cells in the method is from about 0.1% to about 5%, from about 5% to 10%, from about 10% to 15%, from about 15% to 20%, from about 20% to 25%, from about 25% to 30%, from about 30% to 35%, from about 35% to about 40%, from about 40% to about 45%, from about 45% to about 50%, from about 50% to about 55%, from about 55% to about 60%, from about 60% to 65%, or from about 65% to about 70% of total T cells or total immune cells. In some embodiments, a percentage of antigen specific CD8$^+$ T cells in the method is at least about 1%, 2%, 3%, 4%, 5%, 6%, 7%, 8%, 9%, 10%, 11%, 12%, 13%, 14%, 15%, 16%, 17%, 18%, 19%, or 20% of total T cells or total immune cells. In some embodiments, a percentage of antigen specific naïve CD8$^+$ T cells in the method is at least about 1%, 2%, 3%, 4%, 5%, 6%, 7%, 8%, 9%, 10%, 11%, 12%, 13%, 14%, 15%, 16%, 17%, 18%, 19%, or 20% of total T cells or total immune cells. In some embodiments, a percentage of antigen specific memory CD8$^+$ T cells in the method is at least about 1%, 2%, 3%, 4%, 5%, 6%, 7%, 8%, 9%, 10%, 11%, 12%, 13%, 14%, 15%, 16%, 17%, 18%, 19%, or 20% of total T cells or total immune cells. In some embodiments, a percentage of antigen specific CD4$^+$ T cells in the method is at least about 1%, 2%, 3%, 4%, 5%, 6%, 7%, 8%, 9%, 10%, 11%, 12%, 13%, 14%, 15%, 16%, 17%, 18%, 19%, or 20% of total T cells or total immune cells. In some embodiments, a percentage of antigen specific CD4$^+$ T cells in the method is at least about 1%, 2%, 3%, 4%, 5%, 6%, 7%, 8%, 9%, 10, 1%, 12%, 13%, 14%, 15%, 16%, 17%, 18%, 19%, or 20% of total T cells or total immune cells. In some embodiments, a percentage of antigen specific T cells in the biological sample is at most about 0.5%, 1%, 2%, 3%, 4%, 5%, 6%, 7%, 8%, 9%, 10%, 11%, 12%, 13%, 14%, 15%, 16%, 17%, 18%, 19%, or 20%. In some embodiments, a percentage of antigen specific CD8$^+$ T cells in the biological sample is at most about 0.5%, 1%, 2%, 3%, 4%, 5%, 6%, 7%, 8%, 9%, 10%, 11%, 12%, 13%, 14%, 15%, 16%, 17%, 18%, 19%, or 20%. In some embodiments, a percentage of antigen specific naïve CD8$^+$ T cells in the biological sample is at most about 0.5%, 1%, 2%, 3%, 4%, 5%, 6%, 7%, 8%, 9%, 10%, 11%, 12%, 13%, 14%, 15%, 16%, 17%, 18%, 19%, or 20%. In some embodiments, a percentage of antigen specific memory CD8$^+$ T cells in the biological sample is at most about 0.5%, 1%, 2%, 3%, 4%, 5%, 6%, 7%, 8%, 9%, 10%, 11%, 12%, 13%, 14%, 15%, 16%, 17%, 18%, 19%, or 20%. In some embodiments, a percentage of antigen specific CD4$^+$ T cells in the biological sample is at most about 0.5%, 1%, 2%, 3%, 4%, 5%, 6%, 7%, 8%, 9%, 10%, 11%, 12%, 13%, 14%, 15%, 16%, 17%, 18%, 19%, or 20%.

In some embodiments, a biological sample is freshly obtained from a subject or is a frozen sample.

In some embodiments, a method comprises incubating one or more of the APC preparations with a first medium comprising at least one cytokine or growth factor for a first time period. In some embodiments, the first time period is at lease 1, 2, 3, 4, 5, 6, 7, 8, 9, 10, 11, 12, 13, 14, 15, 16, or 17, or 18 days. In some embodiments, the first time period is no more than 2, 3, 4, 5, 6, 7, 8, 9, 10, 11, 12, 13, 14, 15, 16, 17, or 18 days. In some embodiments, the first time period is at least 1, 2 3, 4, 5, 6, 7, 8, or 9 days. In some embodiments, the first time period is no more than 3, 4, 5, 6, 7, 8, 9, or 10 days. In some embodiments, the at least one cytokine or growth factor comprises GM-CSF, IL-4, FLT3L, TNF-α, IL-1β, PGE1, IL-6, IL-7, IFN-γ, LPS, IFN-α, R848, LPS, ss-rna40, poly I:C, or any combination thereof.

In some embodiments, a method comprises incubating one or more of the APC preparations with at least one peptide for a second time period. In some embodiments, the second time period is no more than 1 hour.

In some embodiments, a method comprises incubating one or more of the APC preparations with a second medium comprising one or more cytokines or growth factors for a third time period, thereby obtaining matured APCs. In some embodiments, the one or more cytokines or growth factors comprises GM-CSF (granulocyte macrophage colony-stimulating factor), IL-4, FLT3L, IFN-γ, LPS, TNF-α, IL-1β, PGE1, IL-6, IL-7, IFN-α, R848 (resiquimod), LPS, ss-rna40, poly I:C, CpG, or a combination thereof. In some embodiments, the third time period is no more than 2, 3, 4, 5, 6, 7, 8, 9, 10, 11, 12, 13, 14, 15, 16, 17, or 18 days. In some embodiments, the third time period is at least 1, 2, 3, 4, 5, 6, 7, 8, 9, 10, 11, 12, 13, 14, 15, 16, or 17 days. In some embodiments, the third time period is no more than 2, 3, 4, or 5 days. In some embodiments, the third time period is at least 1, 2, 3, or 4 days.

In some embodiment, the method further comprises removing the one or more cytokines or growth factors of the second medium after the third time period and before a start of the fourth time period.

Antigen Loaded PBMCs for T Cell Induction In Vitro

In some embodiments, the methods provided herein comprise isolating PBMCs from a human blood sample, and directly loading the PBMCs with antigens. PBMCs directly contacted with antigens can readily take up antigens by phagocytosis and present antigens to T cells that may be in the culture or added to the culture. In some embodiments, the methods provided herein comprise isolating PBMCs from a human blood sample, and nucleofecting or electroporating a polynucleotide, such as an mRNA, that encodes one or more antigens into the PBMCs. In some embodiments, antigens delivered to PBMCs, instead of antigen presenting cells maturing to DCs, provides a great advantage in terms of time and manufacturing efficiency. The PBMCs may be further depleted of one or more cell types. In some embodiments, the PBMCs may be depleted of CD3+ cells for an initial period of antigen loading and the CD3+ cells returned to the culture for the PBMCs to stimulate the CD3+ T cells. In some embodiments, the PBMCs may be depleted of CD25+ cells. In some embodiments, the PBMCs may be depleted of CD14+ cells. In some embodiments, the PBMCs may be depleted of CD19+ cells. In some embodiments, the PBMCs may be depleted of both CD14 and CD25 expressing cells. In some embodiments, CD11b+ cells are depleted from the PBMC sample before antigen loading. In some embodiments, CD11b+ and CD25+ cells are depleted from the PBMC sample before antigen loading.

In some embodiments, the PBMCs isolated from a human blood sample may be handled as minimally as possible prior to loading with antigens. Increased handling of PBMCs, for example freezing and thawing cells, multiple cell depletion steps, etc., may impair cell health and viability.

In some embodiments, the PBMCs are allogeneic to the subject of therapy. In some embodiments the PBMCs are allogeneic to the subject of adoptive cell therapy with antigen specific T cells.

In some embodiments, the PBMCs are HLA-matched for the subject of therapy. In some embodiments, the PBMCs are allogeneic, and matched for the subject's HLA subtypes, whereas the CD3+ T cells are autologous. The PBMCs are loaded with the respective antigens (e.g. derived from analysis of a peptide presentation analysis platform such as RECON), cocultured with subject's PBMC comprising T cells in order to stimulate antigen specific T cells.

In some embodiments, mRNA is used as the immunogen for uptake and antigen presenting. One advantage of using mRNA over peptide antigens to load PBMCs is that RNA is self adjuvanting, and does not require additional adjuvants. Another advantage of using mRNA is that the peptides are processed and presented endogenously. In some embodiments, the mRNA comprises shortmer constructs, encoding 9-10 amino acid peptides comprising an epitope. In some embodiments, the mRNA comprises longmer constructs, encoding bout 25 amino acid peptides. In some embodiments, the mRNA comprises a concatenation of multiple epitopes. In some embodiments, the concatemers may comprise one or more epitopes from the same antigenic protein. In some embodiments, the concatemers may comprise one or epitopes from several different antigenic proteins. Several embodiments are described in the Examples section. Antigen loading of PBMCs by antigen loading may comprise various mechanisms of delivery ad incorporation of nucleic acid into the PBMCs. In some embodiments, the delivery or mechanism of incorporation includes transfection, electroporation, nucleofection, chemical delivery, for example, lipid encapsulated or liposome mediated delivery.

Use of antigen loaded PBMCs to stimulate T cells saves the maturation time required in a method that generates DCs from a PBMC sample prior to T cell stimulation. In some embodiments, use of antigen loaded PBMCs, for example, mRNA loaded PBMCs as APCs reduces the total manufacturing time by 1, 2, 3, 4, 5, 6, 7, 8, 9, or 10 days. In some embodiments, use of antigen loaded PBMCs as APCs reduces the total manufacturing time by 3 days. In some embodiments, use of antigen loaded PBMCs as APCs reduces the total manufacturing time by 4 days. In some embodiments, use of antigen loaded PBMCs as APCs reduces the total manufacturing time by 5 days. In some embodiments, use of antigen loaded PBMCs as APCs reduces the total manufacturing time by 6 days. In some embodiments, use of antigen loaded PBMCs as APCs reduces the total manufacturing time by 7 days.

In some embodiments, use of mRNA as antigen may be preferred because it is easy to design and manufacture nucleic acids, and transfect the PBMCs. In some embodiments, mRNA loaded PBMCs can stimulate T cells and generate higher antigen specific T cells. In some embodiments, mRNA loaded PBMCs can stimulate T cells and generate higher yield of antigen specific T cells. In some embodiments, mRNA loaded PBMCs can stimulate T cells and generate antigen specific T cells that have higher representation of the input antigens, i.e., reactive to diverse antigens. In some embodiments, mRNA loaded PBMCs can stimulate T cells that have at least 1, 2, 3, 4, 5, 6, 7, 8, 9, 10 or more antigen reactivity in the pool of expanded cells. In some embodiments, the mRNA loaded PBMCs can stimulate T cells that have at least 1, 2, 3, 4, 5, 6, 7, 8, 9, 10 or more antigen reactivity than conventional antigen loaded APCs (such as peptide loaded DCs).

Methods of Treating

Provided herein is a method for treating cancer in a subject, comprising: I. contacting cancer neoantigen loaded antigen presenting cells (APCs) with isolated T cells ex vivo, wherein, the cancer neoantigen loaded antigen presenting cells (APCs) are CD11b depleted; II. preparing cancer neoantigen primed T cells for a cellular composition for cancer immunotherapy ex vivo; and III. administering the cellular composition for cancer immunotherapy in the subject, wherein at least one or more conditions or symptoms related to the cancer are reduced or ameliorated by the administering, thereby treating the subject, wherein the cancer neoantigen loaded APCs and the cancer neoantigen primed T cells each express a protein encoded by an HLA allele that is expressed in the subject, and to which the neoantigen can specifically bind.

In some embodiments, the method further comprises administering one or more of the at least one antigen specific T cell to a subject. In some embodiments, the therapeutic composition comprising T cells is administered by injection. In some embodiments, the therapeutic composition comprising T cells is administered by infusion. When administration is by injection, the active agent can be formulated in aqueous solutions, specifically in physiologically compatible buffers such as Hanks solution, Ringer's solution, or physiological saline buffer. The solution can contain formulator agents such as suspending, stabilizing and/or dispersing agents. In another embodiment, the pharmaceutical composition does not comprise an adjuvant or any other substance added to enhance the immune response stimulated by the peptide. In some embodiments, the method further comprises administering one or more of the at least one antigen specific T cell as a pharmaceutical composition described herein to a subject. In some embodiments, the pharmaceutical composition comprises a preservative or stabilizer. In some embodiments the preservative or stabilizer is selected from a cytokine, a growth factor or an adjuvant or a chemical substance. In some embodiments, the at least one antigen specific T cell is administered to a subject within 28 days from collecting a PBMC sample from the subject.

In addition to the formulations described previously, the active agents can also be formulated as a depot preparation. Such long acting formulations can be administered by implantation or transcutaneous delivery (for example subcutaneously or intramuscularly), intramuscular injection or use of a transdermal patch. Thus, for example, the agents can be formulated with suitable polymeric or hydrophobic materials (for example as an emulsion in an acceptable oil) or ion exchange resins, or as sparingly soluble derivatives, for example, as a sparingly soluble salt.

Also provided herein are methods of treating a subject with a disease, disorder or condition. A method of treatment can comprise administering a composition or pharmaceutical composition disclosed herein to a subject with a disease, disorder or condition.

The present disclosure provides methods of treatment comprising an immunogenic therapy. Methods of treatment for a disease (such as cancer or a viral infection) are provided. A method can comprise administering to a subject an effective amount of a composition comprising an immunogenic antigen specific T cells according to the methods provided herein. In some embodiments, the antigen comprises a viral antigen. In some embodiments, the antigen comprises a tumor antigen.

Non-limiting examples of therapeutics that can be prepared include a peptide-based therapy, a nucleic acid-based therapy, an antibody based therapy, a T cell based therapy, and an antigen-presenting cell based therapy.

In some other aspects, provided here is use of a composition or pharmaceutical composition for the manufacture of a medicament for use in therapy. In some embodiments, a method of treatment comprises administering to a subject an effective amount of T cells specifically recognizing an immunogenic neoantigen peptide. In some embodiments, a method of treatment comprises administering to a subject an effective amount of a TCR that specifically recognizes an immunogenic neoantigen peptide, such as a TCR expressed in a T cell.

In some embodiments, the cancer is selected from the group consisting of carcinoma, lymphoma, blastoma, sarcoma, leukemia, squamous cell cancer, lung cancer (including small cell lung cancer, non-small cell lung cancer (NSCLC), adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, melanoma, endometrial or uterine carcinoma, salivary gland carcinoma, kidney or renal cancer, liver cancer, prostate cancer, vulval cancer, thyroid cancer, hepatic carcinoma, head and neck cancer, colorectal cancer, rectal cancer, soft-tissue sarcoma, Kaposi's sarcoma, B-cell lymphoma (including low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, and Waldenstrom's macroglobulinemia), chronic lymphocytic leukemia (CLL), acute lymphoblastic leukemia (ALL), myeloma, Hairy cell leukemia, chronic myeloblasts leukemia, and post-transplant lymphoproliferative disorder (PTLD), abnormal vascular proliferation associated with phakomatoses, edema, Meigs' syndrome, and combinations thereof.

The methods described herein are particularly useful in the personalized medicine context, where immunogenic neoantigen peptides identified according to the methods described herein are used to develop therapeutics (such as vaccines or therapeutic antibodies) for the same individual. Thus, a method of treating a disease in a subject can comprise identifying an immunogenic neoantigen peptide in a subject according to the methods described herein; and synthesizing the peptide (or a precursor thereof, such as a polynucleotide (e.g., an mRNA) encoding the peptide); and manufacturing T cells specific for identified neoantigens; and administering the neoantigen specific T cells to the subject. In some embodiments, the method of treating a disease in a subject can comprise identifying an immunogenic neoantigen peptide in a subject according to the methods described herein; and synthesizing the polynucleotide, such as an mRNA, that encodes the immunogenic neoantigen peptide or a precursor thereof, and manufacturing T cells specific for identified neoantigens; and administering the neoantigen specific T cells to the subject.

The agents and compositions provided herein may be used alone or in combination with conventional therapeutic regimens such as surgery, irradiation, chemotherapy and/or bone marrow transplantation (autologous, syngeneic, allogeneic or unrelated). A set of tumor antigens can be identified using the methods described herein and are useful, e.g., in a large fraction of cancer patients.

In some embodiments, at least one or more chemotherapeutic agents may be administered in addition to the composition comprising an immunogenic therapy. In some embodiments, the one or more chemotherapeutic agents may belong to different classes of chemotherapeutic agents.

In practicing the methods of treatment or use provided herein, therapeutically-effective amounts of the therapeutic agents can be administered to a subject having a disease or condition. A therapeutically-effective amount can vary widely depending on the severity of the disease, the age and relative health of the subject, the potency of the compounds used, and other factors.

Subjects can be, for example, mammal, humans, pregnant women, elderly adults, adults, adolescents, pre-adolescents, children, toddlers, infants, newborn, or neonates. A subject can be a patient. In some cases, a subject can be a human. In some cases, a subject can be a child (i.e. a young human being below the age of puberty). In some cases, a subject can be an infant. In some cases, the subject can be a formula-fed infant. In some cases, a subject can be an individual enrolled in a clinical study. In some cases, a subject can be a laboratory animal, for example, a mammal, or a rodent. In some cases, the subject can be a mouse. In some cases, the subject can be an obese or overweight subject.

In some embodiments, the subject has previously been treated with one or more different cancer treatment modalities. In some embodiments, the subject has previously been treated with one or more of radiotherapy, chemotherapy, or immunotherapy. In some embodiments, the subject has been treated with one, two, three, four, or five lines of prior therapy. In some embodiments, the prior therapy is a cytotoxic therapy.

In some embodiments, the disease or condition that can be treated with the methods disclosed herein is cancer. Cancer is an abnormal growth of cells which tend to proliferate in an uncontrolled way and, in some cases, to metastasize (spread). A tumor can be cancerous or benign. A benign tumor means the tumor can grow but does not spread. A cancerous tumor is malignant, meaning it can grow and spread to other parts of the body. If a cancer spreads (metastasizes), the new tumor bears the same name as the original (primary) tumor.

The methods of the disclosure can be used to treat any type of cancer known in the art. Non-limiting examples of cancers to be treated by the methods of the present disclosure can include melanoma (e.g., metastatic malignant melanoma), renal cancer (e.g., clear cell carcinoma), prostate cancer (e.g., hormone refractory prostate adenocarcinoma), pancreatic adenocarcinoma, breast cancer, colon cancer, lung cancer (e.g., non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies.

Additionally, the disease or condition provided herein includes refractory or recurrent malignancies whose growth may be inhibited using the methods of treatment of the present disclosure. In some embodiments, a cancer to be treated by the methods of treatment of the present disclosure is selected from the group consisting of carcinoma, squamous carcinoma, adenocarcinoma, sarcomata, endometrial cancer, breast cancer, ovarian cancer, cervical cancer, fallopian tube cancer, primary peritoneal cancer, colon cancer, colorectal cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, head and neck cancer, glioblastoma, glioma, squamous cell carcinoma of the head and neck, prostate cancer, pancreatic cancer, mesothelioma, sarcoma, hematological cancer, leukemia, lymphoma, neuroma, and combinations thereof. In some embodiments, a cancer to be treated by the methods of the present disclosure include, for example, carcinoma, squamous carcinoma (for example, cervical canal, eyelid, tunica conjunctiva, vagina, lung, oral cavity, skin, urinary bladder, tongue, larynx, and gullet), and adenocarcinoma (for example, prostate, small intestine, endometrium, cervical canal, large intestine, lung, pancreas, gullet, rectum, uterus, stomach, mammary gland, and ovary). In some embodiments, a cancer to be treated by the methods of the present disclosure further include sarcomata (for example, myogenic sarcoma), leukosis, neuroma, melanoma, and lymphoma. In some embodiments, a cancer to be treated by the methods of the present disclosure is breast cancer. In some embodiments, a cancer to be treated by the methods of treatment of the present disclosure is triple negative breast cancer (TNBC). In some embodiments, a cancer to be treated by the methods of treatment of the present disclosure is ovarian cancer. In some embodiments, a cancer to be treated by the methods of treatment of the present disclosure is colorectal cancer.

In some embodiments, a patient or population of patients to be treated with a pharmaceutical composition of the present disclosure have a solid tumor. In some embodiments, a solid tumor is a melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, or Merkel cell carcinoma. In some embodiments, a patient or population of patients to be treated with a pharmaceutical composition of the present disclosure have a hematological cancer. In some embodiments, the patient has a hematological cancer such as Diffuse large B cell lymphoma ("DLBCL"), Hodgkin's lymphoma ("HL"), Non-Hodgkin's lymphoma ("NHL"), Follicular lymphoma ("FL"), acute myeloid leukemia ("AML"), or Multiple myeloma ("MM"). In some embodiments, a patient or population of patients to be treated having the cancer selected from the group consisting of ovarian cancer, lung cancer and melanoma.

Specific examples of cancers that can be prevented and/or treated in accordance with present disclosure include, but are not limited to, the following: renal cancer, kidney cancer, glioblastoma multiforme, metastatic breast cancer; breast carcinoma; breast sarcoma; neurofibroma; neurofibromatosis; pediatric tumors; neuroblastoma; malignant melanoma; carcinomas of the epidermis; leukemias such as but not limited to, acute leukemia, acute lymphocytic leukemia, acute myelocytic leukemias such as myeloblastic, promyelocytic, myelomonocytic, monocytic, erythroleukemia leukemias and myclodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone cancer and connective tissue sarcomas such as but not limited to bone sarcoma, myeloma bone disease, multiple myeloma, cholesteatoma-induced bone osteosarcoma, Paget's disease of bone, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangio sarcoma, neurilemmoma, rhabdomyosarcoma, and synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease (including juvenile Paget's disease) and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but not limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; cervical carcinoma; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; colorectal cancer, KRAS mutated colorectal cancer; colon carcinoma; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as KRAS-mutated non-small cell lung cancer, non-small cell lung cancer, squamous cell carcinoma (epidermoid carcinoma), adenocarcinoma, large-cell carcinoma and small-cell lung cancer; lung carcinoma; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, androgen-independent prostate cancer, androgen-dependent prostate cancer, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acrallentiginous melanoma; kidney cancers such as but not limited to renal cell cancer, adenocarcinoma, hypernephroma, fibrosarcoma, transitional cell cancer (renal pelvis and/or uterer); renal carcinoma; Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas.

In some embodiments, the treatment with adoptive T cells generated by the method described herein is directed to treatment of a specific patient population. In some embodiments, the adoptive T cells are directed to treatment of population of patients that are refractory to a certain therapy. For example, the T cells are directed to treatment of population of patients that are refractory to anti-checkpoint inhibitor therapy. In some embodiments, the patient is a melanoma patient. In some embodiments, the patient is a metastatic melanoma patient. In some embodiments, provided herein are methods of treating unresectable melanoma patient. In some embodiments, unresectable melanoma patients are selected for the T cell therapy described herein (such as NEO-PTC-01). Unresectable melanoma subjects may not be candidates for therapy with tumor infiltrating lymphocytes. In some embodiments, the treatment with adoptive T cells generated by the method described herein is directed to treatment of metatstatic and unresectable melanoma patients. In some embodiments, the patient is refractory to anti-PD1 therapy. In some embodiments, the patient is refractory to anti-CTLA-4 therapy. In some embodiments, the patient is refractory to both anti-PD1 and anti-CTLA-4 therapy. In some embodiments, the therapy is administered by intravenously. In some embodiments, the therapy is administered by injection or infusion. In some embodiments the therapy is administered via a single dose, or 2, 3, 4, 5, 6, 7, 8, 9 or 10 doses. In some embodiments, the therapeutic or pharmaceutical composition comprises about 10^9 or higher total number of cells per dose. In some embodiments, the therapeutic or pharmaceutical composition comprises 10^10 or higher total number of cells per dose. In some embodiments, the therapeutic or pharmaceutical composition comprises 10^11 or higher total number of cells per dose. In some embodiments, the therapeutic or pharmaceutical composition comprises 10^12 or higher total number of cells per dose. In some embodiments, the subject is administered a therapeutic composition as described herein having about 10^10 to about 10^11 total cells per dose, wherein the cells have been validated for quality and have passed the release criteria.

Kits

The methods and compositions described herein can be provided in kit form together with instructions for administration. Typically, the kit can include the desired neoantigen therapeutic compositions in a container, in unit dosage form and instructions for administration. Additional therapeutics, for example, cytokines, lymphokines, checkpoint inhibitors, antibodies, can also be included in the kit. Other kit components that can also be desirable include, for example, a sterile syringe, booster dosages, and other desired excipients.

Kits and articles of manufacture are also provided herein for use with one or more methods described herein. The kits can contain one or more types of immune cells. The kits can also contain reagents, peptides, and/or cells that are useful for antigen specific immune cell (e.g. neoantigen specific T cells) production as described herein. The kits can further contain adjuvants, reagents, and buffers necessary for the makeup and delivery of the antigen specific immune cells.

The kits can also include a carrier, package, or container that is compartmentalized to receive one or more containers such as vials, tubes, and the like, each of the container(s) comprising one of the separate elements, such as the polypeptides and adjuvants, to be used in a method described herein. Suitable containers include, for example, bottles, vials, syringes, and test tubes. The containers can be formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment. A kit typically includes labels listing contents and/or instructions for use, and package inserts with instructions for use. A set of instructions can also be included.

EXAMPLES

The present disclosure will be described in greater detail by way of the following specific examples. The following examples are offered for illustrative purposes, and are not intended to limit the invention in any manner. Those of skill in the art will readily recognize a variety of non-critical parameters that can be changed or modified to yield alternative embodiments according to the invention. All patents, patent applications, and printed publications listed herein are incorporated herein by reference in their entirety.

Summary of Examples

Figures 1B, 1C:
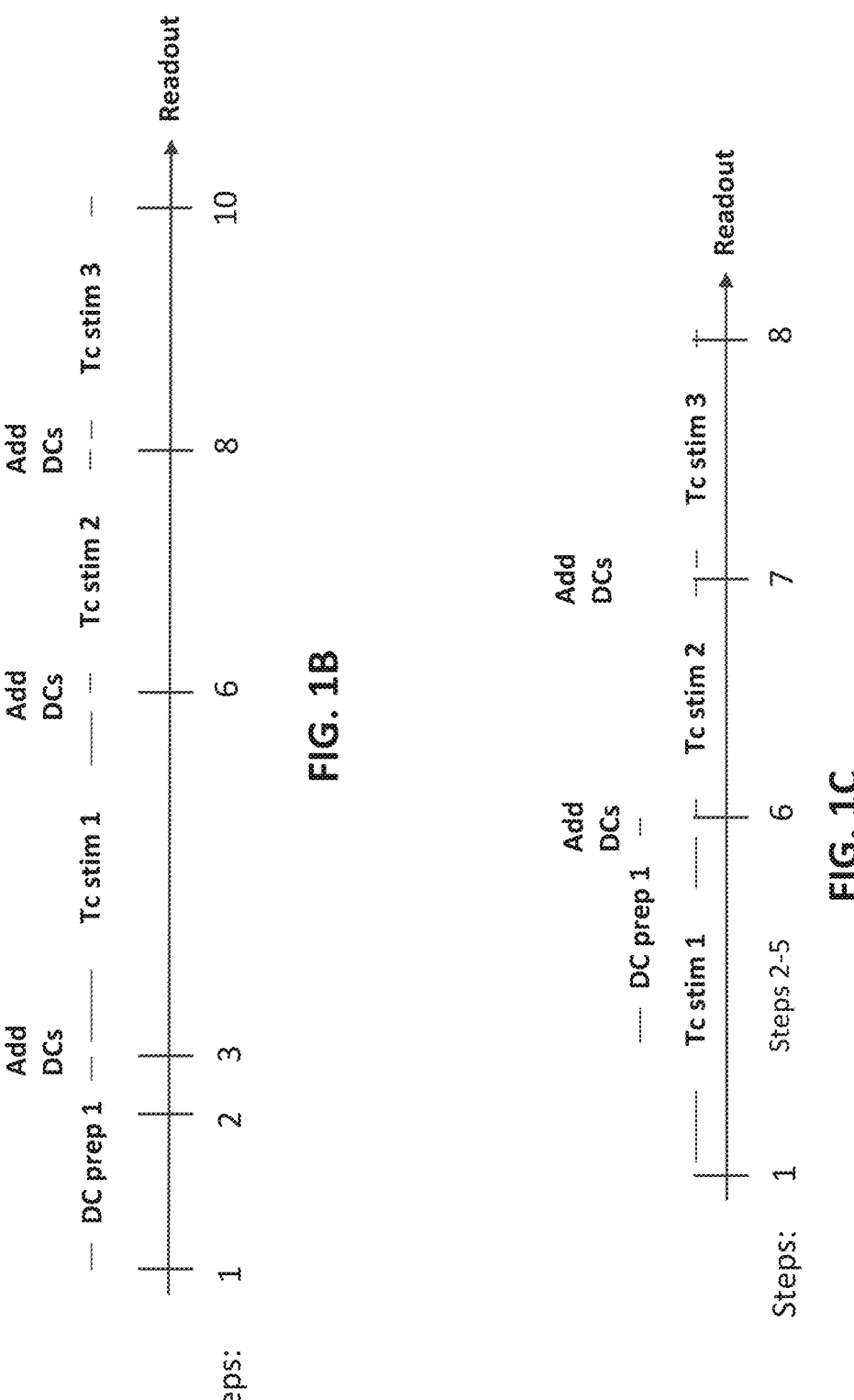
FIG. 1B depicts an example schematic of an antigen specific T cell manufacturing protocol.
FIG. 1C depicts an example alternate schematic of an antigen specific T cell manufacturing protocol.

Examples 1 and 2 below are examples of T cell manufacturing protocols (protocol 1 and protocol 2). Schematics of the example protocols are shown in FIG. 1B and FIG. 1C. Examples 21-23 depicts the steps for preparing APCs and of these two protocols. Examples 12 and 14-16 and Tables 2-5 summarize results obtained from protocols 1 and 2. Example 13 describes parameters of the protocols that will be tested.

Examples 3-7 and 20 are examples of results of CD4$^+$ memory T cell expansion and CD8$^+$ naïve T cell inductions using protocol 1 and protocol 2. Flow cytometric analyses results are show in FIG. 2B, FIGS. 5A and B, FIG. 7, FIG. 10, and FIGS. 12-23.

Figure 25:
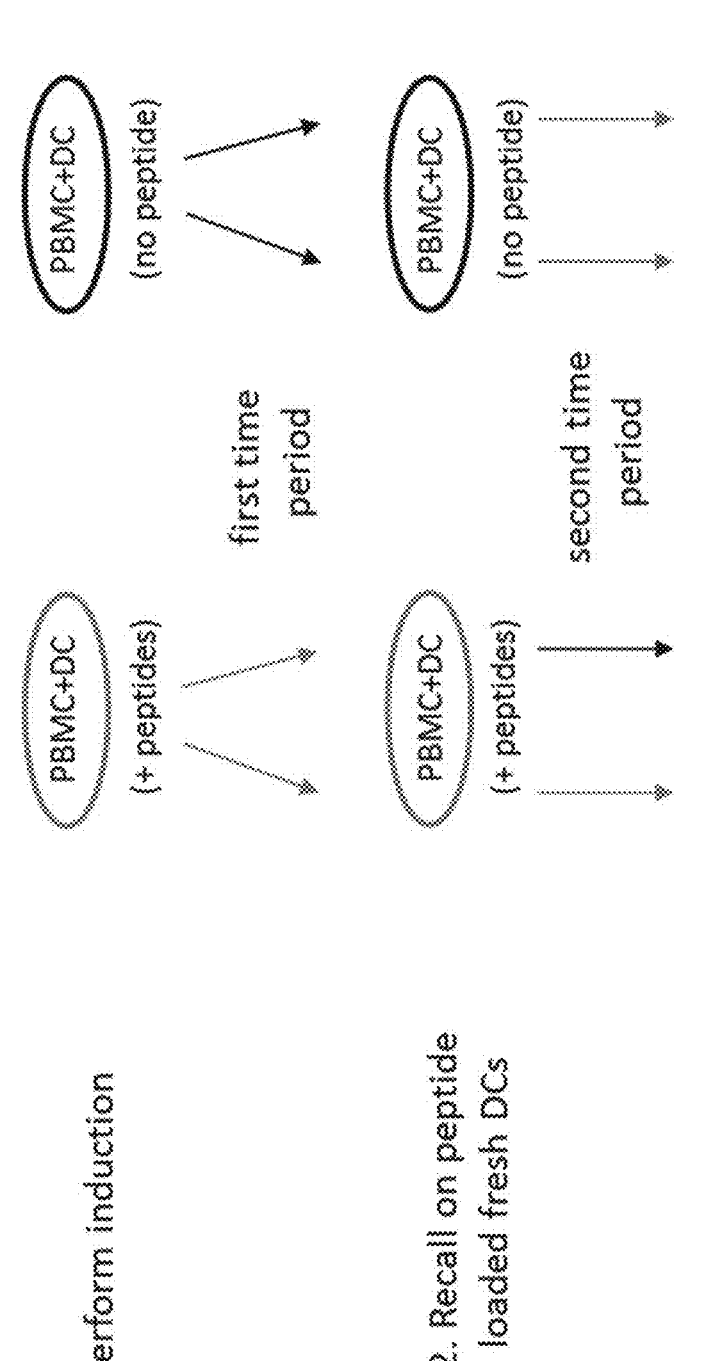
FIG. 25 depicts an exemplary method to test functionality, phenotype and/or function of T cells and/or T cell responses.

Examples 8-11 and 16-19 are examples of results of assays used to assess specificity, phenotype and/or function of T cells expanded or induced using the methods described herein. FIG. 25 depicts a general overview of the T cell manufacturing process and use of these assays specificity, phenotype and/or function of the T cells.

Example 1—T Cell Manufacturing Protocol 1

This example provides an example of T cell manufacturing protocol 1 as illustrated in FIGS. 1B and 1C.
Materials:
  DC media (Cellgenix)
  CD14 microbeads, human, Miltenyi #130-050-201
  Cytokines and/or growth factors
  T cell media (AIM V+RPMI 1640 glutamax+serum+PenStrep)
  Peptide stocks—1 mM per peptide (HIV A02—5-10 peptides, HIV B07—5-10 peptides, DOM—4-8 peptides, PIN—6-12 peptides)
Procedure:
Step 1: Monocyte Isolation for DC Prep
  1. Calculate the approximate number of PBMCs to thaw based on expected DC yield for each donor.
  2. Thaw PBMCs and resuspend at ~1×10$^6$-1×10$^8$ cells/mL in DC media.
  3. Add benzonase (1:1000 dilution) and place in incubator with cap loosened.
  4. Perform CD14$^+$ monocyte enrichment according to manufacturer protocol.
  5. Plate enriched cells in 6-well plates at 1×10$^5$-1×10$^7$ per well in DC media with one or more cytokines and/or growth factors selected from GM-CSF, IL-4, FLT3L, TNF-α, IL-1β, PGE1, IL-6, IL-7, IFN-α, R848, LPS, ss-rna40, and polyI:C.
Step 2: Peptide Loading and Maturation
  1. Count DCs and split the cells according to the experimental conditions in 15 mL tubes; 0.01-1 million cells per condition.
  2. Spin @1200 rpm for 5 min and resuspend in 50-400 μL DC medium. Add peptide(s) and place in incubator with loosened cap for 0.5-3 hrs. Volumes were calculated for peptide pools at a concentration of 1 mM per peptide. A volume of each separate pool of A02 (5 peptides) and B07 (5 peptides) was added per well for a final concentration of 0.001-100 μM per peptide.
  3. After 0.5-3 hrs. add 200 μL to 1.5 mL of DC media containing maturation mix and transfer the cells to 24 well plate. The maturation mix contains one or more cytokines selected from GM-CSF, IL-4, FLT3L, TNF-α, IL-1β, PGE1, IL-6, IL-7, IFN-α, R848, LPS, ss-rna40, and polyI:C.
Step 3: Setting Up Long Term Stimulation (LTS) Experiment
  1. Carefully remove all media from the wells of the DC plates, transferring each well to a separate well in a 24-well deepwell block.
  2. Wash each well with 0.5-3 mL T cell media and combine with DC media in the deepwell block.
  3. Add 100 μL to 2 mL T cell media to each well.
  4. Spin down DCs at 1200 rpm for 5 min.

5. Remove all supernatant, resuspend DCs in 100 μL to 2 mL T cell media and transfer back into the correct wells.
  6. Thaw PBMCs in T cell media and resuspend at 0.5× 10$^6$-4×10$^6$ cells/mL in T cell media with IL-7 and IL-15.
  7. Add 0.5-3 mL of prepared PBMCs to each well.
Step 4: Feeding LTS
  Check with glucose meter if the media is yellow. If glucose remains high, feed culture with IL-7 and IL-15 to the well. If glucose is low, expand the cells to 6 well plate (4 mL/well) and supplement with IL-15 and IL-7. If glucose is very low, expand to 6 mL/well in a 6-well plate.
Step 5: Feeding LTS
  Feed cultures every 1-4 days, adding fresh IL-15/IL-7 and expanding the culture volume as needed when glucose concentration becomes low.
Step 6: Re-Stimulation
  Count T cells and repeat from step 3 on a new batch of peptide-loaded DCs. Freeze leftover cells for analysis.
Step 7: Feeding LTS
  Feed cultures every –1-5 days.
Step 8: Re-Stimulation
  Count T cells and repeat from step 3 on a new batch of peptide-loaded DCs. Freeze leftover cells for analysis.
Step 9: Feeding LTS
  Feed cultures every 1-5 days.
Step 10
  Count T cells and freeze for analysis.

Example 2—T Cell Manufacturing Protocol 2

This protocol can be an alternative to the protocol described in Example 1.

Example 2 provides an example T cell manufacturing protocol (protocol 2) as illustrated in FIG. 1.
Materials:
  AIM V media (Invitrogen)
  Media 1 (RPMI 1640 glutamax+serum+PenStrep)
  Media 2 (AIM V+RPMI 1640 glutamax+serum+PenStrep)
Procedure:
Step 1: Plate 4 million PBMCs in each well of 24 well plate with one or more cytokines in Media 2. The one or more cytokines are selected from GM-CSF, IL-4, FLT3L, TNF-α, IL-1β, PGE1, IL-6, IL-7, IFN-α, R848, LPS, ss-rna40, and polyI:C.
Step 2: Peptide loading and maturation in Media 2
  1. Make stock peptide pool of interest (except for no peptide condition) at 0.001-100 μM for shortmers and 0.001-100 μM for longmers final concentration in respective wells and mix.
  2. Incubate for 0.5-3 hr.
  3. Make stock maturation cocktail and add to each well after incubation and mix. The maturation cocktail contains one or more cytokines selected from GM-CSF, IL-4, FLT3L, TNF-α, IL-1β, PGE1, IL-6, IL-7, IFN-α, R848, LPS, ss-rna40, and polyI:C.
Step 3: Add human serum to each well at a final concentration of 2.5-20% by volume and mix.
Step 4: Carefully replace 50-90% of the media with fresh Media 1 supplemented with IL-7 and IL-15 to a final concentration of 0.005-500 ng/mL each.
Step 5: Carefully replace 50-90% of the media with fresh Media 1 supplemented with IL-7 and IL-15 to a final concentration of 0.005-500 ng/mL each every 1-5 days.

In case the wells turn orange to yellow on non-feeding days (glucose readout in case of clear media), change 25-75% of existing media with fresh Media 1 and IL-7/IL-15.

Step 6: Count and freeze (or proceed to the following steps to carry the T cell simulation to step 8 and/or step 10 of protocol 1).

During the culturing steps from step 1 to step 6, peptide-loaded DCs can be prepared in parallel according to the procedures in protocol 1 "Step 1" and "Step 2".

Count T cells and stimulate T cells with a new batch of peptide-loaded DCs. Freeze leftover cells for analysis. The T cell stimulation procedure can be carried out according to the procedures in protocol 1 "Step 3".

Step 7: Count T cells and repeat T cell stimulation procedures in protocol 1 "step 3" on a new batch of peptide-loaded DCs. Freeze leftover cells for analysis.

Step 8: Count T cells and freeze for analysis.

Example 3—CD8$^+$ T Cell Induction

Figure 3:
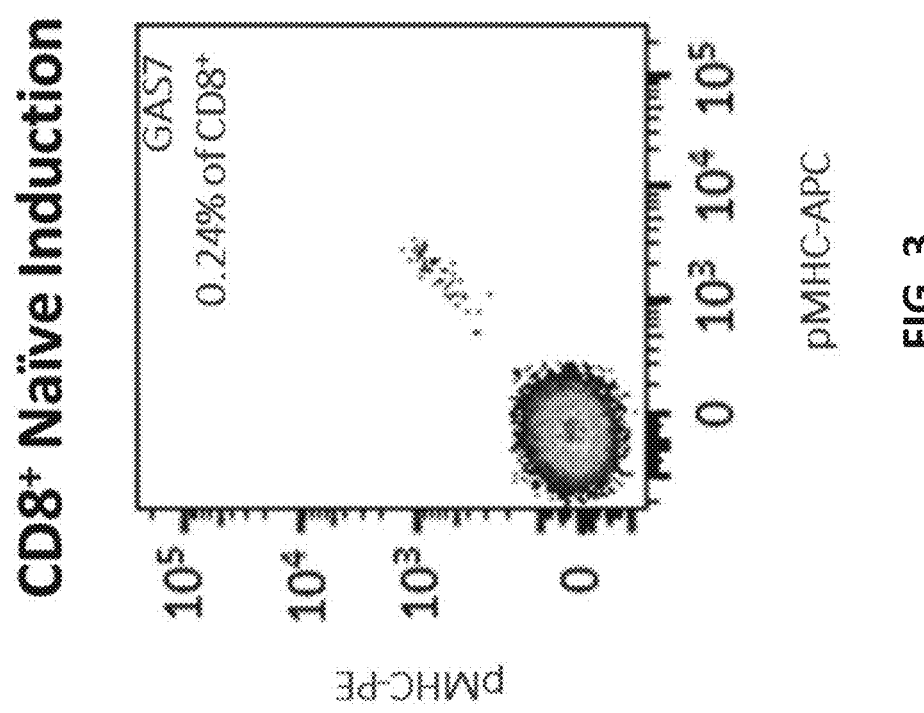
FIG. 3 depicts an example flow cytometry analysis showing the fraction of antigen specific CD8$^+$ naïve T cells induced with a GAS7 peptide.
Figure 2:
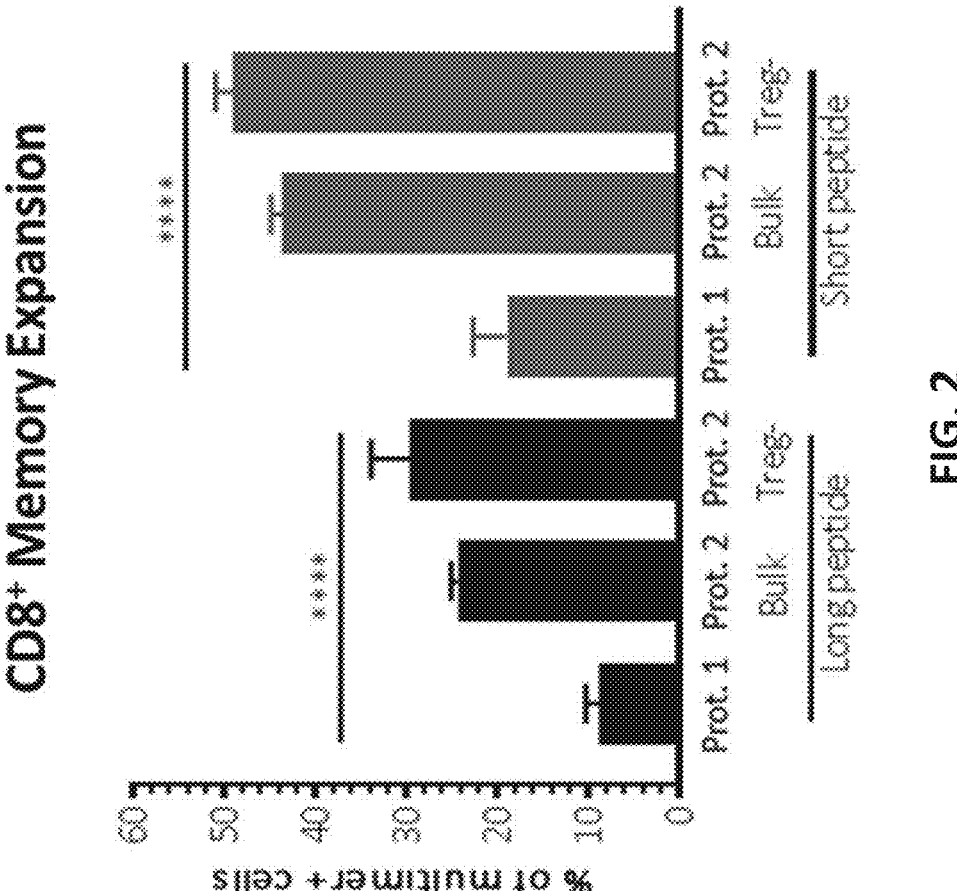
FIG. 2 depicts an example result showing fraction of antigen specific CD8$^+$ memory T cells induced by long peptide or short peptide. "Bulk" indicates the sample containing T cells used for induction is whole peripheral blood mononuclear cell (PBMC). "Treg$^-$" indicates the sample containing T cells used for induction is PBMCs depleted of CD25 expressing cells.

PBMC samples from a human donor were used to perform antigen specific T cell induction according to protocol 1 or protocol 2. CD8$^+$ memory and naïve T cell inductions were analyzed after manufacturing T cells using different protocols. Cell samples can be taken out at different time points for analysis. pMHC multimers were used to monitor the fraction of antigen specific CD8$^+$ T cells in the induction cultures and used to detect multiple T cell responses in parallel by using combinatorial coding. FIG. 2 depicts an exemplary result showing the fraction of antigen specific CD8$^+$ memory T cells induced with long peptides or short peptides using protocol 1 (prot. 1) and protocol 2 (prot. 2). "Bulk" indicates the sample containing T cells used for induction is whole PBMC. "Treg$^-$" indicates the sample containing T cells used for induction is PBMCs depleted of CD25 expressing cells. FIG. 3 depicts an exemplary result of a T cell response assay showing fraction of antigen specific CD8$^+$ naïve T cell responded to GAS7 peptide analyzed by flow cytometry after a shortmer (short) stimulation or induction with a longmer (long). Increase in fraction of antigen specific memory T cells and naïve PIN specific T cells can be observed after short term stimulation. A "long" or a "longmer" is a peptide that is used as an immunogen, and is about 16-25 amino acid long. A "short" or a "shortmer" is a peptide that is used as an immunogen, and is about 8-12 amino acid long.

Example 4—CD8$^+$ T Cell Induction

Figure 4:
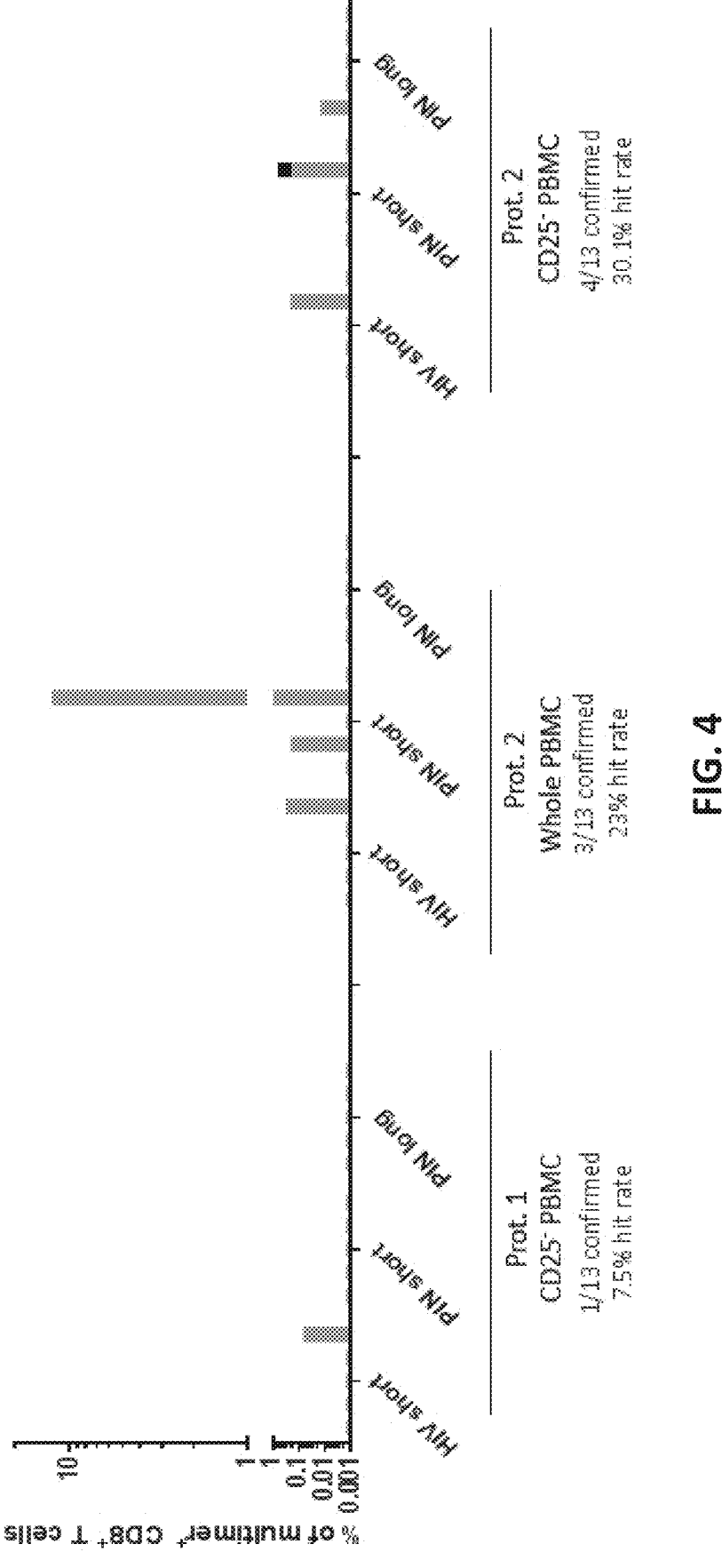
FIG. 4 depicts an example result showing antigen specific CD8$^+$ T cell responses to a peptide pool of HIV short peptides, short previously identified neoantigens (PINs), or long PINs. "Whole PBMC" indicates the sample containing T cells used for induction is whole PBMC. "CD25$^-$ PBMC" indicates the sample containing T cells used for induction is depleted of CD25$^+$ cells. Short, Short peptides, or shortmers; Long, Long peptides, or longmers.

CD8$^+$ T cell induction were analyzed after manufacturing T cells using different protocols. The induced T cells were incubated with different antigen peptides in test wells and the fraction of T cells that responded to the peptides were analyzed by flow cytometry. pMHC multimers were used to monitor the fraction of antigen specific CD8$^+$ T cells in the induction cultures and used to detect multiple T cell responses in parallel by using combinatorial coding. Hit rate can be used to depict how responsive the T cells are to antigen peptides. The hit rate is defined as the number of positive response test wells divided by the total number of test wells. The experiment was done in duplicates, and the hit rate was confirmed in the duplicate wells. FIG. 4 depicts an example of results showing the fraction of CD8$^+$ T cells induced with HIV short peptides, previously identified neoantigen (PIN) short peptides, or PIN long peptides after induction using protocol 1 (prot. 1) and protocol 2 (prot. 2).

Figure 6:
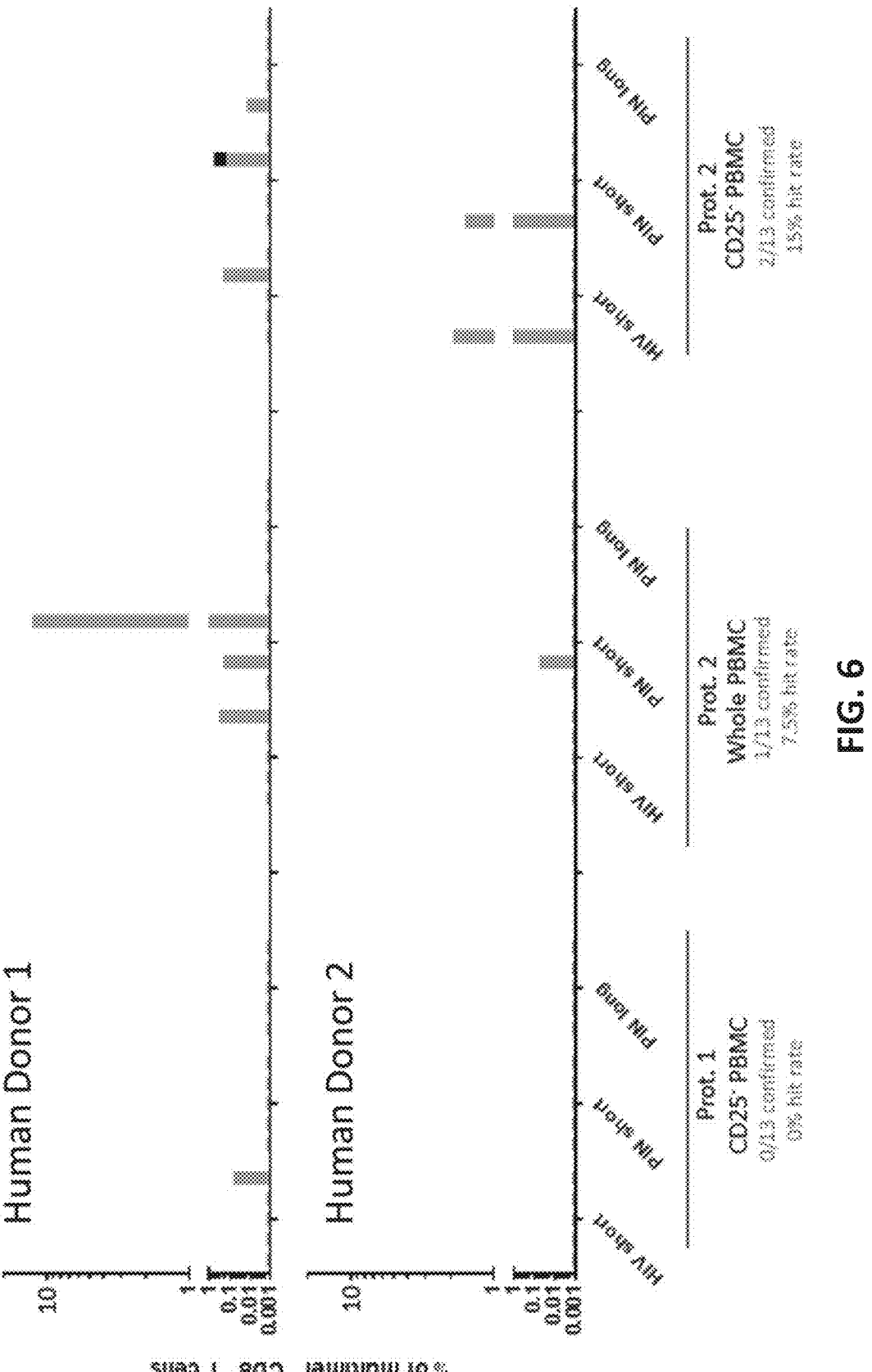
FIG. 6 depicts example results showing antigen specific CD8$^+$ T cell responses to the indicated peptides using PBMC samples from two human donors.

"Whole PBMC" indicates the sample containing T cells used for induction is whole PBMC. "CD25$^-$ PBMC" indicates the sample containing T cells used for induction is depleted of CD25$^+$ cells. Long and short inductions are shown. FIG. 6 depicts exemplary results showing the fraction of cells that are multimer positive CD8 T cells induced by the indicated long and short inductions from two human donors.

Example 5—CD4$^+$ T Cell Responses

Figure 10:
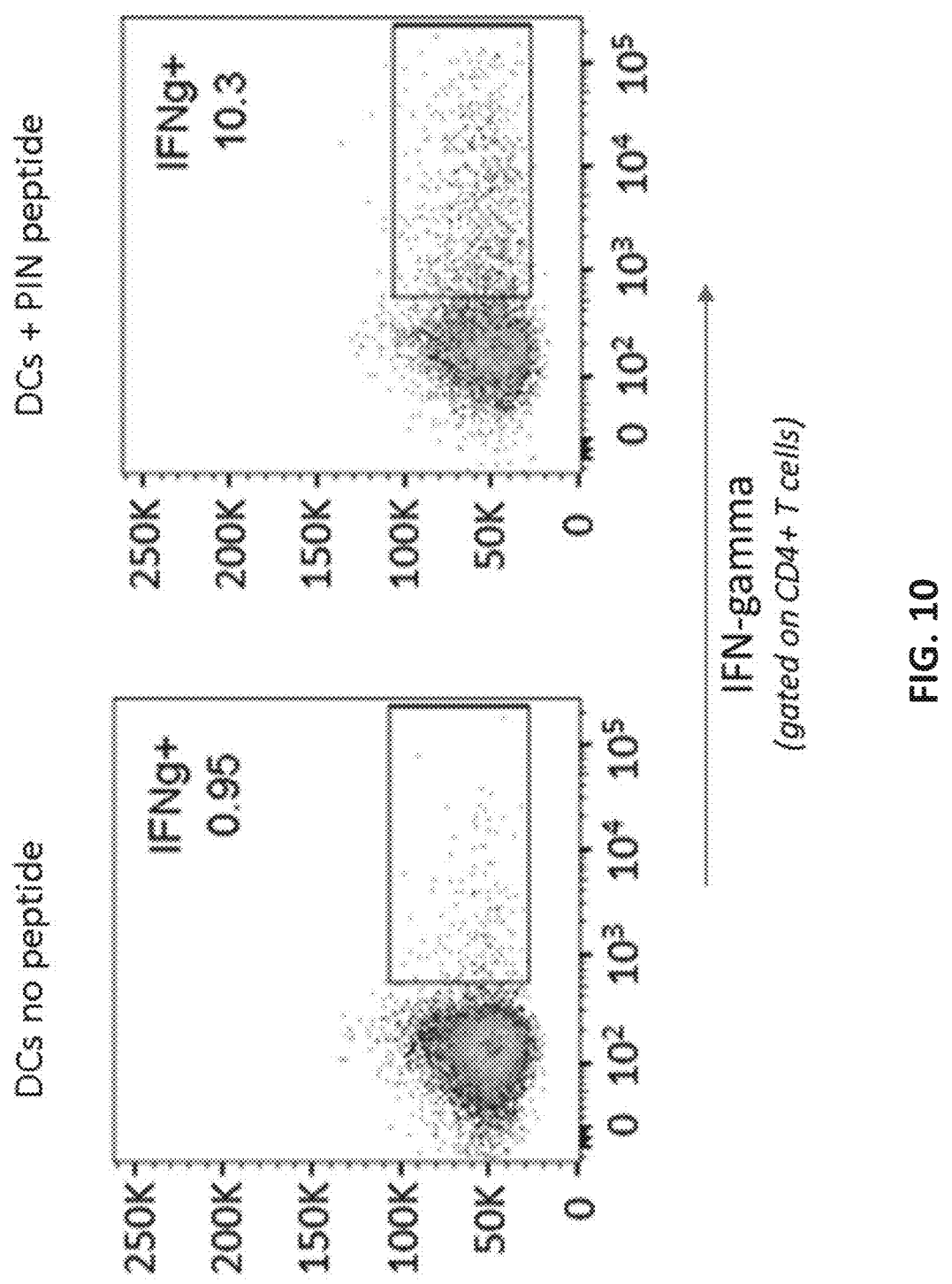
FIG. 10 depicts an example flow cytometric analysis of antigen specific CD4$^+$ T cell responses to peptide loaded antigen presenting cells and then incubated with APCs with and without loaded PINs. The percentage of CD4$^+$ T cells releasing IFNγ is shown.
Figure 11:
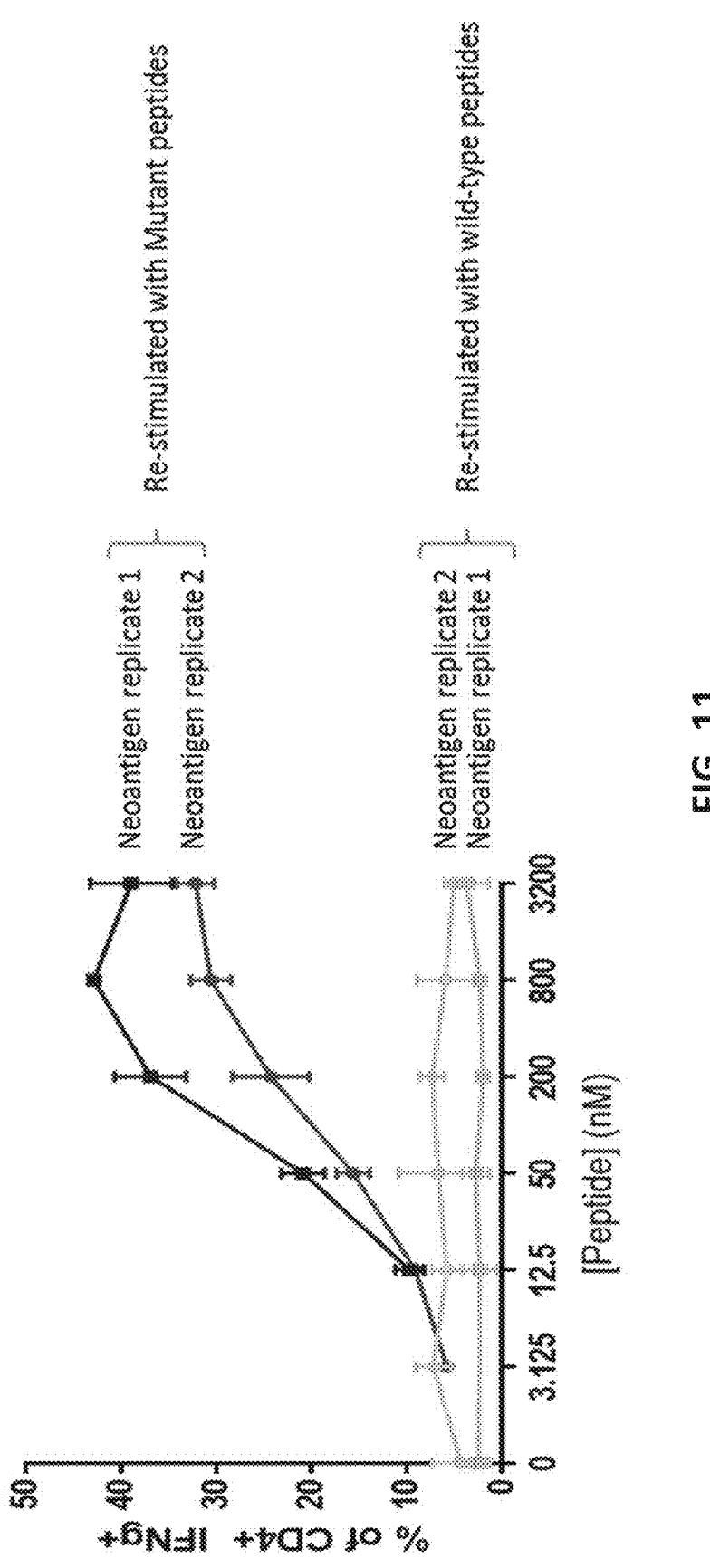
FIG. 11 depicts an example result of the percentage of antigen specific CD4$^+$ T cells releasing IFNγ after being restimulated with mutant peptides or wild-type peptides.
Figure 12:
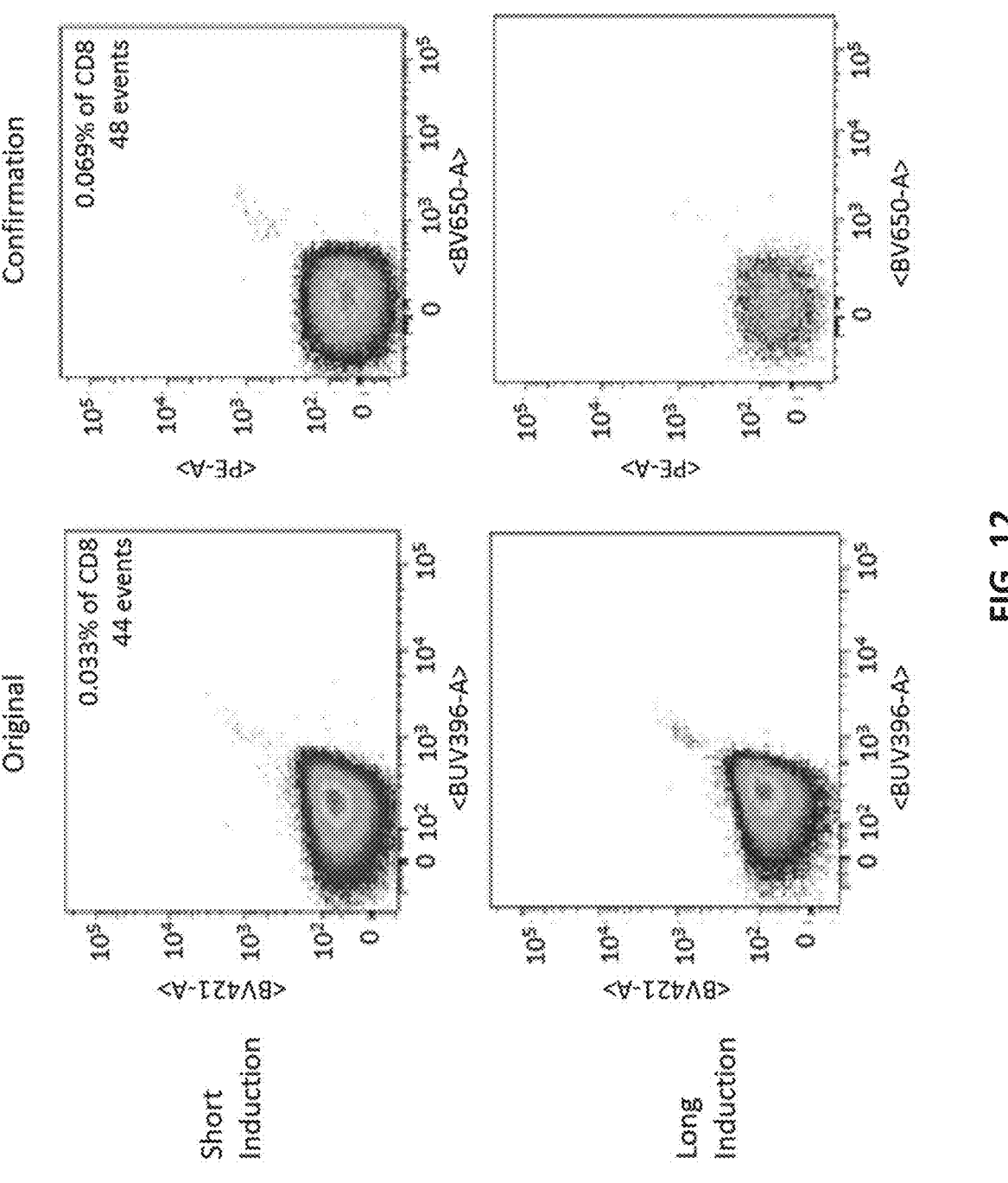
FIG. 12 depicts example flow cytometric analyses showing antigen specific CD8$^+$ naïve T cell responses to short HIV5 peptides. Both short and long term inductions are shown.
Figure 13:
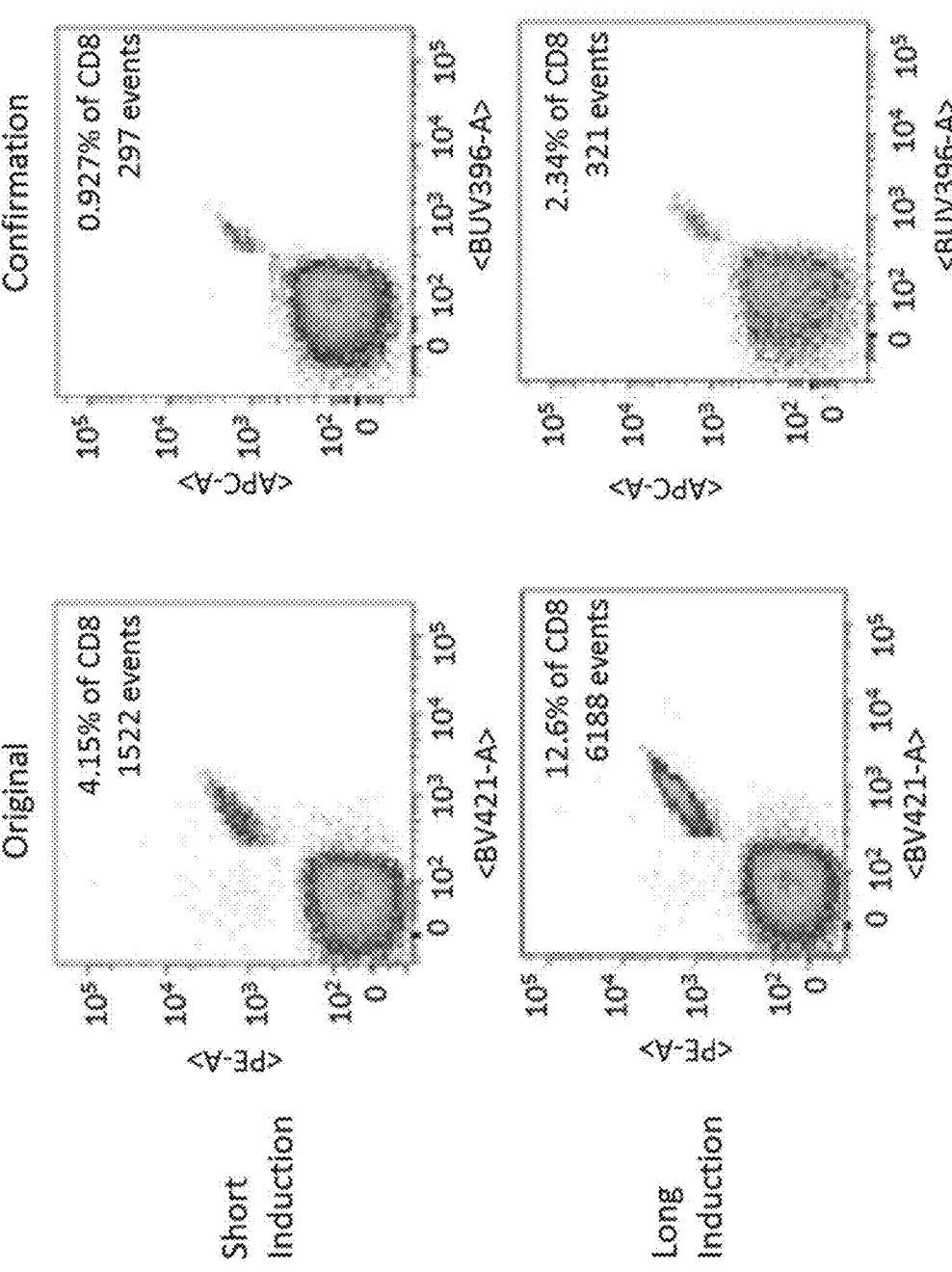
FIG. 13 depicts exemplary flow cytometric analyses showing the fraction of antigen specific CD8$^+$ naïve T cell responses to short ME1 peptides using a whole PBMC sample from a human donor.
Figure 14:
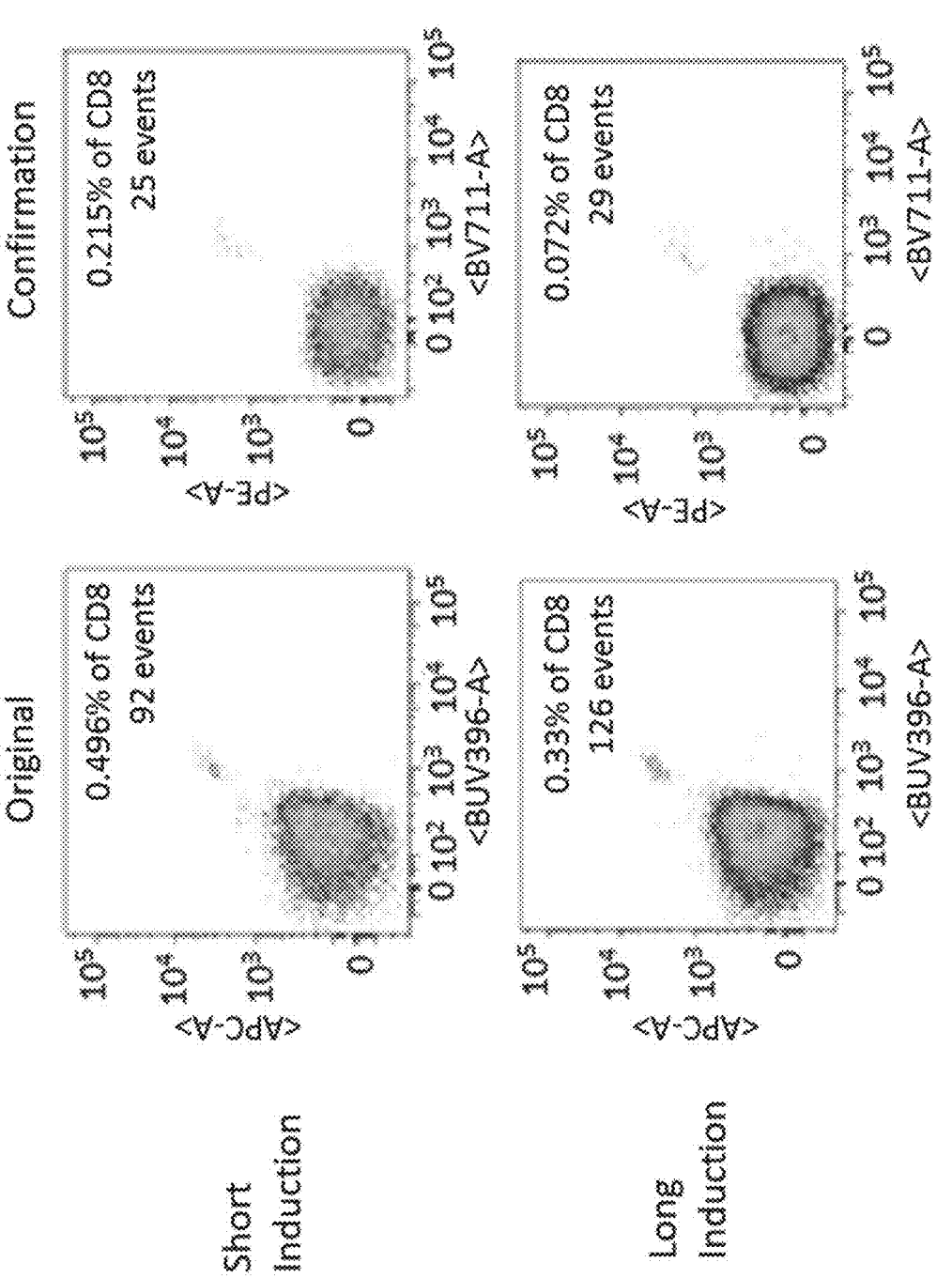
FIG. 14 depicts example flow cytometric analyses showing antigen specific CD8$^+$ naïve T cell responses to short HIV3 peptides using a whole PBMC sample from a human donor.
Figure 15:
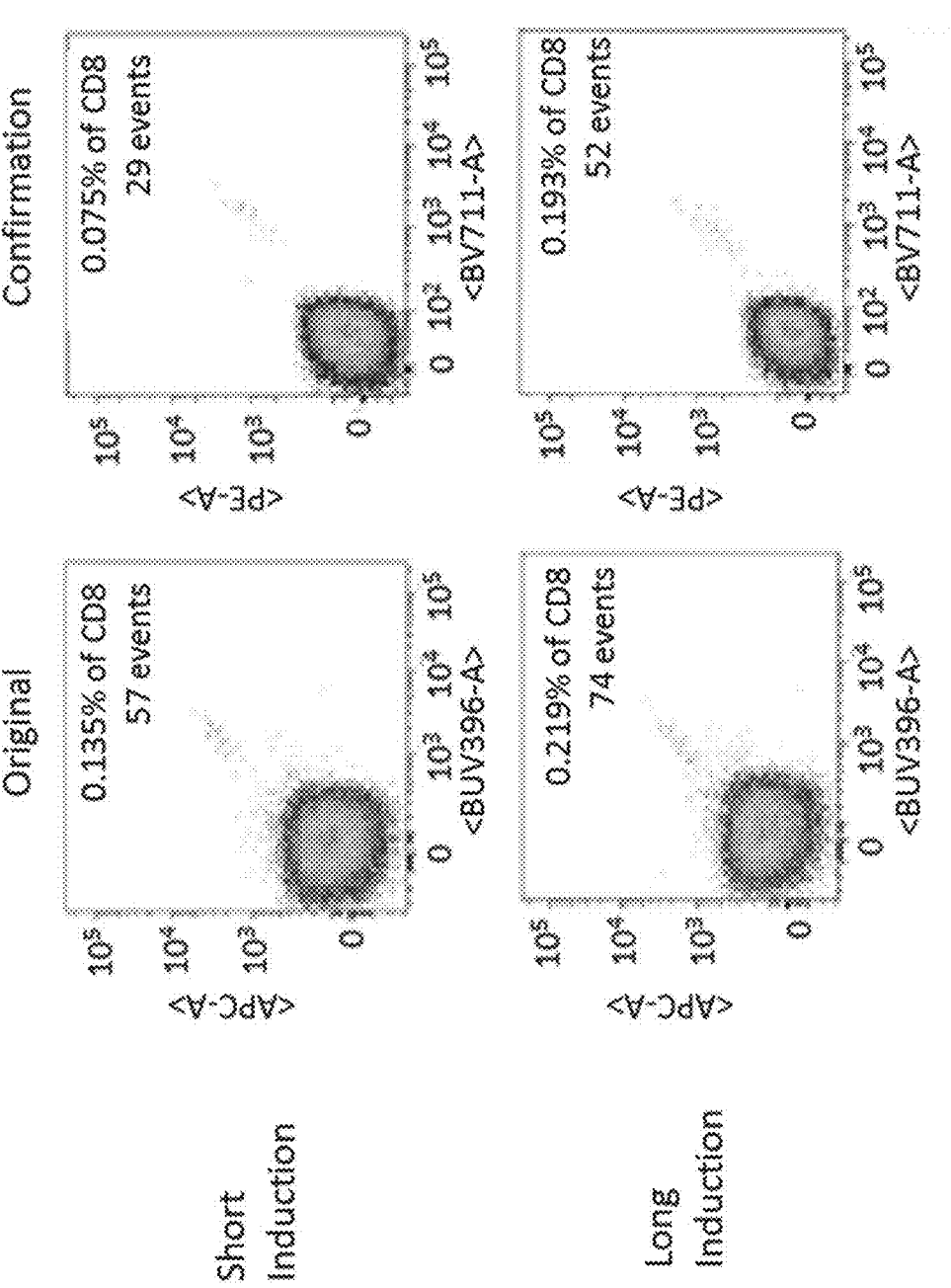
FIG. 15 depicts example flow cytometric analyses showing antigen specific CD8$^+$ naïve T cell responses to long CSNK1A1 peptides using a whole PBMC sample from a human donor.
Figure 16:
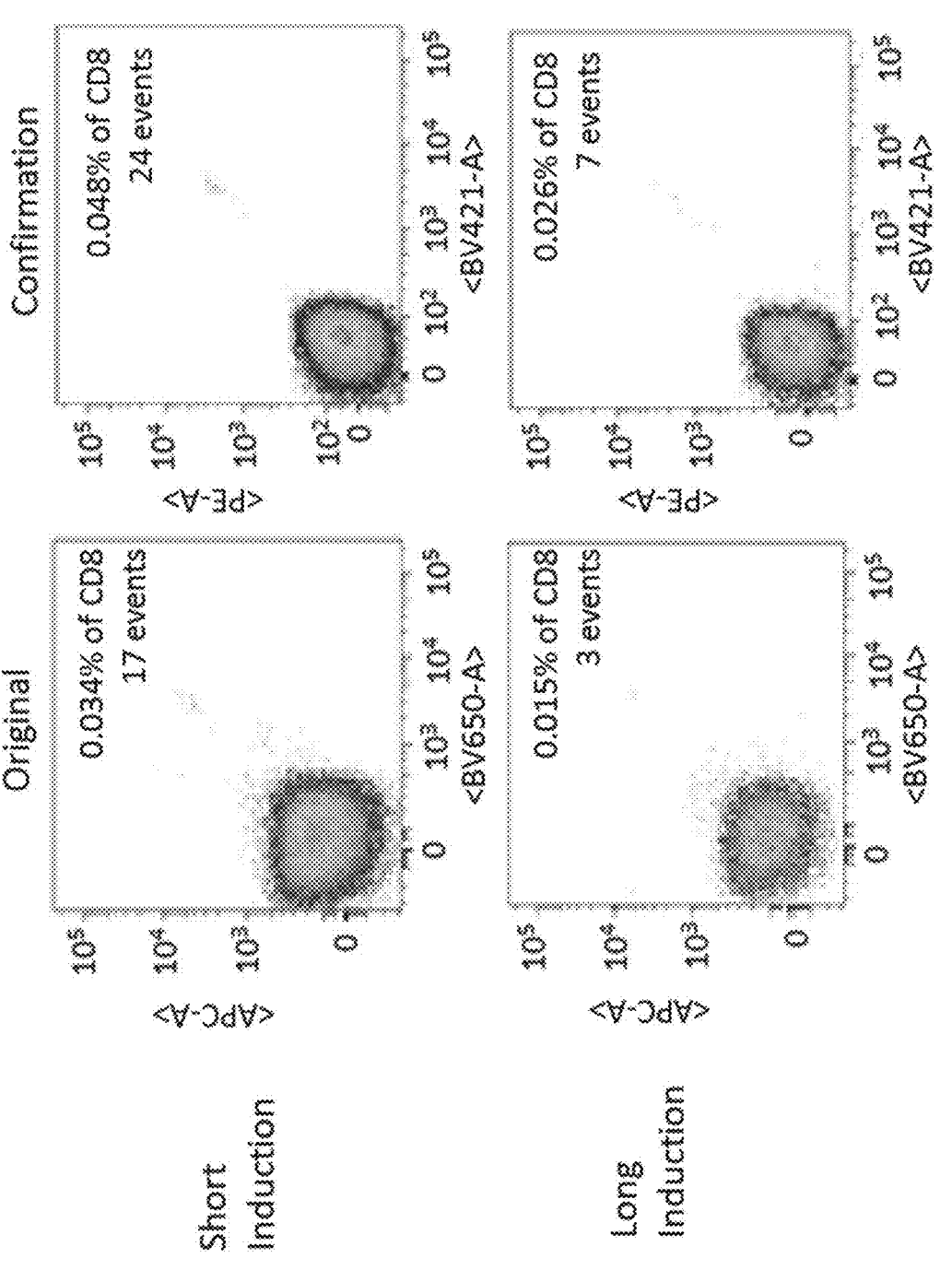
FIG. 16 depicts example flow cytometric analyses showing antigen specific CD8$^+$ naïve T cell responses to long CSNK1A1 peptides using a PBMC sample from a human donor that was depleted of CD25$^+$ cells.
Figure 17:
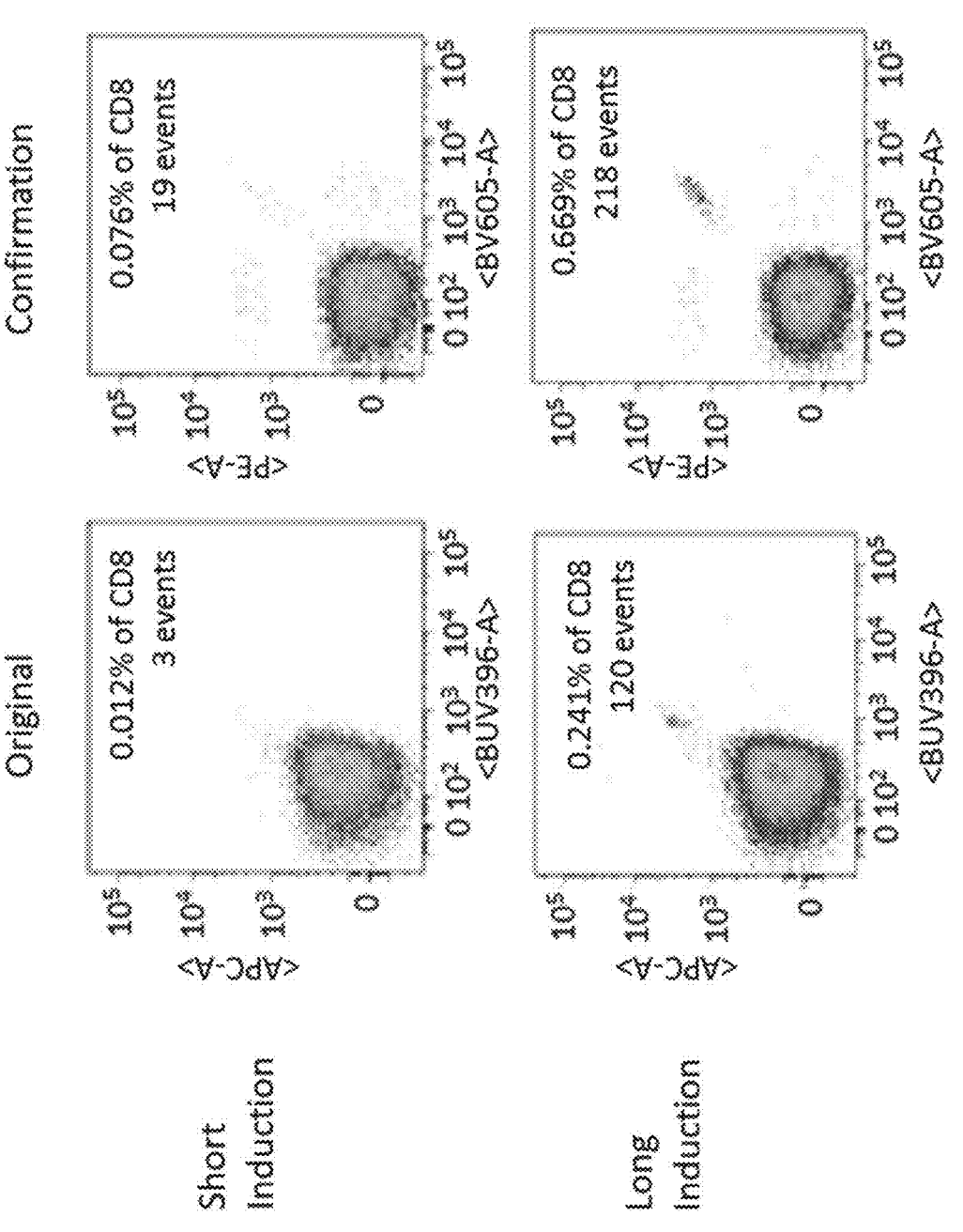
FIG. 17 depicts example flow cytometric analyses showing antigen specific CD8$^+$ naïve T cell responses to short GAS7 peptides using a PBMC sample from a human donor that was depleted of CD25$^+$ cells.
Figure 18:
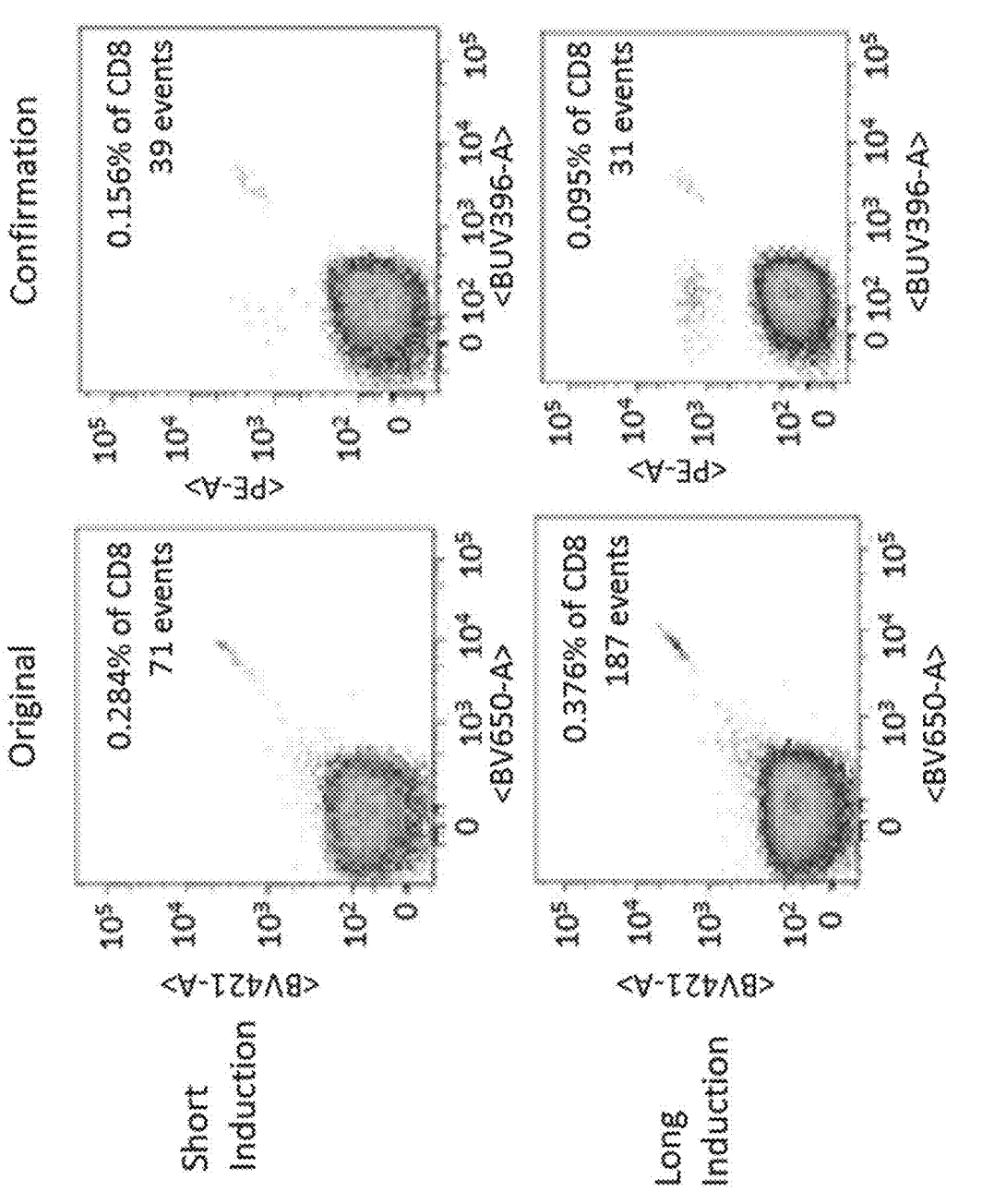
FIG. 18 depicts example flow cytometric analyses showing antigen specific CD8$^+$ naïve T cell responses to short ACTN4 peptides using a PBMC sample from a human donor that was depleted of CD25$^+$ cells.
Figures 19A, 19B:
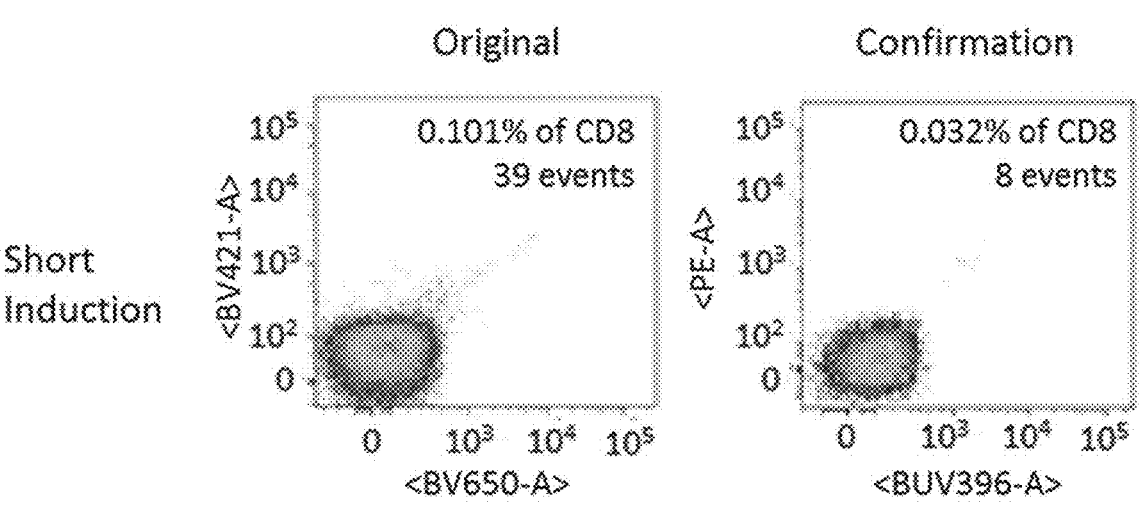
FIG. 19A depicts example flow cytometric analyses showing antigen specific CD8$^+$ naïve T cell responses to short ACTN4 peptides using a PBMC sample from a human donor that was depleted of CD25$^+$ cells. A short term induction is shown.
FIG. 19B depicts example flow cytometric analyses showing antigen specific CD8$^+$ naïve T cell responses to short HIV3 peptides using a PBMC sample from a human donor that was depleted of CD25$^+$ cells. A long term induction is shown.
Figure 20:
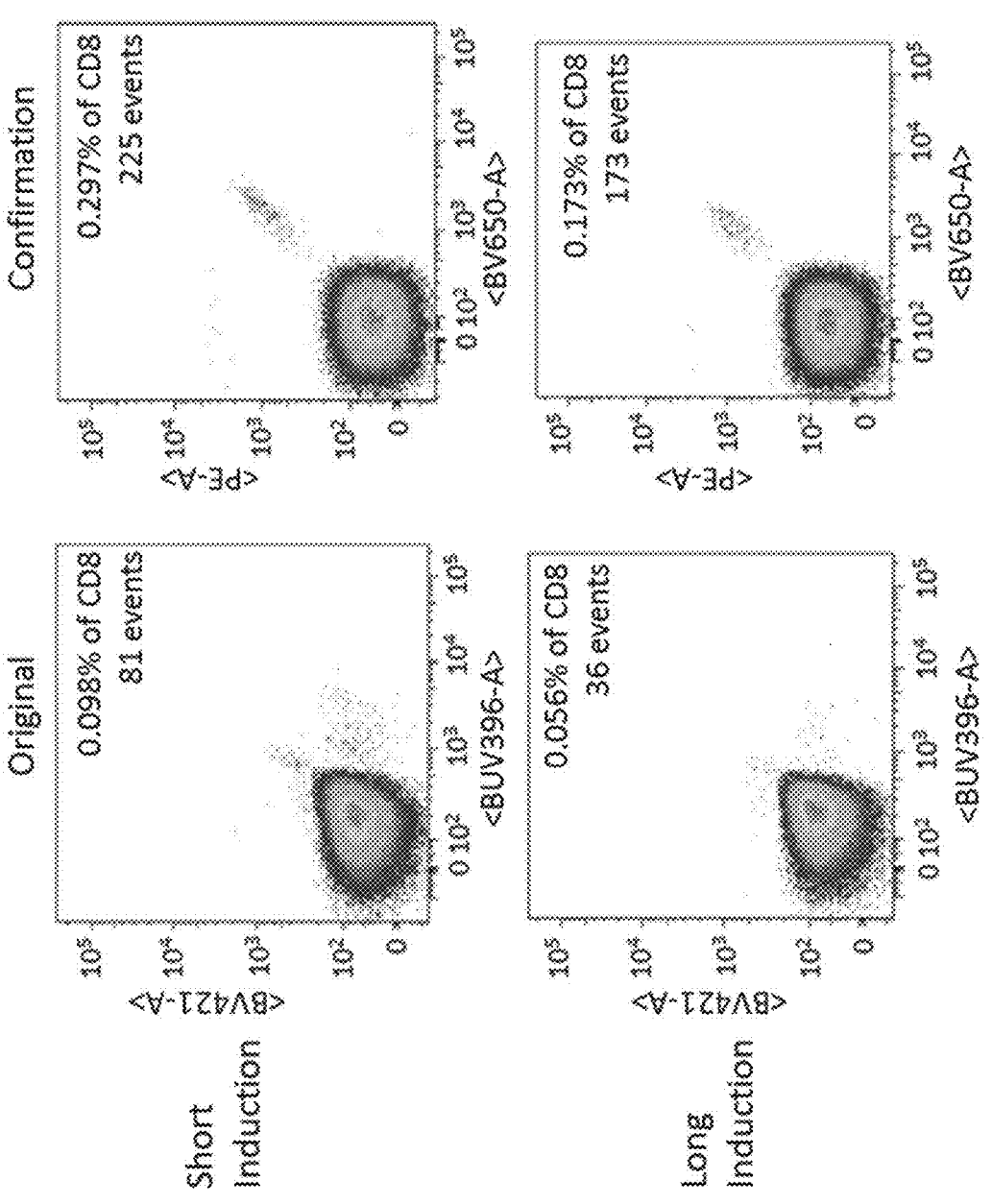
FIG. 20 depicts example flow cytometric analyses of antigen specific CD8$^+$ naïve T cell responses to short HIV5 peptides using a whole PBMC sample from a human donor. Both short and long term inductions are shown.
Figure 21:
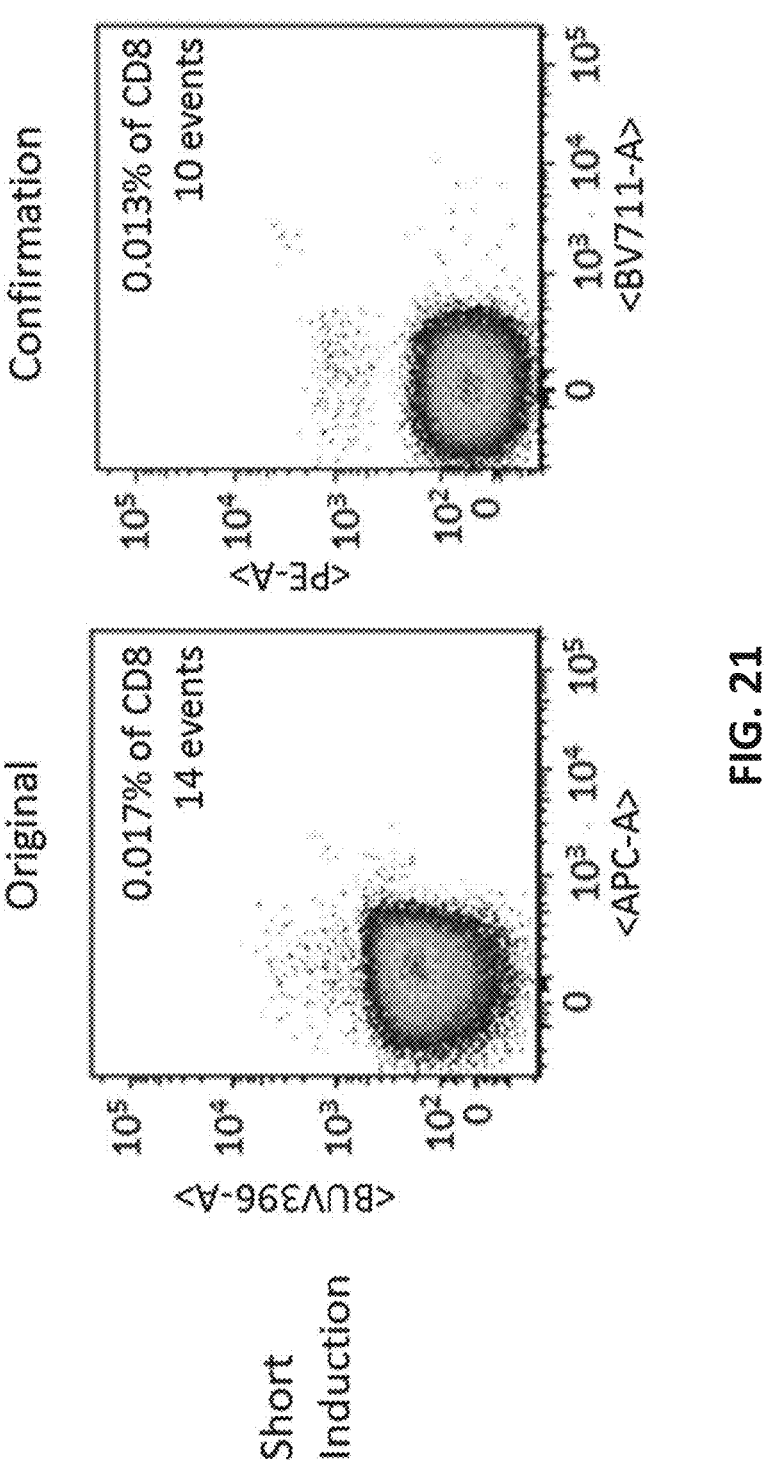
FIG. 21 depicts example flow cytometric analyses showing antigen specific CD8$^+$ naïve T cell responses to short HIV3 peptides using a whole PBMC sample from a human donor. A short term induction is shown.
Figure 22:
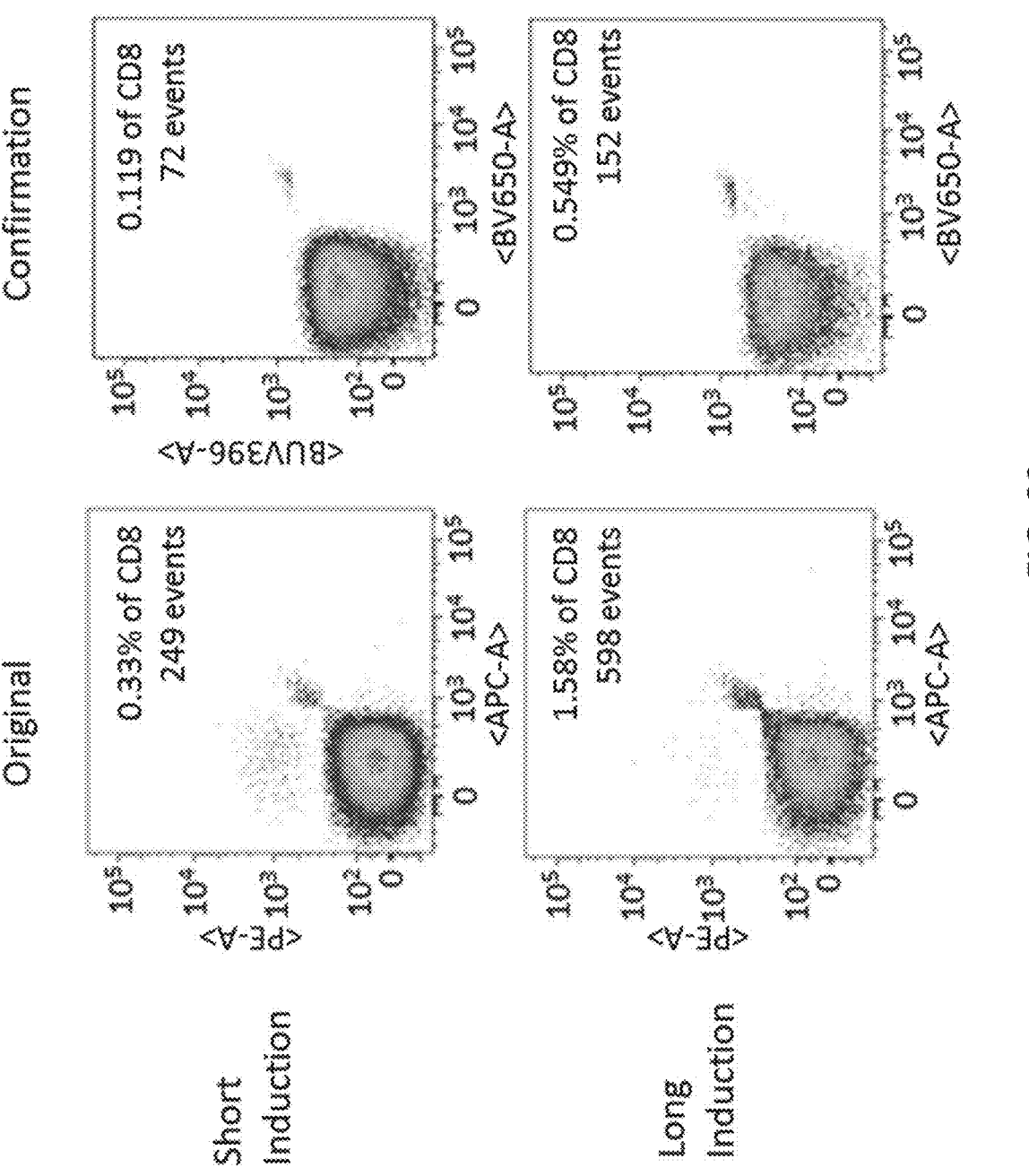
FIG. 22 depicts example flow cytometric analyses showing antigen specific CD8$^+$ naïve T cell responses to short PRDX5 peptides using a PBMC sample from a human donor that was depleted of CD25$^+$ cells. Both very short and long term inductions are shown.
Figure 23:
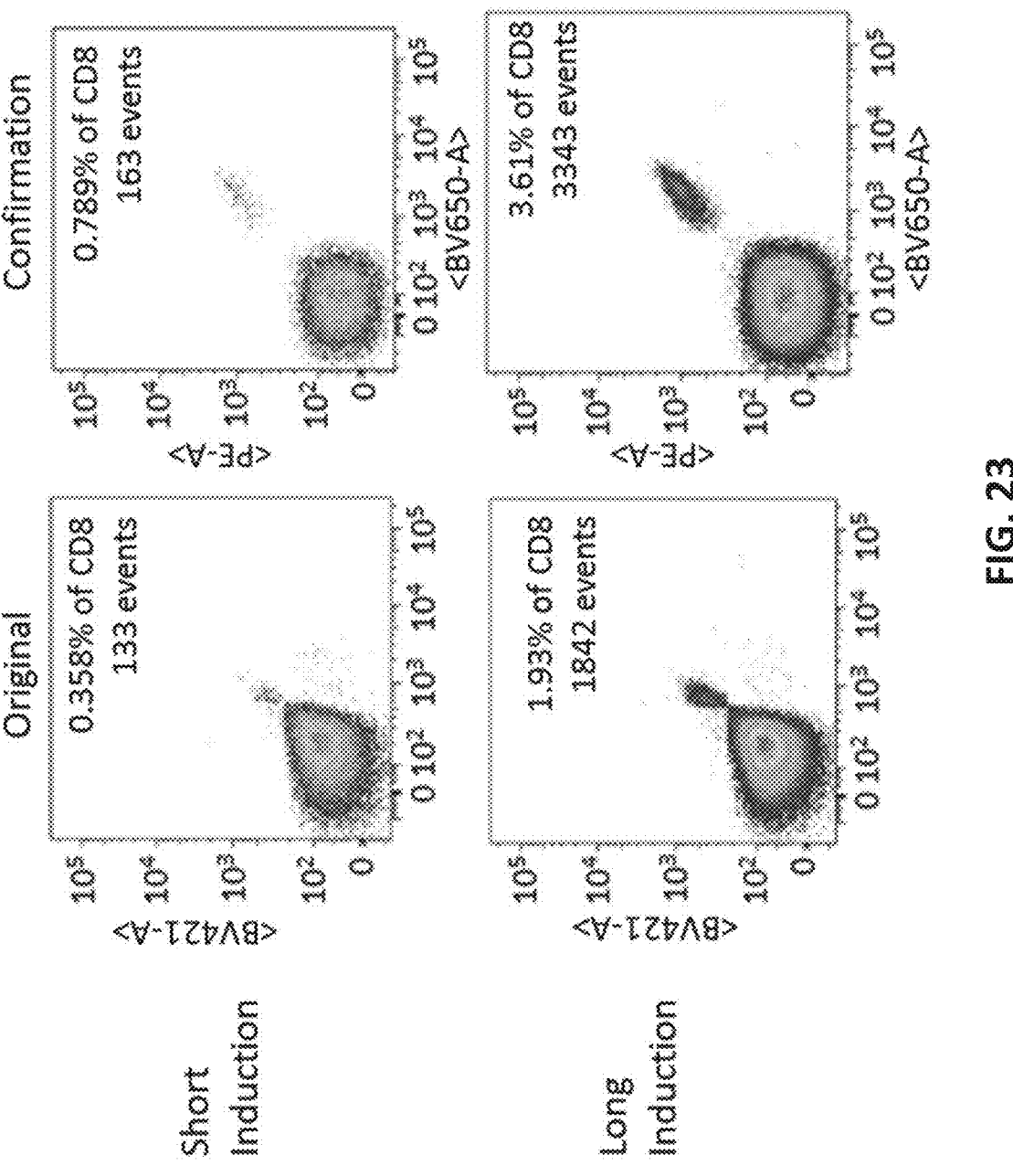
FIG. 23 depicts example flow cytometric analyses showing antigen specific CD8$^+$ naïve T cell responses to short HIV5 peptides using a PBMC sample from a human donor that was depleted of CD25$^+$ cells tides. Both short and long term inductions are shown.

CD4$^+$ T cell responses towards previously identified neo-antigens (PINs) can be induced using an ex vivo induction protocol, such as protocol 1 or 2 described above. In this example, CD4$^+$ T cell responses were identified by monitoring IFNγ production in an antigen specific manner using protocol 1. FIG. 10 shows representative examples of such flow cytometric analysis. Finally, specificity of CD4$^+$ T cell responses for the mutant peptide and not the wildtype was shown by stimulation the induced T cell populations either with mutant or wildtype peptide (FIG. 11).

Example 6—Naïve CD8$^+$ T Cell Induction

Naïve CD8$^+$ T cell induction was analyzed by flow cytometry after T cell manufacturing using protocol 1 or protocol 2. The PBMC samples were from a human donor 1 or human donor 2, and either whole PBMCs or CD25$^-$ depleted PBMCs. The cell samples were analyzed after short or long induction according to the protocols in FIG. 1. Naïve CD8$^+$ Responses of the induced CD8$^+$ T cells were analyzed against different peptides and were plotted in FIGS. 12-23.

Example 7—CD8$^+$ Naïve T Cell Responses

Figure 7:
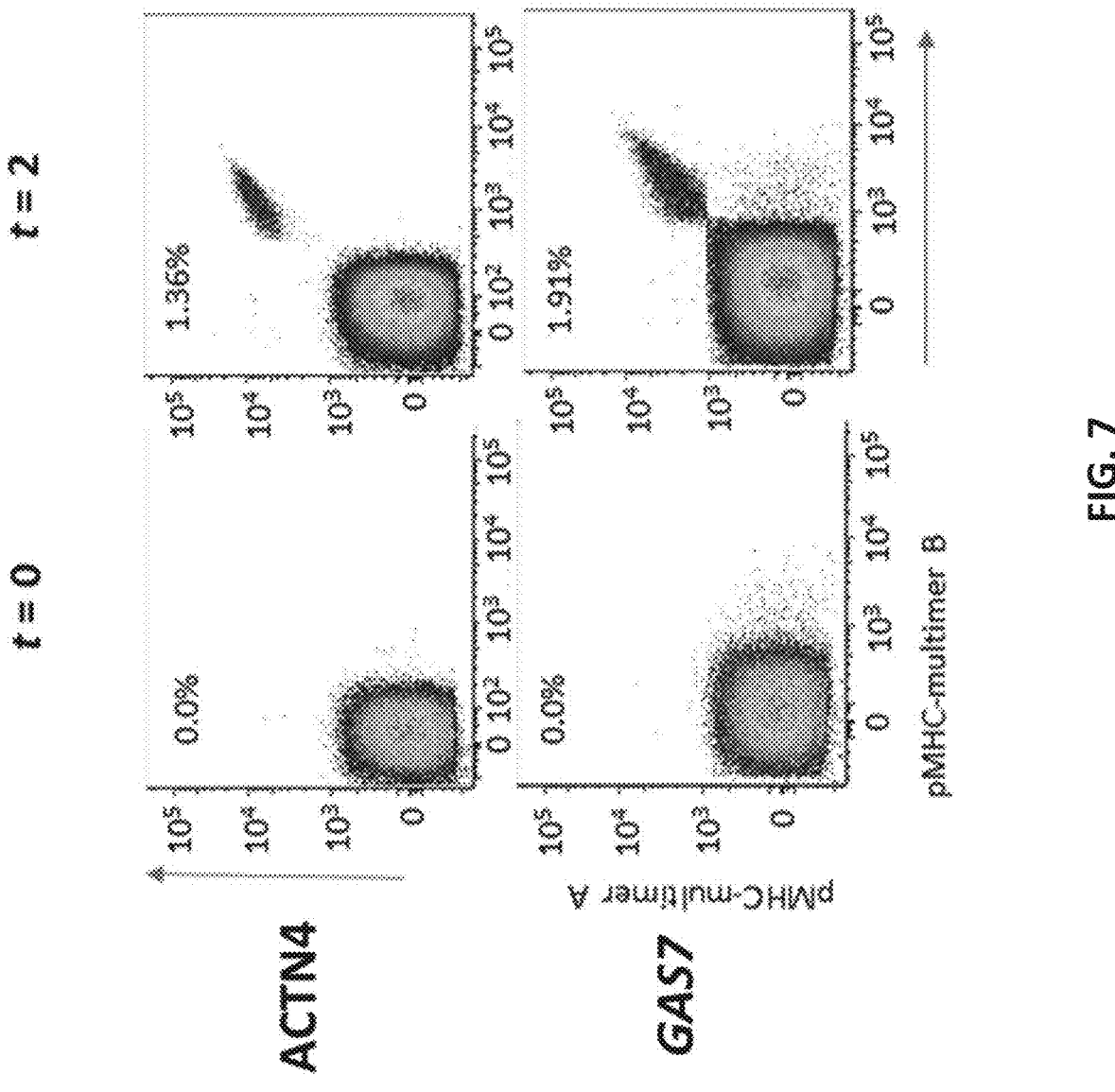
FIG. 7 depicts example flow cytometry plots of antigen specific CD8$^+$ T cell responses to the indicated mutated epitopes in a healthy donor prior to stimulation and after up to three rounds of stimulation.
Figure 8A:
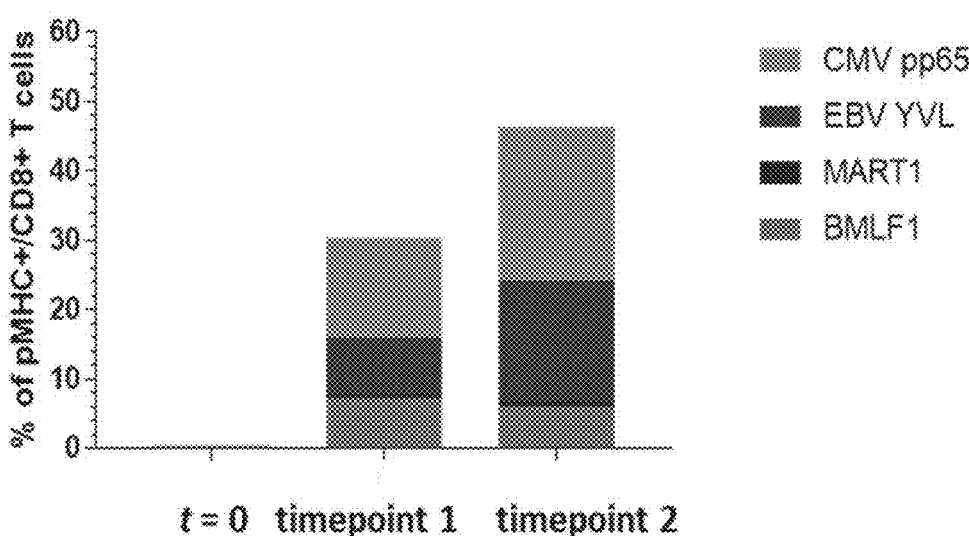
FIG. 8A depicts an example bar graph showing results of antigen specific memory CD8$^+$ T cell responses to viral antigens. After up to three rounds of stimulation, approximately 50% of all CD8$^+$ T cells were specific for the indicated viral epitopes (CMV pp65, EBV YVL, EBV BMLF1 and Mart-1).
Figure 8B:
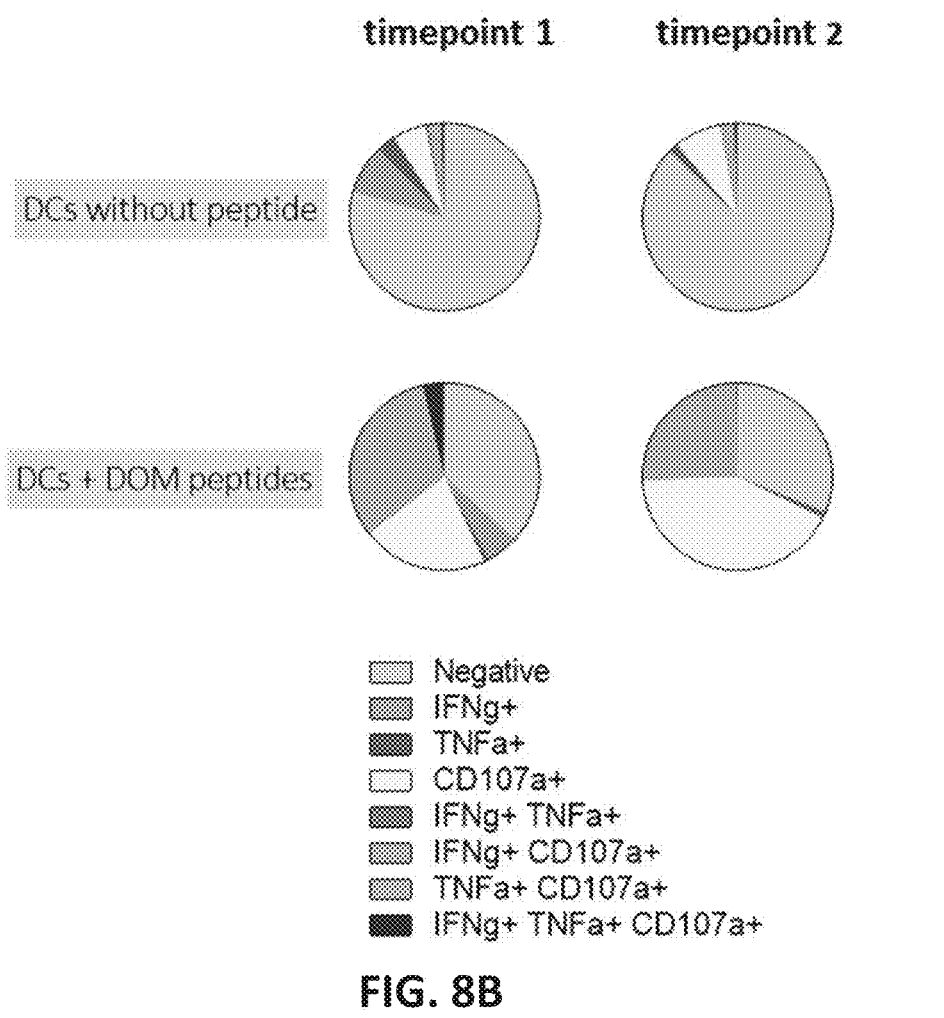
FIG. 8B depicts example results of a recall assay of antigen specific memory CD8$^+$ T cell responses to peptide loaded antigen presenting cells and then incubated with APCs with and without loaded viral antigens. The fraction of CD8$^+$ T cells from two time points that release the indicated cytokines are depicted in the charts.

The T cell manufacturing protocols in Example 1 can successfully be used to induce CD8$^+$ T cell responses from the naïve compartment. FIG. 7 shows representative flow plots of two CD8$^+$ T cell responses that were generated toward mutated epitopes in a healthy donor after two rounds of stimulation. Moreover, CD8$^+$ T cell responses from the memory compartment can be expanded to high numbers. In the representative example shown in FIG. 8A, after up to three rounds of stimulation, approximately 50% of all CD8$^+$ T cells were specific for the immune dominant epitopes, CMV pp65, EBV YVL, EBV BMLF1 and Mart-1. The induced CD8$^+$ memory responses demonstrate poly-functionality in a peptide recall assay (degranulation and cytokine release, FIG. 8B).

Example 8—Flow Cytometry Analysis of T Cells

Figure 5A:
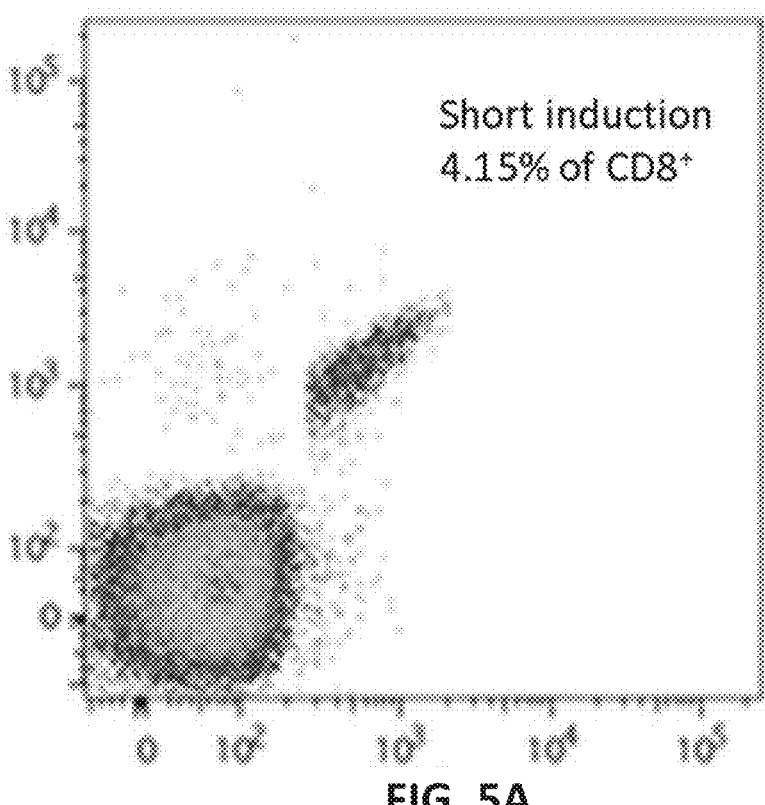
FIG. 5A depicts an example flow cytometry analysis of antigen specific CD8$^+$ naïve T cell responses to a single previously identified neoantigen (PIN) under the indicated conditions.
Figure 5B:
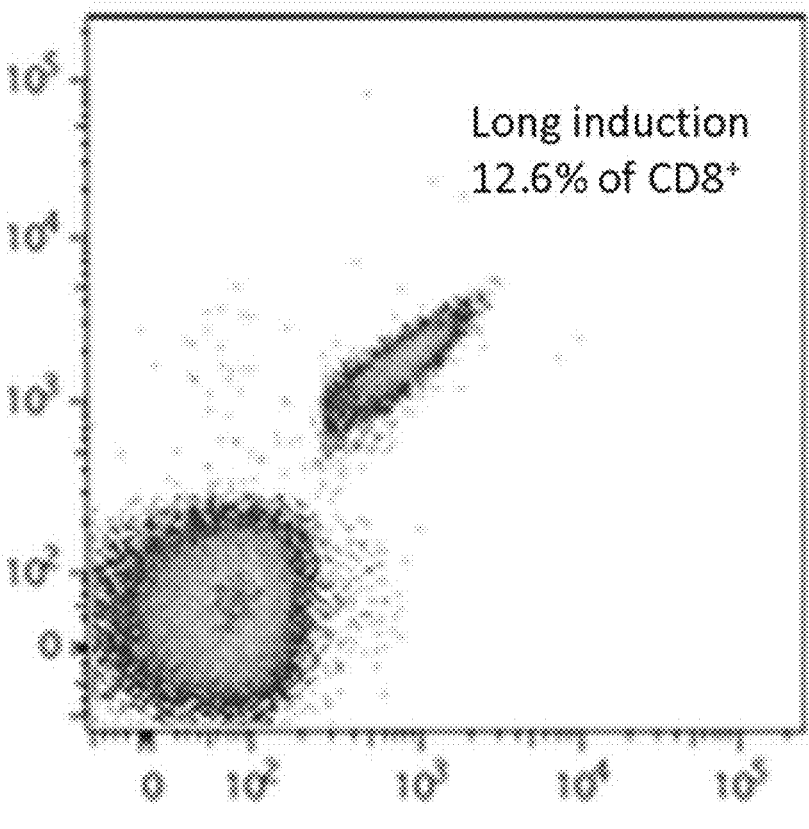
FIG. 5B depicts an example flow cytometry analysis of antigen specific CD8$^+$ naïve T cell responses to a single previously identified neoantigens (PIN) under the indicated conditions.

FIG. 5A depicts an exemplary flow cytometry analysis of ME-1 response of CD8$^+$ naïve T cells induced under condition indicated in the figure using protocol 2. FIG. 5B depicts an example of flow cytometry analysis of ME-1 response of CD8$^+$ naïve T cells induced under longmer induction indicated in the figure. 12.6% of CD8$^+$ T cells were observed to be specific to ME-1 after a long induction.

Example 9—Cytotoxicity Assay of Induced T Cells

Figure 9:
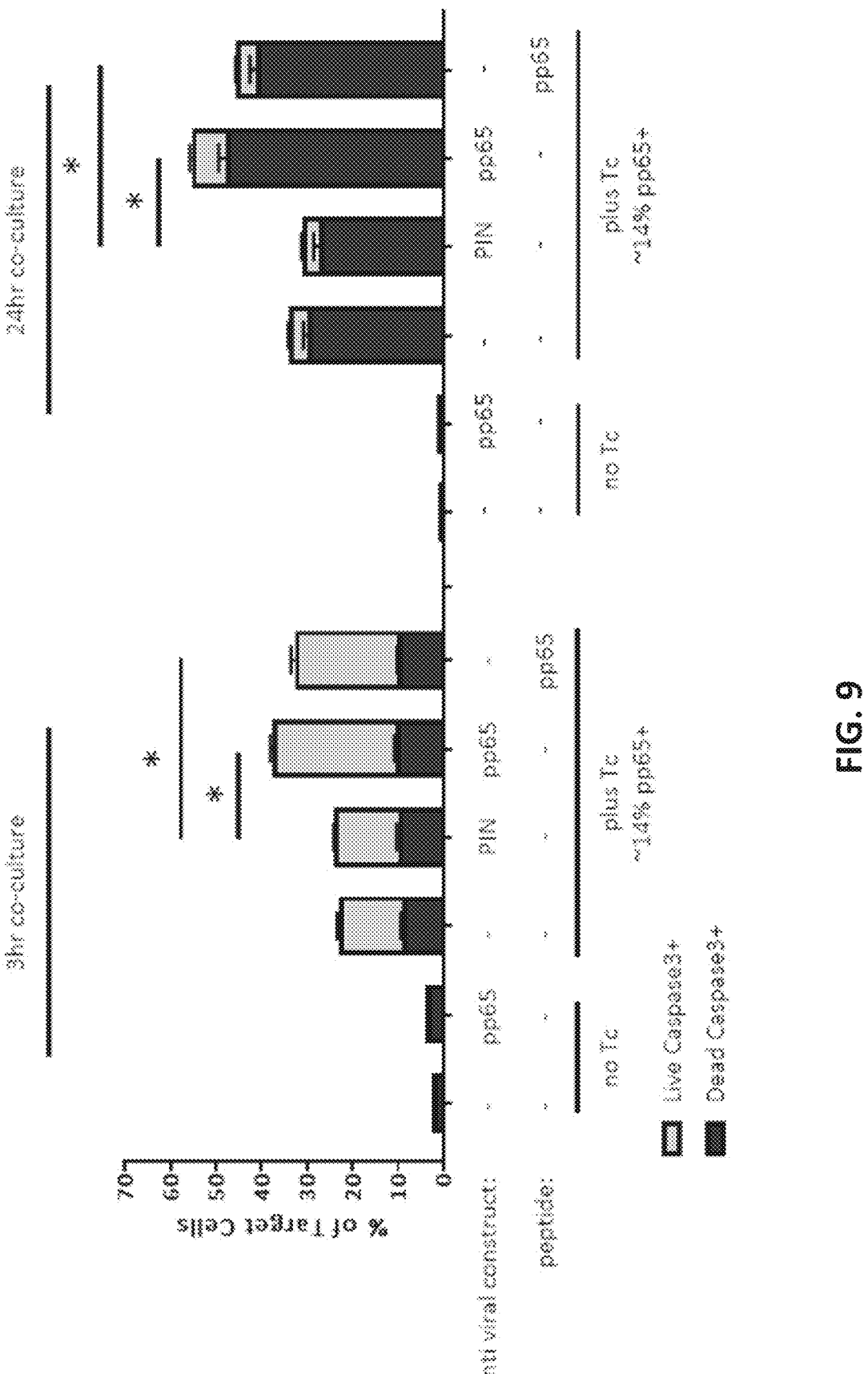
FIG. 9 depicts an example result of a cytotoxicity assay used to assess whether the induced T cell cultures can kill antigen expressing tumor cell lines. The fractions of live and dead caspase 3 positive tumor cells to total tumor cells are shown. Caspase 3 positive alive tumor cells indicate cells undergoing early cell death.

A cytotoxicity assay was used to assess whether the induced T cell cultures can kill antigen expressing tumor lines. In this example, expression of active caspase 3 on alive and dead tumor cells was measured to quantify early cell death and dead tumor cells. In FIG. 9, the induced CD8$^+$ memory responses were capable of killing antigen expressing tumor targets.

Example 10—Phenotypic Analysis of Generated CD8$^+$ T Cells

To analyze the phenotypic expression, $1\times10^4$ to $1\times10^6$ T cells of each culture was washed in PBS containing 0.1-10% FBS and 0.1% sodium azide (FBS-PBS) and resuspended in cytokine concentrations was quantitated by Microplate computer software (Bio-Rad) using a double eight-point standard curve.

Example 12—Protocol 1 and Protocol 2: Summary

In this example, a summary of results from Protocol 1 and Protocol 2 stimulation protocols is provided in the table below.

TABLE 1

| | | Summary of results from protocols 1 and 2 | | | | | |
|---|---|---|---|---|---|---|---|
| | | Prot. 1 CD14$^{depleted}$/CD25$^{depleted}$ | | Prot. 2 | | | |
| | | | | CD25$^{depleted}$ | | CD14$^{depleted}$ CD25$^{depleted}$ | FLT3L × 3 |
| | | LTS 37 | LTS 38 | LTS 37 | LTS 38 | LTS 38 | LTS 38 |
| CD8 Memory | Bulk Fold expansion | 30-1200 | 20-5000 | 20-100 | 5-100 | 5-100 | 5-100 |
| | Absolute # | $1\text{-}50 \times 10^6$ | $20\text{-}1000 \times 10^6$ | $0.1\text{-}1 \times 10^6$ | $2\text{-}10 \times 10^6$ | $2\text{-}20 \times 10^6$ | $0.5\text{-}10 \times 10^6$ |
| | Functionality | decreased at stim 3 | decreased at stim 3 | maintained at stim 3 | maintained at stim 3 | maintained at stim 3 | maintained at stim 3 |
| CD8 Naïve | Hit rate per well | 20-40% | 0-40% | 20-30% | 0-20% | 10% | 0-10% |
| | Hit rate per peptide | 1-3 out of 11 | 0-4 out of 11 | 2 out of 11 | 1 out of 11 | 1-3 out of 11 | 1-2 out of 11 |
| | Absolute # | $0.1\text{-}1 \times 10^6$ | — | $0.01\text{-}0.5 \times 10^6$ | — | — | — |
| | Functionality | TBD* | TBD | TBD | TBD | TBD | TBD |
| CD4 Naïve | Hit rate/well | 78-100% | 56% | 10-100% | 50% | 70% | TBD |
| | Hit rate/peptide | TBD | TBD | TBD | TBD | TBD | TBD |
| | Absolute # | TBD | TBD | TBD | TBD | TBD | TBD |
| | Functionality | good | good | good | TBD | TBD | TBD |

TBD* = To be determined

FBS-PBS containing a 1:100 dilution of fluorochrome-labeled antibody (CD45RA and CD62L). After incubation on ice, the cells were washed and fixed for flow cytometric analysis. If the selected CD8$^+$ T cell cultures express CD62L but not CD45RA, regardless of their reactivity to the various peptides, it can indicate that the selected T cell cultures belong to the CD8$^+$ memory T cell subset.

Example 11—Cytokine Production of CD8$^+$ T Cells

The cytokine profile of CD8$^+$ T cell cultures can be analyzed. T cell cultures will be first challenged with autologous APC pulsed with the antigen peptides. The cytokine profile was determined quantitatively using ELISA kits (PharMingen, San Diego, Calif.). Microtiter plates (96-Wells, NUNC Maxisorp) were coated overnight at 4° C. with 0.2-4 μg/well of a purified mouse capturing monoclonal antibody to human cytokine (IL-4, IL-10, TNF-αt, IFN-γ) (PharMingen). Plates were washed and non-specific binding sites will be saturated with 1000 (w/v) fetal bovine serum (FBS) for 0.5-3 hours and subsequently washed. Superatants and cytokine standards will be diluted with PBS and added in duplicate Wells. Plates will be incubated at 37° C. for 1-3 hours and subsequently washed with PBS-T. Matched biotinylated detecting antibody will be added to each well and incubated at room temperature for 1-3 hours. After washing, avidin-conjugated horseradish peroxidase was added and incubated for 0.5-3 hours. 3,3',5,5'-tetramethylbenzidine (TMB, Sigma) was used as a substrate for color development. Optical density was measured at 450 nm using an ELISA reader (Bio-Rad Laboratories, Hercules, Calif) and

Example 13—Protocol 1 and 2 Parameter Testing

An example experiment for testing parameters of the protocols can be to test protocol 1 in patient samples at small scale. Another example experiment for testing parameters of the protocols can be to characterize the T cell products generated in previous batches, including testing functionality of CD4$^+$ T cells and CD8$^+$ T cells and sorting antigen specific cells and characterizing by single cell RNAseq. Another example of an experiment for testing parameters of the protocols can be to test addition of poly-ICLC/aCD40L during DC Prep and quantify T cell enrichment. Another example experiment for testing parameters of the protocols can be to test functionality of induced CD8$^+$ naïve T cell responses, including assessing antigen specific cytotoxicity in killing assay, performing peptide recall assay with a broader flow panel to measure differentiation and exhaustion, determining sensitivity (peptide titration) and specificity (WT vs mutant, pool deconvolution) for a subset of hits, and enriching for CD8$^+$ to remove the possibility of bystander effects from antigen specific CD4$^+$ T cells. Another example experiment for testing parameters of the protocols can be to interrogate functionality, determining sensitivity (peptide titration) and specificity (WT vs mutant, pool deconvolution) for a subset of hits, performing a recall assay with a differentiation and exhaustion flow panel to better understand the phenotype. Another example experiment for testing parameters of the protocols can be to sort antigen specific T cells (CD8$^+$ memory, CD8$^+$ naïve, CD4$^+$ naïve) and profile by single cell RNAseq, including comparing phenotype of different inductions, comparing phenotype of inductions from different compartments, examining kinetics.

Example 14—T Cell Inputs Depleted of CD14 and/or CD25 Expressing Cells Improve Induction of CD4+ and CD8+ Naïve T Cells Table 2 below shows results from the protocol 1 T cell preparation method demonstrating that CD14−/CD25− depletion can increase CD8+ naïve hit rate and have a consistent CD4+ hit rate.

TABLE 2

| CD14−/CD25− depletion results | | | | |
|---|---|---|---|---|
| | LTS#33 | CD14− | CD25− | CD14−/CD25− |
| CD8 naïve hit rate % | HD34 | 20 | 30 | 50 |
| | HD35 | 0 | 0 | 10 |
| | Average | 10 | 15 | 30 |

TABLE 2-continued

| CD14−/CD25− depletion results | | | | |
|---|---|---|---|---|
| | LTS#33 | CD14− | CD25− | CD14−/CD25− |
| CD4 naïve hit rate % | HD34 | 100 | 80 | 90 |
| | HD35 | 100 | 100 | 100 |
| | Average | 100 | 90 | 95 |

Example 15—CD8 Naïve Inductions Significantly Improved with Use of Protocol 2

Tables 3A and 3B below shows results from both protocol 1 and protocol 2 T cell preparation method described herein. In the two human donors tested, CD8+ naïve inductions significantly improved using depletion of CD25 expressing cells or depletion of CD25 and CD14 expressing cells compared to using depletion of CD14 expressing cells. CD8+ naïve inductions also significantly improved using FLT3L stimulation.

TABLE 3A

| | | Prot. 1 (CD25 depleted) 1/13 confirmed 7.5% success rate | | | | Prot. 2 (bulk) 3/13 confirmed 23% success rate | | | | Prot. 2 (CD25 depleted) 5/13 confirmed 39% success rate | | | |
|---|---|---|---|---|---|---|---|---|---|---|---|---|---|
| | | day 19 | | day 26 | | day 19 | | day 26 | | day 19 | | day 26 | |
| | HD35 | initial | confirmation | initial | confirmation | initial | confirmation | initial | confirmation | initial | confirmation | initial | confirmation |
| Induced with short peptides | HIV replicate 1 | | | | | | | | | | | | |
| | HIV replicate 2 | | | | | | | | | | | | |
| | HIV replicate 3 | | | | | | | | | | | | |
| | HIV replicate 4 | | | | | | | | | | | HIV-3 0.226% | HIV-3 0.0203% |
| | HIV replicate 5 | HIV-5 * 0.0327% | HIV-5 * 0.0691% | HIV-5 | HIV-5 | HIV-3 0.496% | HIV-3 0.215% | HIV-3 0.33% | HIV-3 0.0722% | | | | |
| | PIN replicate 1 | | | | | | | | | | | | |
| | PIN replicate 2 | | | | | CSNK 1A1 0.135% | CSNK 1A1 0.0747% | CSNK 1A1 0.219% | CSNK 1A1 0.193% | | | | |
| | PIN replicate 3 | | | | | | | | | | | | |
| | PIN replicate 4 | | | | | ME-1 4.15% | ME-1 0.927% | ME-1 12.6% | ME-1 2.34% | GAS7/ ACTN4 0.012/ 0.284% | GAS7/ ACTN4 0.076/ 0.156% | GAS7/ ACTN4 0.241/ 0.376% | GAS7/ ACTN4 0.669/ 0.095% |
| | PIN replicate 5 | | | | | | | | | ACTN4 0.101% | ACTN4 0.032% | | |
| Long | PIN LONG replicate 1 | | | | | | | | | CSNK1A1 0.0342% | CSNK1A1 0.0482% | CSNK1A1 0.0156% | CSNK1A1 0.0265% |
| | PIN LONG replicate 2 | | | | | | | | | | | | |

TABLE 3A-continued

| CD8+ naïve induction results from HD35 | | | | | | | | | | | |
| | Prot. 1 (CD25 depleted) 1/13 confirmed 7.5% success rate | | | | Prot. 2 (bulk) 3/13 confirmed 23% success rate | | | | Prot. 2 (CD25 depleted) 5/13 confirmed 39% success rate | | | |
| | day 19 | | day 26 | | day 19 | | day 26 | | day 19 | | day 26 | |
| HD35 | initial | confir-mation | initial | confir-mation | initial | confir-mation | initial | confir-mation | initial | confir-mation | initial | confir-mation |
| PIN LONG replicate 3 | | | | | | | | | | | | |

TABLE 3B

| CD8+ naïve induction results from HD34 | | | | | | | | | | | | |
| | Prot. 1 0/13 confirmed 0% success rate | | | | Prot. 2 bulk input 2/13 confirmed 15% success rate | | | | Prot. 2 CD25 depleted input 2/13 confirmed 15% success rate | | | |
| | day 19 | | day 26 | | day 19 | | day 26 | | day 19 | | day 26 | |
| HD34 | initial | confir-mation | initial | confir-mation | initial | confir-mation | initial | confir-mation | initial | confir-mation | initial | confir-mation |
| Induced with short HIV replicate 1 | | | | | | | | | HIV-5 0.358% | HIV-5 0.789% | HIV-5 1.93% | HIV-5 3.61% |
| HIV replicate 2 | | | | | HIV-3 & HIV-5 0.017/0.09% | HIV-3 & HIV-5 0.013/0.279% | HIV-5 0.0556% | HIV-5 0.173% | | | | |
| HIV replicate 3 | | | | | | | | | | | | |
| HIV replicate 4 | | | | | | | | | | | | |
| HIV replicate 5 | | | | | | | | | | | | |
| PIN replicate 1 | | | | | | | | | PRDX5 0.33% | PRDX5 0.119% | PRDX5 1.58% | PRDX5 0.549% |
| PIN replicate 2 | | | | | | | | | | | | |
| PIN replicate 3 | | | | | | | | | | | | |
| PIN replicate 4 | | | | | | | | | | | | |
| PIN replicate 5 | | | | | | | | | | | | |

Example 16—UV Mediated Peptide Exchange Assay to pMHC Specific Reagents

Antigen specific pMHC multimers are generated through UV mediated peptide exchange of HLA specific monomers and subsequent multimerization. These were used for detecting antigen specific T cells.

UV-mediated cleavage of the conditional ligand can be time dependent. With the set-up described below, peptide cleavage can be detected after 1 min and can be essentially complete after approximately 15 min. A 30 to 60 min incubation time can be normally used to ensure optimal exchange of the conditional ligand with the peptide of interest. Protein concentration may influence the rate of UV-mediated cleavage, as both the nitrophenyl moiety and the reaction product absorb long wavelength UV light. In addition, path length may affect the reaction speed. Empty, peptide receptive MHC molecules that are formed upon UV exposure can be rescued by performing the UV-mediated cleavage in the presence of an MHC ligand of interest. In most experiments, a 100 fold molar excess of peptide over MHC is used. UV induced peptide exchange is routinely performed using 25 μg/mL of UV sensitive MHC class I complexes. However, peptide exchange reactions may be performed with MHC class I concentrations up to 100-200 μg/mL.

Materials:

96-well plates (cat. #: 651201 polypropylene microplate 96 well V sharp, Greiner Bio-one) UV-lamp 366 nm CAMAG UV Cabinet 3 (catalog #: 022.9070, CAMAG) fitted with UV Lamp long-wave UV, 366 nm, 2×8 W (cat. #: 022.9115, CAMAG) or Uvitec tube light, with 2×15W, 365 nm blacklight blue tubes (Model—LI215BLB sizes L×W×H 505×140×117 mm)

Centrifuge with rotor for microtiter plates.

Procedure:

1. In a 96-well plate, add the following reagents to each well as shown in Table 4:

TABLE 4

| Reagent | Amount | Final concentration |
|---|---|---|
| PBS | 100 μL | Not applicable |
| 10x Exchange peptide (500 μM in PBS) | 12.5 μL | 50 μM |
| 10x UV-sensitive MHC class I molecules (250 μg/mL; ~5 μM) | 12.5 μL | 25 μg/mL (approx. 0.5 μM) |

2. Place the 96-well plate under a UV lamp (366 nm) for 1 hr., with a distance between the UV lamp and sample of approximately 5 cm.

3. Spin the plate at 3,300 g for 5 minutes. Transfer 100 μL of supernatant (keep the plate at an angle to avoid transferring any pellet) to a new 96-well plate for downstream applications.

Example 17—Assemble Fluorochrome Conjugated pMHC Multimers

MHC class I complexes may be complexed with fluorophore-labeled streptavidin to form MHC class I tetramers for T cell analysis. Commonly used fluorophores include allophycocyanin and phycoerythrin, and the formation of MHC multimers with these conjugates is described below. However, streptavidin-coated quantum dots or any streptavidin-coupled fluorophores may also be used to prepare MHC multimers for T cell detection.

Materials:

PE-streptavidin solution 1 mg/mL (cat. #: S866, Molecular Probes) or APC streptavidin solution 1 mg/mL (cat. #: S868, Molecular Probes)

Microtiter plates with exchanged MHC class I complexes, containing 25 μg/mL of pMHC in 100 μL/well. This corresponds to 2.5 μg or 0.05 nmol MHC class I per well.

Procedure:

1. Generate dilutions of 27 μg/mL of streptavidin-PE in PBS, or of 14.6 μg/mL of streptavidin-APC in PBS, preparing 100 μL for each well of MHC class I.

2. Add streptavidin-PE or -APC to MHC class I by four sequential additions of 25 μL with 10 minute intervals.

Example 18—Combinatorial Encoding of MHC Multimers

UV-Mediated MHC Peptide Exchange

1. Thaw the stock solution of biotinylated p*MHC complexes on ice.

2. Dilute the biotinylated p*MHC complexes of interest in PBS to 200 μg/mL. A volume of 60 μL is needed per exchange reaction. For the pMHC complexes to be conjugated to Qdot585, 80 μL is needed per exchange reaction.

3. Dilute peptide stocks to 400 μM in PBS. Prepare a minimum of 70 μL per peptide; for peptides used to make pMHC complexes to be conjugated to Qdot585, prepare a minimum of 90 μL per peptide.

4. In a 96-well polypropylene microplate with a V-bottom, mix 60 μL 200 μg/mL p*MHC of the chosen allele and 60 μL of a 400 μM peptide solution per well (final concentrations: 100 μg/mL p*MHC and 200 M peptide). For the pMHC complexes to be conjugated to Qdot585, mix 80 μL of 200 μg/mL p*MHC and 80 μL of 400 μM peptide solution.

5. Expose the 96-well microplate to UV light (~366 nm) for 1 hr. at RT. The distance to the UV lamp should be 2-5 cm.

6. Centrifuge the plate at 3,300 g for 5 min at RT.

7. Repeat Step 6 if the pause point was included, and transfer 2×50 μL of the supernatant to two fresh 96-well polypropylene microplates with V-bottoms and keep them on ice. For the pMHC complexes to be conjugated to Qdot585, transfer 2×70 μL. Be careful not to transfer the bottom pellet (often invisible), as the transfer of aggregates will potentially increase the background of the final MHC multimer staining.

8. Multimerize the pMHC monomers by conjugation to fluorochrome-streptavidin conjugates. The differential conjugation is described below: option A for conjugation to Qdot605-, 625-, 655- or 705-streptavidin; option B for conjugation to Qdot585-streptavidin; and option C for conjugation to PE-, APC- or PE-Cy7-streptavidin.

(A) Conjugation to Qdot605-, 625-, 655- or 705-streptavidin: (i) Add 3.5 μL of Qdot-streptavidin conjugate (stock concentration 1 M) per 50 μL of pMHC monomer (to a final concentration of 66 nM).

(B) Conjugation to Qdot585-streptavidin: (i) Add 4.9 μL of Qdot585-streptavidin conjugate (stock concentration 1 M) per 70 μL of pMHC monomer (to a final concentration of 66 nM).

(C) Conjugation to PE-, APC- or PE-Cy7-streptavidin: (i) Add 4.6 μL of PE-, APC- or PE-Cy7-streptavidin conjugate (stock concentration 200 μg/mL) per 50 μL of pMHC monomer (to a final concentration of 16.8 μg/mL).

9. Mix well and leave to conjugate for 30 min on ice.

10. Add D-biotin and $NaN_3$ to a final concentration of 25 μM D-biotin and 0.02% (wt/vol) $NaN_3$. Do this by adding 2.5 μL of a 20-fold stock solution (500 μM D-biotin with 0.4% (wt/vol) $NaN_3$) to each well; for MHC multimers conjugated to Qdot585, add 3.5 μL to each well. Mix well and incubate on ice for 20 min.

11. Add 50 μL of PBS containing 25 μM D-biotin and 0.02% (wt/vol) $NaN_3$ to the MHC multimers conjugated to PE, APC or PE-Cy7 (twofold dilution).

12. Mix the different complexes. When mixing, use a 2:1 ratio of Qdot585 to every other color complex. Mix all other color complexes in a 1:1 ratio.

T Cell Staining with MHC Multimers

13. Mix MHC multimers for all the 27 color combinations to obtain one ready-to-use sample and centrifuge it at 3,300 g for 5 min at 4° C. and transfer the supernatant. In total, 54 μL of supernatant will be required for each T cell staining (i.e., 2 μL for each individual pMHC complex present in the mix).

14. Thaw the PBMC samples (or other relevant T cell samples) and wash them twice with RPMI. It is recommended to treat with DNase upon thawing to reduce clotting of the cells (e.g., by thawing cells in medium containing 0.025 mg/mL Pulmozyme and 2.5 mM MgCl$_2$).

15. Resuspend cells in PBS with 2% (vol/vol) FBS (FACS buffer) and distribute them a 96-well polystyrene U-bottom microplate, up to 3×10$^6$ cells per well in 200 μL of FACS buffer.

16. Spin the plate at 490 g for 5 min at RT.

17. Throw out buffer by tipping the plate upside down-cells are left as a pellet in the bottom of the well.

18. Add 54 μL of the MHC multimers from Step 13 and mix well.

19. Incubate for 15 min at 37° C.

20. Move the plate onto ice and add 20 μL of antibody mix from a 5× stock.

21. Add 4 μL of a 40-fold dilution of the near-IR dead cell stain and mix well.

22. Incubate for 30 min on ice.

23. Spin the plate at 490 g for 5 min at 4° C.

24. Throw out the supernatant by tipping the plate upside down.

25. Wash twice with 200 μL of FACS buffer (centrifuge twice at 490 g for 5 min at 4° C. and tip the plate upside down after each spin to remove the supernatant).

26. Resuspend the pellet in 50-100 μL of FACS buffer and transfer it to 1.4 mL or 5 mL FACS tubes. The samples are now ready for acquisition on the flow cytometer.

Single Color Compensation Controls

27. Add 100 μL of FACS buffer and one drop of negative compensation beads to 11 FACS tubes (nos. 1-11).

28. Add one drop of anti-mouse Ig-κ compensation beads to tubes 1-10 from Step 27 and one drop of ArC amine reactive beads to a new tube (no. 12).

29. Add 5 μL of 1 mg/mL anti-CD8-biotin to tubes 1-8 and mix.

30. Incubate tubes 1-8 for 20 min on ice.

31. Wash tubes 1-8 twice with 2 mL of FACS buffer (centrifuge at 490 g for 5 min at 4° C.).

32. Add 1 μL of near-IR dead cell stain to tube 12 (from Step 28); mix and incubate for 30 min at RT in the dark.

33. Dilute the streptavidin-fluorochrome conjugates ten-fold (except for Qdot585), add 5 μL of each to tubes 1-7, add 1 μL of undiluted Qdot585-streptavidin to tube 8, and then incubate for 20 min on ice in the dark.

34. Add 5 μL of FITC antibody (use one of the dump channel antibodies) or 5 μL of the Alexa Fluor 700 anti-CD8a antibody to tubes 9 and 10 (from Step 28); incubate for 20 min on ice in the dark. 35. Wash tubes 1-11 twice with 2 mL of FACS buffer, and wash tube 12 twice with 2 mL of PBS (centrifuge at 490 g for 5 min at 4° C.).

36. Resuspend all tubes in 150 μL of FACS buffer. Add one drop of ArC-negative beads to tube 12 and mix. The compensation controls are ready for acquisition on the flow cytometer.

Gating Strategy

37. Gate first on lymphocytes, and subsequently on single cells (FSC-α, FSC-W), live cells, dump channel-negative cells and CD8$^+$ cells.

38. Draw separate gates that define positive events in the eight different MHC multimer channels.

39. Invert the eight MHC multimer-positive gates, to obtain eight gates that select CD8$^+$ and MHC multimer-negative cells for each MHC multimer channel.

40. Intersect gates for two MHC multimer-positive populations with the inverted gates for each of the other six MHC multimer populations. This combination of gates selects for CD8$^+$ cells that are positive in two and only two MHC multimer channels (i.e., if a cell is positive in one or in three or more MHC multimer channels, it is gated out). An example of such a gate is PE$^+$ and APC$^+$ and PE-Cy7$^-$ and Qdot585$^-$ and Qdot605$^-$ and Qdot625$^-$ and Qdot655$^-$ and Qdot705$^-$.

41. Make these intersected gates (described in Step 40) for all 28 possible two-color combinations of MHC multimers.

42. Join all the 28 gates from Step 41 (e.g., gate 1 or gate 2 or . . . or gate 28).

43. Intersect the eight inverted gates from Step 39 (PE- and APC- and PE-Cy7$^-$ and Qdot585$^-$ and Qdot605$^-$ and Qdot625$^-$ and Qdot655$^-$ and Qdot705$^-$).

44. Join the two gates from Steps 42 and 43.

45. Make 28 dot plots with all the possible two-color codes, showing the events gated for in Step 44. These plots will only show CD8$^+$ cells that are negative for all MHC multimers or positive for two; all background events are gated out.

46. Also make 28 dot plots with all the possible two-color codes, showing all CD8$^+$ cells. These plots will provide a good indication of the background level in the sample and can also be used to reveal improper compensation. It is recommended comparing these 'nongated' plots with the gated plots in order to gain experience in separating responses from background. This may be especially of importance for low-intensity populations.

Example 19—Fluorescent Cell Barcoding

Cellular barcoding can be used to perform multiplexed phenotypic and functional analysis by flow cytometry. The phospho flow can be performed with slight modifications to include FCB labeling. After formaldehyde fixation, samples will be resuspended in 100% 20-25° C. methanol (typically 500 μL per 10$^6$ cells) containing the indicated concentration of Alexa Fluor or Pacific Blue succinimidyl esters, with each sample receiving a different concentration of fluorescent dye. In some cases, samples can be resuspended in methanol and then FCB fluorophores dissolved in DMSO (typically at 1:50 dilution) will be added. This can be done to allow prior preparation and storage of FCB staining matrices in DMSO, necessary for 96-well plate experiments. After labeling for 15 min at 20-25° C., cells will be washed twice with staining medium (phosphate-buffered saline (pH 7.0) containing 0.5% BSA and 0.02% sodium azide). Labeling at 4° C. or colder can produce very low labeling intensities, allowing storage of samples at −80° C. in the methanol staining solution without increasing FCB staining levels.

The differentially labeled samples will be combined into one FACS tube or well, and pelleted again if the resulting volume is greater than 100 μL. The combined, barcoded sample (typically 100 μL) will be stained with phospho-specific and/or surface marker antibodies, washed and analyzed by flow cytometry. Flow cytometry can be performed on a BD LSR2 flow cytometer, equipped with 405 nm, 488 nm and 633 nm lasers, and manufacturer's stock filters, with replacement of the 405 nm octagon bandpass filter for Cascade Yellow with a 610/20 bandpass filter for detection of Quantum Dot 605.

Example 20—CD4$^+$ Naïve Inductions

Protocol 1 and 2 were carried out using PIN peptides. Antigen specific CD4$^+$ naïve inductions were assessed. The results can be seen below in Table 5. 'Y' indicates a T cell response was observed.

TABLE 5

| CD4+ naïve induction results from donors 1 and 2 | | | | | | |
|---|---|---|---|---|---|---|
| long term | | Donor 2 | | | Donor 1 | | |
| induction read-out LTS#35 | | Prot. 1 (CD25⁻) | Prot. 2 whole PBMC | Prot. 2 CD25⁻ | Prot. 1 (CD25⁻) | Prot. 2 whole PBMC | Prot. 2 CD25⁻ |
| Induced with | PIN replicate 1 | Y | Y | Y | Y | Y | Y |
| Long peptide | PIN replicate 2 | Y | Y | Y | Y | — | — |
| | PIN replicate 3 | — | Y | Y | Y | Y | — |
| | Results | 2/3 66% | 3/3 100% | 3/3 100% | 3/3 100% | 2/3 66% | 1/3 33% |

Example 21—Manufacturing Process: DC Derivation

TABLE 6

| An exemplary protocol followed for DC derivation | | |
|---|---|---|
| Step 1 | Monocyte Enrichment and DC Culture | Autologous Cells Apheresis Bag #1 |
| Step 2 | | Monocyte Enrichment |
| Step 3 | | DC culture |
| Step 4 | Peptide Loading and DC Maturation | DC Harvest, resuspension in DC Media |
| Step 5 | | Addition Patient Specific Peptides and incubation |
| Step 6 | | DC Maturation |

Example 22—T Cell Induction Protocol 1

TABLE 7A

| T Cell Induction #1 | |
|---|---|
| Step 7 | Autologous Cells Apheresis Bag #2 |
| Step 8 | CD25+ depletion (+/− CD14+ depletion) |
| Step 9 | DC wash and resuspension in T Cell culture Media |
| Step 10 | Incubation of T cells with Matured DCs (from DC Derivation) |

TABLE 7B

| T cell induction #2 | |
|---|---|
| Step 11 | T Cell Washing and Resuspension in T cell Media |
| Step 12 | Incubation of T cells with Matured DC (from DC Derivation) |

TABLE 7C

| T cell induction #3 | |
|---|---|
| Step 11 | T Cell Washing and Resuspension in T cell Media |
| Step 12 | Incubation of T cells with Matured DC (from DC Derivation) |

TABLE 7D

| Harvest & cryopreservation | | | |
|---|---|---|---|
| Step 15 | | T Cell Harvest | Release Testing: Mycoplasma |
| Step 16 | drug substance | Wash and Suspension in Final Formulation | Release Testing: Sterility, Endotoxin, Cell Phenotype, TNC |

TABLE 7D-continued

| Harvest & cryopreservation | | | |
|---|---|---|---|
| | | | Count, Viability, Cell Concentration |
| Step 17 | drug product | DS Fill and Cryopreservation Store in vapor phase of liquid nitrogen | |

Example 23—T Cell Induction Protocol 2

TABLE 8A

| T cell induction #1 | |
|---|---|
| Step 7 | Autologous Cells Apheresis Bag #2 |
| Step 8 | CD25+ depletion (+/− CD14+ depletion) |
| Step 8a | Add FLT3L |
| Step 9 | Addition Patient Specific Peptides and incubation |
| Step 10 | Incubation of depleted PMBCs with FLT3L and peptides |

TABLE 8B

| T cell induction #2 | |
|---|---|
| Step 11 | T Cell Washing and Resuspension in T cell Media |
| Step 12 | Incubation of T cells with Matured DC (from DC Derivation) |

TABLE 8C

| T cell induction #3 | |
|---|---|
| Step 11 | T Cell Washing and Resuspension in T cell Media |
| Step 12 | Incubation of T cells with Matured DC (from DC Derivation) |

TABLE 9

| Harvest & cryopreservation | | | |
|---|---|---|---|
| Step 15 | | T Cell Harvest | Release Testing: Mycoplasma |
| Step 16 | drug substance | Wash and Suspension in Final Formulation | Release Testing: Sterility, Endotoxin, Cell Phenotype, TNC Count, Viability, Cell Concentration |

TABLE 9-continued

| Harvest & cryopreservation | | |
| --- | --- | --- |
| Step 17 | drug product | Drug substance Fill and Cryopreservation Store in vapor phase of liquid nitrogen |

Example 24—Simultaneous Detection and Functional Characterization of CD4$^+$ and CD8$^+$ Neoantigen-Specific T Cell Responses Using Multiplexed, Multiparameter Flow Cytometry Neoantigens, which arise in cancer cells from somatic mutations that alter protein-coding gene sequences, are emerging as an attractive target for immunotherapy. They are uniquely expressed on tumor cells as opposed to healthy tissue and may be recognized as foreign antigens by the immune system, increasing immunogenicity. T cell manufacturing processes were developed to raise memory and de novo CD4$^+$ and CD8$^+$ T cell responses to patient-specific neoantigens through multiple rounds of ex-vivo T cell stimulation, generating a neoantigen-reactive T cell product for use in adoptive cell therapy. Detailed characterization of the stimulated T cell product can be used to test the many potential variables these processes utilize.

Figure 26:
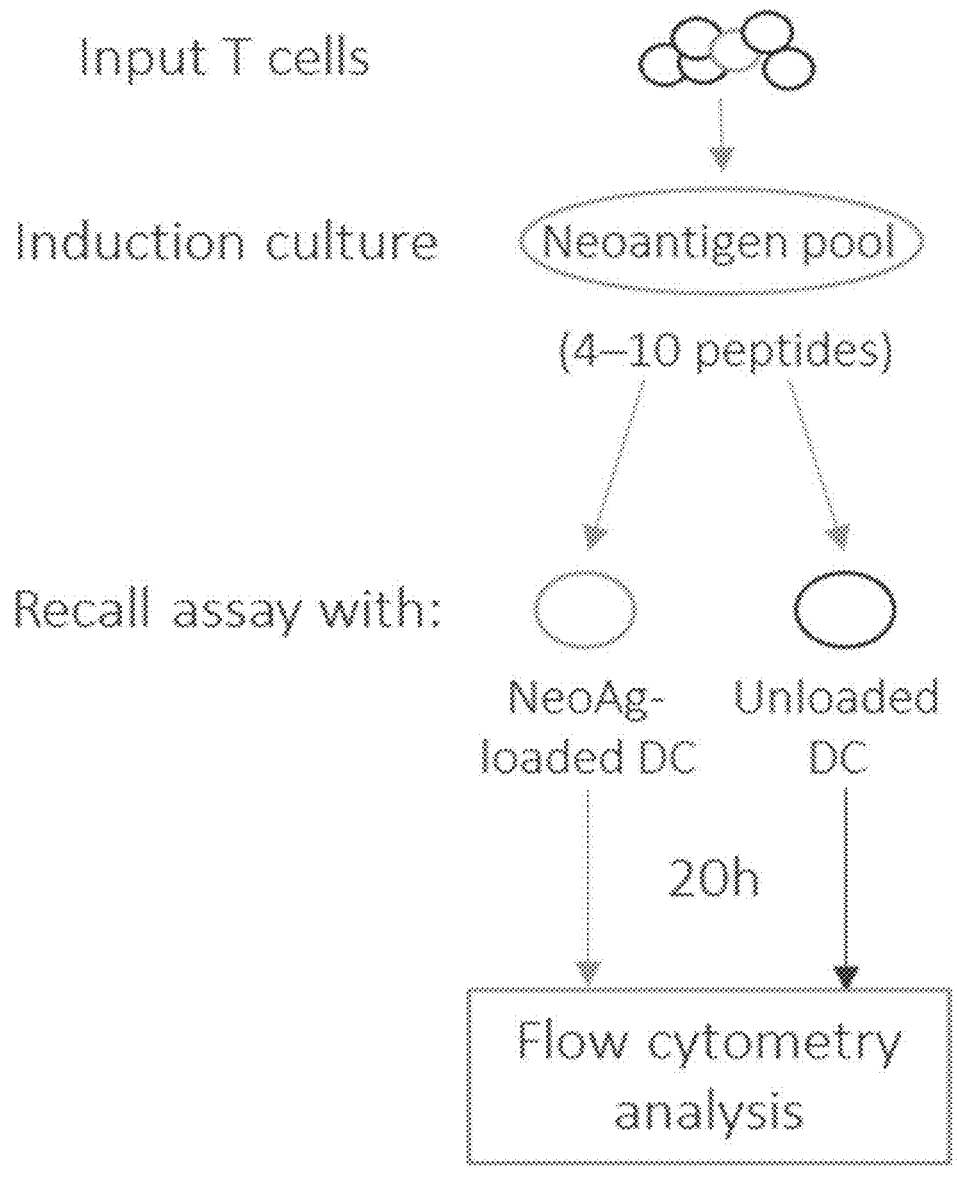
FIG. 26 depicts an example of a recall assay to test functionality, phenotype and/or function of T cells and/or T cell responses.

To probe T cell functionality and/or specificity, an assay was developed to simultaneously detect antigen-specific T cell responses and characterize their magnitude and function. This assay employed the following steps. First T cell-APC co-cultures were used to elicit reactivity in antigen-specific T cells. Optionally, sample multiplexing using fluorescent cell barcoding was employed. To identify antigen-specific CD8$^+$ T cells and to examine T cell functionality, staining of peptide-MHC multimers and multiparameter intracellular and/or cell surface cell marker staining were probed simultaneously using FACS analysis. The results of this streamlined assay demonstrated its application to study T cell responses induced from a healthy donor. Neoantigen-specific T cell responses induced toward peptides were identified in a healthy donor. The magnitude, specificity and functionality of the induced T cell responses were also compared. FIG. 25 and FIG. 26 depict exemplary processes for simultaneous analysis of a cell marker profile and MHC tetramer staining of a T cell sample.

Briefly, different T cell samples were barcoded with different fluorescent dyes at different concentrations (see, e.g., Example 19). Each sample received a different concentration of fluorescent dye or combination of multiple dyes at different concentrations. Samples were resuspended in phosphate-buffered saline (PBS) and then fluorophores dissolved in DMSO (typically at 1:50 dilution) were added to a maximum final concentration of 5 μM. After labeling for 5 min at 37° C., excess fluorescent dye was quenched by the addition of protein-containing medium (e.g. RPMI medium containing 10% pooled human type AB serum). Uniquely barcoded T cell cultures were challenged with autologous APC pulsed with the antigen peptides as described above.

The differentially labeled samples were combined into one FACS tube or well, and pelleted again if the resulting volume is greater than 100 μL. The combined, barcoded sample (typically 100 μL) was stained with surface marker antibodies including LAMP-1 (see, e.g., Example 11) and incubated with assembled fluorochrome conjugated peptide-MHC multimers (see, e.g., Examples 17 and 18 above).

After fixation and permeabilization, the sample was additionally stained intracellularly with antibodies targeting TNF-α and IFN-γ.

The cell marker profile and MHC tetramer staining of the combined, barcoded T cell sample were then analyzed simultaneously by flow cytometry on a flow cytometer. Unlike other methods that analyze cell marker profiles and MHC tetramer staining of a T cell sample separately, the simultaneous analysis of the cell marker profile and MHC tetramer staining of a T cell sample described in this example provides information about the percentage of T cells that are both antigen specific and that have increased cell marker staining. Other methods that analyze cell marker profiles and MHC tetramer staining of a T cell sample, separately determine the percentage of T cells of a sample that are antigen specific, and separately determine the percentage of T cells that have increased cell marker staining, only allowing correlation of these frequencies. The simultaneous analysis of the cell marker profile and MHC tetramer staining of a T cell sample described in this example does not rely on correlation of the frequency of antigen specific T cells and the frequency of T cells that have increased cell marker staining; rather, it provides a frequency of T cells that are both antigen specific and that have increased cell marker staining. The simultaneous analysis of the cell marker profile and MHC tetramer staining of a T cell sample described in this example allows for determination on a single cell level, those cells that are both antigen specific and that have increased cell marker staining.

To evaluate the success of a given induction process, a recall response assay was used followed by a multiplexed, multiparameter flow cytometry panel analysis. A sample taken from an induction culture was labeled with a unique two-color fluorescent cell barcode. The labeled cells were incubated on antigen-loaded DCs or unloaded DCs overnight to stimulate a functional response in the antigen-specific cells. The next day, uniquely labeled cells were combined prior to antibody and multimer staining according to the Table 10 below.

TABLE 10

| Assay targets (markers), fluorochromes and purpose | | |
| --- | --- | --- |
| Marker | Fluorochrome | Purpose |
| CD19/CD16/CD14 | BUV395 | Cell exclusion |
| Live/Dead | Near-IR | Dead cell exclusion |
| CD3 | BUV805 | Lineage gating |
| CD4 | Alexa Fluor 700 | Lineage gating |
| CD8 | PerCP-Cy5.5 | Lineage gating |
| Barcode 1 | CFSE | Sample multiplexing |
| Barcode 2 | TagIT Violet | Sample multiplexing |
| Multimer 1 | PE | CD8+ antigen specificity |
| Multimer 2 | BV650 | CD8+ antigen specificity |
| IFNγ | APC | Functionality |
| TNFα | BV711 | Functionality |
| CD107a | BV786 | Cytotoxicity |
| 4-1BB | PE/Dazzle 594 | Activation |

Figure 27A:
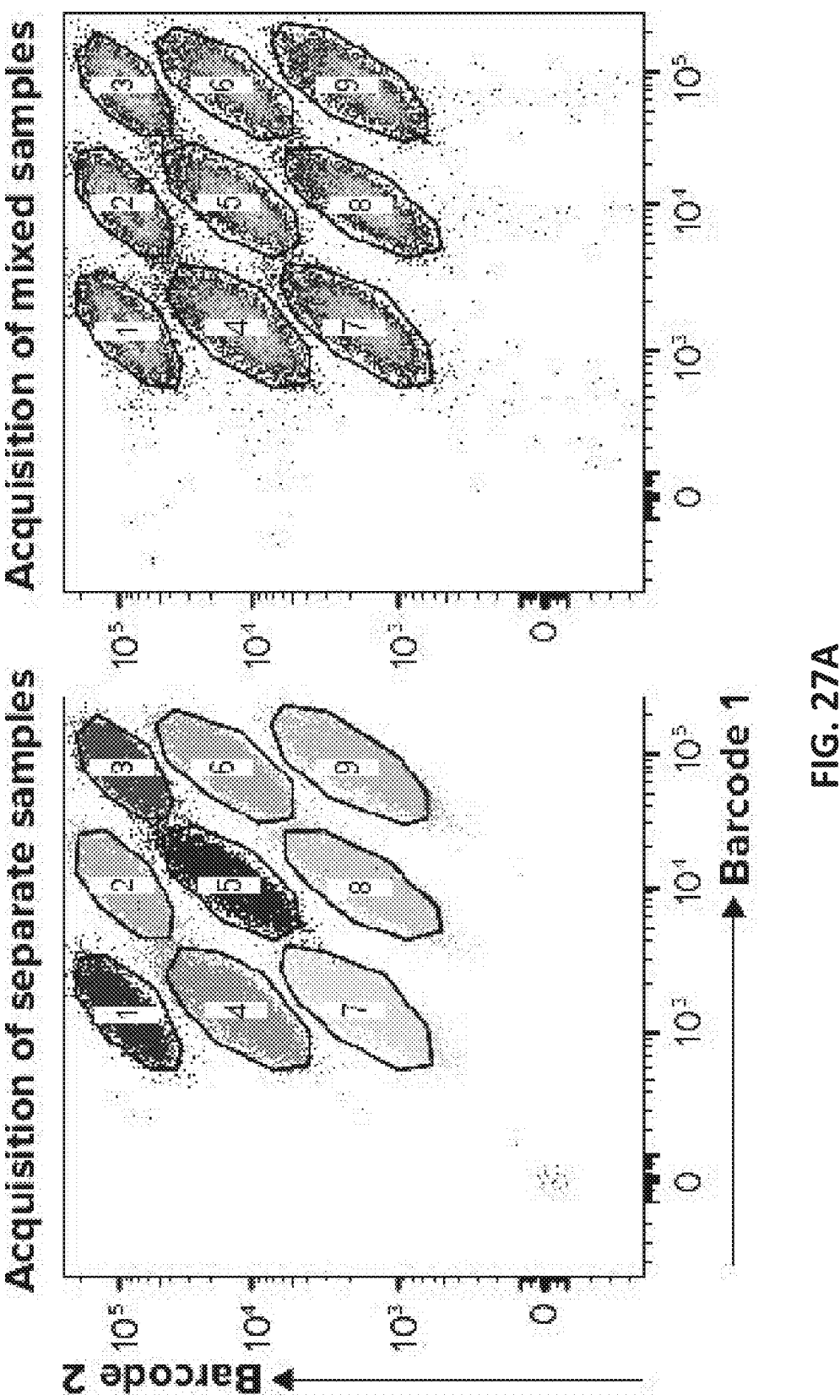
FIG. 27A depicts example flow cytometric analyses showing the ability to deconvolute multiplexed samples by labeled samples, acquired either separately or as a mixture, in a recall assay. Uniquely labeled samples were resolved with minimal to no cross-contamination to other barcodes.
Figure 27B:
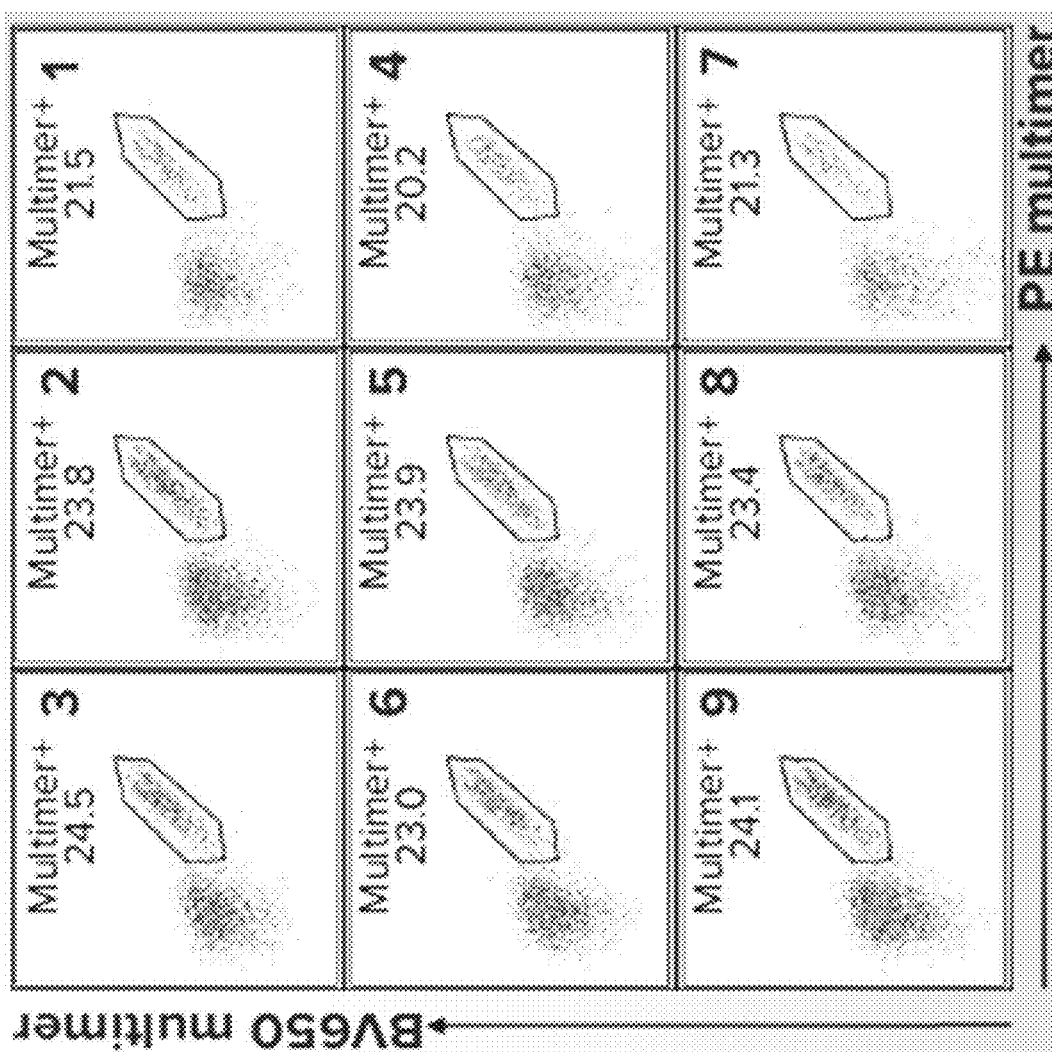
FIG. 27B depicts example flow cytometric analyses showing detection of antigen-specific CD8$^+$ T cells by multimer staining of a mixture of nine uniquely labeled samples in a recall assay.

The ability to fully deconvolute multiplexed samples by labeled, acquired either separately or as a mixture, was determined (FIG. 27A). Uniquely labeled samples could be fully resolved with minimal to no cross-contamination to other barcodes. Detection of antigen-specific CD8$^+$ T cells by multimer staining was maintained with sample multiplexing. A sample of an induction culture containing ~20% of CD8$^+$ T cells with specificity for CMV pp65, EBV BRLF1, EBV BMLF1 and/or MART-1 was split, labeled with nine unique two-color barcodes, and then combined for staining with tetramers targeting all four specificities in the same two-color combinations (brilliant violet 650 [BV650] and phycoerythrin [PE]) (FIG. 27B). All nine barcodes yielded comparable tetramer staining pattern and detected frequency of tetramer$^+$ cells.

Figure 28A:
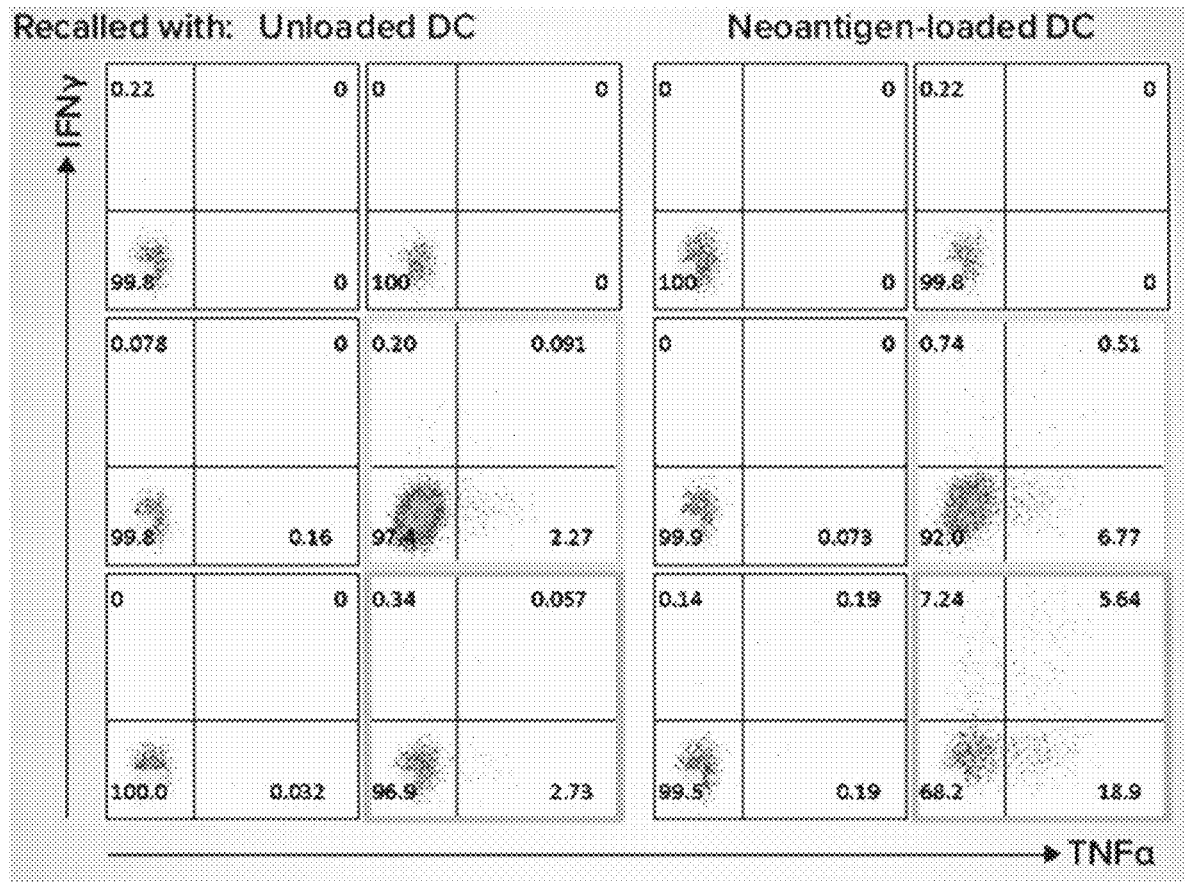
FIG. 28A depicts example flow cytometric analyses of a recall assay using six uniquely barcoded samples recalled with unloaded DCs and neoantigen-loaded DCs.

Samples of two induced cultures containing de novo CD4$^+$ T-cell responses were also analyzed in a recall response assay, either alone without barcoding or mixed with irrelevant samples (FIG. 28A and FIG. 28B). The number of functions and magnitude of response elicited from the cells was not significantly changed with sample barcoding.

Figure 29A:
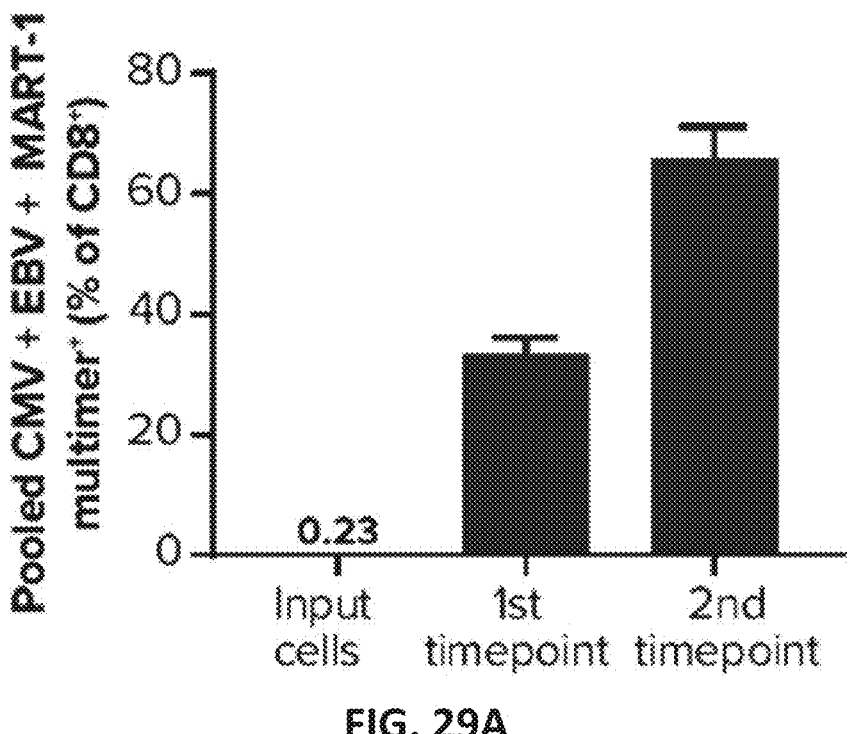
FIG. 29A depicts an example bar graph showing results of antigen specific memory CD8$^+$ T cell responses to viral antigens. CD8$^+$ memory responses toward CMV pp65, MART-1 and EBV BRLF1 and BMLF1 epitopes could be raised from 0.23% of CD8$^+$ T cells in the starting healthy donor material to >60%.

Simultaneous analysis of specificity and functionality of induced CD8$^+$ memory responses demonstrated that CD8$^+$ memory responses toward CMV pp65, MART-1 and EBV BRLF1 and BMLF1 epitopes could be raised from 0.23% of CD8$^+$ T cells in the starting healthy donor material to ≥60% (FIG. 29A)

Figure 29B:
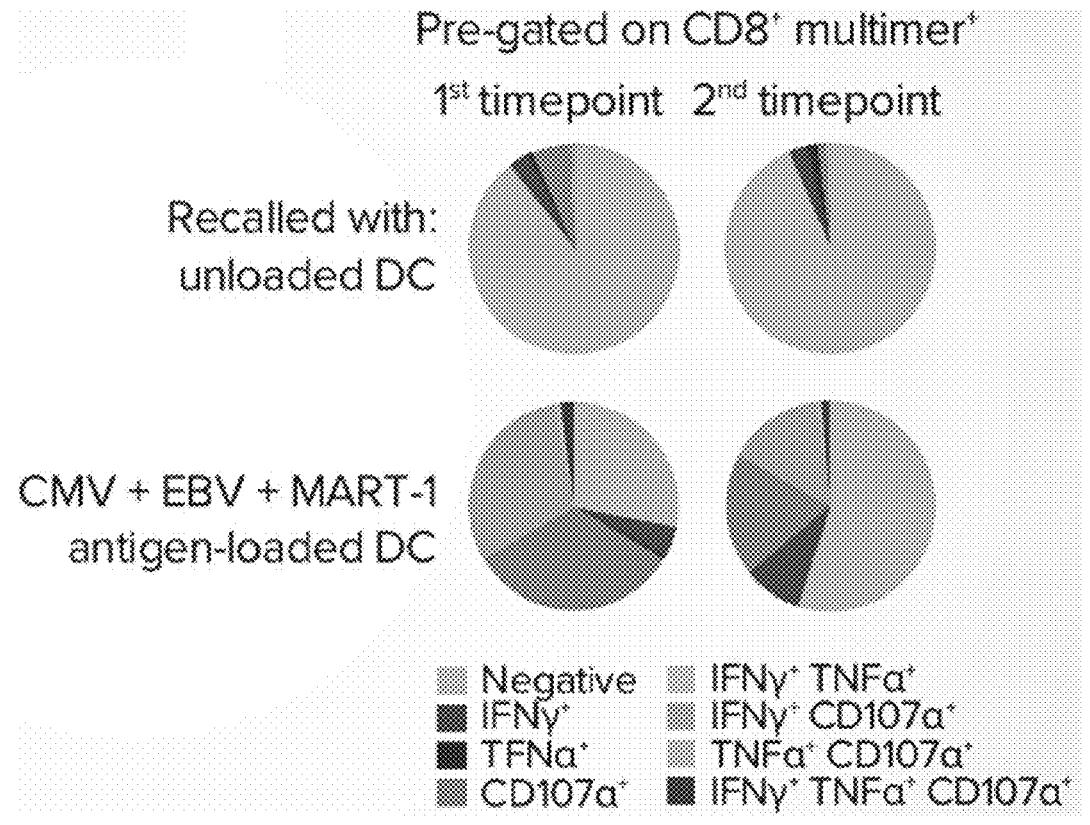
FIG. 29B depicts example results of a recall assay of antigen specific memory CD8$^+$ T cell responses to viral antigens and then recalled with DCs loaded with and without viral antigens. The fraction of CD8$^+$ T cells from two time points that release the indicated cytokines are depicted in the charts.

By pre-gating on the CD8$^+$ multimer$^+$ cells, the function of antigen-specific T cells was selectively interrogated (FIG. 29B). Cells exhibited cytotoxic function (CD107a surface exposure) and IFNγ secretion upon exposure to antigen-loaded DCs.

Figure 30A:
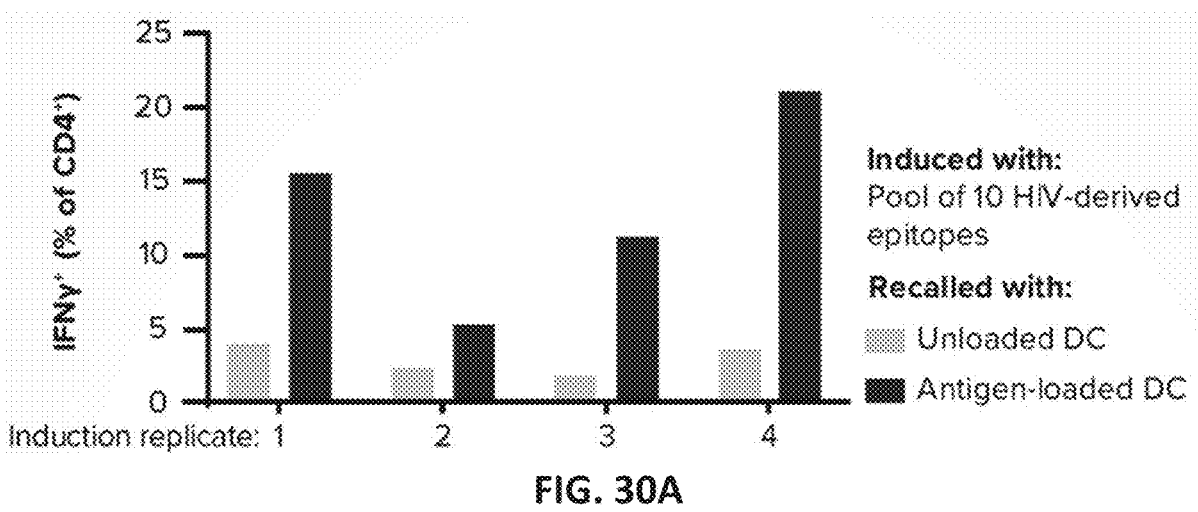
FIG. 30A depicts an example result of hit identification by detection and functional characterization of de novo induced CD4$^+$ responses with multiple specificities in the same culture. In the example shown, an induction was performed in four replicate cultures targeting 10 HIV-derived epitopes, which are naïve targets in an HIV-negative healthy donor. Antigen-specific responses are detected in 4/4 biological replicates, with varying magnitude of response.
Figure 30B:
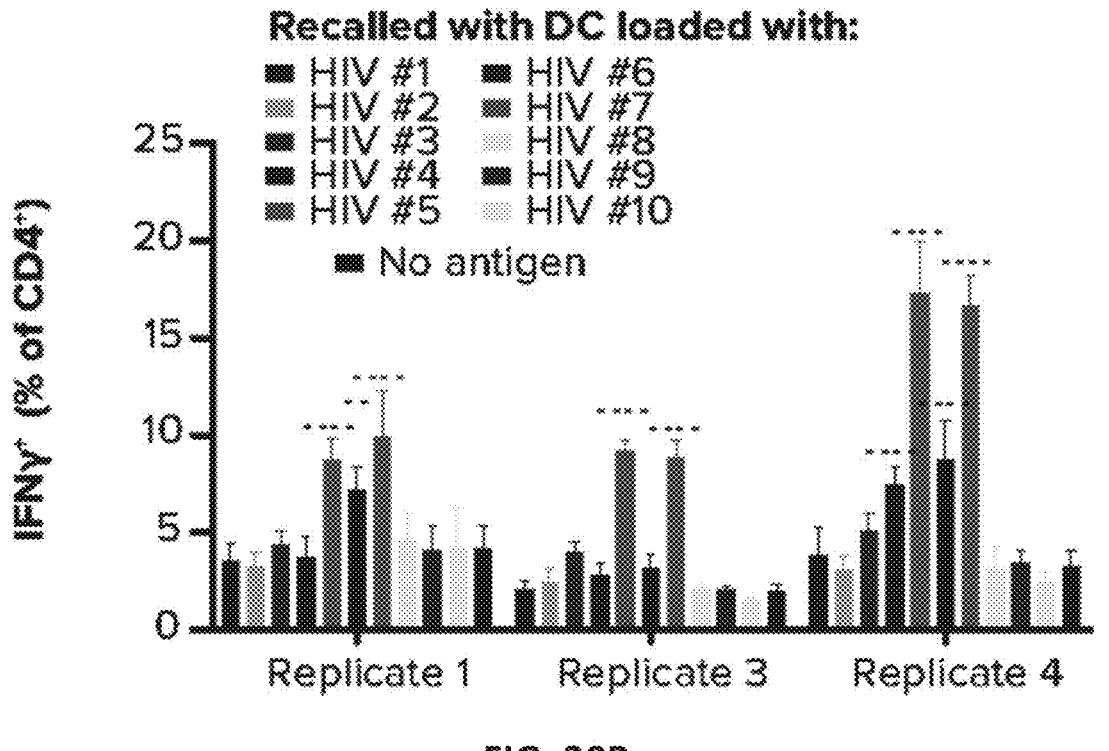
FIG. 30B depicts an example result of pool deconvolution by detection and functional characterization of de novo induced CD4$^+$ responses with multiple specificities in the same culture. Multiple responses were detected in each replicate tested, and the same two epitopes (HIV #5 and HIV #7) yielded the highest magnitude response in each case.
Figure 31:
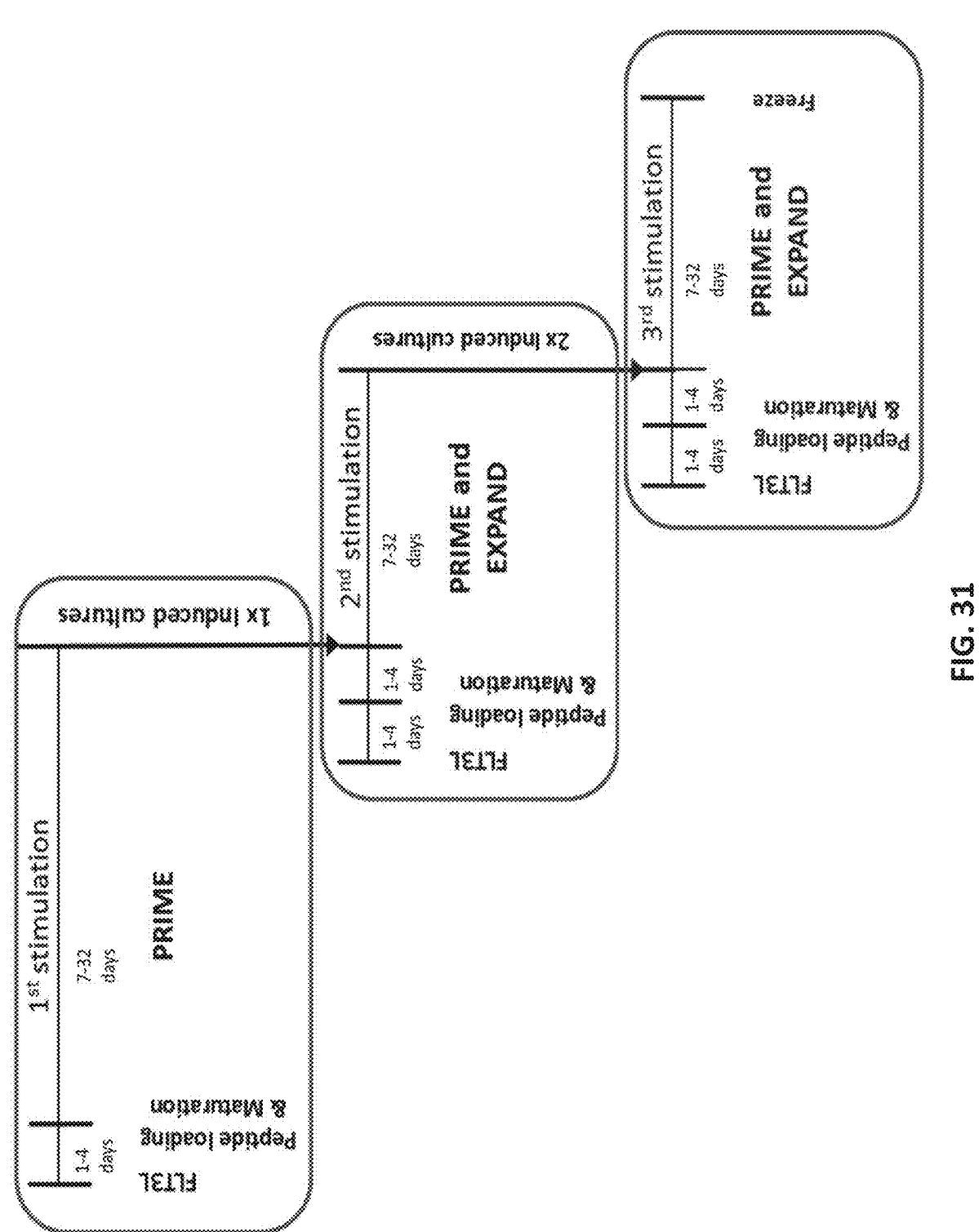
FIG. 31 depicts an example schematic of an antigen specific T cell manufacturing protocol.
Figure 32:
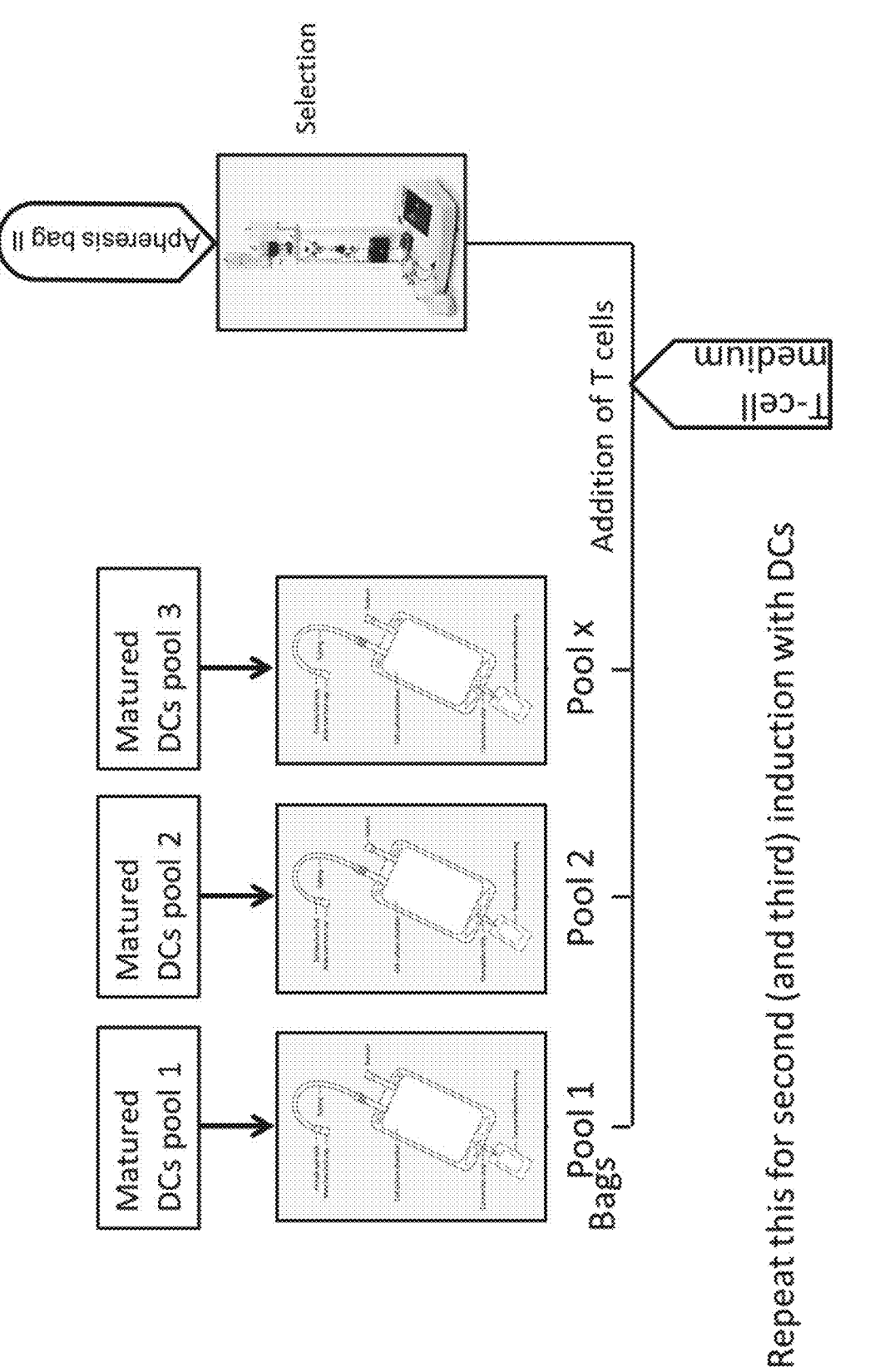
FIG. 32 depicts an example schematic of a T cell induction protocol.
Figure 33:
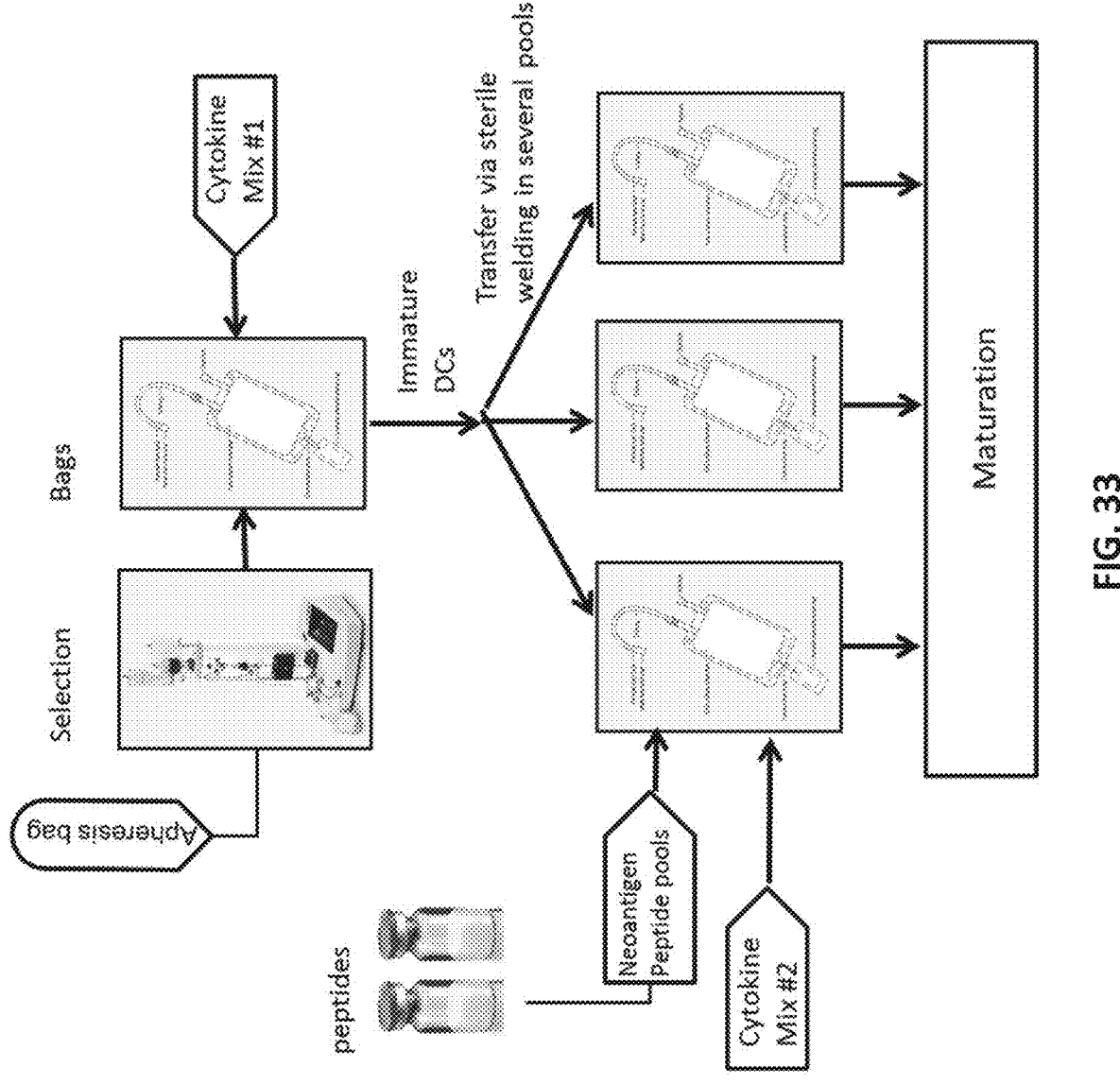
FIG. 33 depicts an example schematic of a dendritic cell generation protocol.

Detection and functional characterization of de novo induced CD4$^+$ responses with multiple specificities in the same culture was also demonstrated. Antigen-specific functionality was utilized to identify induced CD4$^+$ T-cell responses (FIG. 30A). In the example shown, an induction was performed in four replicate cultures targeting 10 HIV-derived epitopes, which are naïve targets in an HIV-negative healthy donor. Antigen-specific responses were detected in all four biological replicates. Three of the detected responses were selected for further follow-up by pool deconvolution to identify the specificity of the induced responses (FIG. 30B). Multiple responses were detected in each replicate tested, and the same two epitopes (HIV #5 and HIV #7) induced the highest magnitude response in each case. Without being bound to any theory, this may reflect greater immunogenicity of these epitopes in this donor due to MHC class II haplotype or a greater precursor frequency of T cells targeting these epitopes in the naïve repertoire. Sensitivity to antigen was determined for three selected responses by peptide titration during DC loading (FIG. 30C). The responses to HIV #5, HIV #6 and HIV #4 demonstrated an EC$_{50}$ of 0.45 μM, 0.43 μM and 9.1 μM, respectively.

Example 25—T Cell Manufacturing Protocol 3

Materials:
  AIM V media (Invitrogen)
  Human FLT3L, preclinical CellGenix #1415-050 Stock 50 ng/μL
  TNF-α, preclinical CellGenix #1406-050 Stock 10 ng/μL
  IL-1β, preclinical CellGenix #1411-050 Stock 10 ng/μL
  PGE1 or Alprostadil—Cayman from Czech republic Stock 0.5 μg/μL
  R10 media—RPMI 1640 glutamax+10% Human serum+1% PenStrep 20/80 Media—18% AIM V+72% RPMI 1640 glutamax+10% Human Serum+1% PenStrep
  IL7 Stock 5 ng/μL
  IL15 Stock 5 ng/μL
Procedure:
  Step 1: Plate 5 million PBMCs (or cells of interest) in each well of 24 well plate with FLT3L in 2 mL AIM V media Step 2: Peptide loading and maturation-in AIMV
  1. Mix peptide pool of interest (except for no peptide condition) with PBMCs (or cells of interest) in respective wells.
  2. Incubate for 0.5 to 4 hr.
  3. Mix Maturation cocktail (including TNF-α, IL-1β, PGE1, and IL-7) to each well after incubation.
Step 3: Add human serum to each well at a final concentration of 10% by volume and mix.
Step 4: Replace the media with fresh RPMI+10% HS media supplemented with IL7+IL 15.
Step 5: Replace the media with fresh 20/80 media supplemented with IL7+IL15 during the period of incubation every 1-6 days.
Step 6: Plate 5 million PBMCs (or cells of interest) in each well of new 6-well plate with FLT3L in 2 ml AIM V media
Step 7: Peptide loading and maturation for re-stimulation—(new plates)
  1. Mix peptide pool of interest (except for no peptide condition) with PBMCs (or cells of interest) in respective wells
  2. Incubate for 1 hr.
  3. Mix Maturation cocktail to each well after incubation
Step 8: Re-stimulation:
  1. Count first stimulation FLT3L cultures and add 5 million cultured cells to the new Re-stimulation plates.
  2. Bring the culture volume to 5 mL (AIM V) and add 500 μL of Human serum (10% by volume) Step 9: Remove 3 ml of the media and add 6 ml of RPMI+10% HS media supplemented with IL7+IL15.
Step 10: Replace 75% of the media with fresh 20/80 media supplemented with IL7+IL 15.
Step 11: Repeat re-stimulation if needed.

Example 26—Experimental Data Using T Cell Manufacturing Protocol 3

Figure 34:
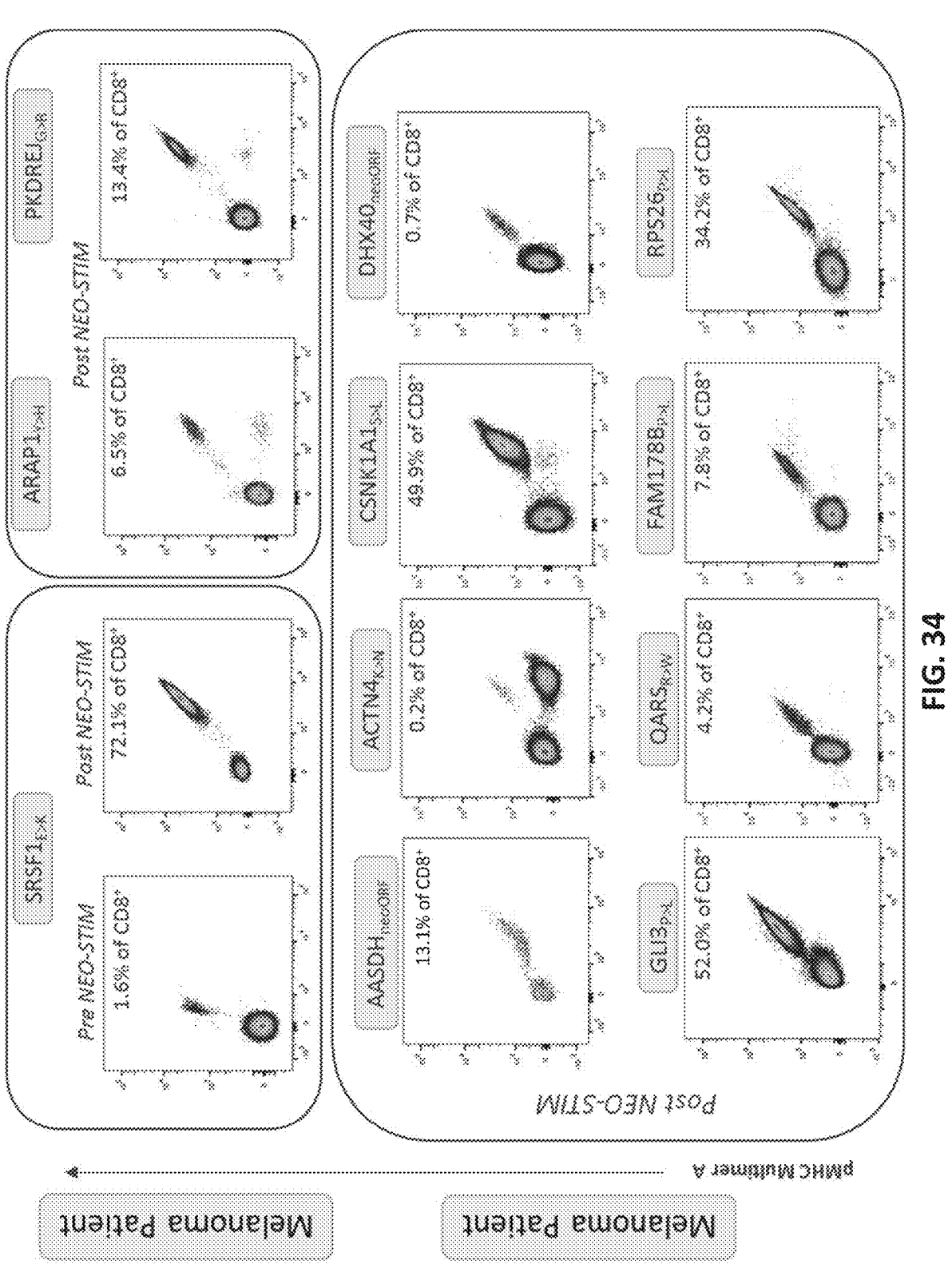
FIG. 34 depicts example pMHC multimer plots showing CD8+ T cell responses induced in leukapheresis material from a melanoma patient targeting patient-specific epitopes: SRSF1$_{E>K}$, ARAP1$_{Y>H}$ & PKDREJ$_{G>R}$, a melanoma patient targeting a patient-specific epitope (AASDH neoORF and seven model neoantigens: ACTN4$_{K>N}$, CSNK1A1$_{S>L}$, DHX40neoORF, GLI3$_{P>L}$ QARSR$_{>W}$, FAM178B$_{P>L}$ and RPS26$_{P>L}$. The first panel plots in the first and second rows indicate memory responses and the remaining plots indicate de novo responses.
Figure 35:
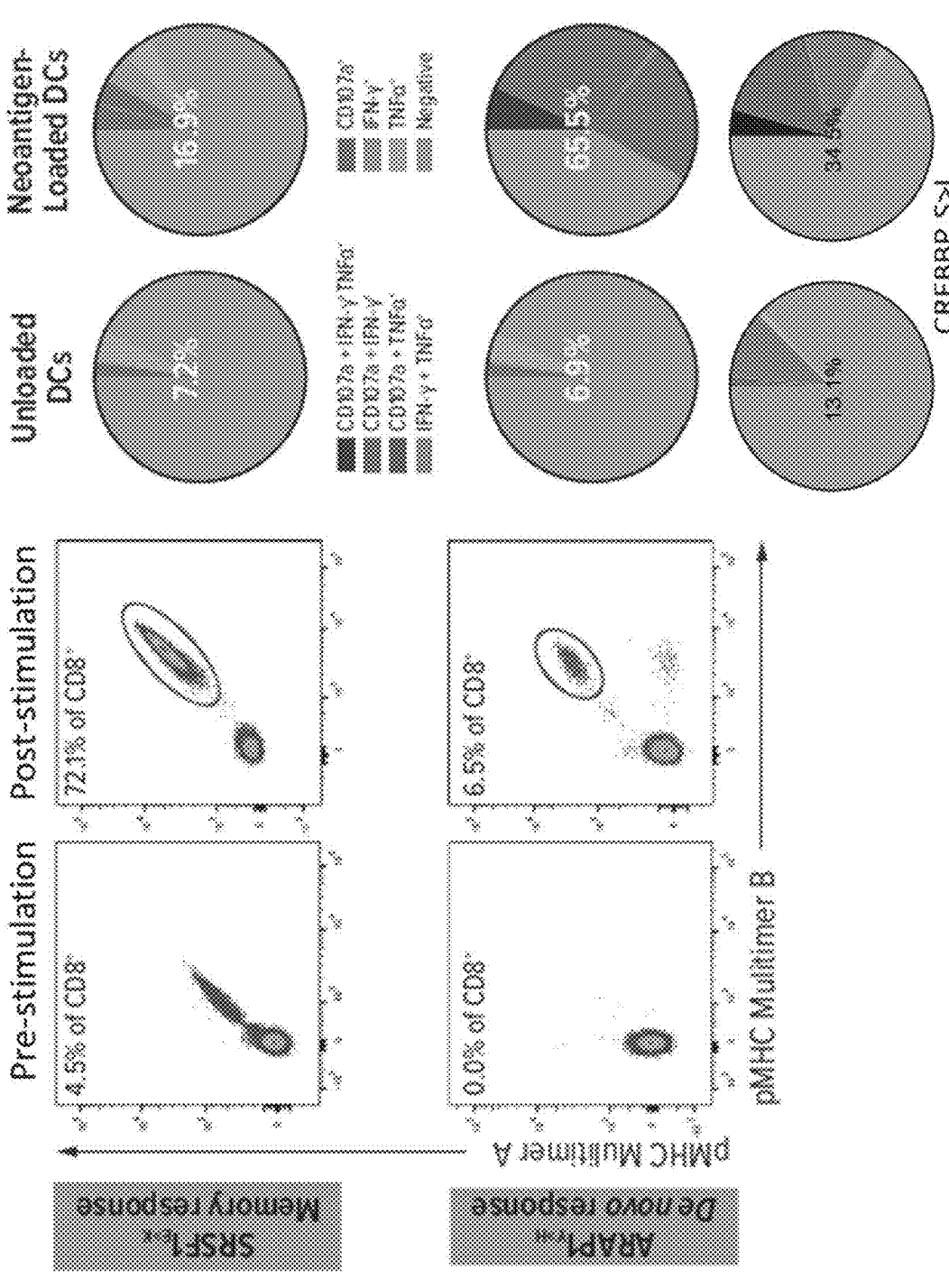
FIG. 35 depicts example data of pMHC multimer plots of SRSF1$_{E>K}$ and ARAP1$_{Y>H}$ pre and post peptide stimulation (left panels), pie charts depicting the functionality of neoantigen specific T cells upon re-challenge with neoantigen loaded DCs; gated on pMHC multimer$^+$ CD8$^+$ or CD4+ T cells. The polyfunctional profile of a CD8+ memory, CD8+ de novo and CD4+de novo responses induced in a patient with melanoma are shown by a combination of 1, 2, or 3 functions (e.g., the one or more functions are production of one or more factors selected from IFNγ, TNFα, CD107a and 4-1BB).
Figure 36:
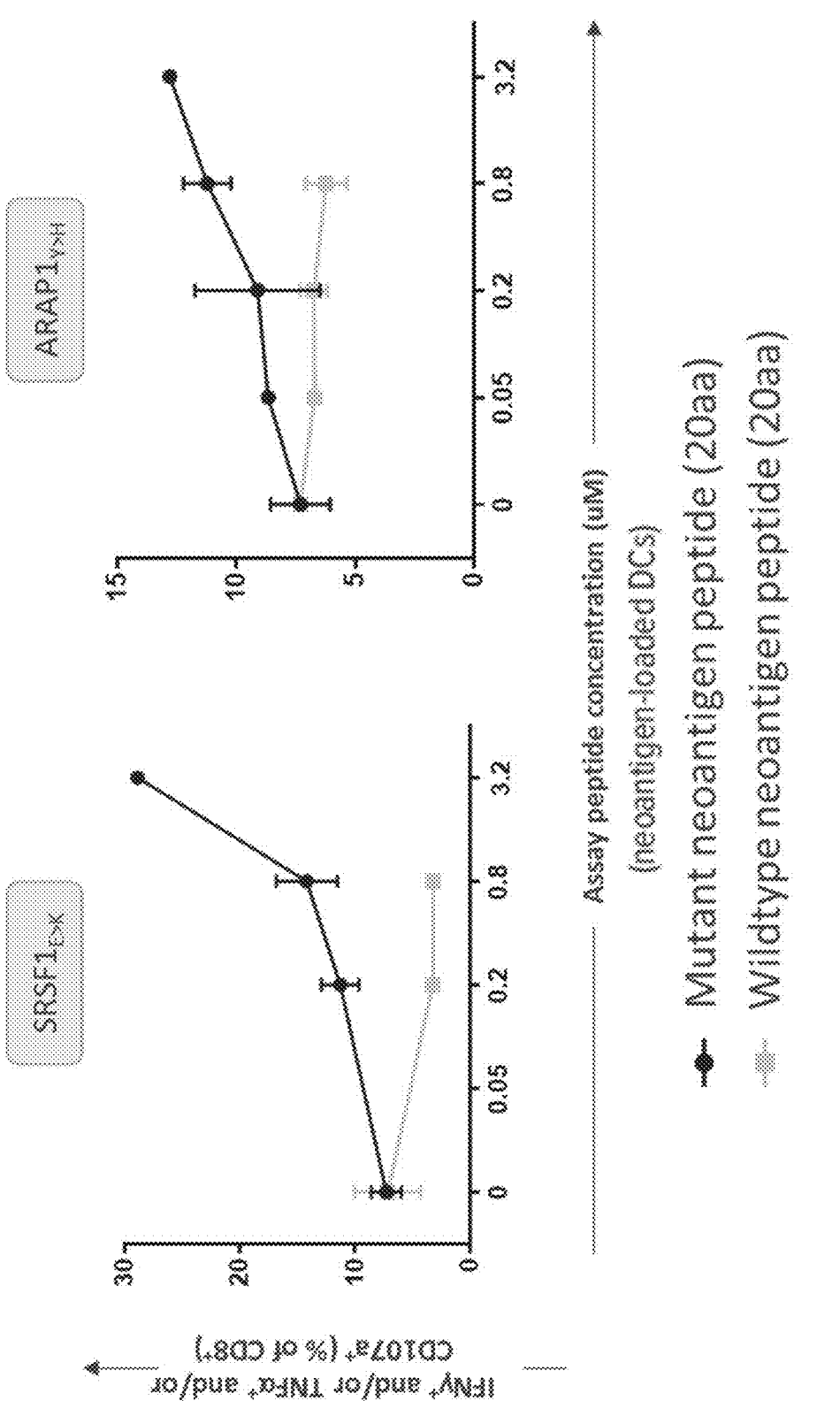
FIG. 36 depicts the specificity of a memory and de novo response induced in a patient with melanoma towards mutated and wildtype peptide. SRSF1$_{E>K}$ and ARAP1$_{Y>H}$ specific T cell responses were challenged with DCs loaded with mutant or wildtype neoantigen peptides at different concentrations (X axis: 0 μM, 0.05 μM, 0.2 μM, 0.8 μM, and 3.2 μM) and measured IFN-γ+ and/or TNFα+ and/or CD107a+ of total CD8+ T cells (Y axis) in the samples; Both responses show significant difference to 0 μM concentration and not responsive to wild type neoantigen peptide. Statistical analysis: FDR for adjusted p value, P values: *≤0.05, *≤0.001, **≤0.0001.
Figure 37A:
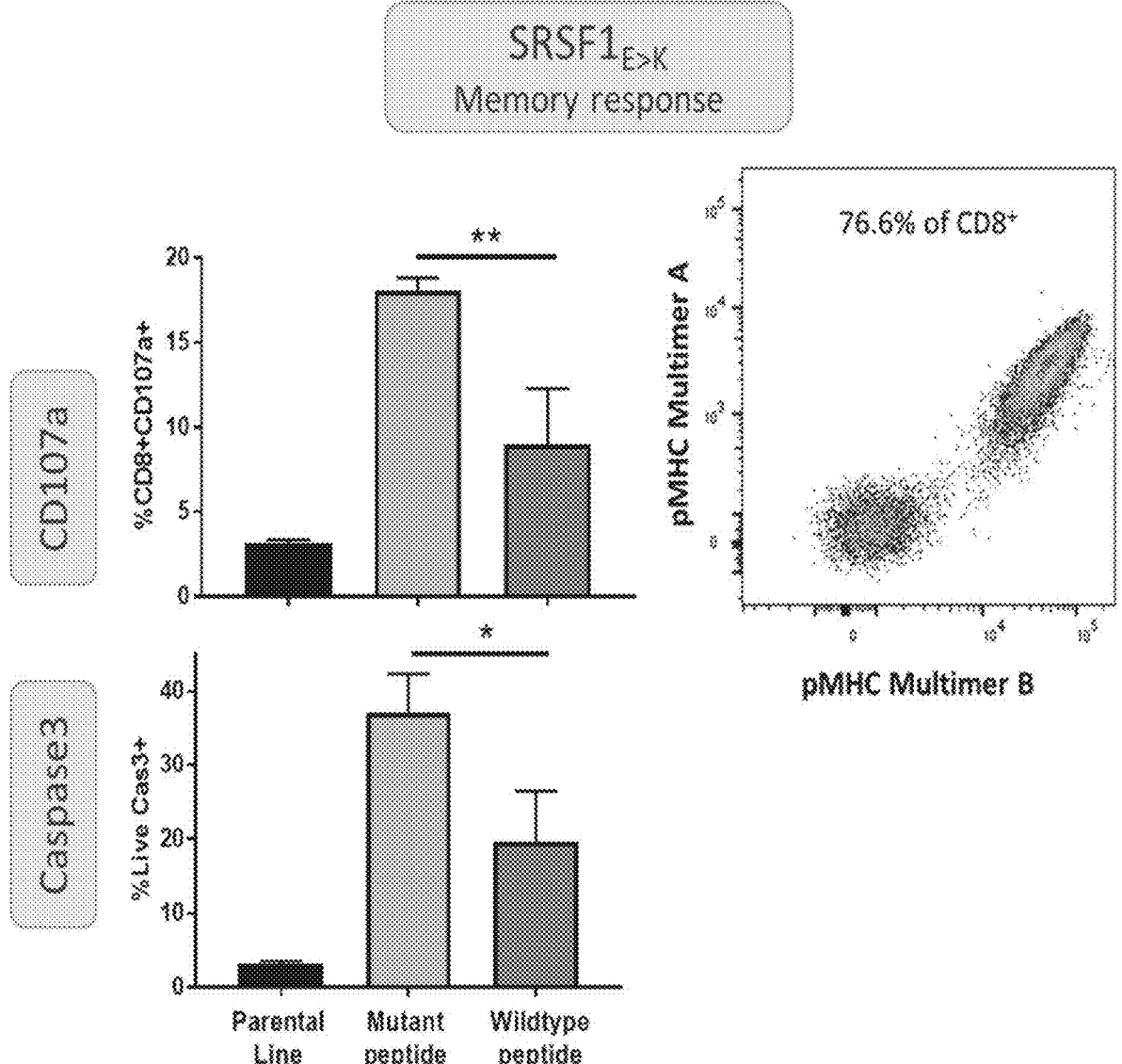
FIG. 37A depicts the cytotoxicity profile of a memory response induced in a patient with melanoma as quantified by the frequency of CD8$^+$CD107a$^+$ T cells. It also depicts target cell killing by these T cell responses as quantified by the frequency of aCAS3+ tumor cells. The cytotoxic capacity of the induced CD8+ T cell responses was assessed by re-challenging with mutant or wildtype neoantigen transduced tumor cells. Un-transduced tumor cells (parental A375 line) or tumor cells transduced with a 200aa construct were used. The construct either contained the mutant or wildtype sequence, mutation in the center. Upregulation of CD107a on CD8+ T cells and active Caspase3 on tumor cells were measured upon co-culture. Target ratio: 3.3:1 (SRSF1$_{E>K}$).
Figure 37C:
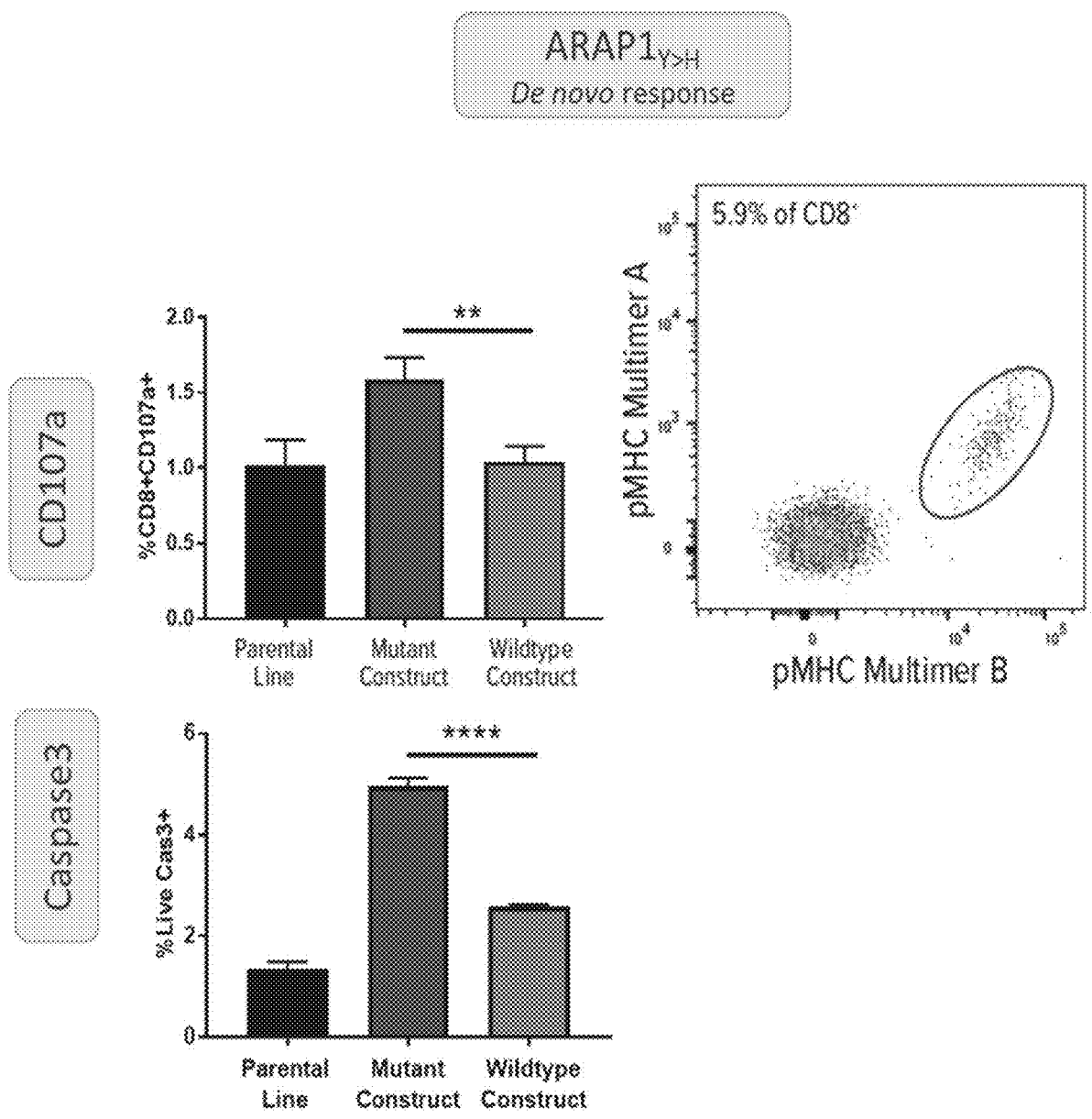
FIG. 37C depicts the cytotoxicity profile of a de novo response induced in a patient with melanoma as quantified by the frequency of CD8$^+$CD107a$^+$ T cells. It also depicts target cell killing by these T cell responses as quantified by the frequency of aCAS3+ tumor cells. The cytotoxic capacity of the induced CD8+ T cell responses was assessed by re-challenging with mutant or wildtype neoantigen transduced tumor cells. Un-transduced tumor cells (parental A375 line) or tumor cells transduced with a 200aa construct were used. The construct either contained the mutant or wildtype sequence, mutation in the center. Upregulation of CD107a on CD8+ T cells and active Caspase3 on tumor cells were measured upon co-culture. The circles highlight the pMHC+ fractions. Effector:Target ratio: 0.66:1 (ARAP1$_{Y>H}$). Statistical analysis: unpaired T test, P values ≤0.01, **≤0.0001.

T cells were prepared using the T cell manufacturing protocol 3 and the stimulated T cells were analyzed. The samples were obtained from two patients with melanoma. T cells were analyzed using similar assays as described in Example 24. FIG. 34 shows pMHC multimer plots quantifying CD8$^+$ T cell responses induced from the two patients with melanoma. As used herein, NEO-STIM refers to the T cell manufacturing protocol. FIG. 35 shows data of the polyfunctional profile of a memory and de novo CD8+ T cell response induced in a patient with melanoma, as shown by a combination of 1, 2, 3, or 4 functions. The one or more functions are production of one or more factors selected from IFNγ, TNFα, CD107a and 4-1BB). FIG. 36 shows the specificity of a memory and de novo CD8+ T cell response induced in a patient with melanoma towards mutated and wildtype peptide. FIGS. 37A and 37B and 37C show the cytotoxicity profile of a memory and de novo response induced in a patient with melanoma as quantified by the frequency of CD8$^+$CD107a$^+$ T cells (top panels). The bottom panels of FIGS. 37A and 37B and 37C show target cell killing by these T cell responses as quantified by the frequency of aCAS3$^+$ tumor cells. FIG. 38A shows the identification of neoantigen specific CD4$^+$ T cell responses in a melanoma patient. FIG. 38B shows the specificity of these CD4$^+$ T cell responses identified in FIG. 38A towards mutated and wildtype peptides. FIG. 38C shows the polyfunctionality profile of these CD4$^+$ T cell responses, as shown by a combination of 1, 2, 3, or 4 functions. The one or more functions are production of one or more factors selected from IFNγ, TNFα, CD107a and 4-1BB.

Example 27—Experimental Data Using T Cell Manufacturing Protocol 1 or 2

Figure 39:
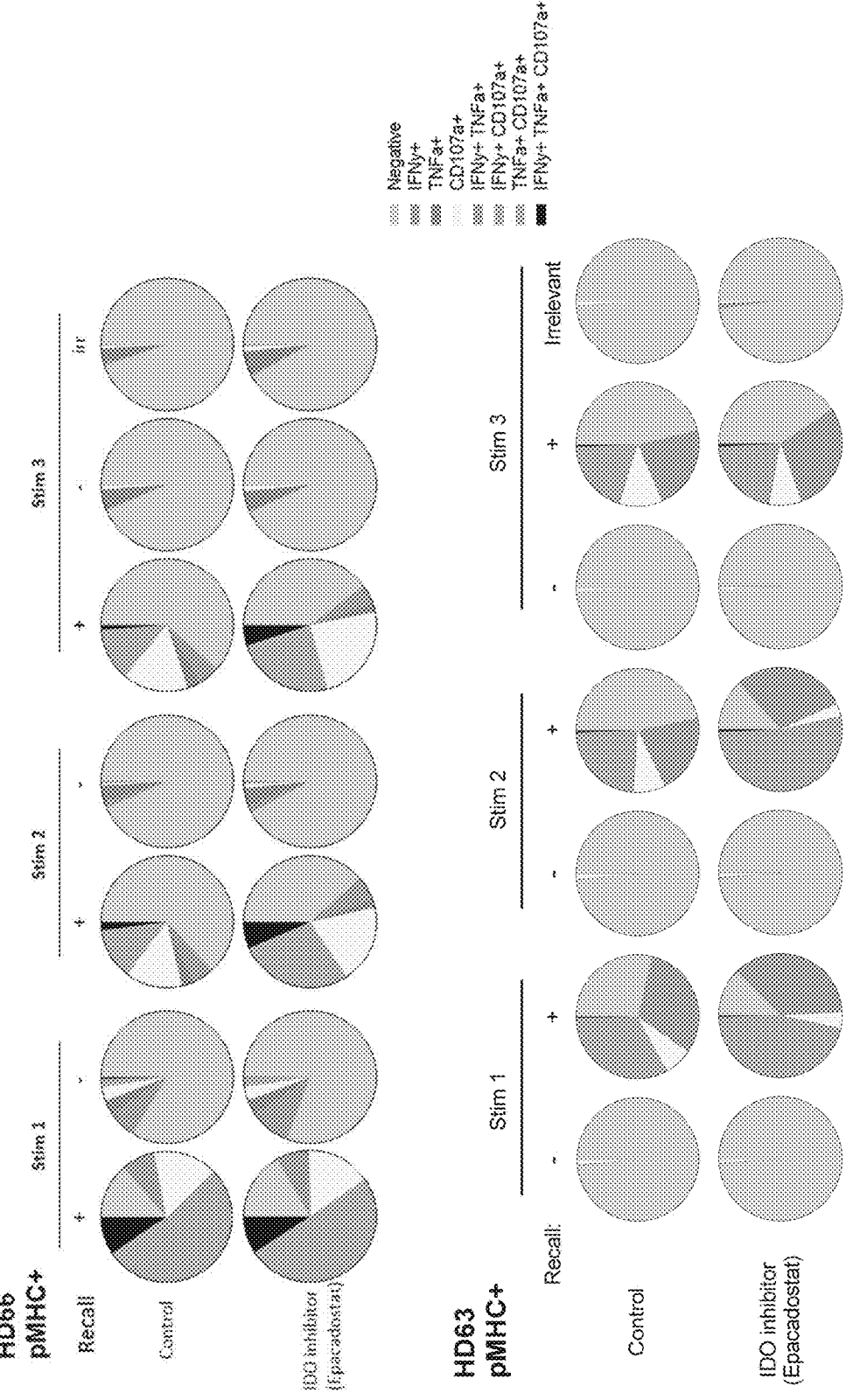
FIG. 39 depicts the functionality of memory responses induced in two healthy donors with or without the addition of Epacadostat, as shown by a combination of 1, 2 or 3 functions (e.g., the one or more functions are production of one or more factors selected from IFNγ, TNFα and CD107a).
Figures 40, 41A, 41B:
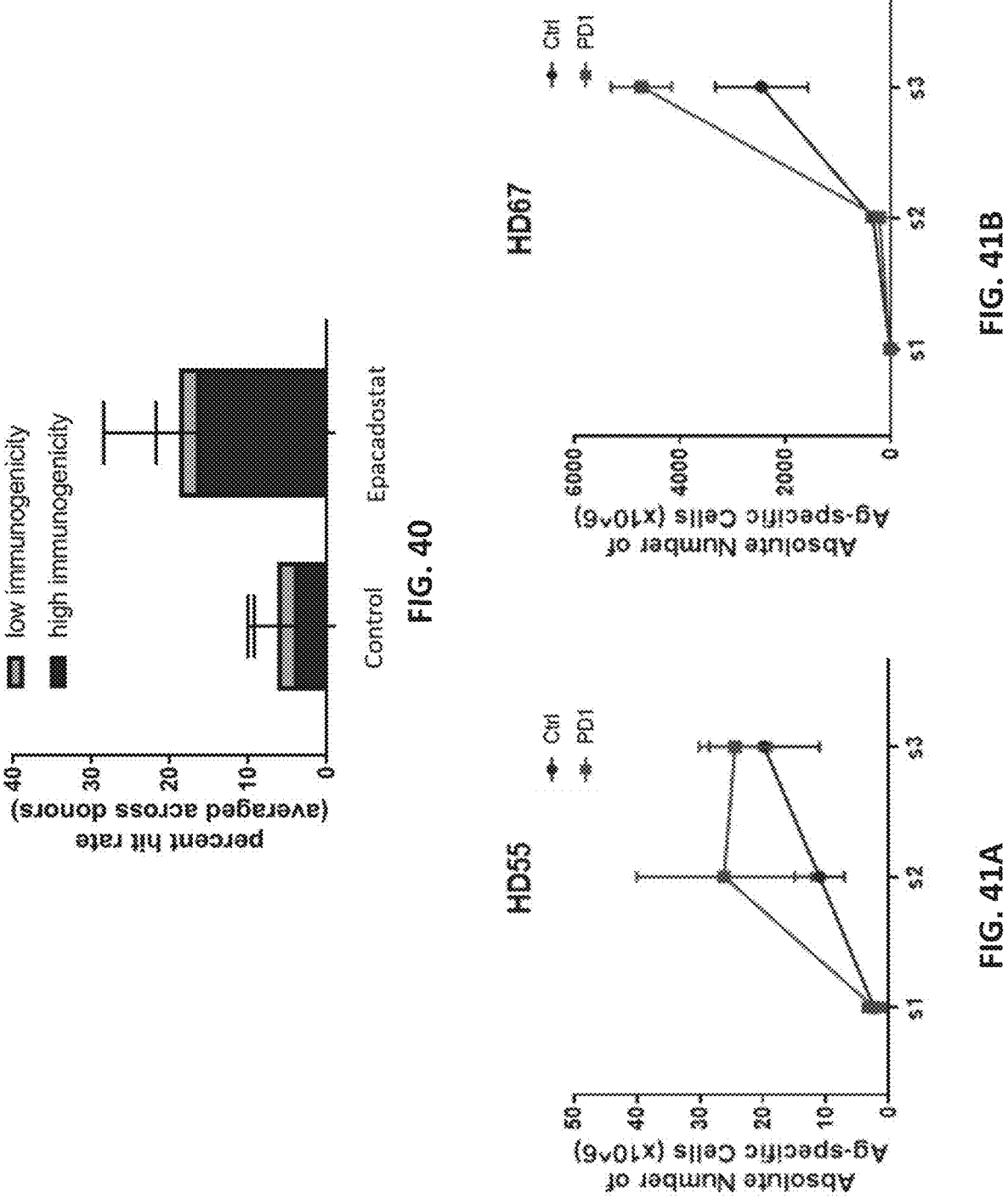
FIG. 40 depicts the percent induced de novo CD8$^+$ T cell responses ('hit rate', averaged across four healthy donors) in six replicate inductions with or without the addition of Epacadostat.
FIG. 41A depicts the absolute number of antigen specific cells from a healthy donor after induction with T cell manufacturing protocol provided herein, with or without the addition of PD-1 blocking antibody.
FIG. 41B depicts the absolute number of antigen specific cells from a healthy donor after induction with T cell manufacturing protocol provided herein, with or without the addition of PD-1 blocking antibody.
Figure 42B:
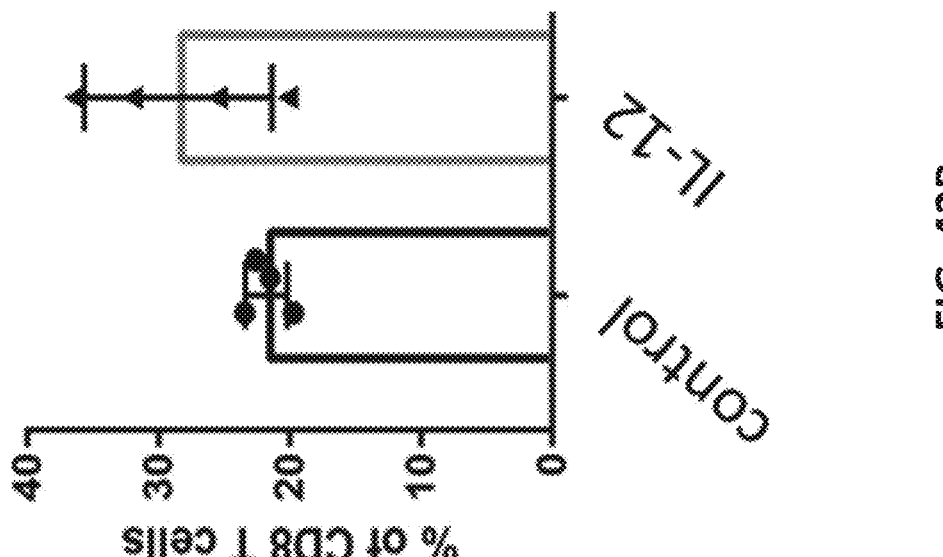
FIG. 42B depicts an exemplary graphical representation of the percentage of CD8+ T cells from the de novo CD8+ T cell compartment with or without the addition of IL-12.
Figure 42A:
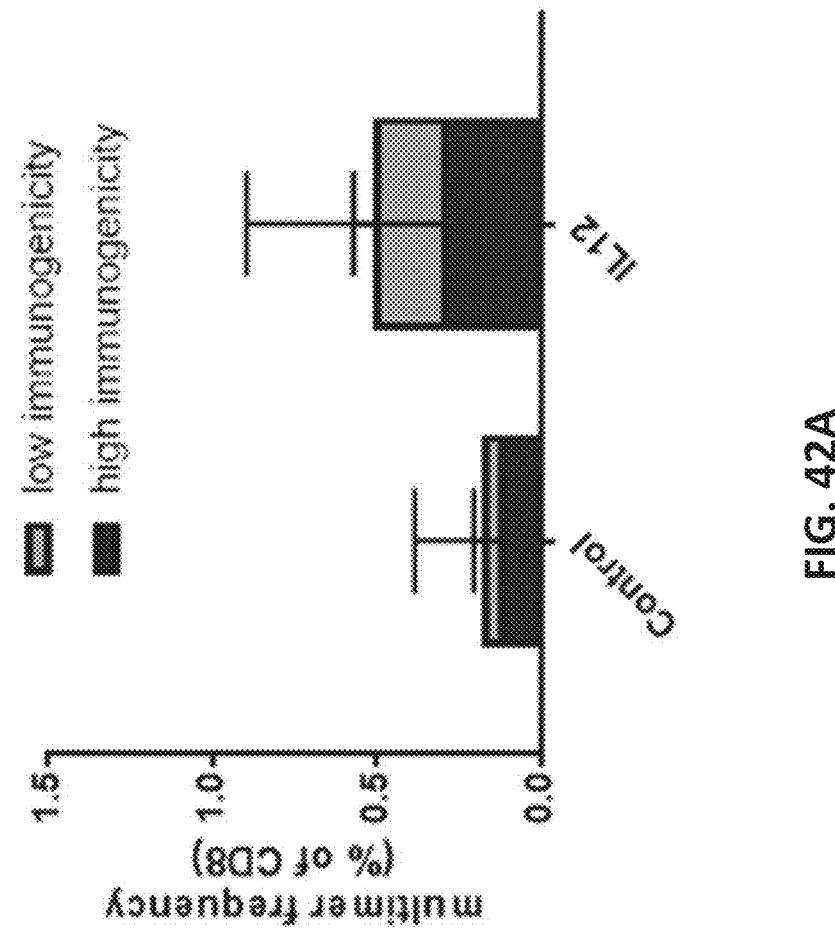
FIG. 42A depicts the multimer positive frequency as a percentage of CD8$^+$ T cells from the de novo CD8+ T cell compartment with or without the addition of IL-12.
Figure 43:
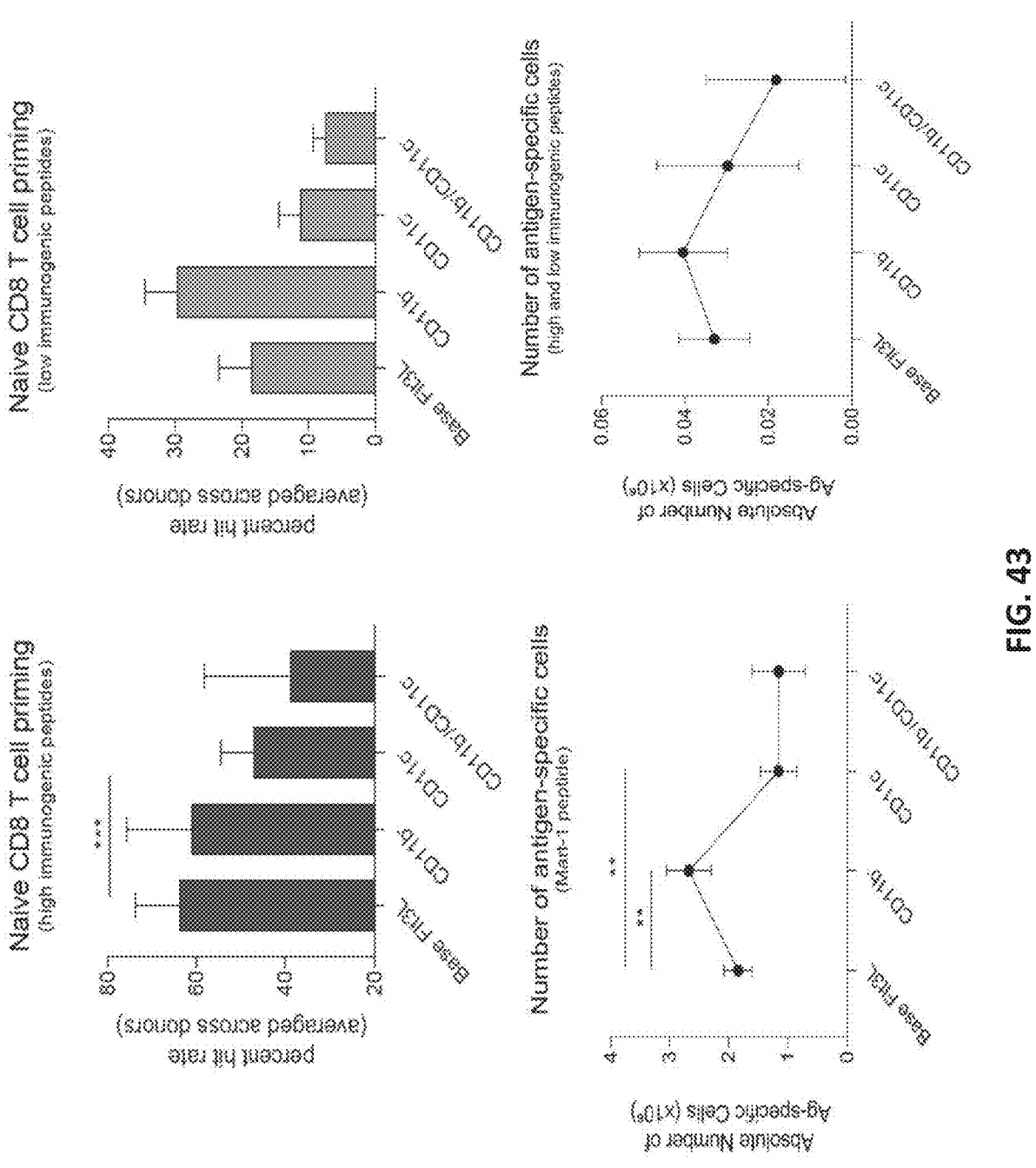
FIG. 43 depicts exemplary graphical representations of the percent hit rate for highly immunogenic and low immunogenic antigens that naive CD8 cells are responsive to after performing different antigen presenting cell enrichment and antigen loading protocols using PBMCs derived from healthy donors. Also depicted are exemplary graphical representations of the absolute number of antigen specific cells after performing different antigen presenting cell enrichment and antigen loading protocols using PBMCs derived from healthy donors using a Mart-1 peptide or highly immunogenic and low immunogenic antigens.
Figure 44A:
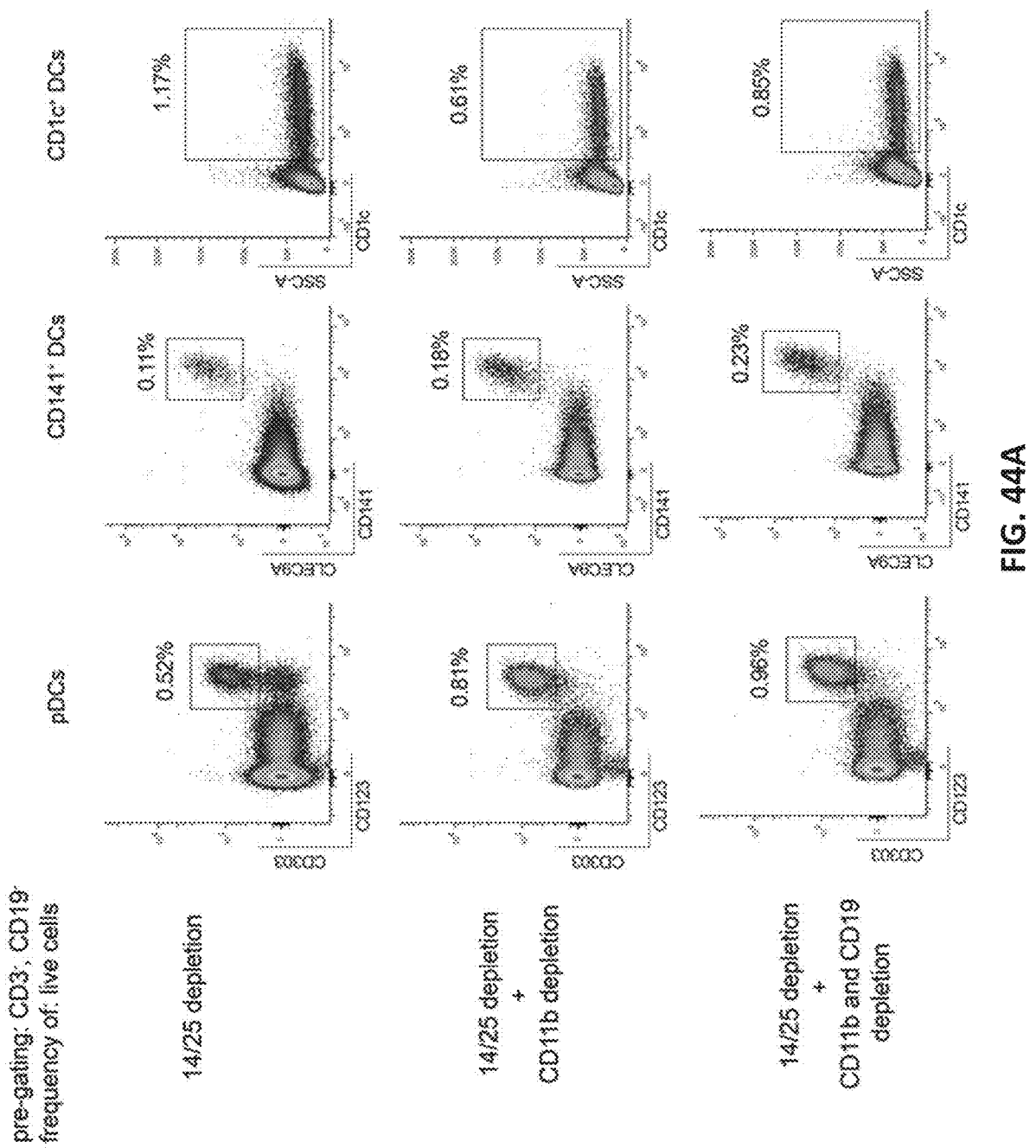
FIG. 44A depicts exemplary flow cytometric results of CD123 positive cells after performing the indicated antigen presenting cell enrichment and antigen loading protocols using PBMCs from three different healthy donors.
Figure 44B:
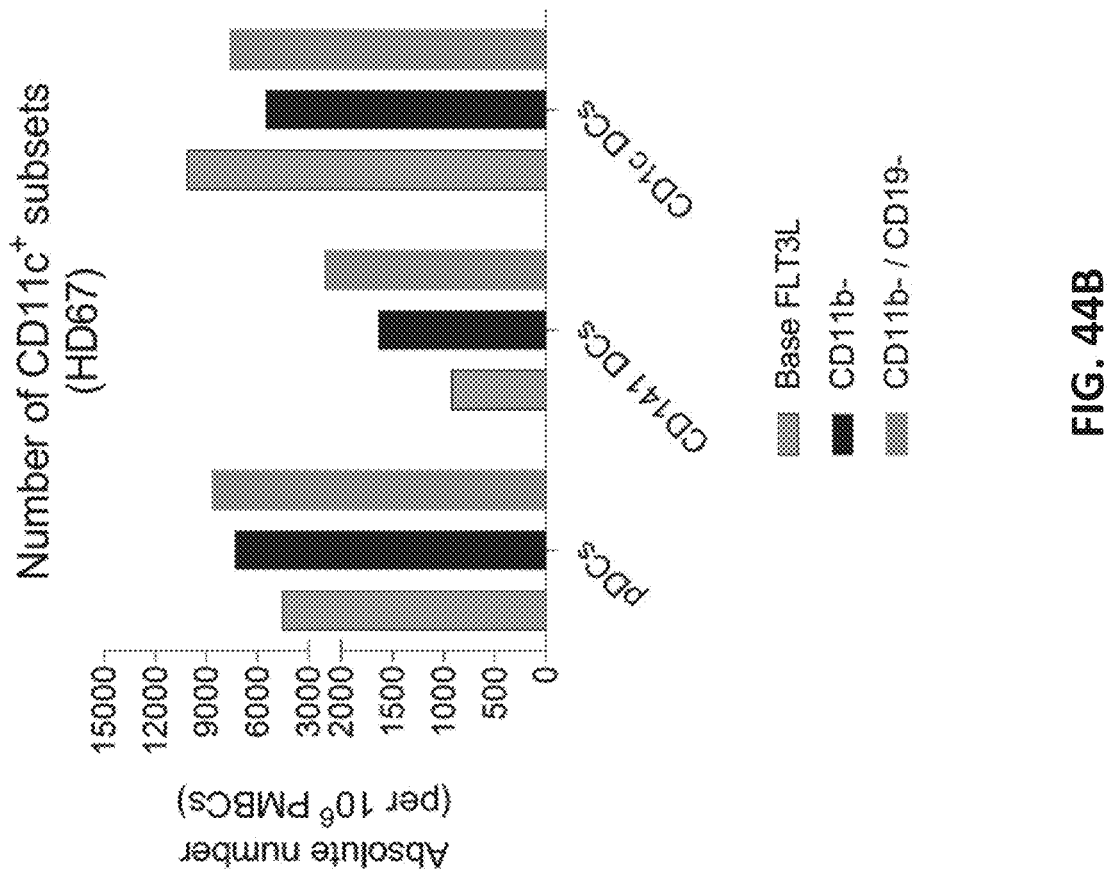
FIG. 44B depicts an exemplary graphical representation of the absolute number of the indicated CD11c+ cell subsets after performing three antigen presenting cell enrichment and antigen loading protocols using PBMCs from a healthy donor. The treatments are: Base Flt3L, FLT3L treatment alone; CD11b, FLT3L treatment and depletion of CD11b expressing cells; CD11b–/CD19–, FLT3L treatment and depletion of CD11b expressing cells and CD19 expressing ells.
Figure 45:
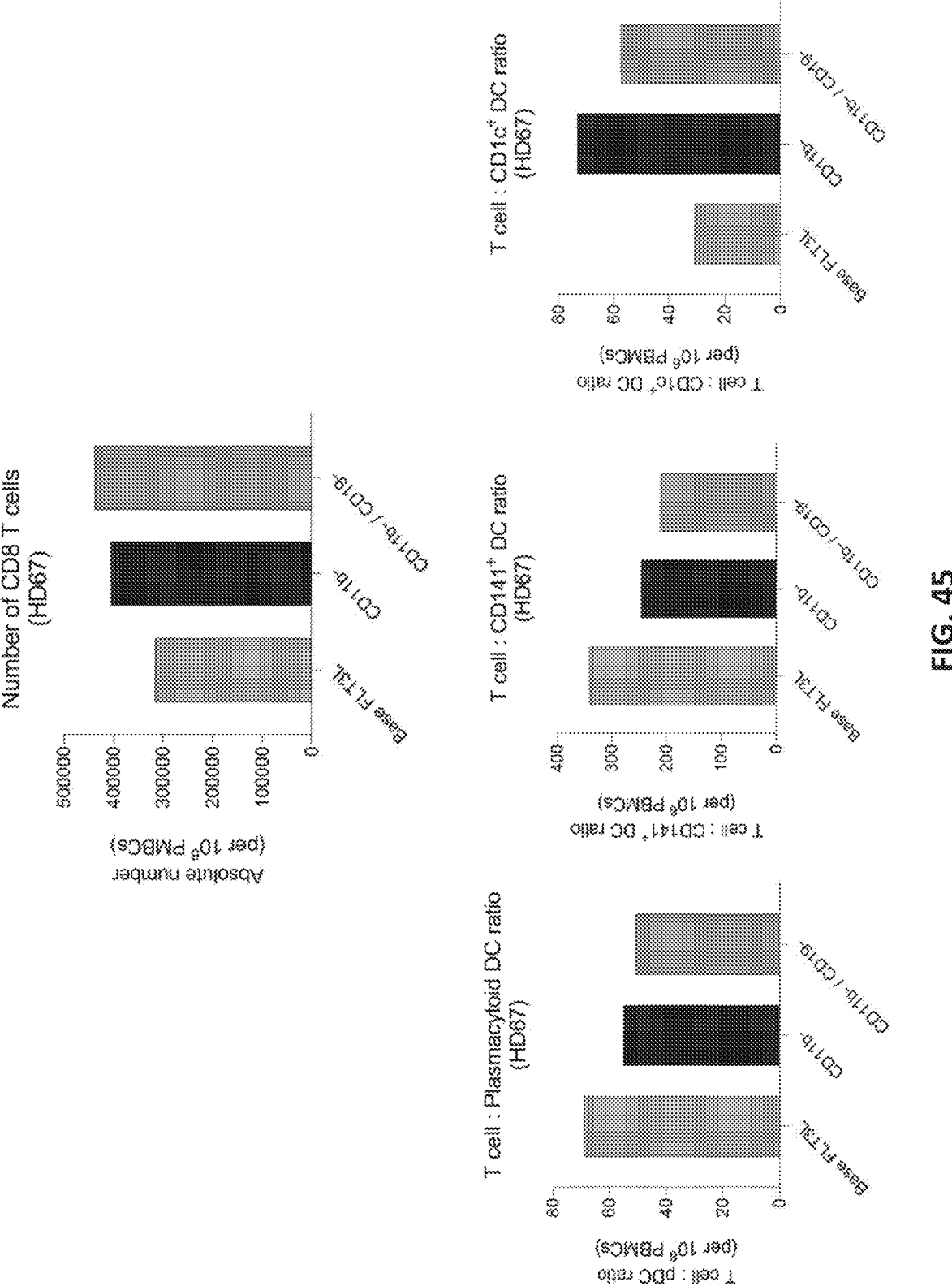
FIG. 45 depicts exemplary graphical representations of the total number of CD8 T cells and the indicated cell ratios after performing three antigen presenting cell enrichment and antigen loading protocols using PBMCs from a healthy donor. The treatments are: Base Flt3L, FLT3L treatment alone; CD11b, FLT3L treatment and depletion of CD11b expressing cells; CD11b–/CD19–, FLT3L treatment and depletion of CD11b expressing cells and CD19 expressing cells.

T cells were prepared using the T cell manufacturing protocol 1 or, as an alternative, protocol 2. The stimulated T cells were analyzed using similar assays as described in Example 24. FIG. 39 shows the functionality of memory responses induced in two healthy donors (e.g., HD66 and HD63) with or without the addition of Epacadostat, as shown by a combination of 1, 2 or 3 functions (e.g., the one or more functions are production of one or more factors selected from IFNγ, TNFα and CD107a). FIG. 40 shows the percent induced de novo CD8+ T cell responses ('hit rate', averaged across four healthy donors) in six replicate inductions with or without the addition of Epacadostat. FIG. 41A shows the absolute number of antigen specific cells from donor HD55 after induction with T cell manufacturing protocol provided herein, with or without the addition of PD-1 blocking antibody. FIG. 41B shows the absolute number of antigen specific cells from donor HD 67 after induction with T cell manufacturing protocol provided herein, with or without the addition of PD-1 blocking antibody. FIG. 42A shows the fraction of pMHC$^+$ CD8$^+$ T cells of de novo CD8$^+$ T cell responses with or without the addition of IL-12. FIG. 42B shows the percentage of CD8$^+$ T cells within the de novo CD8$^+$ T cell responses with or without the addition of IL-12.

Example 28: In-Depth Characterization of Immune Responses Induced Against Patient-Specific Neoantigens Patient-specific neoantigens were predicted using bioinformatics engine. Synthetic long peptides covering the predicted neoantigens were used as immunogens in the stimulation protocol to assess the immunogenic capacity. The stimulation protocol involves feeding these neoantigen-encoding peptides to patient-derived APCs, which are then co-cultured with patient-derived T cells to prime neoantigen specific T cells.

Multiple rounds of stimulations are incorporated in the stimulation protocol to prime, activate and expand memory and de novo T cell responses. The specificity, phenotype and functionality of these neoantigen-specific T cells was analyzed by characterizing these responses with the following assays: Combinatorial coding analysis using pMHC multimers was used to detect multiple neoantigen-specific CD8+ T cell responses. A recall response assay using multiplexed, multiparameter flow cytometry was used to identify and validate CD4+ T cell responses. The functionality of CD8+ and CD4+ T cell responses was assessed by measuring production of pro-inflammatory cytokines including IFN-γ and TNFα, and upregulation of the CD107a as a marker of degranulation. A cytotoxicity assay using neoantigen-expressing tumor lines was used to understand the ability of CD8+ T cell responses to recognize and kill target cells in response to naturally processed and presented antigen. The cytotoxicity was measured by the cell surface upregulation of CD107a on the T cells and upregulation of active Caspase3 on neoantigen-expressing tumor cells. In this study, melanoma patient samples (NV6 and NV10) were obtained under IRB approval.

The stimulation protocol was successful in the expansion of pre-existing CD8+ T cell responses, as well as the induction of de novo CD8+ T cell responses (Table 11).

TABLE 11

| Patient | HUGO Symbol | Full Gene Name | Type |
|---|---|---|---|
| NV10 | SRSF1E > K | Serine and Arginine Rich Splicing Factor 1 | CD8 |
| | ARAP1Y > H | Ankyrin Repeat And PH Domain | |
| | PKDREJG > R | Polycystin Family Receptor For Egg Jelly | |
| | MKRN1$_{S>L}$ | Makorin Ring Finger Protein 1 | CD4 |
| | CREBBP$_{S>L}$ | CRREB Binding Protein | |
| | TPCN1$_{K>E}$ | Two Pore Segment Channel 1 | |
| NV6 | AASDH$_{neoORF}$ | Aminoadipate-Semialdehyde Dehydrogenase | CD8 |
| | ACTN4$_{K>N}$ | Actinin Alpha 4 | |
| | CSNK1A1$_{S>L}$ | Casein Kinase 1 Alpha 1 | |
| | DHX40$_{neoORF}$ | DEAH-Box Helicase 40 | |
| | GLI3$_{P>L}$ | GLI Family Zinc Finger 3 | |
| | QARS$_{R>W}$ | Glutamyl-tRNA Synthetase | |
| | FAM178B$_{P>L}$ | Family With Sequence Similarity 178 Member 8 | |
| | RPS26$_{P>L}$ | Ribosomal Protein S26 | |

Using PBMCs from melanoma patient NV10, expansion of a pre-existing CD8+ T cell response was observed from 4.5% of CD8+ T cells to 72.1% of CD8+ T cells (SRSF1$_{E>K}$). Moreover, the stimulation protocol was effective in inducing two presumed de novo CD8+ T cell responses towards patient-specific neoantigens (ARAP1$_{Y>H}$: 6.5% of CD8+ T cells and PKDREJ$_{G>R}$: 13.4% of CD8+ T cells; no cells were detectable prior to the stimulation process) (FIG. 34). The stimulation protocol successfully induced seven de novo CD8+ T cell responses towards both previously described and novel model neoantigens using PBMCs from another melanoma patient, NV6, up to varying magnitudes (ACTN4$_{K>N}$ CSNK1A1$_{S>L}$ DHX40neoORF 7, GLI3$_{P>L}$, QARSR$_{>W}$, FAM178B$_{P>L}$ and RPS26$_{P>L}$, range: 0.2% of CD8+ T cells up to 52% of CD8+ T cells). Additionally, a CD8+ memory T cell response towards a patient-specific neoantigen was expanded (AASDH neoORF, up to 13% of CD8+ T cells post stimulation).

The induced CD8+ T cells from patient NV10 was characterized in more detail. Upon re-challenge with mutant peptide loaded DCs, neoantigen-specific CD8+ T cells exhibited one, two and/or all three functions (16.9% and 65.5% functional CD8+ pMHC+ T cells for SRSF1$_{E>K}$ and ARAP1$_{Y>H}$, respectively (FIG. 35).

When re-challenged with different concentrations of neoantigen peptides, the induced CD8+ T cells responded significantly to mutant neoantigen peptide but not to the wildtype peptide (FIG. 36).

In patient NV10, CD4+ T cell responses were identified using a recall response assay with mutant neoantigen loaded DCs (FIGS. 38A-38C). Three CD4+ T cell responses were identified (MKRN1$_{S>L}$, CREBBP$_{S>L}$ and TPCN1$_{K>E}$) based on the reactivity to DCs loaded with mutant neoantigen peptide. These CD4+ T cell responses also showed a polyfunctional profile when re-challenged with mutant neoantigen peptide. 31.3%, 34.5% & 41.9% of CD4+ T cells exhibited one, two and/or three functions; MKRN1$_{S>L}$, CREBBP$_{S>L}$ and TPCN1$_{K>E}$ responses, respectively.

The cytotoxic capacity of the induced CD8+ responses from patient NV10 was also assessed (FIGS. 37A-37C). Both SRSF1$_{E>K}$ and ARAP1$_{Y>H}$ responses showed a significant upregulation of CD107a on the CD8+ T cells and active Caspase3 on the tumor cells transduced with the mutant construct after co-culture.

Using the stimulation protocol, predicted patient-specific neoantigens, as well as model neoantigens, were confirmed to be immunogenic by the induction of multiple neoantigen-specific CD8+ and CD4+ T cell responses in patient material. The ability to induce polyfunctional and mutant-specific CD8+ and CD4+ T cell responses proves the capability of predicting high-quality neoantigens and generating potent T cell responses. The presence of multiple enriched neoanti-gen-specific T cell populations (memory and de novo) at the end of the stimulation process demonstrates the ability to raise new T cell responses and generate effective cancer immunotherapies to treat cancer patients.

Example 29—Effect of Selective Depletion of Cells

In this example, the effect of selective depletion of non-essential cells from a PBMC culture on the cell population, rate of cell expansion ex vivo and generation of activated T cells was investigated. The purpose of the depletion studies was to enhance CD8 T cell priming by enriching for essential APC populations (via depletion of non-essential PBMCs).

PBMCs were isolated from donors, HD66, HD67, HD69; and cell culture was set up in G-Rex 24 well plates. Cells were cultured in the presence of peptide concentration: 0.4 µM (0.4 mM peptide stock). Peptide pool: Two sets of peptides were tested: highly immunogenic and low immu-nogenic HIV3, ACTN4, CSNK1A1 peptides. Additionally, MART-1 was used to assess the expansion of cells with a high precursor frequency, as is the case for memory T cell responses. PBMCs were first subjected to the depletion as indicated per experimental group, and then stimulated with Flt3L. The groups include CD14/25 depletion (Base Flt3L); Base Flt3L+CD11b depletion (using CD11b biotin AB); Base Flt3L+CD11b/CD19 depletion (using CD11b biotin AB, CD19 microbeads).

Figure 46:
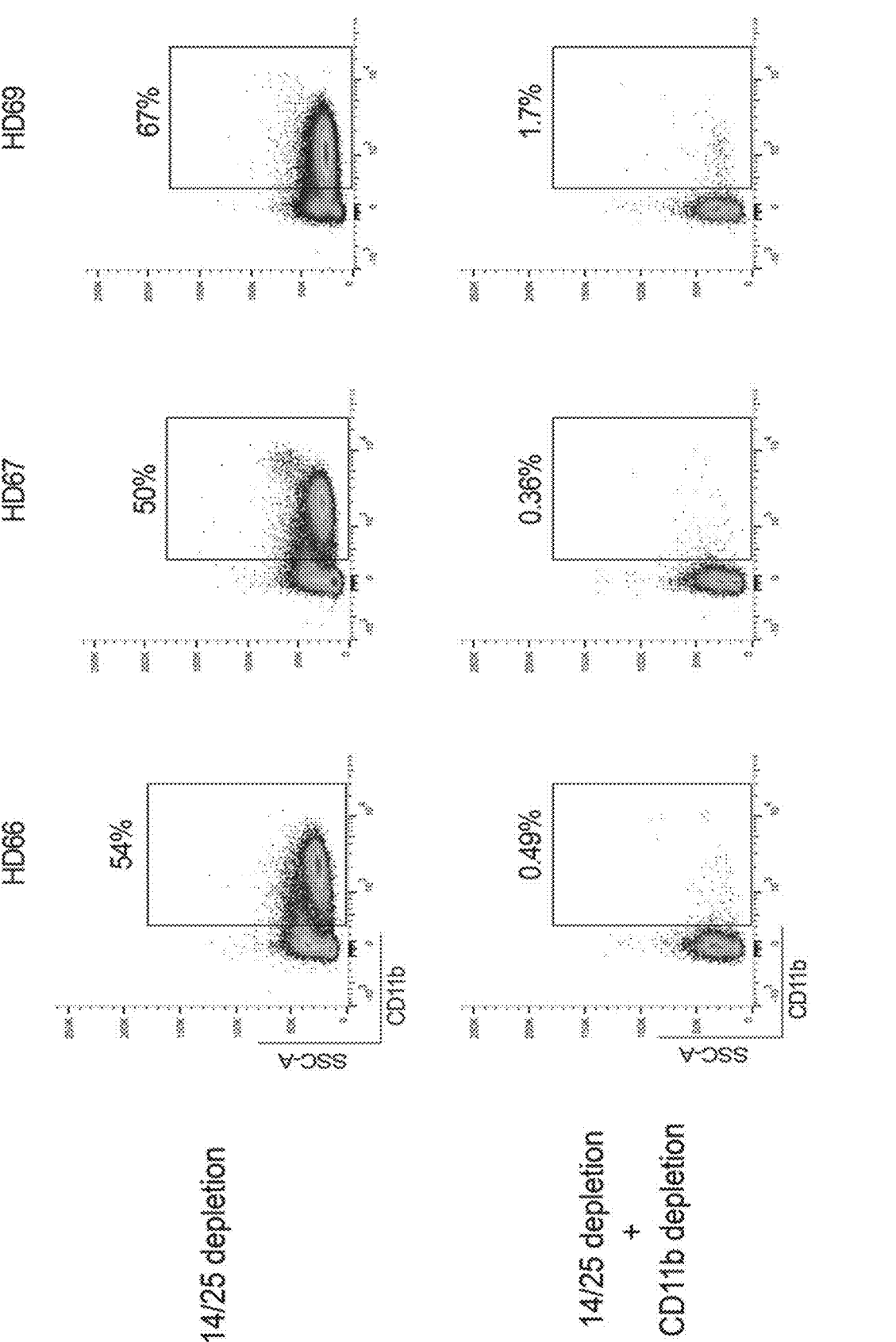
FIG. 46 depicts exemplary flow cytometric results of CD11b positive cells after performing the indicated antigen presenting cell enrichment and antigen loading protocols using PBMCs from three different healthy donors.
Figure 47:
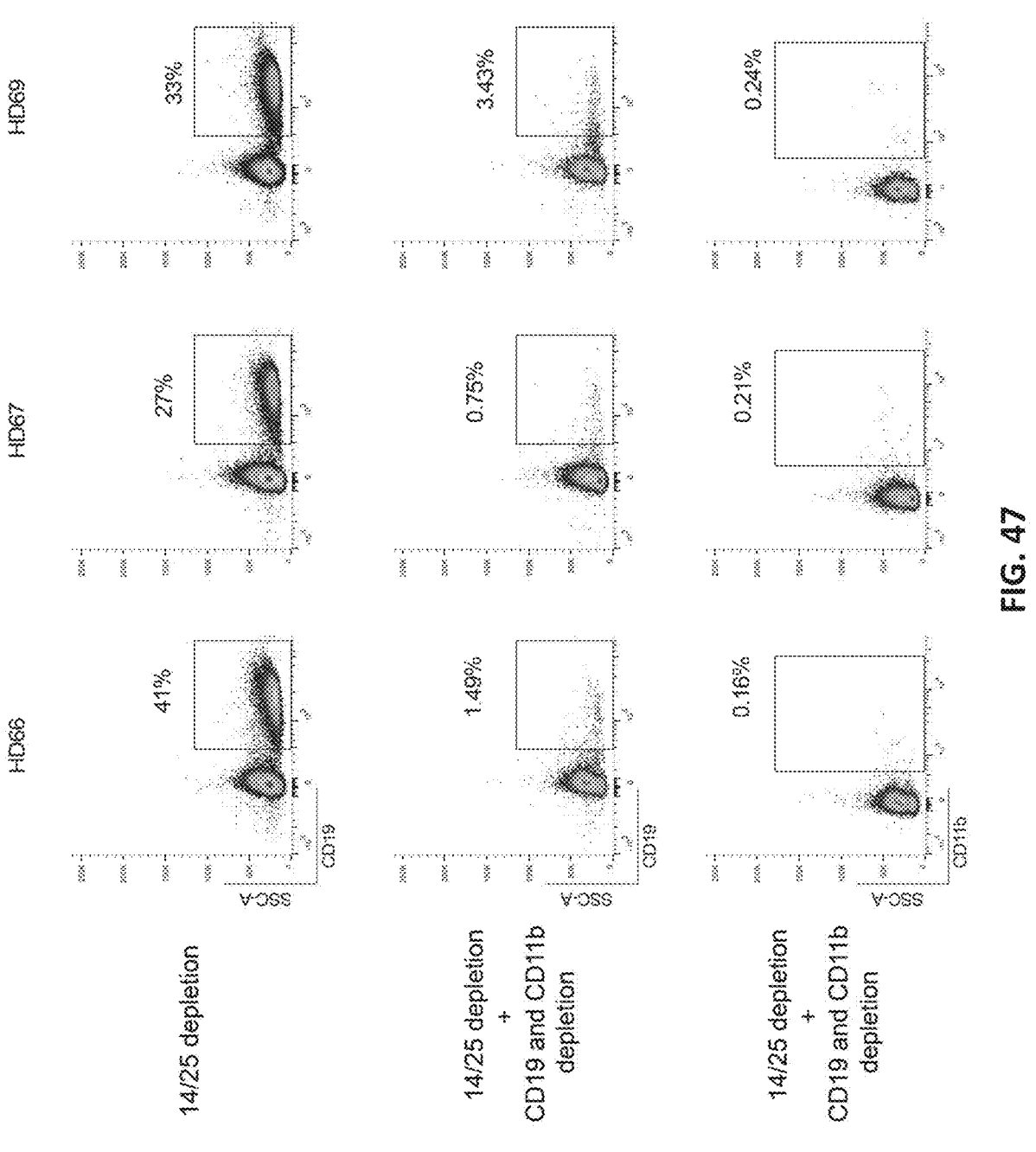
FIG. 47 depicts exemplary flow cytometric results of CD19 positive cells after performing the indicated antigen presenting cell enrichment and antigen loading protocols using PBMCs from three different healthy donors.
Figure 48:
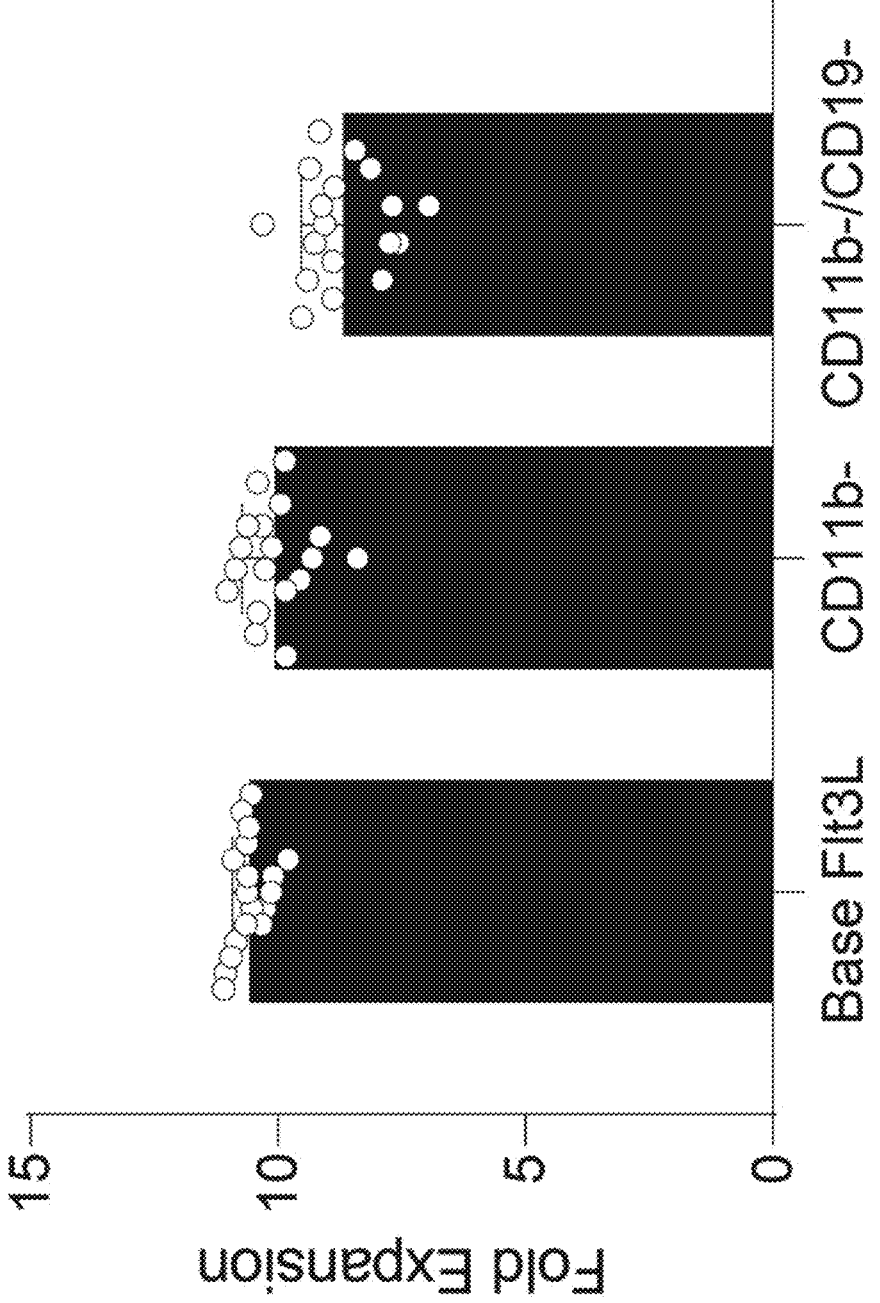
FIG. 48 depicts an exemplary graphical representation of the fold expansion of cells after performing three antigen presenting cell enrichment and antigen loading protocols. The treatments are: Base Flt3L, FLT3L treatment alone; CD11b, FLT3L treatment and depletion of CD11b expressing cells; CD11b–/CD19–, FLT3L treatment and depletion of CD11b expressing cells and CD19 expressing cells.
Figure 49A:
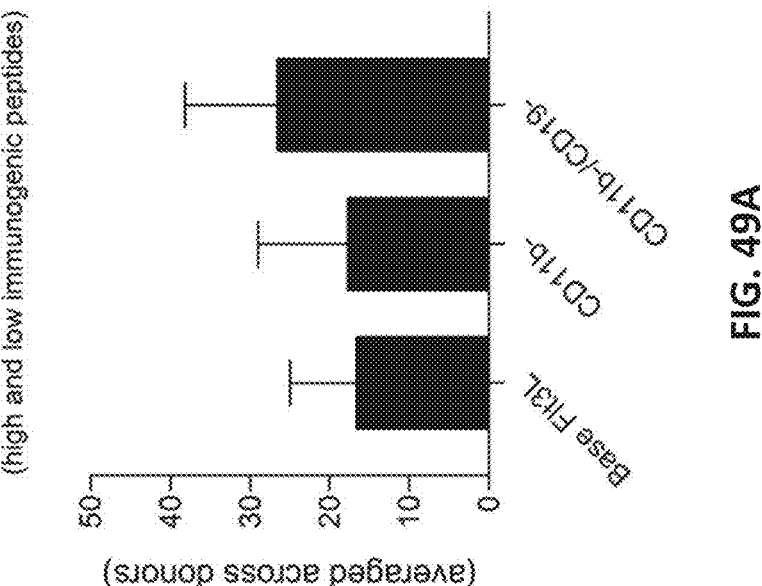
FIG. 49A depicts exemplary data indicating the number of specific antigens that naive CD8 T cells are responsive to after performing three antigen presenting cell enrichment and antigen loading protocols using PBMCs derived from healthy donors. The results were averaged across three healthy donors. The treatments are: Base Flt3L, FLT3L treatment alone; CD11b, FLT3L treatment and depletion of CD11b expressing cells; CD11b–/CD19–, FLT3L treatment and depletion of CD11b expressing cells and CD19 expressing cells. An exemplary graphical representation of the data is shown in the bottom graph.
Figure 49B:
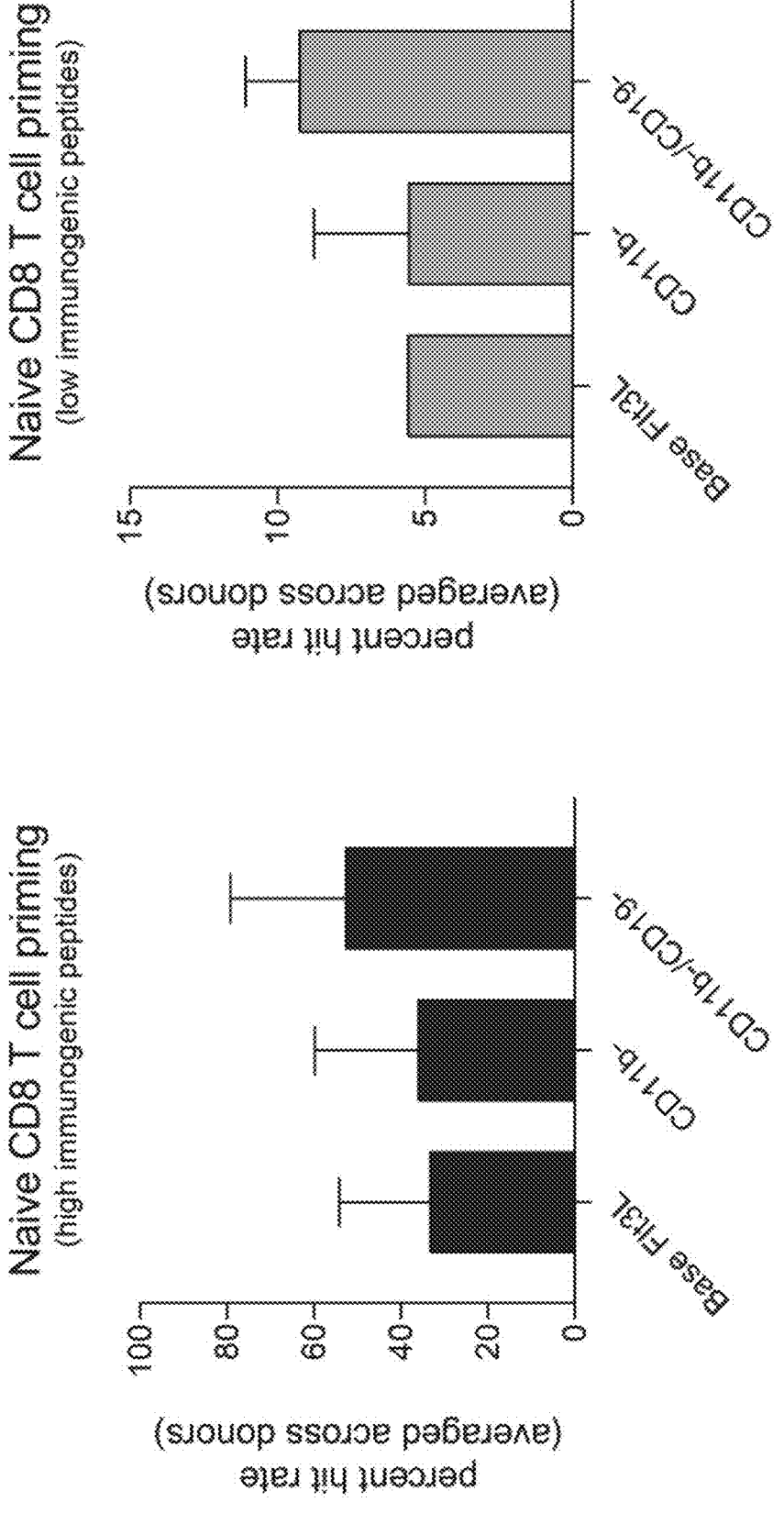
FIG. 49B depicts exemplary graphical representations of the percent hit rate for highly immunogenic (left) and low immunogenic (right) antigens that naive CD8 cells are responsive to after performing three antigen presenting cell enrichment and antigen loading protocols using PBMCs derived from healthy donors. The results were averaged across three healthy donors. The treatments are: Base Flt3L, FLT3L treatment alone; CD11b, FLT3L treatment and depletion of CD11b expressing cells; CD11b–/CD19–, FLT3L treatment and depletion of CD11b expressing cells and CD19 expressing cells.

Read-outs—The following assays were performed at D16 post induction: Fold expansion of cells, Multimer analysis. Cell counts were expressed as absolute number or percent of the total population. FIGS. 46-47 show the resultant cells at Day 0 after performing the indicated depletion. FIG. 48 shows that the depletion of CD11b and CD19 cells had no effect on fold change of expansion. FIG. 49A and FIG. 49B show that depletion of CD11b or CD11b and CD19 actually increases the hit rate of naïve T cells, which are primed by peptide loaded DCs. No difference was observed when either low or high immunogenic peptides were used. Depletion of CD11b and CD11b/CD19 cells shows remarkable improvement of antigen specific CD8+ T cells after the first stimulation with antigen loaded APCs. As shown in FIG. 50, for the MART-1 peptide there was greater than two-fold increase (left) in CD8+ antigen specific T cells, after a single stimulation. Similar increase is found when cells were stimulated with high and low immunogenic peptide. With multiple inductions, the increase was further magnified (data not shown). Overall, the increase frequencies of pDCs and CD141+ DCs correlated with improved T cell inductions.

Figures 51A, 51B, 51C:
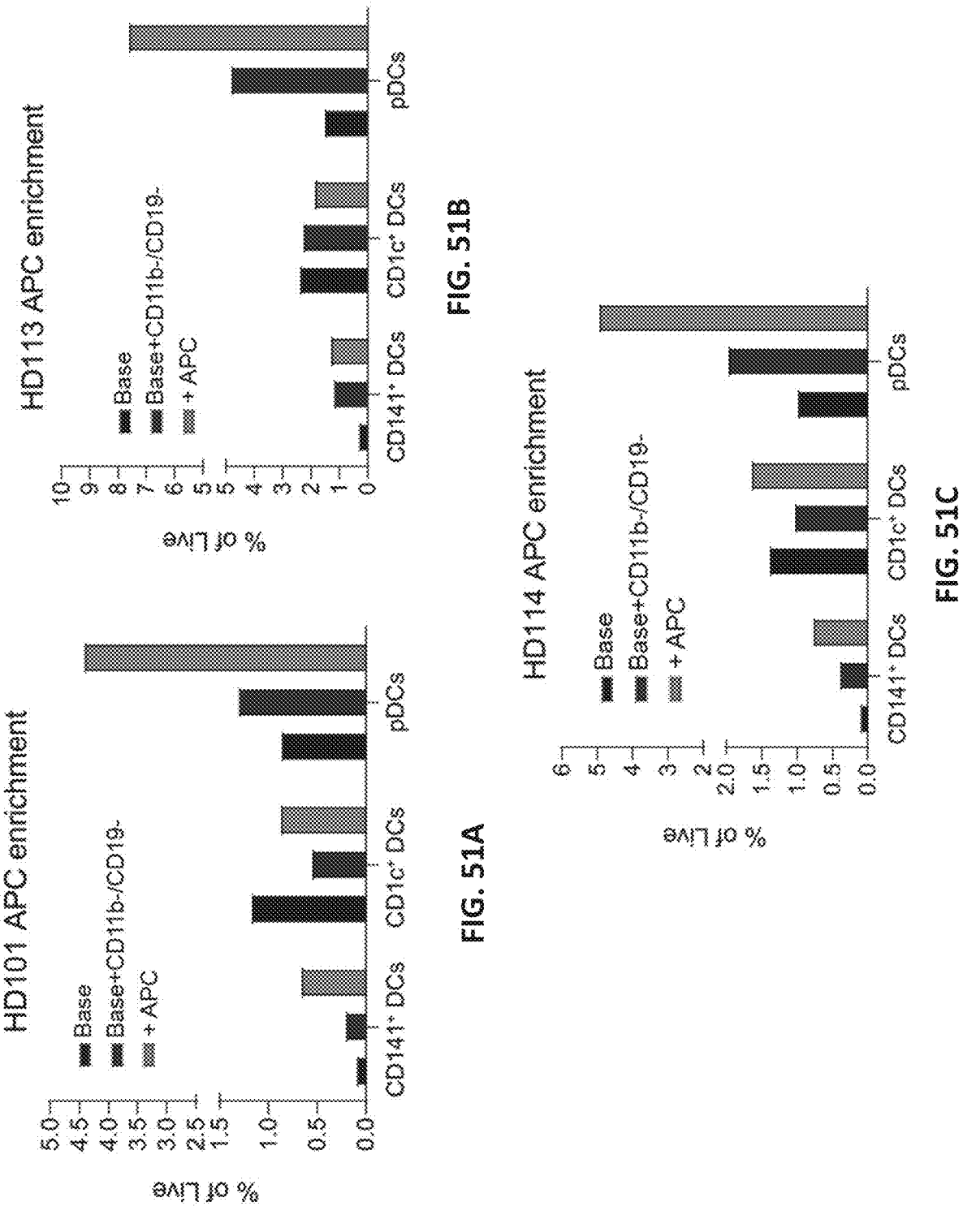
FIG. 51A depicts an exemplary graphical representation of the percentage of live cells after performing three antigen presenting cell enrichment and antigen loading protocols using PBMCs derived from a healthy donor. The treatments are: Base, FLT3L treatment alone; Base+CD11b–/CD19–, FLT3L treatment, and depletion of CD11b expressing cells and CD19 expressing cells; +APC, additional PBMC fraction added to Base+CD11b–/CD19–, where the additional fraction was depleted of CD3, CD19, CD11b, CD25, and CD14 expressing cells.
FIG. 51B depicts an exemplary graphical representation of the percentage of live cells after performing three antigen presenting cell enrichment and antigen loading protocols using PBMCs derived from a healthy donor. The treatments are: Base, FLT3L treatment alone; Base+CD11b–/CD19–, FLT3L treatment, and depletion of CD11b expressing cells and CD19 expressing cells; +APC, additional PBMC fraction added to Base+CD11b–/CD19–, where the additional fraction was depleted of CD3, CD19, CD11b, CD25, and CD14 expressing cells.
FIG. 51C depicts an exemplary graphical representation of the percentage of live cells after performing three antigen presenting cell enrichment and antigen loading protocols using PBMCs derived from a healthy donor. The treatments are: Base, FLT3L treatment alone; Base+CD11b–/CD19–, FLT3L treatment, and depletion of CD11b expressing cells and CD19 expressing cells; +APC, additional PBMC fraction added to Base+CD11b–/CD19–, where the additional fraction was depleted of CD3, CD19, CD11b, CD25, and CD14 expressing cells.
Figures 51D, 51E:
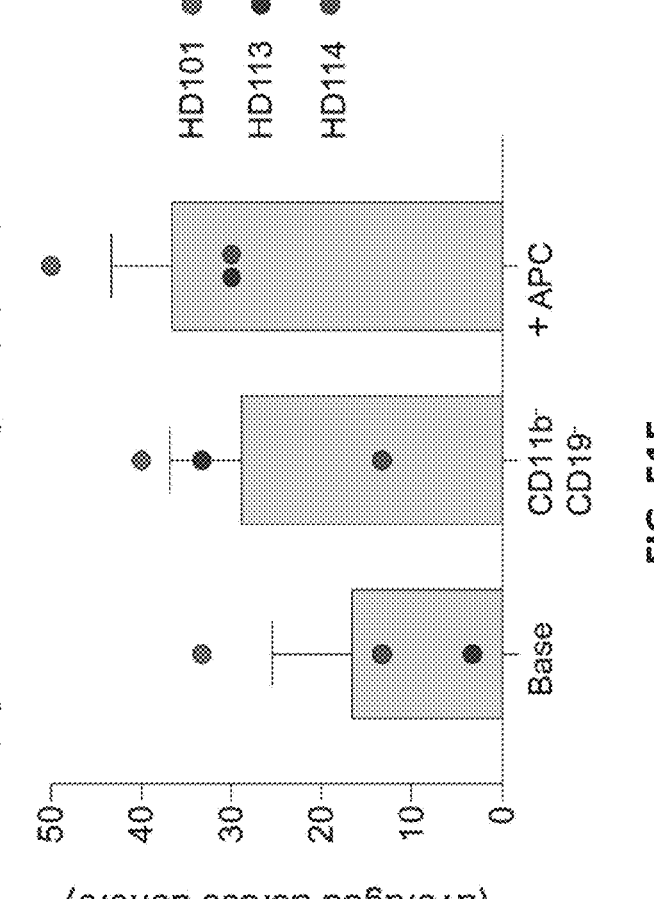
FIG. 51D depicts exemplary data indicating the number of specific antigens that CD8 cells are responsive to, per donor, using exemplary antigen presenting cell enrichment protocols.
FIG. 51E depicts an exemplary graphical representation of the percent hit rate for the indicated peptides that CD8 cells are responsive to averaged across three healthy donors.

Further enrichment of antigen presenting cells (APCs) by selective depletion of CD3+, CD19+, CD11b+, CD14+ and CD25+ cells from a PBMC culture on cell population, rate of cell expansion ex vivo and generation of activated T cells was investigated. PBMCs were isolated from donors, HD101, HD113, HD114; and cell culture was set up in G-Rex 24 well plates. Three sets of cells were depleted as follows: 5×10^6 cells were CD14/CD25 depleted (Base);

5×10^6 cells were CD14/CD25/CD11b/CD19 depleted (Base+CD11b/CD19); 5×10^5 cells were CD3/CD19/CD11b/CD25/CD14 depleted and mixed with 5×10^6 Base+CD11b/CD25 cells, and the set designated as APC in the figures described for this example. The various cell populations were identified by cell surface markers as follows: CD141+ DCs were identified by detection of CD141 and Clec9A expression; CD1c+ DCs were identified by detection of CD1c expression; plasmacytoid DCs (pDCs) were identified by CD303 and CD123 expression. As shown in FIGS. 51A-51C, pDCs were the most over-represented APCs within the enrichment set (APCs). APC enrichment during first stimulation improves hit rates (antigen specific CD8+ T cells) (FIGS. 51D and 51E).

Figure 52A:
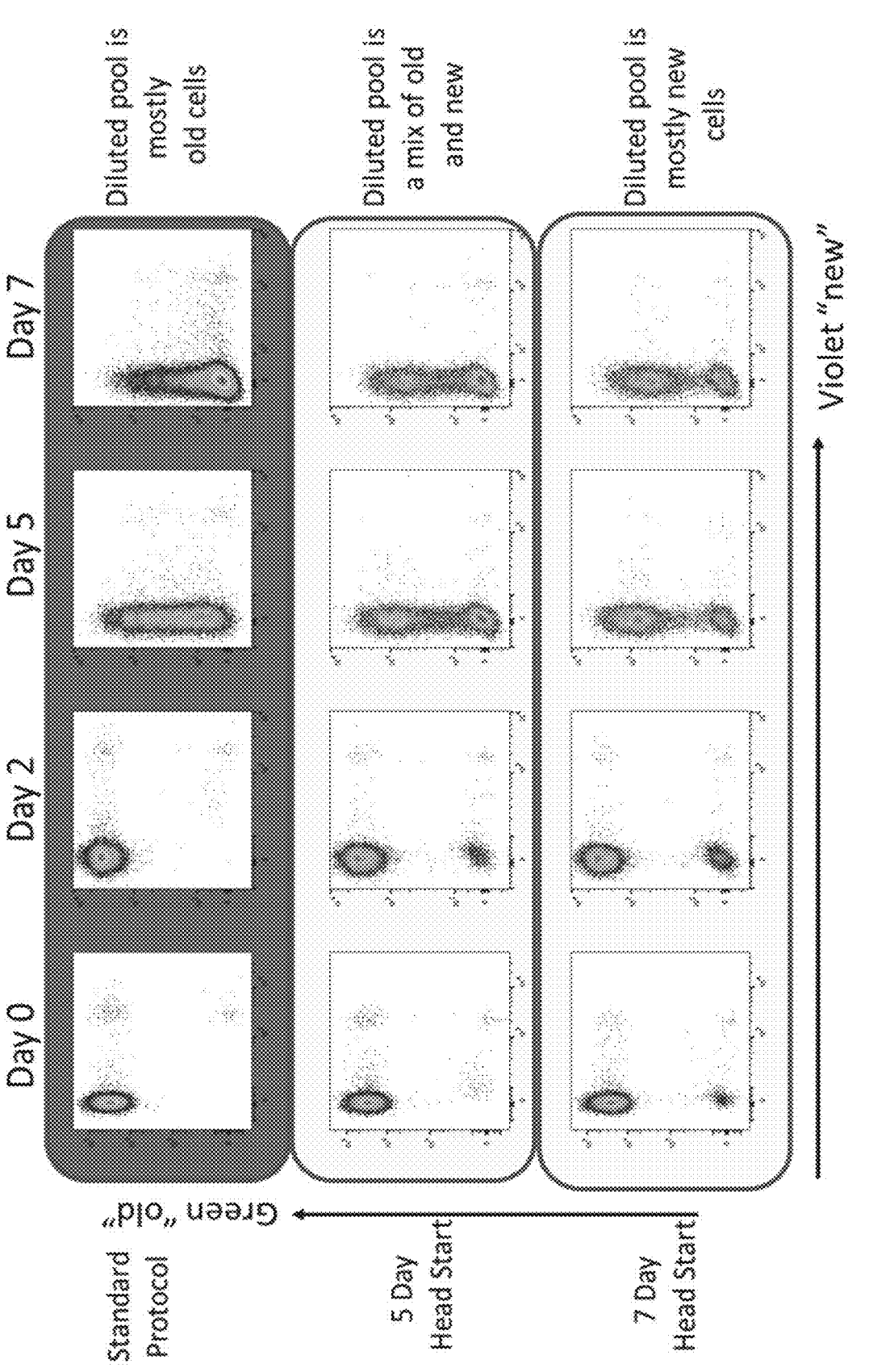
FIG. 52A depicts exemplary flow cytometric analysis results from an experiment in which populations of cells added to the culture process at different times were labeled with membrane-permeable amine-reactive dyes (e.g. Carboxyfluorescein succinimidyl ester or TagIT Violet™) prior to stimulation with antigen loaded APCs. When applied to the second stimulation, a population of cells already cultured for 14 days was labeled with one dye, while another population of cells containing a new preparation of antigen loaded APCs and T cells was labeled with another dye, and the two populations were mixed together to perform a restimulation or expansion. The relative contribution of each of these populations to the overall antigen specific T cell pool was noted by the presence and rate of dilution of each dye. In all cases, a population of cells was cultured for 14 days ($1^{st}$ stimulation), labeled with one dye, and then added to another populations of cells labeled with another dye that had been antigen-stimulated 1 day in advance (standard protocol), 4 days in advance (5 day head start), or 6 days in advance (7 day head start).
Figures 52B, 52C:
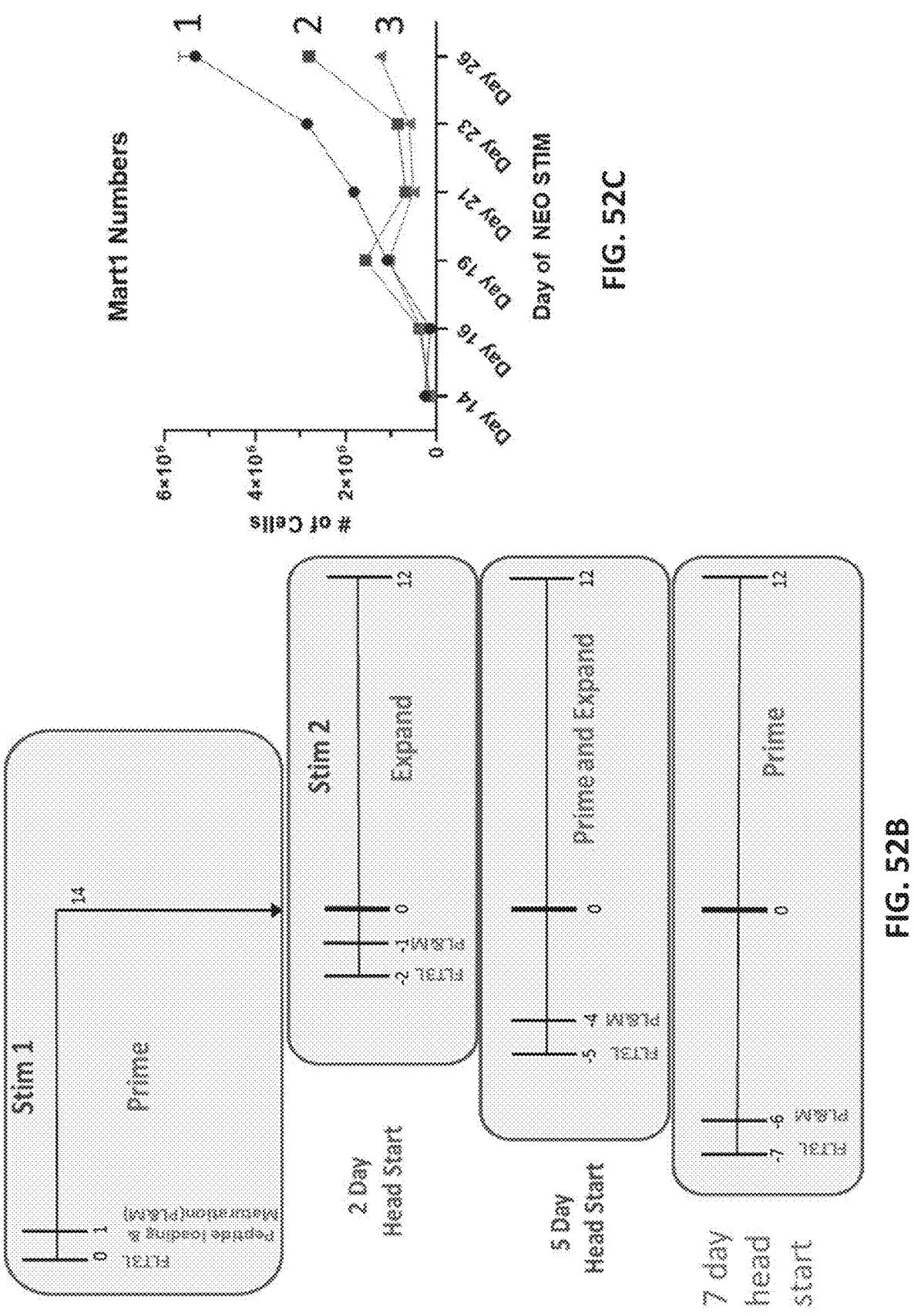
FIG. 52B shows an exemplary schematic representation of three different T cell expansion protocols, each with two stimulations including a head start for antigen loading APCs at 2 or 5 or 7 days prior to contacting with T cells.
FIG. 52C shows an exemplary graph of the number of antigen specific T cells over time using the three different T cell expansion protocols depicted in FIG. 52B. 1, Standard protocol; 2, 5 day headstart; 3, 7 day headstart.

Example 30. Contribution of Earlier or Later Stimulated Cells Towards Antigen Responsiveness To investigate the contribution of cell populations added earlier or later to the antigen responsiveness, cells (including T cells) were labeled with membrane-permeable amine-reactive dyes (e.g. Carboxyfluorescein succinimidyl ester or TagIT Violet™) prior to stimulation with antigen loaded APCs and the expansion of antigen specific T cells was noted by the presence and rate of dilution of the dye. When applied to the second stimulation, a population of cells already cultured for 14 days was labeled with one dye, while another population of cells containing a new preparation of antigen loaded APCs and T cells was labeled with another dye, and the two populations were mixed together to perform a restimulation or expansion. The relative contribution of each of these populations to the overall antigen specific T cell pool was noted by the presence and rate of dilution of each dye (FIG. 52A). Using this experimental design, it was noted that the newly prepared population of cells did not yield antigen specific T cells at day 21. It was noted that when the newly prepared APCs were preloaded with antigens either 4 days or 6 days in advance (5 day head start or 7 day head start, respectively) of adding the already-cultured cells, as opposed to 1 day in advance (standard protocol, schema shown in FIG. 52B), the newly prepared T cells did contribute substantially to the antigen specific fraction. Simultaneously, it was noted that the proliferation rate of the already-cultured T cells was reduced when restimulated using APCs preloaded either 4 days or 6 days in advance, resulting in overall a lower number of antigen specific cells compared to the standard protocol (FIG. 52C).

Example 31—Induction of Immune Cells Using Messenger RNA Encoding Neoantigenic Peptides In this example, a study comparing induction of immune cells with neoantigenic peptides and messenger RNA encoding neoantigenic peptides are compared.

Materials: AIM V media (Invitrogen); LS columns, Miltenyi Biotec #130-042-401, CD14 MicroBeads, Human, Miltenyi Biotec #130-050-201; CD25 MicroBeads II, Human, Miltenyi Biotec #130-092-983; MACS Buffer: 1:20 dilution of MACS BSA Stock Solution (#130-091-376) with autoMACS Finsing Solution (Miltenyi Biotec #130-091-22); Human FLT3L, preclinical CellGenix #1415-050 Stock 50 ng/µL; CD3 Microbeads, Human, Miltenyi Biotec #130-050-101; TNF-α, preclinical CellGenix #1406-050 Stock 10 ng/µL; IL-1β, preclinical CellGenix #1411-050 Stock 10 ng/µL; PGE1 or Alprostadil—Cayman from Czech republic Stock 0.5 µg/µL; AIMV media+2, 5, 10% Human serum+1% PenStrep; IL7 Stock 5 ng/µL; IL15 Stock 5 ng/µL; 24 well G-Rex Plates; IVT mRNA (1 μg/μL); RNAse zap; Lonza P3 Nucelofection kit and buffer with 100 ul cuvettes.

Procedure:

Day 0: CD14 and CD25 Depletion of PBMCs and Treatment with FLT3L

1. PBMCs were thawed and counted in AIM V media at 10 million cells/mL.
2. Cells were then pelleted by centrifugation at 300×g for 5 minutes and resuspended in warm media containing benzonase (1 uL/mL) for 1 hour. After benzonase treatment, cells were counted.
3. MACS LS columns were washed three times with 3 mL of cold MACS buffer.
4. PBMCs were then spun at 300×g for 5 minutes and resuspended in 60 uL MACS buffer per $10^7$ cells in a 50 mL tube
5. 20 ul of CD2511 Microbeads and 20 μL of CD14 Microbeads were added to cells plus MACs buffer per $10^7$ cells and incubated for 15 minutes in 4 degree fridge or on ice
6. After incubation, the total volume of cells were made to 50 mL by adding cold MACS buffer and cells were spun at 300×g for 10 minutes. The supernatant was then decanted and cells were resuspended in 500 μL per $2×10^8$ cells.
7. Cells were passed through the LS Column attached to Miltenyi MidiMACS columns. Columns were then washed three times with 3 mL of MACS buffer.
8. Cells that pass through the magnet into the collection tube are counted and spun down. Cells were then counted and 5 million cells in 2 mL of AIM V with 50 ng/mL of FLT3L and were plated in a 24 well plate.

Day 1: Nucleofection of FLT3L Treated PBMCs

1. Two ml of AIM V media were plated in a well of a 24 well GREX plate. Plates were put into the incubator to equilibrate along with a separate 5 mL of media in a 15 mL conical tube.
2. Using a cell lifter, cells that were stimulated with FLT3L overnight were harvested from the well
3. All cells were collected in a 50 mL conical tube and wells were washed with an additional 1 ml of COLD media. Cells are then spun at 300×g for 7 minutes
4. CD3 isolation was performed on the FLT3L stimulated PBMCs per manufacturer's protocol. CD3 isolated cells left on the magnet are expelled from the column, counted and plated into the appropriate wells of the equilibrated 24 well plate and placed into the incubator.
5. The remaining cells collected as flow through from the Miltenyi bead separation were spun down (300×g for 7 minutes) and pellets were placed on ice.
6. 1 μg-10 μg of appropriate RNA were added to each AMAXA nucleocuvette vessel and placed on ice (volume was kept less than 10 μL; RNA was diluted with RNAse free water if needed)
7. Cells were resuspended cells in P3 buffer using 100 ul of P3 buffer per million cells per cuvette
8. 100 ul of P3 buffer plus cells were mixed with RNA in the nucleocuvette and nucleofected by manufacturer's protocol using CB150, DU100, EA100, EU100 or CU110 protocols as appropriate.
9. Cuvettes were then incubated for 10 minutes on ice and after incubation, 100 ul of pre-warmed media was added.
10. Cells were then plated in the appropriate wells of a 24 well plate and placed in the incubator.

Day 2: Cell Maturation and Addition of Human Serum

1. Maturation cocktail containing TNF-α, IL-1β, PGE1, IL-7 was added 2-3 hours after nucleofection. Plates were then returned to the incubator. After 8-12 hours, human serum was added to each well to bring the human serum to 10% of well volume. Plates were then added to the incubator for culturing.

Day 5, 8, 10 and 12: Media Replacement and Feeding of IL-7 and IL-15

1. AIMV containing 10% human serum supplemented with 5 ng/mL IL-7 and 5 ng/mL of IL-15 were added to cultures as needed determined by culture growth.

Day 12-14: Repeat of Protocol for Day 0-Day 2 for Restimulation of Cultured T Cells Day 14: Restimulation of Cultured T Cells 1. T cell cultures are harvested, counted and replated with new nucleofected cultures at a 1:1 ratio of induced cultures to nucleofected PBMCs. Human serum is added to the cultures so the culture volume of human serum is 10% in AIMV.

Day 16 and 19: Media Replacement and Feeding of IL-7 and IL-15

1. AIMV containing 10% human serum supplemented with 5 ng/mL IL-7 and 5 ng/mL of IL-15 were added to cultures as needed determined by culture growth.

Day 19-21: Repeat of Protocol for Day 0-Day 2 for Restimulation of Cultured T Cells Day 21: Restimulation of Cultured T Cells 1. T cell cultures are harvested, counted and replated with new nucleofected cultures at a 1:1 ratio of induced cultures to nucleofected PBMCs. Human serum is added to the cultures so the culture volume of human serum is 10% in AIMV. Any additional cells are saved frozen for additional analysis.

Day 23 and 26: Media Replacement and Feeding of IL-7 and IL-15

1. AIMV containing 10% human serum supplemented with 5 ng/mL IL-7 and 5 ng/mL of IL-15 were added to cultures as needed determined by culture growth.

Day 28: Harvest of Induced T Cells

2. T cell cultures are harvested, counted and frozen for additional analysis.

Figure 53:
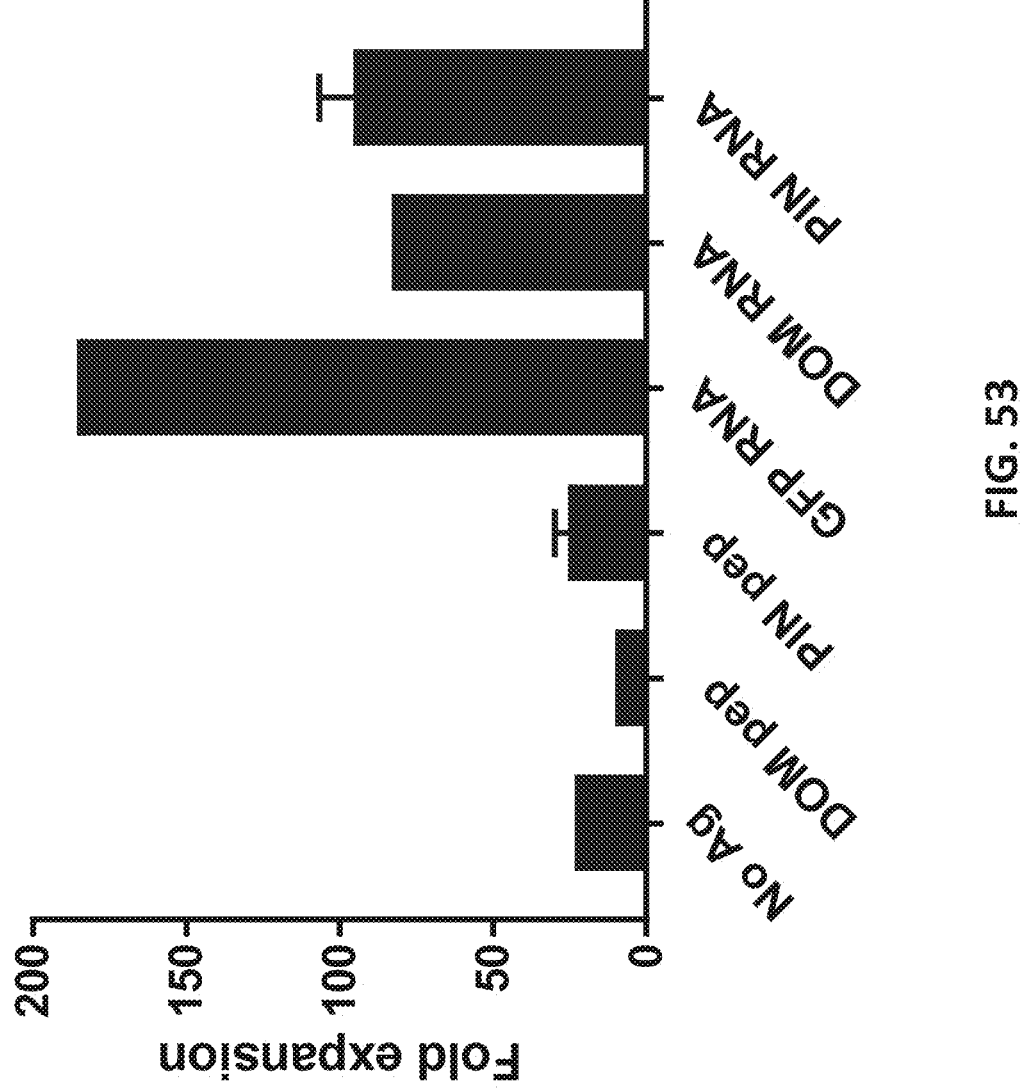
FIG. 53 shows an exemplary graph of fold expansion of cultures treated with the indicated neoantigen peptides (pep) or neoantigen RNA. CD14/CD25 depleted PBMC cells, after separating out or removing CD3 lymphocytes, were stimulated with antigen (peptide or mRNA encoding antigen). CD3 lymphocyte cells were reintroduced and stimulated for 14 days.

Results: FIG. 53 shows an exemplary data from the study described above. Fold expansion evaluated at the end of the study from stimulation of the cells using neoantigenic peptides (dominant peptides) or pre-identified neoantigenic peptides or with mRNA encoding the peptides, or mRNA encoding an irrelevant mRNA (GFP). mRNA induced cells exhibit surprising increase in fold change. Of note, there was only one sample for GFP expressing mRNA set, and so further experiments will be performed to validate the data. Nonetheless, the trend shows impressive increase in fold change of mRNA induced cells.

Figure 54:
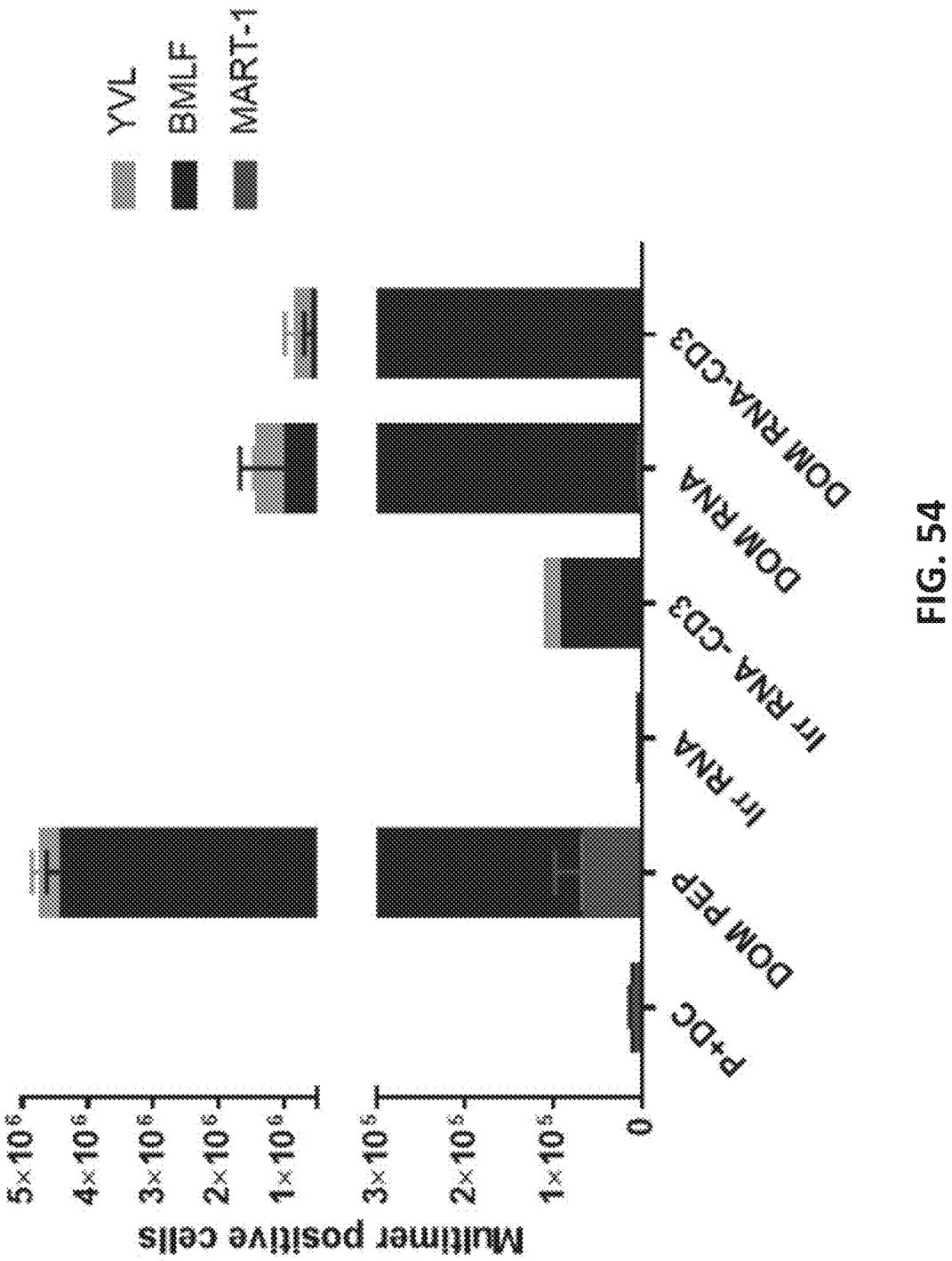
FIG. 54 shows an exemplary graph of the number of multimer positive antigen specific cells in cultures nucleofected with the indicated neoantigen peptides (pep) or neoantigen RNA. The cultures were nucleofected in the presence of T cells or in the absence of T cells (–CD3). Irr, irradiated.

FIG. 54 shows an exemplary data from the study where a selection of dominant peptides (mixture of viral peptides) were used. Irr RNA=irrelevant RNA. In this experiment, CD3+ cells were removed in some samples (designated in the figure as —CD3) prior to induction with mRNA. Comparing DOM-RNA and DOM RNA-CD3 samples, in which the cells were induced with the same mRNAs, only CD3 cells were first removed from the set designated as DOM RNA-CD3, it was seen that the presence or absence of CD3 did not result in drastic differences in the induction profiles. In general, stimulation with neoantigenic peptide encoding mRNA led to high level of induction of T cells which are antigen specific, as shown by multimer positive cells.

FIG. 55 shows an exemplary data, where CD8+ T cells obtained at the end of the stimulation and expansion were evaluated by flow cytometry for antigen specific memory T cell response. CD8+ T cells in an experimental set induced by viral peptides are shown in FIG. 54 upper panel (EBV BMLF peptide, left; mRNA encoding EBV BMLF peptide, right) which showed similar specificity profiles, approximately 46% of the CD8+ T cells were specific for the multimers. FIG. 55 lower panel (a pre-identified ME-1 peptide, left; mRNA encoding the ME-1 peptide, right), exhibited higher induction of the T cells with mRNA. This study shows that it could be even more beneficial to use mRNA for induction in case of low immunogenic antigens.

Figure 56A:
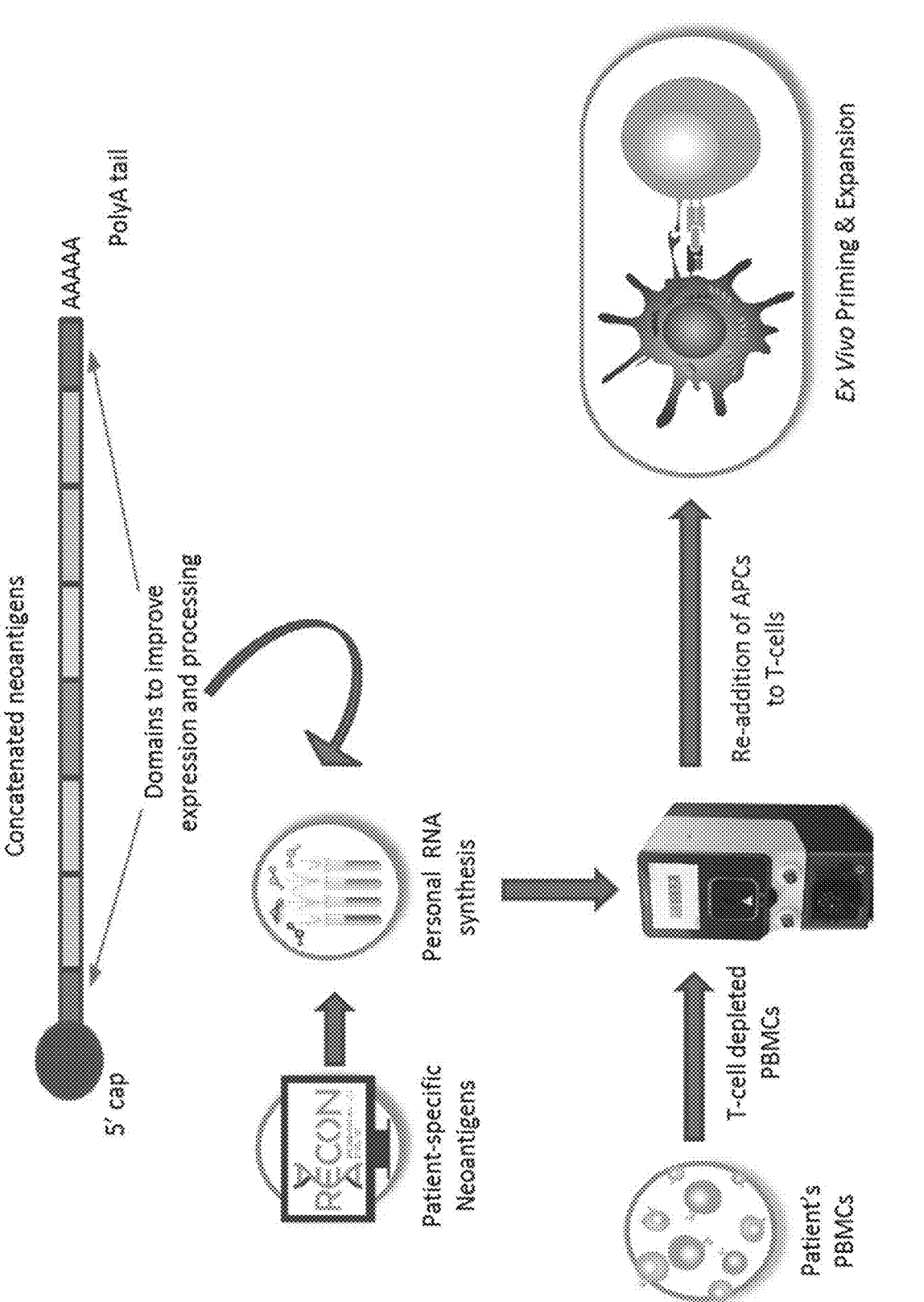
FIG. 56A depicts a schematic of an exemplary process for generation of RNA comprising sequences encoding neoantigen and using them for loading PBMCs and activating T cells.

Example 32—Methods for Increasing T Cell Priming Efficiency and Antigen Specific T Cell Yield In this example, PBMCs are directly electroporated with an mRNA encoding antigen encoding sequences into a PBMC population for increasing efficiency of T cell priming and yield of antigen specific T cells. The process is represented by a simplified work flow in FIGS. 56A and 56B. Personalized antigens (for example, neoantigens) for a particular subject can also be developed from a reliable MHC-peptide binding predictor platform, based on the subject's genomic or exomic sequencing result and identification of subject specific neoantigens. A reliable MHC-peptide binding predictor platform was disclosed at least in part in the international applications PCT/US2018/017849 and PCT/US2019/068084 and which are hereby fully incorporated by reference. Following determination of subject's HLA repertoire, potential antigen epitopes specific for a cancer type are run in the predictor, and top predicted binders are identified. One or more RNA constructs are generated. Each RNA construct comprises nucleic acid encoding multiple antigens comprising the identified epitopes. The mRNA is incorporated into PBMCs by electroporation or nucleofection. PBMCs express and present the RNA-encoded antigen peptides to T cells that are in proximity, for example, where the antigen presenting cells are cocultured with the T cells, such as in a PBMC sample (FIG. 56A).

Figure 56B:
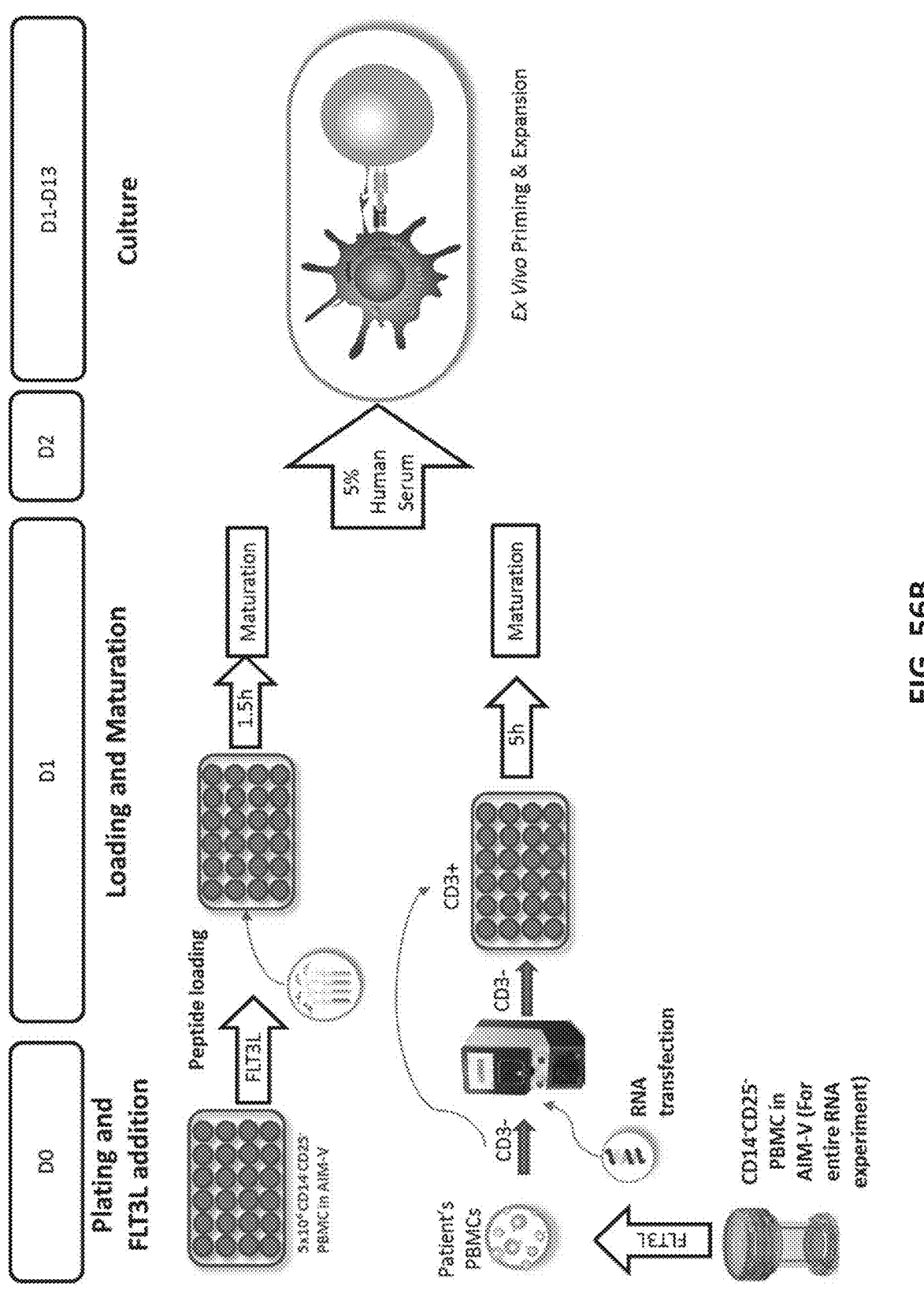
FIG. 56B depicts a schematic of an exemplary process for generation of RNA comprising sequences encoding neoantigen and using them for loading PBMCs and activating T cells.

For exemplary parallel comparison of peptide and mRNA stimulation, PBMC samples are depleted of CD14 and CD25 expressing cells and taken through the basic workflow as depicted in FIG. 56B.

Figures 57A, 57B:
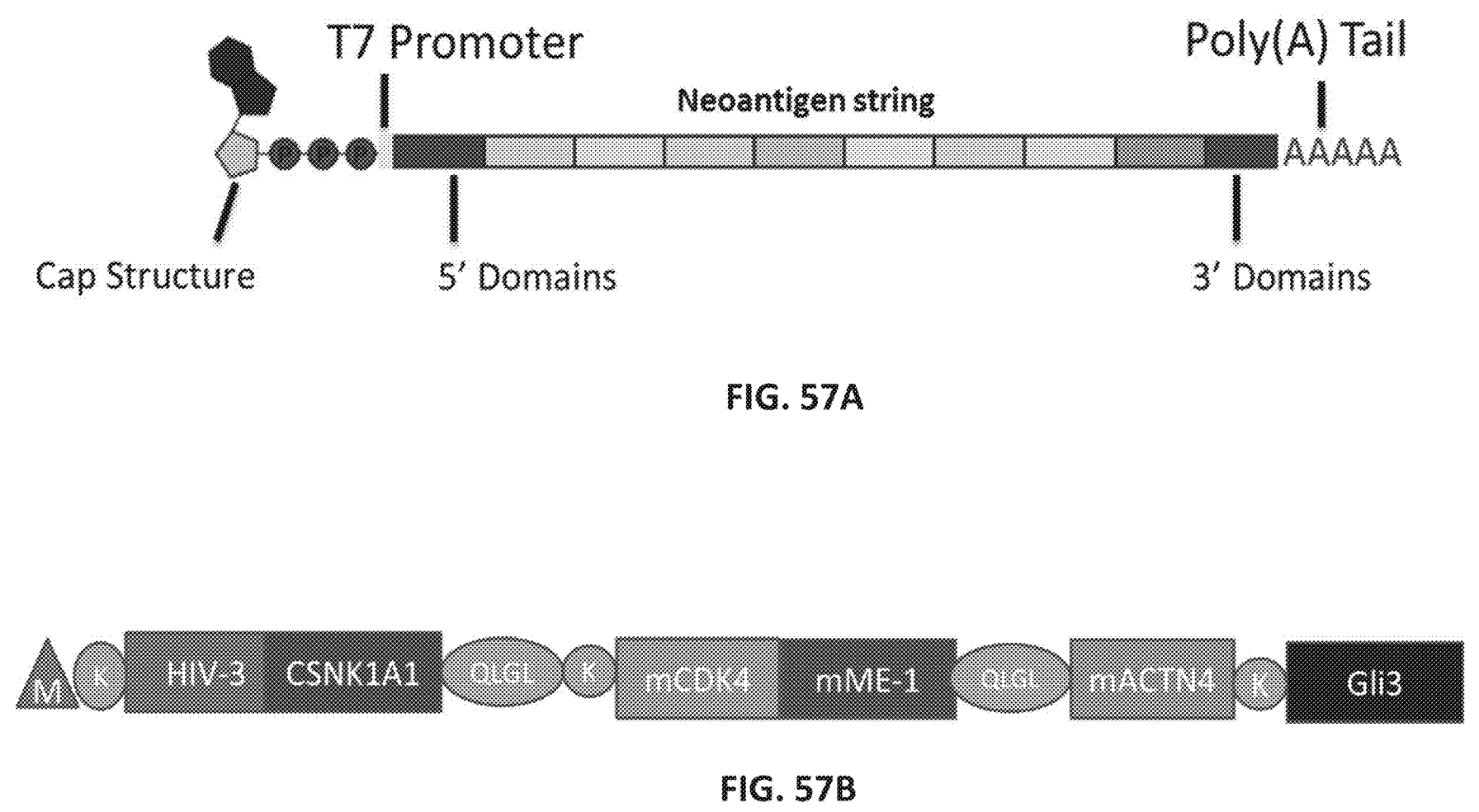

RNA Construct Design for Delivery of Polynucleotide Encoding Multiple Immunogenic Epitopes for Expression on PBMC for Antigen Presentation An exemplary RNA construct is shown in FIG. 57A. The RNA construct comprises a neoantigen string, where multiple mRNA sequences encoding multiple antigenic epitopes are ligated to generate a 5'-3' concatamer. At least one antigen encoded by the mRNA is a neoantigen. The mRNA comprises a 5'-CAP, a 3'poly A tail and a polynucleotide sequence encoding a concatenated string of antigens, operably linked to a promoter sequence, exemplified in this case by a T7 promoter. The constructs used in loading PBMCs vary extensively in sequences that encode neoantigen strings as it varies on a case by case basis. An elaborate view of the neoantigen string portion of the construct is depicted in FIG. 57B. Cleavage sequences, for example, QLGL (SEQ ID NO: 29), and K are carefully optimized and placed in between sequences encoding one or more antigens within the concatenated neoantigen string. The specific sequences as well as the arrangement of sequences encoding antigens and cleavage sequences in a single mRNA chain are individually optimized for obtaining superior epitope presentation by the PBMC, and in turn maximizing the yield of antigen responsive T cells. Exemplary antigen or neoantigen sequences are obtained from HIV-3 epitope, CSNK1A1 epitope, mCDK4 epitope, mME1 epitope, and a Gli3 epitope. Designing and placement of the cleavage facilitating sequences carefully juxtaposed to certain epitope-encoding sequences ensures that an encoded epitope is not inadvertently cleaved within the epitope sequence naturally when the mRNA is transfected, so that each epitope is represented for expression and presentation by the PBMC.

5'-CAP and Poly A Elements

Experiments were performed with and without the 5'-CAP inclusion in the mRNA. PBMCs were transfected with mRNA with a 5'CAP (Cap1 or Cap0). It was noted that CAP1 structures was important for effective mRNA delivery and expression. FIG. 58A shows that an Adenosine is incorporated at the 5'-UTR region to help with co-transcriptional incorporation the Cap1 structure (CleanCap). As shown in FIG. 58B-58C, Cap1 incorporation had greater advantage over Cap0, in terms of reduced cellular toxicity (FIG. 58B) and higher expression of GFP encoded by the mRNA (FIG. 58C). The length of poly A tail was optimized. Poly A tail of about 120 nucleotides was considered effective for mRNA expression (data not shown).

Nucleotide Modification within mRNA and Effect on T Cell Induction:

mRNA is further modified by replacing cytidine (C) or uridine (U) residues to increase mRNA stability and resistance to degradation. In this example, PBMCs selectively depleted of CD3, CD14 and CD25 expressing cells were nucleofected with GFP mRNA in which all natural uridine-triphosphate, all cytosine triphosphates or partial amounts of both nucleosides are modified and GFP expression was followed at different time points. Flow cytometry was performed at 24 hours (middle and bottom rows). At 72 hours GFP positive live cells were measured using the Inucyte (top row). The Uridine residues were modified to Pseudouridine and Cytidines are modified to 5methylcytidines, and percent modifications in different experimental sets are shown in Table 13.

TABLE 13

| Uridine and Cytidine modifications in mRNA | |
| --- | --- |
| Sample | Substitution % (U/C) |
| Partial UTP | 30/0 |
| Full UTP | 100/0 |
| Partial UTP/Partial CTP | 30/30 |
| Full UTP/Full CTP | 100/100 |
| Full UTP/Partial CTP | 100/30 |
| Standard | 0/0 |

Figure 59A:
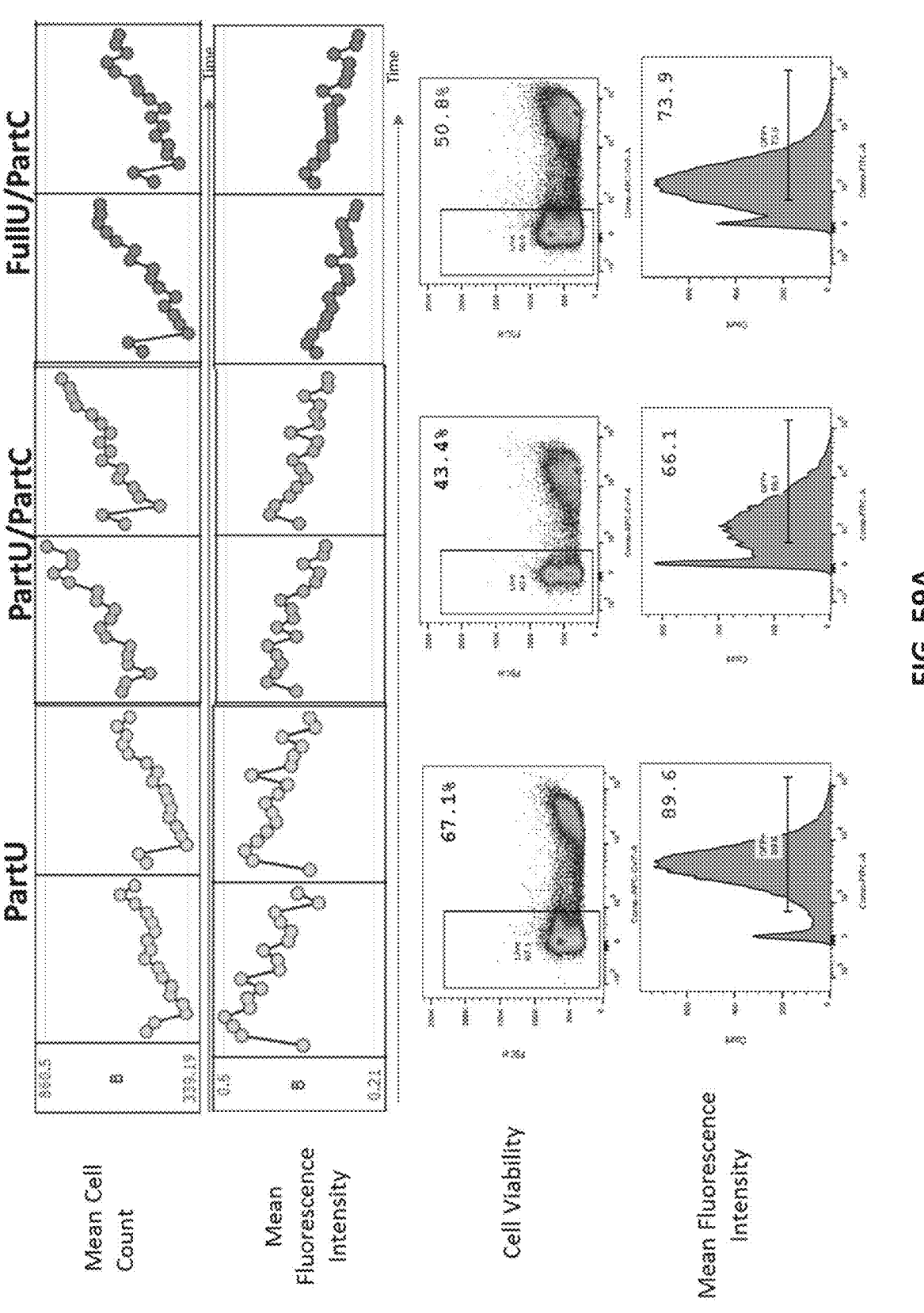
FIG. 59A depicts exemplary results indicating using modified nucleotides to make mRNA. The mRNA was modified either by substituting all (Full) or some (Part) of the Uridine (U) and Cytidine (C) residues within the mRNA. E.g., Part C set contains 30% C residues replaced by methyl cytidine. Results showing the effect on expression of the mRNA encoded peptide in the transfected PBMCs over time.
Figure 59B:
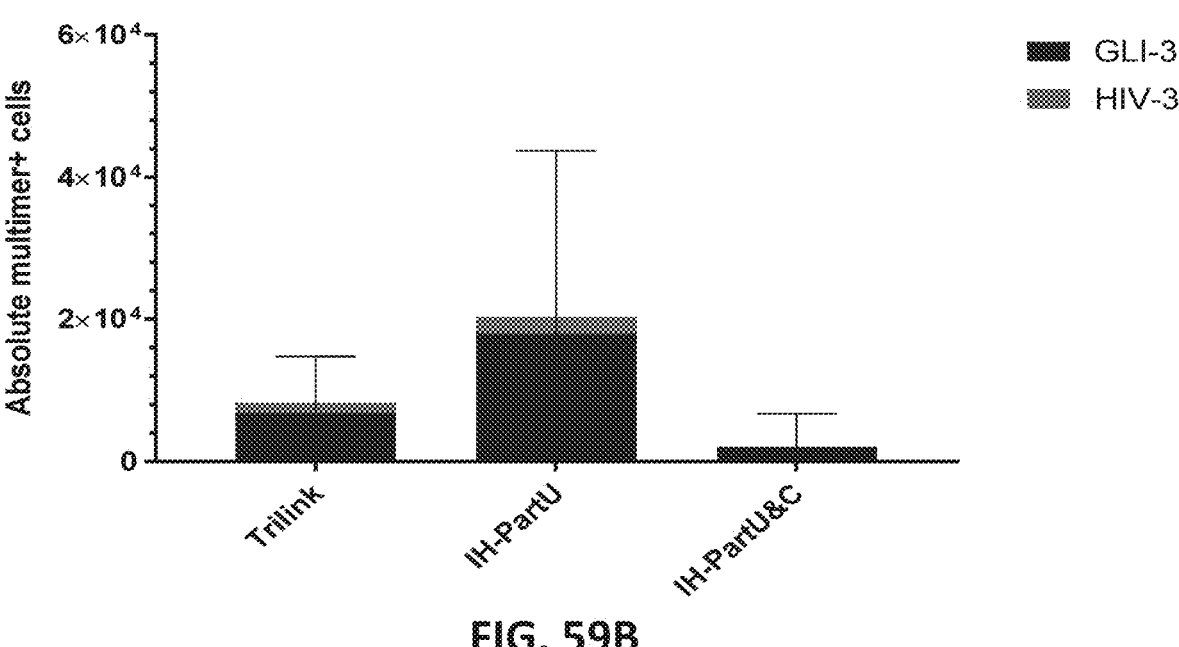
FIG. 59B depicts exemplary data comparing the effect of commercial and in-house preparation of mRNA comprising substituted uridines and/or cytidines on generating multimer specific T cells that are stimulated with PBMCs loaded with the mRNA.
Figure 59C:
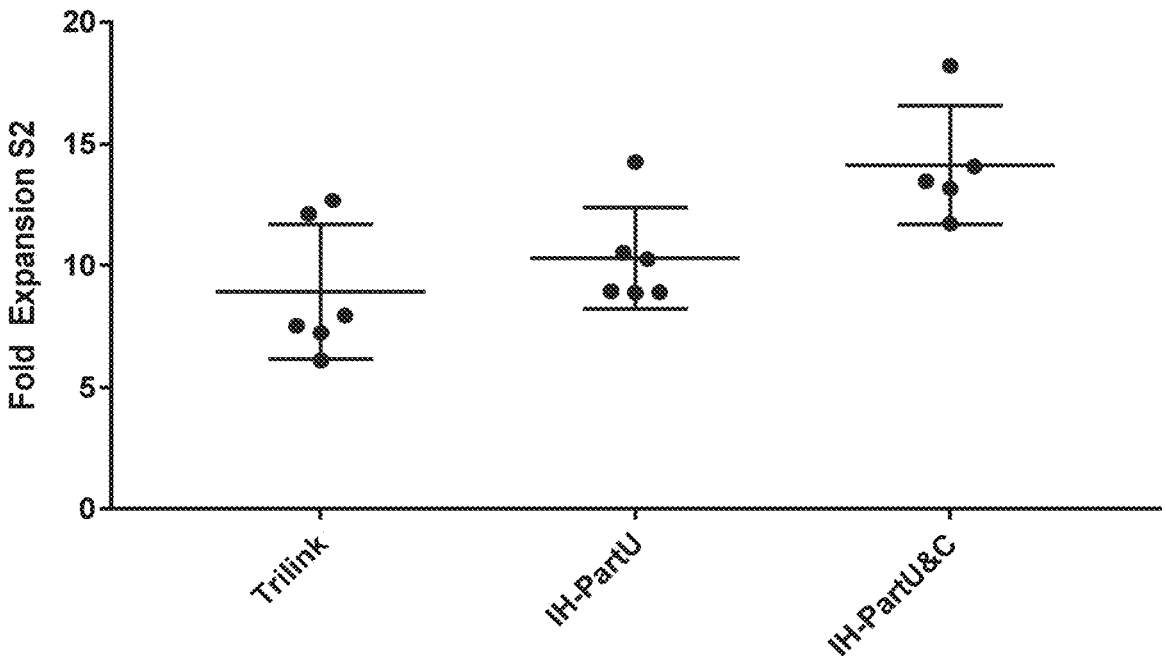
FIG. 59C depicts exemplary data comparing expansion of the stimulated T cells generated as described in FIG. 59B.

The data as shown in FIG. 59A-59C indicate that partial and full substitutions of Uridine and Cytidine with Pseudouridine and 5methylcytidine helps in better translation and a partial UTP substitutions have give rise to higher numbers of neoantigen specific cells (FIG. 58B).

High CD8 Hit Rate when APCs were Stimulated with mRNA Encoding Peptides:

Shortmers (9-10 amino acids) or longmers (25 amino acids) were constructed in the form of a concatenated neoantigen string as shown graphically in FIG. 60A. PBMCs nucleofected with a multi-antigen encoding mRNA construct as described above were used to stimulate T cells, and side by side comparison was performed with peptides comprising the same epitopes. Short and long RNA sequences raise similar CD8+ T cell responsive to multimers (Table 14). Noteably, robust CD8 responses were observed using mRNA encoding longmers (and shortmers).

TABLE 14

Comparison of peptide and RNA longer and shortmer mediated activation

| | | CD8 Hit Rate (%) | Mean Neoantigen+ Frequency (% CD8 cells) | Diversity of responses (out of 6) | CD4 responses |
|---|---|---|---|---|---|
| Donor 1 | Peptide Short | 7 | 0.03% | 1 | N.A. |
| | Peptide Long | 19 | 0.09% | 2 | 0 |
| | RNA Short | 11 | 1.50% | 2 | N.A. |
| | RNA Long | 8 | 0.36% | 2 | 0 |
| Donor 2 | Peptide Short | 11 | 0.03% | 2 | N.A. |
| | Peptide Long | 17 | 0.21% | 3 | 1 |
| | RNA Short | 19 | 0.39% | 2 | N.A. |
| | RNA Long | 20 | 0.05% | 2 | 0 |

As shown in FIG. 60B, Gli3 epitope is well represented and presented by the peptides as well as mRNA, however, mRNA encoded Gli3 shortmer epitope loaded PBMCs resulted in higher Gli3-specific CD8+ T cells (as detected by a multimer assay). Representative flow cytometry results for a multimer assay are shown in FIG. 60C. In contrast, HIV-3 or CDK4 epitopes used herein are not well represented by the mRNA chain comprising a longer or a shortmer sequence. Peptide shortmer sequence generates higher proportions of CDK4-specific CD8+ T cells; and a peptide longmer generates HIV-3 specific CD8+ T cells, and mRNA sequences encoding the same do not generate respective antigen specific CD8+ T cells.

Increased Multimer Positive CD8+ T Cells with Induction of PBMCs

Figures 61A, 61B, 61C:
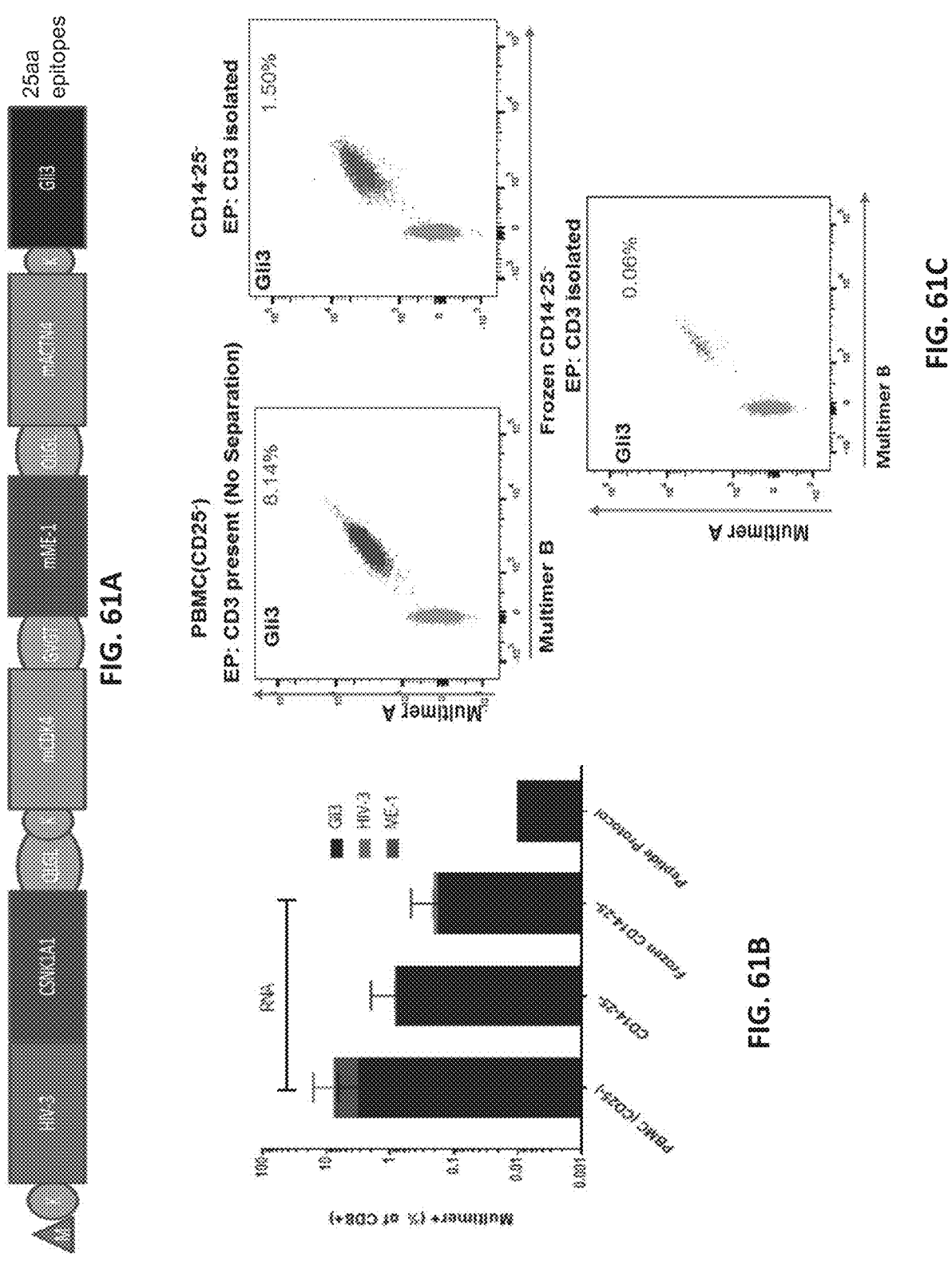
FIG. 61A depicts a schematic of an exemplary RNA construct with which the cells of the experiments shown in FIGS. 61B-61D are transfected.
FIG. 61B depicts an exemplary graphical representation of results from a multimer assay. Under all three conditions of PBMC handling, the RNA transfected PBMCs were better than peptide loaded PBMCs in generating antigen specific T cells. For Gli3 antigen, greater than 10 fold increase in multimer positive cells are noticed compared to peptide loaded PBMCs.
FIG. 61C depicts exemplary flow cytometry data showing detection of Gli3 multimer positive T cells in each indicated set with and without depletion of CD3 cells. Transfection of CD25+ PBMCs directly yields increased multimer positive cells than PBMCs depleting CD14 and CD25 cells or PBMCs that are thawed from a frozen stock.

In this experiment, PBMCs were variously treated for depletion of certain populations and their expansion and multimer specificity was investigated. Yield of multimer specific T cells was tested by nucleofecting three sets of PBMC preparations with RNA constructs: (i) CD25 depleted PBMCs, (ii) CD14 and CD25 depleted PBMCs, (iii) Frozen CD14 and CD25 depleted PBMCs. In preparation (i), T cells were not separated from the APCs during nucleofection like in preparation (ii) and (iii). These were compared with a set of PBMCs loaded with peptides. All cells were treated with FLT3L prior to electroporation. Various mRNA constructs were tested, a representative is shown in FIG. 61A. Collectively, RNA loaded PBMCs depleted of CD25 exhibited superior multimer specific CD8+ T cells as represented in FIG. 61B. mRNA-loaded CD25 depleted PBMCs were superior over fresh or frozen CD14 and CD25 depleted cells that were similarly loaded with RNA, and all RNA loaded PBMCs had advantage in generating CD8+ T cells that were responsive to multimers. It could be possible that less handling of PBMCs before RNA loading step was advantageous. Depletion of multiple cell components in the PBMC population required subjecting the cell population to multiple antibodies, washing steps and recovery steps, which amounts to handling stress for the cells.

mRNA loaded PBMCs showed greater diversity in antigen representation, as shown in FIG. 61B and Tables 15A and Table 15B below. CD25 depleted PBMCs had detectable Gli3 specific CD8+ T cells, and ME1 specific CD8+ T cells. ME1 specific CD8+ T cells were negligible in all the other sets. FIG. 61C shows representative flow cytometry data indicating Gli3 specific cells.

TABLE 15A

| | | | Donor 1 | | | | | | | | |
|---|---|---|---|---|---|---|---|---|---|---|---|
| | IL-7 and IL-15 | | | | | | Hit Rate (%) | Mean Frequency | Starting Material | Immunogen |
| | 1 | 2 | 3 | 4 | 5 | 6 | | | | |
| Gli3 | | √ | √ | √ | √ | √ | 83% | 6.09% | PBMC | RNA |
| HIV-3 | | | | | | | 0% | | (CD25−) | (25 mer |
| CSNK1A1 | | | | | | | 0% | | | epitopes) |
| ME-1 | | | | | | | 0% | | | |
| ACTN4 | | | | | | | 0% | | | |
| CDK4 | | | | | | | 0% | | | |
| Gli-3 | √ | √ | √ | √ | √ | √ | 100% | 0.52% | CD14- | |
| HIV-3 | | | | | | | 0% | | CD25- | |
| CSNK1A1 | | | | | | | 0% | | (Frozen) | |
| ME-1 | | | | | | | 0% | | | |
| ACTN4 | | | | | | | 0% | | | |
| CDK4 | | | | | | | 0% | | | |
| Gli-3 | √ | √ | √ | √ | √ | √ | 100% | 0.98% | CD14- | |
| HIV-3 | | | | | | | 0% | | CD25- | |
| CSNK1A1 | | | | | | | 0% | | (Base | |
| ME-1 | | | | | | | 0% | | Arm) | |
| ACTN4 | | | | | | | 0% | | | |
| CDK4 | | | | | | | 0% | | | |

TABLE 15B

| | | | | | | | Hit Rate | Mean | Starting | |
| | IL-7 and IL-15 | | | | | | | | | |
| | 1 | 2 | 3 | 4 | 5 | 6 | (%) | Frequency | Material | Immunogen |
|---|---|---|---|---|---|---|---|---|---|---|
| Gli3 | | √ | √ | √ | √ | √ | 83% | 2.68% | PBMC | RNA |
| HIV-3 | | | | | | | 0% | | (CD25–) | (25 mer |
| CSNK1A1 | | | | | | | 0% | | | epitopes) |
| ME-1 | | √ | √ | | √ | √ | 67% | 2.97% | | |
| ACTN4 | | | | | | | 0% | | | |
| CDK4 | | | | | | | 0% | | | |
| Gli-3 | √ | √ | | | √ | √ | 67% | 0.12% | CD14- | |
| HIV-3 | √ | √ | √ | √ | √ | √ | 100% | 0.02% | CD25- | |
| CSNK1A1 | | | | | | | 0% | | (Frozen) | |
| ME-1 | | | | √ | | | 0% | 0.01% | | |
| ACTN4 | | | | | | | 0% | | | |
| CDK4 | | | | | | | 0% | | | |
| Gli-3 | √ | √ | √ | √ | √ | √ | 100% | 0.79% | CD14- | |
| HIV-3 | √ | √ | √ | | | √ | 67% | 0.01% | CD25- | |
| CSNK1A1 | | | | | | | 0% | | (Base | |
| ME-1 | √ | √ | √ | √ | √ | | 83% | 0.01% | Arm) | |
| ACTN4 | | | | | | | 0% | | | |
| CDK4 | | | | | | | 0% | | | |

Figure 61D:
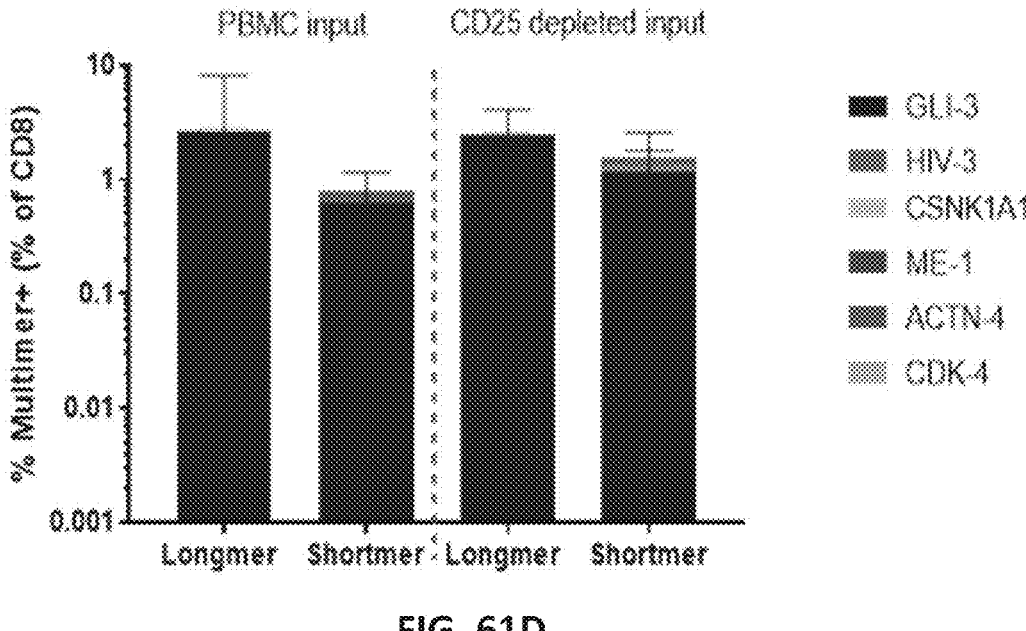
FIG. 61D depicts an exemplary graphical representation of results from a multimer assay. PBMCs or CD25 depleted PBMCs treated with FTL3L cells overnight were electroporated with RNA encoding either 25 amino acid lengths of neoantigen sequences (longmer) or epitope length neoantigen sequences (shortmer). The percent of neoantigen positive cells in the culture were assayed using multimer technology.
Figure 61E:
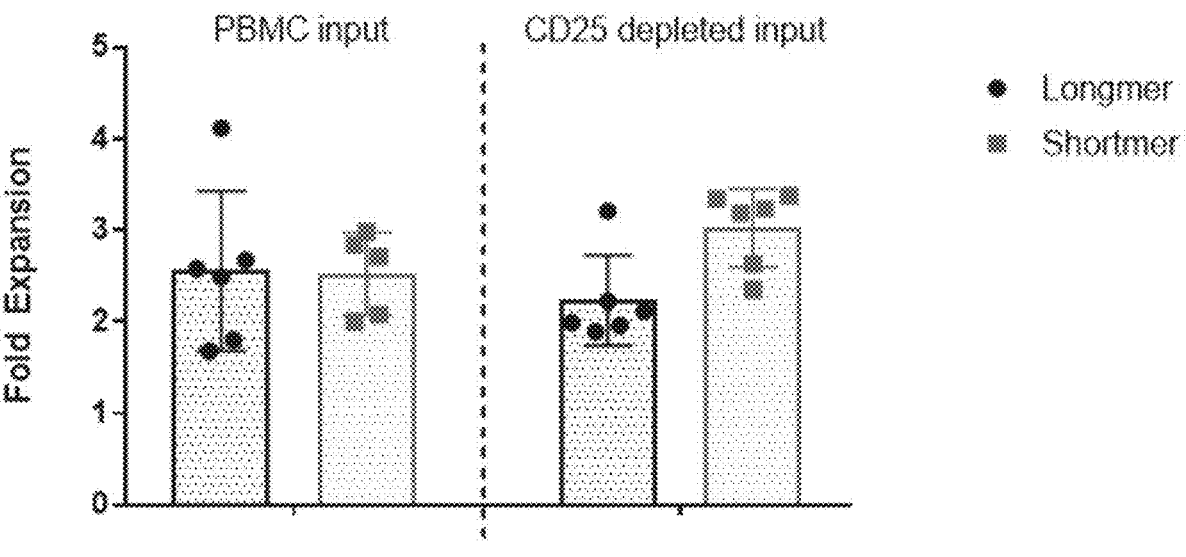
FIG. 61E depicts an exemplary graphical representation of fold expansion results from the experiment described in FIG. 61D. PBMCs or CD25 depleted PBMCs treated with FTL3L cells overnight were electroporated with RNA encoding either 25 amino acid lengths of neoantigen sequences (longmer) or epitope length neoantigen sequences (shortmer). Fold expansion of cells after 26 days in culture and two stimulations is depicted.

PBMCs and CD25 depleted PBMCs treated with FLT3L overnight, were electroporated with shortmer or longer RNA constructs and antigen specificity (FIG. 61D) as well as fold expansions (FIG. 61D) were investigated at 26 days after two stimulations. These data illustrate that the length of the epitope encoded is not critical to achieve robust CD8 induction, contrasting with observations in case of using peptide longmer and shortmer stimulation.

Effect of Different Maturation Mixes

Several cocktails of cytokines and growth factors for inclusion in a T cell culture media for expansion of PBMC stimulated T cells were investigated. The components in the media are collectively termed T cell maturation mixes. In an exemplary set of experiments, PBMCs from two donors were nucleofected with mRNA constructs as previously indicated, and different maturation mixes for T cell expansion were tested in sample sets from each donor's cells. Various cytokine cocktails tested are listed below in Table 15C. Additional cytokine cocktails to-be tested include IFN-γ LPS, Poly I and Poly C, and CD40; and TLR-7/8 and LPS.

TABLE 15C

| Cytokines and growth factor cocktails tested in maturation mix. | |
|---|---|
| Sets | Maturation Mix |
| 1 | IFN-γ, LPS |
| 2 | TNF-α, IL-1β, IL-6, PGE-2 [TIIP (IL6)] |
| 3 | TNF-α, IL-1β, IL-7, PGE-2 [TIIP (IL7)] |

Figures 62A, 62B, 62C:
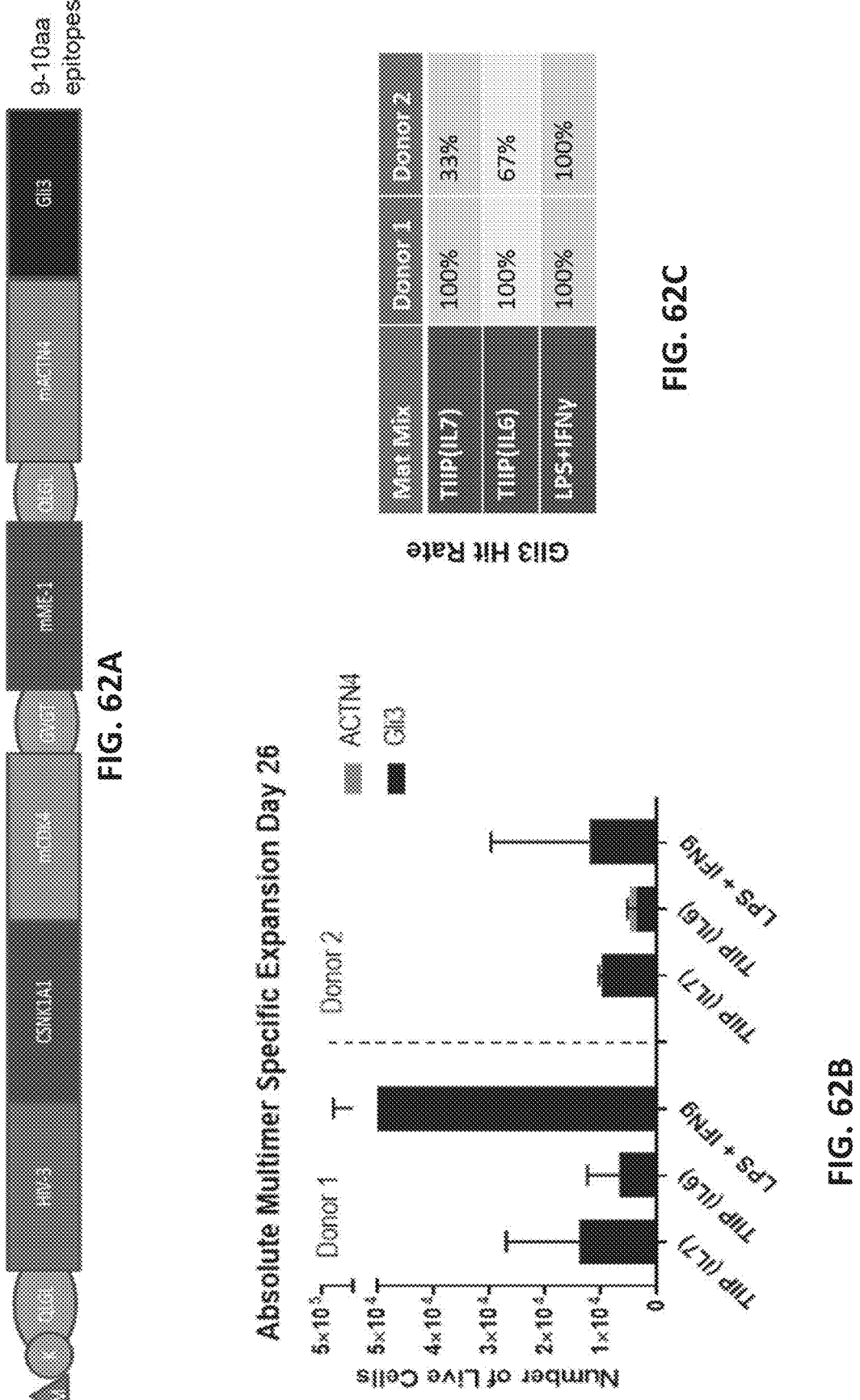
FIG. 62A depicts a schematic of an exemplary RNA construct with which the cells of the experiments shown in FIGS. 62B-62D are transfected.
FIG. 62B depicts an exemplary graphical representation of the number of ACTN4 and Gli3 responsive live T cells from two donors at Day 26 after maturation with the indicated combinations on the X-axis.
FIG. 62C depicts exemplary data of the percentage of Gli3 responsive T cells from live cells that were grown in the presence of the indicated maturation mixes.

The results are shown in FIGS. 62B-62D. Addition of LPS+IFN-γ is associated with higher multimer-specific cells at day 26. Also tested whether each of the epitopes were expressed by PBMCs over time, or whether expression of one or more were compromised.

Figure 63A:
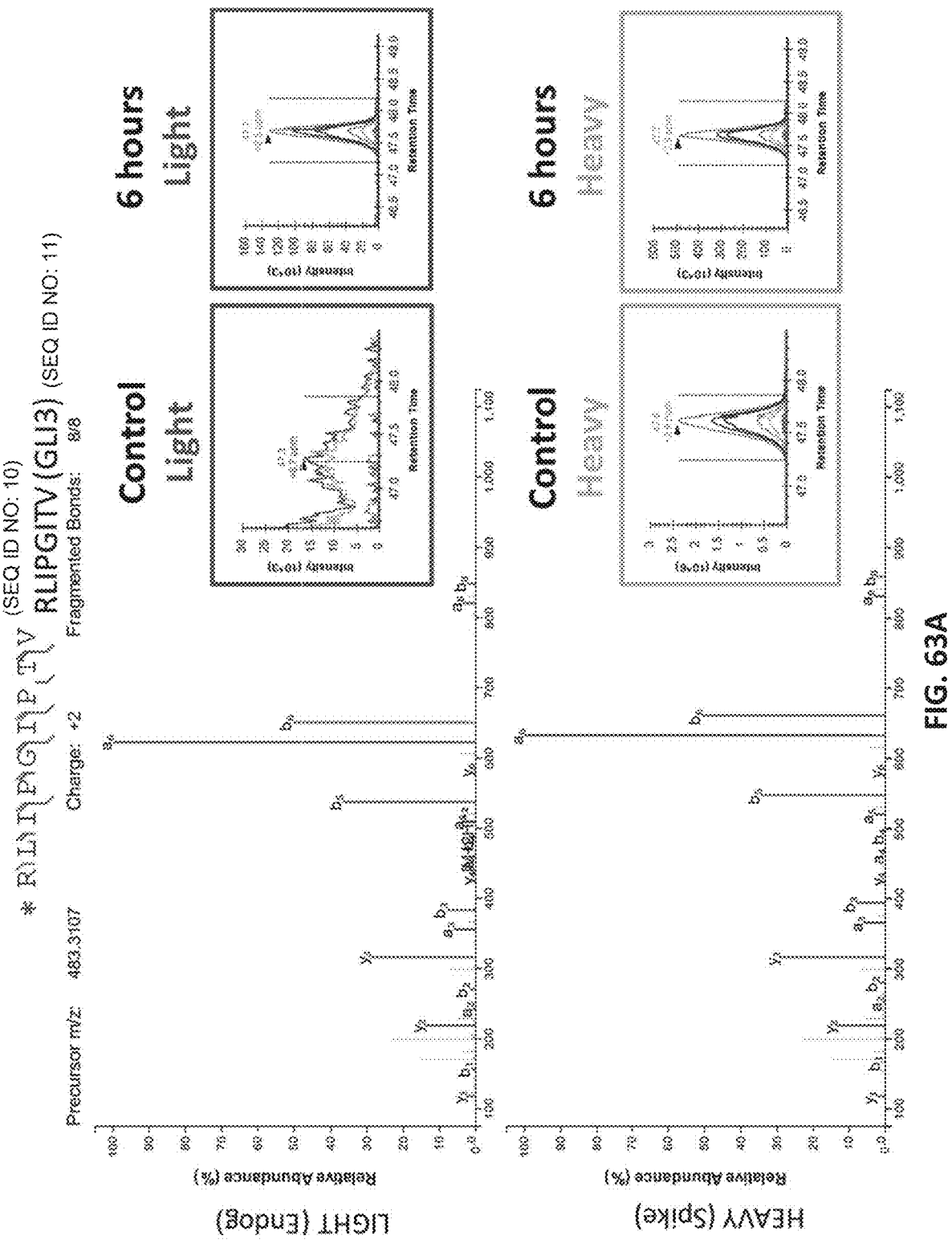
FIG. 63A depicts representative mass spectrometry data showing detection of presentation of the indicated Gli3 epitope by PBMCs using radioactive isotope incorporation. PBMCs transfected with mRNA encoding multiple epitopes (including the Gli3 epitope) and expression of the peptides are detected using reference peptides labeled with heavier isotope. Figure discloses SEQ ID NOS 10-11, respectively, in order of appearance.
Figure 63B:
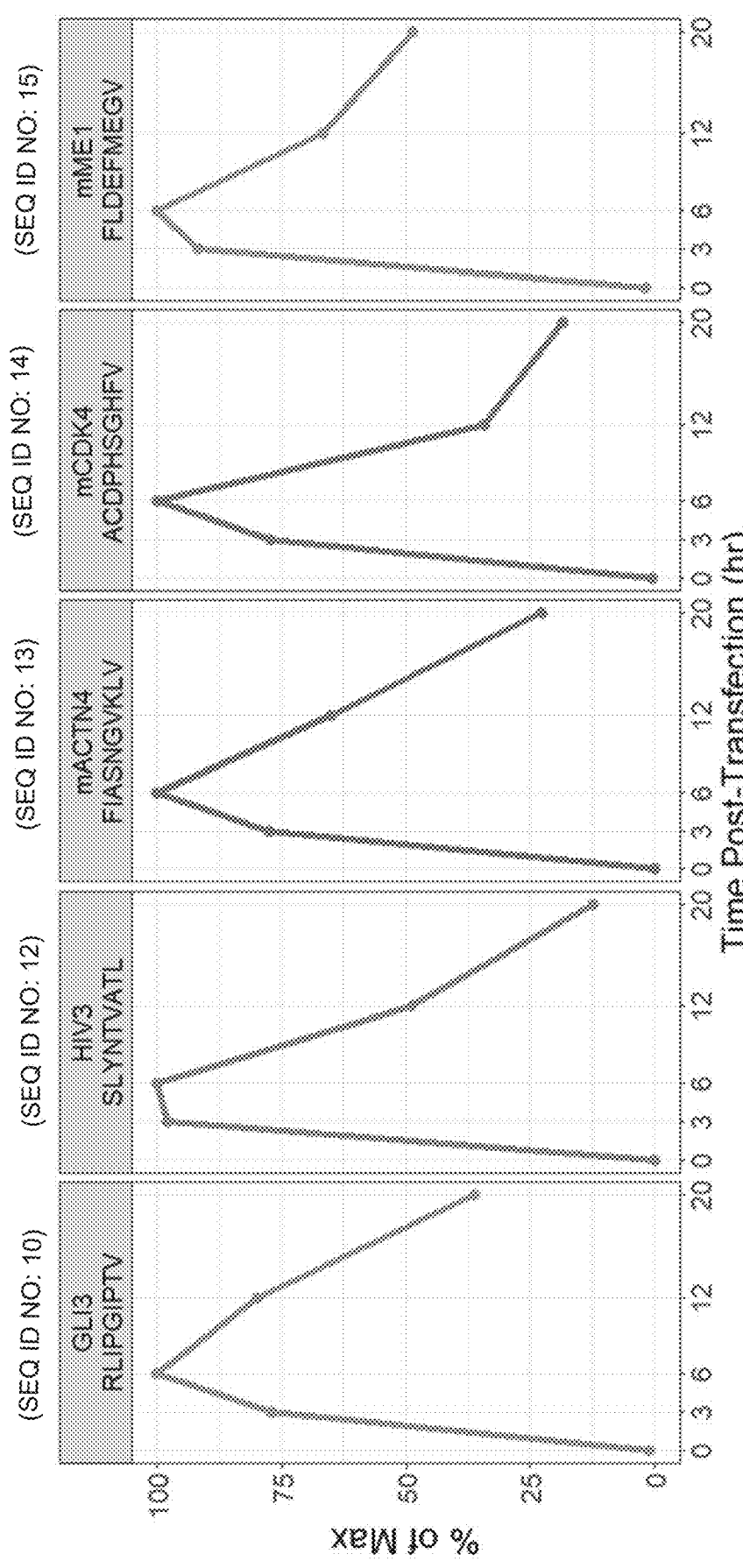
FIG. 63B depicts exemplary graphical representations of the percentage of maximum presentation by HLA-A02:01 of the indicated epitopes over time after transfection of PBMCs with an mRNA encoding each of the epitopes. Each isotope-labeled epitope was detected by mass spectroscopy. Maximum surface presentation was observed 6 hours after transfection. Figure discloses SEQ ID NOS 10 and 12-15, respectively, in order of appearance.

CD25 depleted PBMC cells were electroporated with RNA (depicted in FIG. 60C) and cultured over a period of 24 hours. Cells were harvested at the indicated times, pelleted and flash frozen. HLA-A02:01-peptide complexes were immunoprecipitated and then peptides were eluted and analyzed by LC-MS/MS. Peptide eluted from electroporated cells (Light) were compared to heavy labelled standard peptides (Heavy) for positive identification. (FIG. 63A). FIG. 63B shows that each of the peptides, Gli3, HIV3, mACTN4, mCDK4 and mME1 were expressed readily as dominant epitopes.

Figure 65:
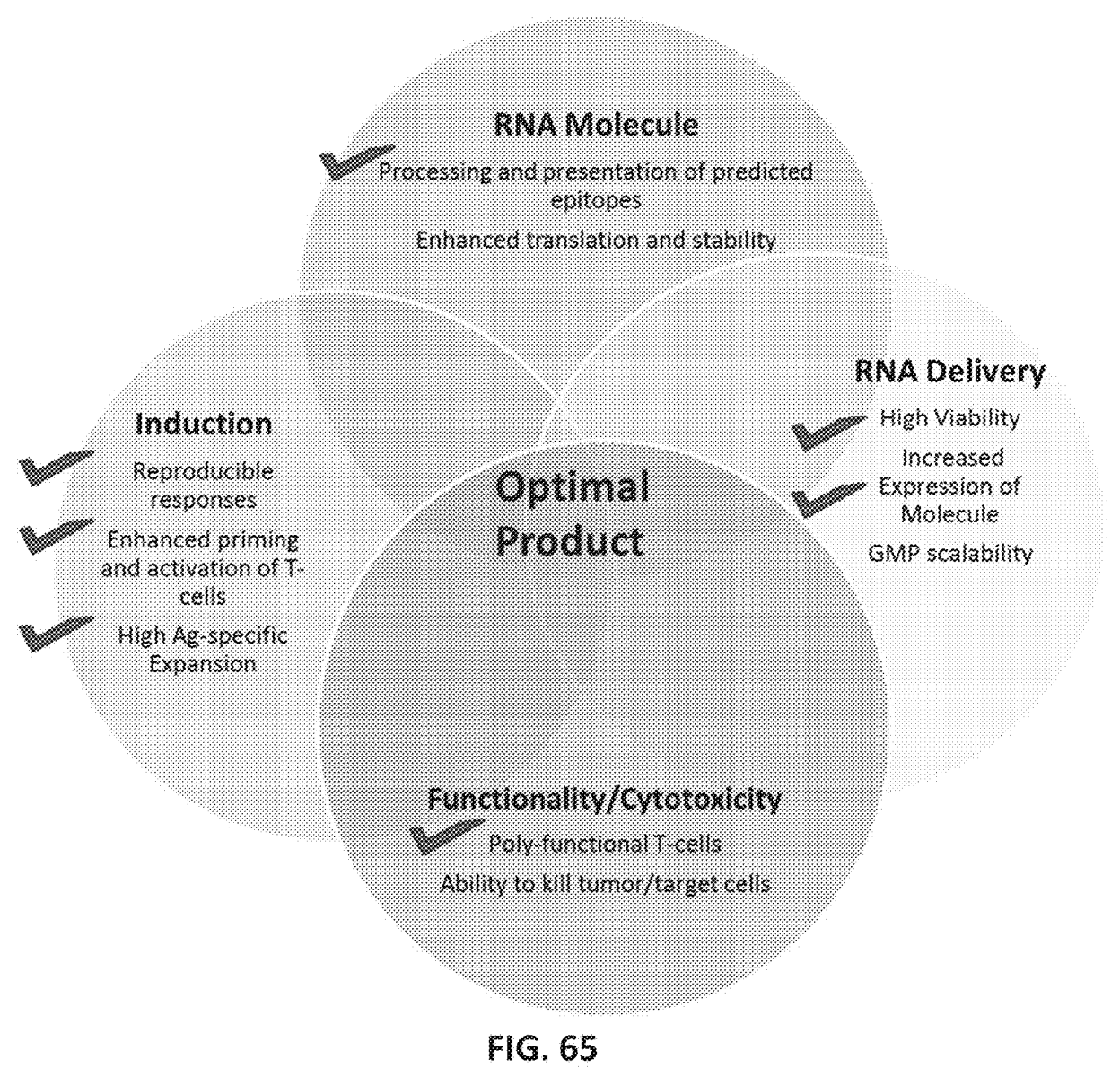

In addition to the multimer assay, functionality of these expanded T cells was assessed. CD8 T cells generated by this method were immunoresponsive to the specific epitopes and released TNF-α and/or IFN-γ or CD107a at different doses indicated (FIGS. 64A-64B). In keeping with the data above, cytokine response was higher for highly immunogenic peptides such as Gli3, in comparison to the peptides that generated fewer specific T cells. FIG. 65 indicates criteria considered for generating an optimum product.

Example 33—Manufacturing Protocol for a T Cell Therapeutic

Figure 66:
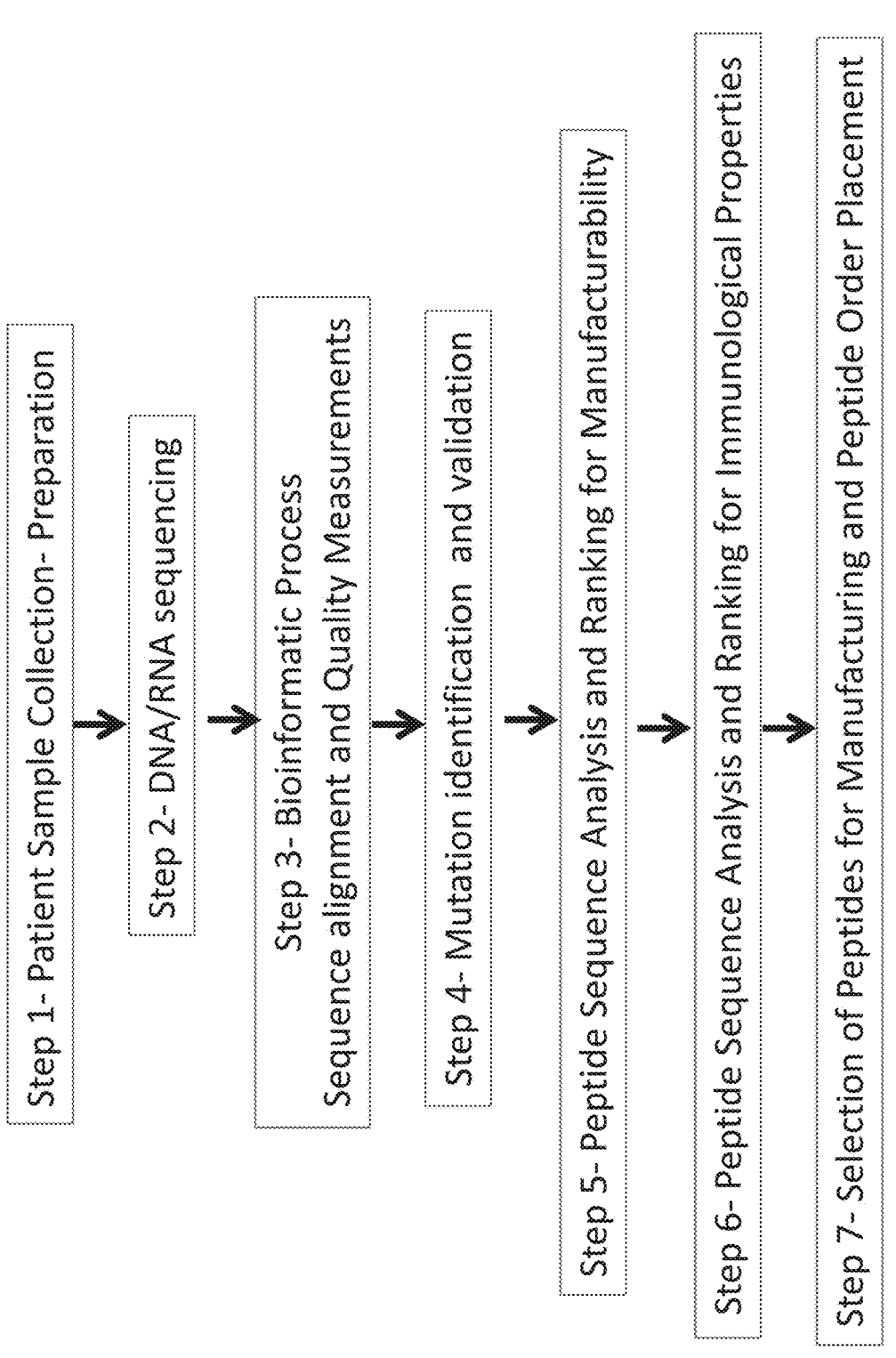
FIG. 66 depicts an exemplary flow diagram showing steps for selection of peptide sequences for preparing a patient specific T cell product.

The T cell therapeutic product is manufactured in a multi-step process summarized below (FIG. 66). The manufacturing process comprises the steps: (A) Tumor biopsy: A tumor biopsy is performed to provide tissue for DNA and ribonucleic acid (RNA) sequencing. A sample of peripheral blood from the patient serves as a 'normal' tissue control. (B) Sequencing and bioinformatics: Whole exome DNA sequencing and RNA sequencing of the patient's tumor and normal samples and RNA Sequencing of the tumor are used to identify and validate mutations. Immunogenic epitopes are predicted and prioritized and used to design peptides that will subsequently be manufactured. The bioinformatics process utilizes a combination of publicly available and proprietary software components. FIG. 66 illustrates the sequence of functions starting from sample collection through identification of mutation in the patient to the generation of peptides in a stepwise manner. (C) Manufacture of selected synthetic peptides: Two sets of peptides will be manufactured, with up to 30-35 peptides per set. Set 1 will be 8-11 amino acids (mostly 9-10 amino acids) to specifically target generation of CD8+ cells through direct MHC Class I binding to Antigen presenting cells (APCs) and set 2 will be approximately 25 amino acids to specifically target induction of CD4+ cells following internalization and re-presentation by APCs. (D) Cell isolation:

Apheresis is performed to provide patient APCs and T cells as the starting materials for T cell therapeutic. (E) Isolation of antigen-presenting cells: Antigen-autologous CD14+ dendritic cells (antigen-presenting cells) are isolated from the apheresis starting material. These dendritic cells are subsequently loaded with the neoantigen peptides described above. (F) T-cell expansion: T cells isolated from the apheresis product are co-incubated with the peptide-loaded dendritic cells. The patient's neoantigen-specific T cells are induced, stimulated, and expanded. The resulting cell product, capable of directly or indirectly recognizing and destroying tumor cells, are reinfused into the patient following lymphodepleting chemotherapy.

Without wishing to be bound by theory, the mode of action of the T cell therapeutic is based on treating patients with autologous CD3+ T cells which recognize the patient's own neoantigen-specific epitopes. Once administered to the patient, the antigen specific T cells are expected to expand in vivo and eliminate tumor cells expressing the antigens, through apoptosis-inducing ligands or release of lytic granules, leading to patient tumor regression and progression free survival.

Starting Material: The patient's own dendritic cells and T cells procured via apheresis (apheresis product). Apheresis will be performed in the clinic under standard protocol as authorized locally according to best practices. Table 16 indicates exemplary acceptance criteria for patient apheresis product.

TABLE 16

Acceptance Criteria for Patient Apheresis Product

| Parameter | Acceptance Criteria |
| --- | --- |
| Visual appearance - cell solution | Minimal or no clumping |
| Visual appearance - bag | No leaking, damaged or cracked bags |
| Documentation and labels | Unique subject identifiers match paperwork (e.g., 2 unique identifiers) |
| Shipping conditions | Conforms with required shipping conditions |

A bioinformatics process is used resulting in the selection of patient specific peptides which are subsequently manufactured and used in the manufacture of T cell product. The bioinformatics software consists of a combination of commercially and publicly available software licensed by the Applicant, and proprietary algorithms, which are used in series to identify mutations and select sequences for the manufacture of peptides. The bioinformatics process starts with data from standard sequencing technologies. First, software algorithms are required for the identification and selection of patient specific mutations. Second, predictions of peptide-MHC binding are performed for all candidates using standard approaches. Combining these well-established techniques enables the ranking and selection of peptides for T-cell stimulation. All software has been evaluated to demonstrate fit-for-intended-use to support a Phase 1 clinical trial. Proprietary algorithms were tested and verified to perform to specification and the resulting epitope sequence selection was consistently obtained as expected.

Critical Raw Material: The synthetic neoantigen peptides manufactured to provide two sets of peptides, with up to 30-35 peptides per set. Set 1 will be 8- to 11-mers (used to induce CD8+ neoantigen specific T cells) and Set 2 would be approximately 25-mers (used to induce CD4+ neoantigen specific T cells) based on the predicted patient specific neoantigen sequences from the bioinformatics process.

The synthetic peptides are not part of the drug product delivered to the patient and therefore do not constitute a starting material. They are obtained and used as purified products that are at least 90% pure. The peptides are added prior to the maturation of monocyte derived DCs, which are subsequently added to the patient's T cells for the induction, stimulation and expansion of neoantigen specific T cells capable of recognizing and directly or indirectly eliminating patient tumor cells. Peptides are highly likely to be cleared through degradation (incubation under aqueous conditions for extended periods of time at 37° C.), cell washing and dilutive manufacturing unit operations and will not tested as part of drug product release.

The 2 sets of peptides are synthesized to help ensure the stimulation of both CD8+ and CD4+ cells based on presentation of the peptides on both MHC Class I and class II alleles.

Non-clinical development: Results from the in vitro pharmacology studies to date have demonstrated the following: In cells from healthy donors, neoantigen specific CD4+ and CD8+ T cells can be induced from the naïve T cell compartment—thereby potentially broadening the repertoire of T cells that can recognize and eliminate tumors of interest. Pre-existing CD8+ memory T cell responses can be further expanded. This has been shown in the context of T cell responses toward common viral epitopes, which are expected to behave in the same manner as neoantigen specific memory T cell responses. Multiple T cell effector functions as measured by secretion of multiple inflammatory cytokines following stimulation, that is, polyfunctionality of neoantigen and viral specific T cells, has been demonstrated, which are believed to be associated with clinically effective immune response. Studies from multiple groups have demonstrated that T cells possessing an effector memory and central memory phenotype are the optimal population for adoptive cell therapy. These populations have been shown to persist following transfer and also possess the ability to proliferate and maintain cytotoxic function. Consistently, more than 75% of the neoantigen induced T cells in T cell therapeutic product are of effector memory phenotype after approximately 4 weeks in culture (CD45RA–/CD62L–).

Cross reactivity evaluation has demonstrated that neoantigen-specific CD4+ T cells from healthy donors, which are induced from the naïve compartment, clearly respond to the mutant but not corresponding native peptides when challenged with a titration of a neoantigen peptide pool and its wild type counterpart. These findings indicate that the induced T cell product is highly specific for the mutated targets. Further studies are planned, including using cells from tumor-bearing patient donors and demonstration of proof-of-concept based on killing of tumor cell lines from tumor-bearing patient donors (ovarian and non-small cell cancer) that express neoantigens of interest.

Starting with the derivation of the dendritic cell culture to the completion of manufacture of drug product, the manufacturing process is continuous. Therefore, considering the product release testing scheme shown in Table 17, the drug substance is the resuspended cells in the cryopreservation medium just prior to filling into the infusion bag. The drug product is the formulated drug substance in its final container and closure system.

The drug substance is the T cell therapeutic autologous CD3+ T cells resuspended in cryopreservation medium.

The drug product is the T cell therapeutic autologous CD3+ T cells resuspended in cryopreservation medium and filled into the final bag for infusion.

Release Tests

Appearance Testing

Appearance testing is performed by visual examination of the NEO-PTC-01 drug product infusion bag.

CD3+ T Cell Identity and Purity

A flow cytometry assay is used to measure the identity and purity of NEO-PTC-01. Multi-color flow cytometry enables the analysis of heterogeneous cellular products and provides multiparametric information on a per cell basis. The flow cytometry method used for NEO-PTC-01 testing contains four markers in the panel for analysis; CD3, CD14, CD25 and live/dead. The assay is performed by thawing a QC cryovial of NEO-PTC-01. Cells are added to a 96 well plate and stained with anti-CD3, anti-CD14, anti-CD25 and live dead stain. CD3 is a marker for T Cells. CD14 and CD25 are included in the panel for process monitoring. The assay reported result is the % viable CD3+ cells.

Viability

Viability testing for NEO-PTC-01 is performed using the Trypan Blue exclusion test in accordance with EP 2.7.29. A NEO-PTC-01 QC cryovial is thawed and mixed with Trypan Blue at a 1:1 ratio. Percent viability is determined using the following equation:

$$((\text{Viable Cell})/(\text{Total Cell Count})) \times 100 = \text{percent viability}.$$

Cell Count

A final cell count is performed using a QC cryovial of NEO-PTC-01. The cell count is performed using a hemocytometer in accordance with EP 2.7.29. The cell concentration is determined based on the number of cells counted, the sample dilution factor, and the volume of sample for analysis. The viable cell count is used for determining the cell dose for the patient.

Endotoxin

Endotoxin testing is performed using the Endosafe-Portable Test System (PTS) system (Charles River) using a QC cryovial of NEO-PTC-01. The Endosafe-PTS system is a spectrophotometer that measures color intensity directly related to the endotoxin concentration in a sample. The color is developed by reaction of the sample with chromogenic Limulus Amebocyte Lysate (LAL) (kinetic chromogenic test method). The Endosafe-PTS system meets all the requirements of EP 2.6.14. The system utilizes FDA-licensed disposable cartridges. Spike recovery controls are used in the assay to confirm the absence of inhibition/enhancement from the sample matrix.

Mycoplasma

Mycoplasma testing for NEO-PTC-01 is perform using nucleic acid amplification (NAT). In this method, a NEO-PTC-01 cell-containing final harvest sample is inoculated into two types of broth medium. Appropriate positive (broth spiked with 50 colony forming units (CFU) of Mycoplasma) and negative controls (broth spiked with saline) are included in the assay. The inoculated samples are incubated at 35-37° C. for 96±4 hours. At the end of the incubation period, DNA is extracted from each sample. The DNA is used as a template in a qPCR reaction using SYBR green as the fluorochrome. The test method complies with the test for Mycoplasma using NAT techniques as described in EP 2.6.7. Spike recovery controls are used in the assay to confirm that the sample matrix does not interfere with the ability of the test method to detect Mycoplasma contamination.

Sterility

Sterility testing for NEO-PTC-01 will be performed using the BacT/Alert sterility system (BioMerieux). The BacT/Alert system is an automated growth-based system that utilizes the metabolism of the microorganism itself to identify sterility contamination. Microbial contaminants metabolize the growth medium contained in the BacT/Alert bottles and produce $CO_2$ as a by-product. Each vial contains a colorimetric sensor. As the sensor absorbs $CO_2$ produced by microorganisms, it creates an irreversible color change. Once the threshold for detection is reached, the instrument marks the test vial as positive. An automatic reading is taken every 10 minutes during the incubation period. The BacT/Alert system is used for in-process (Day 14 supernatant, each individual vessel) and final formulated NEO-PTC-01. Sterility testing for NEO-PTC-01 final product will be performed in accordance with EP 2.6.27 and EP 2.6.1 until the validation of the BacT/Alert system is complete. The sample volume for NEO-PTC-01 testing is ≥1% of total product volume, divided between two media types (anaerobic and aerobic) The BacT/Alert system will be validated using product-specific matrices NEO-PTC-01 testing. Further details are provided in Section 3.2.P.5.3. The data will be used to support a sterility test method that is <14 days.

Characterization Testing Flow Cytometry to Evaluate Cell Types in NEO-PTC-01

Flow cytometry panels have been developed to evaluate CD3+ T cell subpopulations and non-CD3+ cell types in NEO-PTC-01 (including cells of myeloid lineage, B Cells, and NK cells). Additionally, markers are used to define the differentiation status of the product. Markers include CD3, CD4, CD8, Vγ9, CD56, CD14, CD19, CD11c, CD11b, CD62L, CD45RA. The percentages of CD4+ and CD8+ subpopulations in NEO-PTC-01 are reported as a percent of viable CD3+ positive cells Evaluation of Residual IL-7 and IL-15 in NEO-PTC-01

In some embodiments, levels of residual IL-7 and IL-15 in NEO-PTC-01 may be determined using a sandwich immunoassay with electrochemiluminescence detection assay kit (MesoScale Discovery).

Combinatorial Coding Analysis Using pMHC Multimers

Combinatorial coding analysis using peptide-MHC (pMHC) multimers is used to identify the number and the magnitude of the neoantigen specific CD8+ T cell responses. T cells recognize their targets by binding of the T cell receptor (TCR) to peptide MHC complexes expressed on the surface of the target cell. By recombinantly producing the pMHC complexes and coupling these to fluorophores, they can be used as reagents to detect antigen specific T cells by flow cytometry. A pMHC multimer is generated for each of the patient specific short peptides used for NEOPTC-01 manufacture. This allows for the enumeration of the total fraction of neoantigen specific CD8+ T cells and identifies epitopes which are recognized by NEO-PTC-01. To perform the assay, NEO-PTC-01 is thawed, washed, and stained with the pMHC multimers and a panel of surface markers including CD8, CD4, CD14, CD16, and CD19. The fraction of CD4−/CD14−/CD16−/CD19−, CD8+, pMHC+ T cells is quantified using flow cytometry. There are no pMHC multimer reagents available to identify CD4+ T cell responses. Therefore, the antigen recall assay is used for this analysis.

Antigen Recall Assay

Flow cytometry in combination with a 24-hour recall assay is used to assess the number and magnitude of neoantigen specific CD4+ T cell responses in NEO-PTC-01 as well as the polyfunctionality profile of the induced CD4+ and CD8+ T cells. NEO-PTC-01 is co-cultured with dendritic cells loaded with or without the patient specific peptides. After 24 hours, the cell product is characterized using two assay outputs: •Flow cytometry is used to identify the neoantigen specific CD4+ T cell populations, defined as the increased expression of IFNγ and/or TNFα on CD4+ T cells in the presence of target antigen compared to the negative control. •Flow cytometry is used to assess the polyfunctional profile of the neoantigen specific CD4+ and CD8+ T cells. A polyfunctional profile is defined by the increased expression of IFNγ, TNFα, and/or CD107a in the presence of target antigen compared to the negative control. In the context of CD8+ reactivity, neoantigen specific cells are pre-gated on CD8+ pMHC+ T cells, after which polyfunctionality is assessed.

Recognition of Autologous Tumor

The detection of functional T cells upon exposure to autologous tumor cells is used to determine that antigen-specific T cells are present and sensitive to the level of antigen presented on the tumor cell surface. The assay uses autologous tumor digest derived from the patient. NEO-PTC-01 is co-cultured for 4 hours with the autologous tumor cells. Increased expression of IFNγ, TNFα, and/or CD107a in the presence of target antigen compared to the negative control (NEOPTC-01 alone) allows for the identification of T cells in NEO-PTC-01 capable of recognizing autologous tumor.

Cytotoxicity Assay

A cytotoxicity assay using peptide-loaded or stably trans-duced target cells establishes that the antigen-specific T cells are capable of killing tumor cells upon antigen recognition. The assay uses a melanoma tumor cell line, A375 which can be engineered to stably express antigens of interest as well as relevant human leukocyte antigen (HLA) alleles. NEO-PTC-01 is co-cultured for 6 hours with the A375 tumor cells after which cytotoxicity is measured by degranulation of CD107a on CD8+ T cells and upregulation of active Caspase3 on tumor cells, a marker for early apoptosis.

Table 17 shows the exemplary release tests and specification. Table 18 shows exemplary characterization of the product.

TABLE 17

| | | Release tests and specification | |
|---|---|---|---|
| | Test | Method | Specification |
| Identity and | Total nucleated | Hemocytometer | ≥1.0 × 10⁹ cells |

TABLE 17-continued

| | | Release tests and specification | |
|---|---|---|---|
| | Test | Method | Specification |
| Potency | cell count | | |
| | CD3+ cell identity | Flow Cytometry | Positive for CD3+: ≥40% of total cell population. |
| | Cell viability | Trypan Blue Exclusion | ≥70% |
| | CD3+ cell fraction | Flow Cytometry | A quantitative specification will be established based on process development and engineering run data and assay qualification data. |
| Purity and Safety | Sterility | Bact Alert | No Growth |
| | Endotoxin | Endosafe-Portable Test System (PTS) system (Charles River) | ≤1.0 EU/mL Specification based on an average subject weight of 70 kg. Final dose of endotoxin administered to a subject will not exceed 5.0 EU per kg patient weight per hour. |
| | Mycoplasma[a] | Detection of Mycoplasma DNA by nucleic acid amplification (NAT) | None Detected (negative) |

[a]Mycoplasma sample will be taken at the time of harvest of the T cell induction culture, the manufacturing step where the cells have been in culture longest but prior to cell washing. Therefore, this manufacturing step represents a worst case with regards to the risk of detecting contamination Abbreviations:

DNA = deoxyribonucleic acid;

ELISA = enzyme-linked immunosorbent assay;

PCR = polymerase chain reaction

To reduce the risk of introducing contamination into the filled drug product infusion bag, release test samples will be taken from the drug substance manufacturing process step (CD3+ T cells resuspended in the final formulation). An exception to this approach is the sample taken for *Mycoplasma* testing, which will be taken at the time of harvest of the T cell culture. This is the manufacturing step where the cells have been in culture longest but prior to cell washing. Therefore, this manufacturing stage represents a worst case with regards to the risk of detecting *Mycoplasma* contamination.

TABLE 18

| | | Characterization Tests | |
|---|---|---|---|
| Process Step # | Process Step | Test | Purpose |
| Starting Material | Apheresis product | Volume | Consistency of patient cell procurement |
| | | Phenotype | Determine variability of patient cell subpopulations (markers include: CD3, CD4, CD8, CD19, CD14, CD16, CD56, CD11c, live/dead) |
| | | Determine presence of pre-existing CD4+ and CD 8+ memory responses using pMHC multimers and 24-hr recall assay | Determine the % of pre-existing neo-antigen specific CD4+ and CD8+ T cells prior to expansion |
| | | Differentiation status | Assess differentiation status of apheresis product prior to expansion (CD3, CD4, CD8, CD45RA, CD62L) |
| Drug product test | Post Resuspension in final formulation | Phenotype | Determine variability of drug product cell subtype populations (markers include: CD3, CD4, CD8, CD19, CD14, CD16, CD56, CD11c, live/dead) |
| | | Induction of CD4+/CD8+ cells from naïve compartment using pMHC | Determine variability in and range of % cell populations induced from the naïve compartment patient to patient |

TABLE 18-continued

| | | Characterization Tests | |
|---|---|---|---|

Process
| Step # | Process Step | Test | Purpose |
|---|---|---|---|
| | | multimers and 24 hr recall assay | |
| | | Pre-existing CD4+ and CD8+ memory response expansion using pMHC multimers and 24 hr recall assay | Determine variability in and range of % pre-existing CD4+ and CD8+ cell expansion patient to patient |
| | | Specificity | Establish consistency of product by demonstration of neoantigen specificity by exclusive or preferential reactivity to mutant but not wildtype epitope |
| | | Functionality | 1) Establish consistency of product by demonstration of polyfunctionality of CD4+ and CD8+ neoantigen specific T cell responses in response to peptide-loaded target or neoantigen-expressing tumor lines (IFNγ, TNFα, 41B-B, CD107) 2) Establish consistency of product by demonstration of cell killing using engineered cell line (if assay is available) |

TABLE 19

T cell therapeutic Drug Product Stability
Testing Intervals and Tests

| Time Point | Assays |
|---|---|
| T Initial | Cell Count, Viability, Identity, Potency, Sterility, Endotoxin, Mycoplasma |
| T1 M | Cell Count, Viability, Identity, Potency, Sterility, Endotoxin |
| T3 M | Cell Count, Viability, Identity, Potency |
| T6 M | Cell Count, Viability, Identity, Potency, Sterility, Endotoxin |

Example 34—Protocol for Use of T Cell Therapy
(the T Cell Therapeutic Disclosed Above) in
Patients with Ovarian Cancer This example describes a proposed an open-label, single arm, Phase I study of neoantigen activated T cells therapy (hereafter "T cell therapeutic") in patients with platinum-sensitive, high grade serous ovarian carcinoma.

Primary Objective: To evaluate the safety of a single therapeutic infusion of T cell therapeutic in metastatic ovarian cancer patients with platinum-sensitive disease who are experiencing asymptomatic recurrence. Secondary Objectives: (i) To determine anti-tumor activity as assessed by progression free survival based on Response Criteria in Solid Tumors (RECIST) v1.1. (ii) To determine anti-tumor activity as assessed by chemotherapy-free interval, time to first subsequent therapy, and overall survival. Exploratory Objectives include: (i) To characterize immunogenicity by evaluation of cellular immune responses including antigen-specific CD8+ and CD4+ T cell responses in both peripheral blood and tumor biopsies before, during, and following treatment with the T cell therapeutic. (ii) To characterize the clonal expansion, persistence, and phenotype of infused cells. (iii) To correlate patient responses with exploratory biomarkers, such as PD-L1 expression, somatic mutational load, and neoantigen load.

Study Design: Dose Evaluation:

The T cell therapeutic, an autologous personalized, neoantigen-specific adoptive T cell therapy, will be administered to patients with platinum-sensitive, high grade serous ovarian cancer treated with no more than one prior platinum-based therapy. Patients will be enrolled following documented elevation of CA 125 at least twice the baseline level in two measurements at least one week apart. 15 patients are planned to complete the treatment. The study will be conducted in a dose escalation format, to a maximum dose of $1 \times 10^{11}$ CD3+ cells. There is no minimal dose defined. As a result of the personalized nature of the product, the cell dose may vary from patient to patient. The maximal dose of $1 \times 10^{11}$ CD3+ cells is based on comparable products such as TIL therapy. In existing studies with TIL therapy, patients have received a wide range of cell doses and there has not been any clear association between cell dose and clinical benefit. Infused cells are expected to expand variably from patient to patient. As there is no evidence that this expansion is related to patient weight or body surface area, a flat-fixed dose escalation scheme has been employed.

Treatment:

At the time T cell therapeutic is released for administration to the patient, they will undergo repeat radiographic evaluation and begin the pre-conditioning regimen with cyclophosphamide 30 mg/kg/d for 2 days (days −5 and −4) and fludarabine 25 mg/m²/d for 3 days (days −3, −2, and −1). On day 0, T cell therapeutic will be administered as a single IV infusion. An initial dose of $1 \times 10^{10}$ CD3+ cells will be evaluated in the first three patients. Infusion of patients in this dose level will be staggered by a minimum of 2 weeks to assess for toxicity. If infusions at this dose level are well tolerated, the second dose level (3 patients) will receive $1 \times 10^{11}$ CD3+ T cells. Cell infusions at this higher dose will also be staggered by a minimum of 2 weeks to assess for toxicity. If infusion of $1 \times 10^{11}$ cells is well tolerated by the three patients, all subsequent patients will receive up to $1 \times 10^{11}$ cells. All treatments will be administered in the in-patient setting. T cell therapeutics manufactured on a per patient basis and there is expected to be heterogeneity in the number of cells manufactured. If the dose manufactured is above $1 \times 10^{10}$ CD3+ in dose level 1, or above $1 \times 10^{11}$ CD3+ cells in dose level 2, only a portion of the manufactured dose representing the target dose level will be given. If the dose manufactured is below these targeted dose levels, the dose will be given, but the patient will not be considered evaluable for DLT and will be replaced for the purposes of the 3+3 design. Maximally Tolerated Dose (MTD) definition: The highest dose of infused cells with acceptable side effects.

TABLE 20

| Dose Cohorts | | |
| --- | --- | --- |
| Dose Cohort | Lymphodepletion | Dose Range (single intravenous dose) |
| 1 | Fludarabine + Cyclophosphamide | Up to $1 \times 10^{10}$ total CD3+ cells |
| 2 | Fludarabine + Cyclophosphamide | Up to $1 \times 10^{11}$ total CD3+ cells |

Dose Range:

There is no minimal dose defined. As a result of the personalized nature of the product, the cell dose may vary from patient to patient. The maximal dose of $1 \times 10^{11}$ CD3+ cells is based on comparable products such as TIL therapy. In existing studies with TIL therapy, patients have received a wide range of cell doses and there has not been any clear association between cell dose and clinical benefit. Infused cells are expected to expand variably from patient to patient. As there is no evidence that this expansion is related to patient weight or body surface area, a flat-fixed dose escalation scheme has been employed. $1 \times 10^{10}$ CD3+ cells will be evaluated in the first three patients. If infusion at this dose is well tolerated, subsequent patients will receive up to $1 \times 10^{11}$ CD3+ cells.

Dose Limiting Toxicity (DLT):

The definition of dose limiting toxicity is as follows: Grade 3 or greater toxicity occurring within 24 hours post cell infusion (related to cell infusion). Toxicity must not be reversible to less than or equal to grade 2 within 8 hours with two doses of 1000 mg of oral (PO) acetaminophen or two doses of 2 mg of oral (PO) clemastine. Grade 3 autoimmunity. Toxicity must not be resolved or reversed to less than or equal to a grade 2 autoimmune toxicity within 10 days. Any grade 4 autoimmune toxicity. Any grade 3 or greater non-hematologic toxicity Expected toxicities due to the lymphodepleting chemotherapy regimen or supportive medication administration will not be considered DLTs.

Cytokine Release Syndrome (CRS) Definition and Treatment:

Cytokine release syndrome is a severe toxicity of the immune system that has been observed with chimeric-antigen receptor (CAR)-modified T cells and bi-specific T cell engaging antibodies. These therapies are characterized by supraphysiologic T cell activation, which has resulted in impressive clinical efficacy while also inducing the notable and occasionally severe toxicity of CRS. CRS is a constellation of inflammatory symptoms resulting from cytokine elevations associated with T cell engagement and proliferation. While in most cases, these symptoms include mild fever and myalgia they can also present as a severe inflammatory syndrome with vascular leak, hypotension, pulmonary edema, and coagulopathy.

While CRS risk exists for any immune-activating therapy, the Applicant is of the view that the risk of CRS with T cell therapeutic is extremely low. The T cell therapeutic cellular product is not genetically modified and T cells are not stimulated, activated, or engineered to function at supraphysiologic levels. Of note, CRS has not been observed with TIL therapy.

Per the experience with CRS from CAR-T cell clinical studies, the Applicant will monitor for CRS following T cell infusion with measurement of peripheral blood C-reactive protein, ferritin, and IL-6 daily following T cell infusion. Rapid reversal of severe cytokine-release syndrome has been achieved by treatment with the interleukin-6-receptor blocking antibody tocilizumab and tocilizumab will be incorporated into the management of severe CRS in this study.

Safety Review Committee (SRC)

The SRC will be made up of the site investigator, sponsor medical monitor, sponsor head of research and development, and ad hoc members as appropriate. Careful evaluation to ascertain the toxicity, immunologic effects, and anti-tumor efficacy of cell infusions will be performed continuously.

Study Stages:

(1) Pre-screening for CA 125. Platinum-sensitive patients (defined as clinical response to first-line platinum chemotherapy for greater than or equal to six months) will undergo CA 125 testing every three months. The baseline CA 125 level is defined as the nadir value documented within the first six months following the completion of first-line platinum chemotherapy.

Screening upon asymptomatic CA 125 rise. Upon a detected elevation of CA 125 at least twice the baseline level, patients will undergo a CT scan to determine the extent of disease burden; all scans will be reviewed locally and held for central review if needed. Patients who have at least one site of measurable disease will undergo screening to determine eligibility. Screening procedures consist of a complete medical history including prior cancer therapies and related surgeries, concurrent medications, complete physical examination, Eastern Cooperative Oncology Group (ECOG) performance status (PS), vital signs, 12-lead electrocardiogram (ECG), and clinical laboratory assessments (hematology, chemistry, urinalysis, pregnancy test, thyroid testing).

Pre-treatment including biopsy and apheresis. Patients meeting screening criteria as described above will be enrolled in the trial. Following enrollment, patients will have a tumor biopsy or surgical resection within 14 days of screening to obtain tissue for sequencing and individualized mutation analysis. Tumor biopsies must be formalin-fixed, paraffin-embedded (FFPE), and contain a minimum of 30% tumor cellularity as assessed by pathology. A sample of peripheral blood will be obtained in parallel to serve as a 'normal' tissue control as well as for human leukocyte antigen (HLA) class I and II typing. DNA will be generated from both tumor and normal and submitted for whole-exome sequencing in order to identify the unique mutational landscape of the patient. Tumor RNA will be sequenced in parallel to characterize gene expression. Remaining tumor tissue will also be submitted for immunohistochemical analysis of tumor markers and immune cell markers. During pre-treatment, patients will also undergo an apheresis of minimum 6-blood volumes. T cells and antigen-presenting cells isolated from the apheresis will be used for generation of the T cell therapeutic drug product.

T cell therapeutic production. Production of T cell therapeutic will occur over a 12-16 week period following tumor biopsy and apheresis. The product, an autologous personalized, neoantigen-specific adoptive T cell therapy, consists of CD3+ T cells that have been expanded ex vivo with autologous antigen-presenting cells loaded with neoantigen peptides derived from each individual patient's tumor. The neoantigen peptides are both specific to the patient's tumor cells and unique to the patient as they are designed based on sequence analysis of mutations in each patient's tumor.

Treatment

At the time a patient's T cell product is released, they will undergo repeat radiographic evaluation and begin pre-conditioning regimen with cyclophosphamide 30 mg/kg/d for 2 days (days −5 and −4) and fludarabine 25 mg/m2/d for 3 days (days −3, −2, and −1). On day 0, T cell therapeutic will be administered by IV infusion. An initial target dose of $1\times10^{10}$ CD3+ cells will be evaluated in the first three patients. Patients will be staggered by a minimum of 2 weeks for the first three patients receiving $1\times10^{10}$ cells to assess for toxicity. If infusions at this dose level are well tolerated, the second dose level patients will receive $1\times10^{11}$ CD3+ cells. Cell infusions at this higher dose will be staggered by a minimum of 2 weeks for the first three patients receiving $1\times10^{11}$ cells to assess for toxicity. If infusion of $1\times10^{11}$ cells is well tolerated by three patients, all subsequent patients will receive a single infusion of T cell therapeutic on day 0 of up to $1\times10^{11}$ cells. All treatments will be administered in the in-patient setting. T cell therapeutic is manufactured on a per patient basis and there is expected to be heterogeneity in the dose. If the dose manufactured is above $1\times10^{10}$ CD3+ in dose cohort 1 or above $1\times10^{11}$ CD3+ cells in dose cohort 2, only a portion of the manufactured dose representing the dose target level will be given. If the dose manufactured is below these targeted dose levels, the dose may be given, but the patient will not be considered evaluable for DLT and will be replaced for the purposes of the 3+3 design.

Beginning on day 1, filgrastim will be administered subcutaneously at a dose of 5 mcg/kg/day (not to exceed 300 mcg/day). Filgrastim administration will continue daily until neutrophil count $>1.0\times10^9$/L×3 days or $>5.0\times10^9$/L. If, during the 12-16 week production phase, patients experience symptomatic progression requiring immediate therapy, they may remain on study and if clinically appropriate, receive T cell therapeutic at the time of second relapse as documented by CA 125 2× elevation above baseline.

Follow-Up

The primary treatment phase of this study is Week 1 to Week 52. Safety assessments conducted during the primary treatment phase include adverse event (AE) collection, symptom-directed physical examinations, measurement of vital signs, ECOG PS, and safety laboratory assessments. Radiographic assessments to evaluate response to treatment will be conducted at Weeks 12, 24, and 48. Approximately 4-6 weeks after filgrastim administration, patients will undergo a complete tumor evaluation and evaluation of toxicity and immunologic parameters. Patients will receive no other experimental agents while on this protocol. Peripheral blood mononuclear cells (PBMCs) for comprehensive immune monitoring will be obtained from an 80-120 cc peripheral blood draw following T cell therapeutic infusion at time points of 4 hours, 4 days, 14 days, 1 month, and monthly thereafter. In addition to the biopsy prior to treatment, core or surgical biopsies must be conducted between Weeks 20 and 24 and/or at the time of disease progression.

Figure 67:
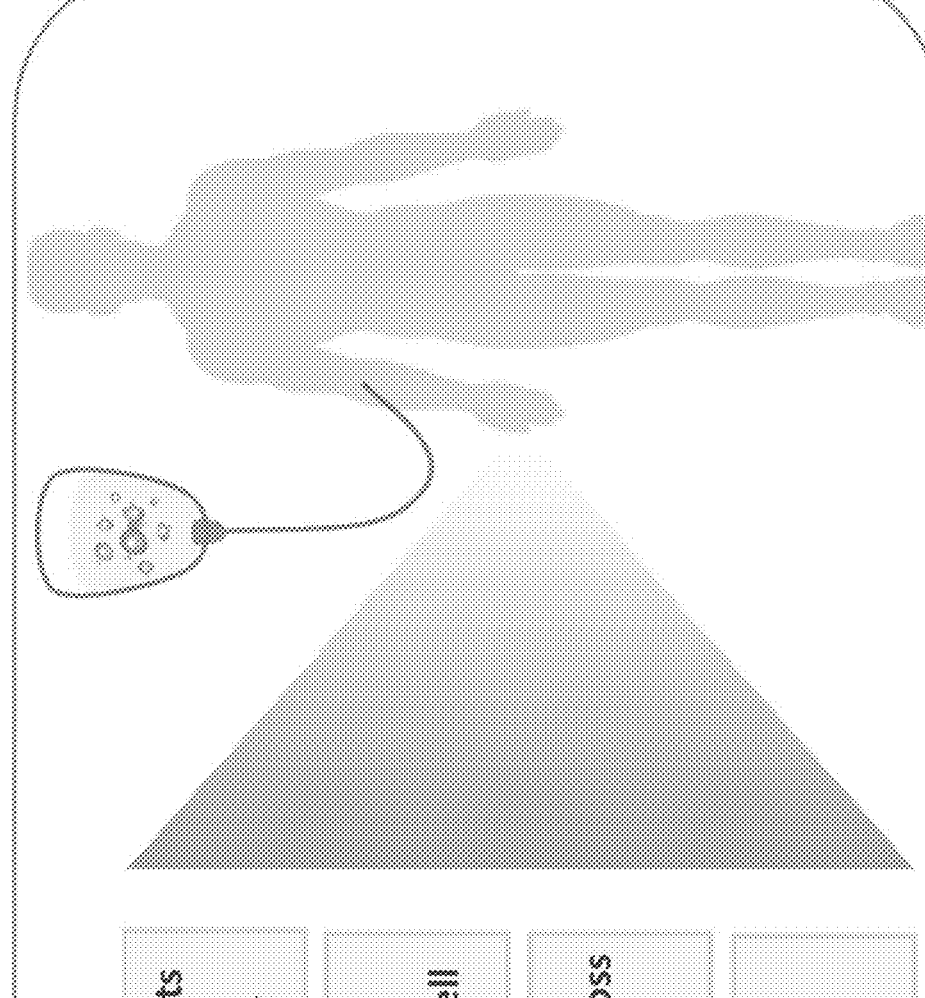
FIG. 67 exemplifies the multiple aspects that are advantageous for the clinical approach using T cells manufactured by the process shown in FIG. 1A.

Example 35—Development of an Autologous Neoantigen-Specific T Cell Product for Adoptive Cell Therapy of Metastatic Melanoma Scalable Process Engineering, T Cell Manufacture, and Quality Control In this example, results of multiple successful process engineering runs using leukapheresis from metastatic melanoma patients are shown. NEO-STIM is a proprietary ex vivo induction process, a neoantigen-specific T cell product (NEO-PTC-01) was generated that contains highly specific T cell responses targeting multiple neoantigens from each individual patient's tumor; these T cell responses are polyfunctional and can recognize autologous tumor. A clinical trial program will commence using the processes described here. A generalized workflow for a clinical program on NEO-PTC-01 is graphically represented in FIGS. 1A and 67). The envision advantages of this program is outlined in FIG. 67.

An induction process, NEO-STIM™, which primes, activates, and expands out multiple neoantigen-specific T cell responses is described. The characteristics of the drug product NEO-PTC-01—specificity, functionality, and phenotype—are expected to confer a clinical benefit and overcome challenges that other cell therapy modalities are facing, including, but no limited, to reducing risk of antigen escape, reducing risk of off-target toxicity, selecting optimal T cell phenotype to drive persistence and tumor cell killing, covering broad clinical opportunity across solid tumors, and making use of an advantage that the a non-engineered cell product is generated that has limited expectations of toxicity. A neoantigen-specific T cell product (NEO-PTC-01) was generated that contains highly specific T cell responses targeting multiple neoantigens from each individual patient's tumor; these T cell responses are polyfunctional and can recognize autologous tumor.

Four process engineering runs were performed by the Biotherapeutics Unit of Netherlands Cancer Institute—Antoni van Leeuwenhoek (NKI-AVL) using PBMCs from a healthy donor and 3 melanoma patient samples that were obtained under IRB approval (Table 22).

For the melanoma patients, patient-specific neoantigens were predicted using a T cell epitope prediction program. For HD108, previously identified neoantigens and model antigens restricted to the donor HLA alleles were used to execute NEO-STIM. Synthetic peptides were generated of 8 to 25 aa in length. NEO-STIM was used to prime, activate, and expand memory and de novo T cell responses, using up to $50\times10^6$ PBMCs per vessel.

The specificity, phenotype, and functionality of these neoantigen-specific T cells were analyzed by characterizing these responses with the following assays:

Combinatorial coding analysis using pMHC multimers.

Detailed flow characterization. Markers included but were not limited to CD3, CD4, CD8, CD45RA, and CD62L.

A recall response assay using multiplexed, multiparameter flow cytometry to a) identify and validate CD4+ T cell responses, b) assess the polyfunctionality of CD8+ and CD4+ T cell responses, and c) assess the ability to recognize autologous tumor. Pro-inflammatory cytokines IFN-γ and TNFα, and upregulation of CD107a as a marker of degranulation, were measured.

A cytotoxicity assay using neoantigen-expressing tumor lines to understand the ability of neoantigen-specific CD8+ T cell responses to recognize and kill target cells in response to naturally processed and presented or exogenously loaded antigen.

Results

Preclinical development activities to inform manufacturing of NEO-PTC-01, the adoptive T cell therapeutic product, successfully resulted in the execution of 4 process engineering runs using leukapheresis from a healthy donor and 3 metastatic melanoma patients.

The final drug product generated met the release specifications for all 4 process engineering runs (Table 21).

TABLE 21

| Results of drug product meeting acceptance criteria Acceptance criteria for NEO-PTC-01 for all runs | |
|---|---|
| Test | Result |
| Cell Count | Pass |
| Viability | Pass |
| T Cell Purity/Identity (CD3$^+$ cells) | Pass |
| Mycoplasma | Pass |
| Endotoxin | Pass |
| Sterility | Pass |

Figure 68:
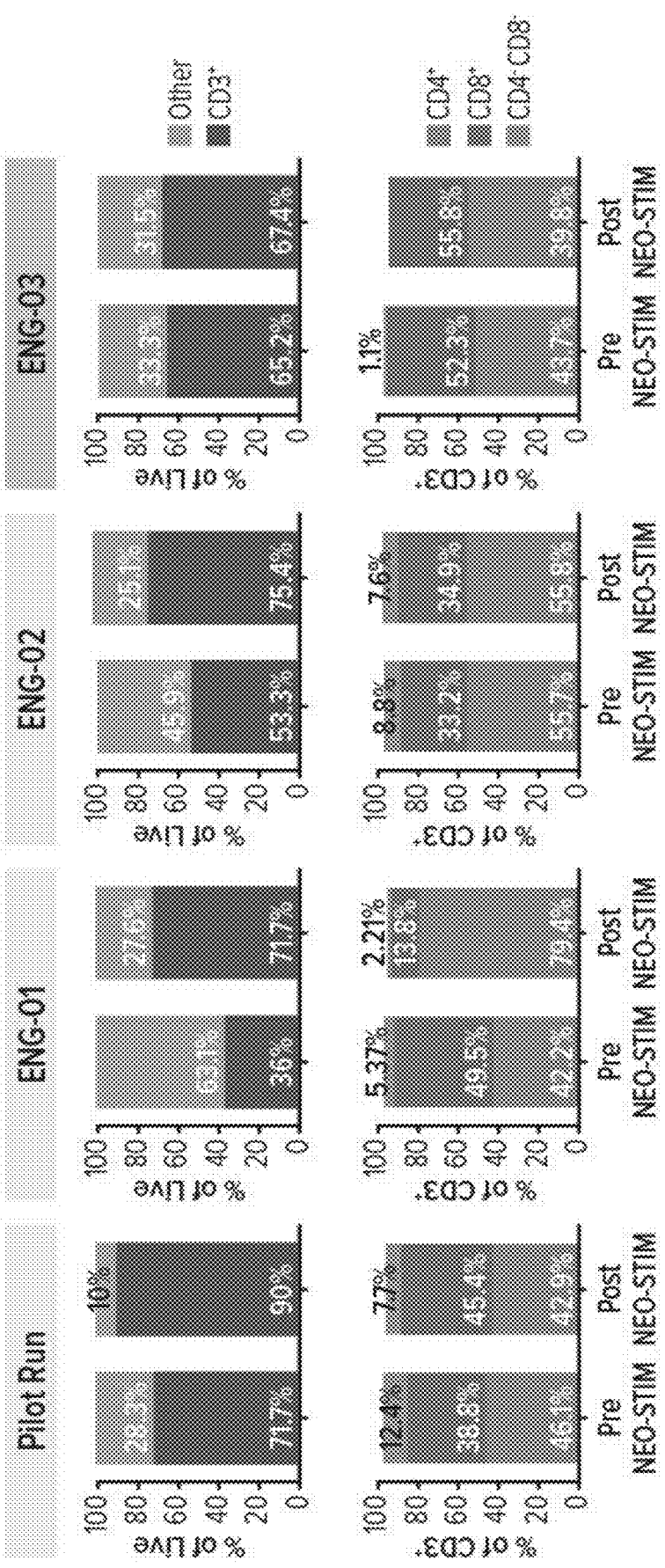
FIG. 68 depicts exemplary representative flow cytometry data showing characterization of a patient specific T cell product prepared by multiple engineering runs. The CD3+as a fraction of live cells (Upper Panel) and CD8+ and CD4+as a fraction of live CD3+ T cells (Lower Panel) are depicted.

The majority of the final drug product consisted of CD3$^+$ T cells (range: 67.4% to 90%). B cells, NK cells, and APCs made up the non-CD3$^+$ fraction (FIG. 68).

Figure 72:
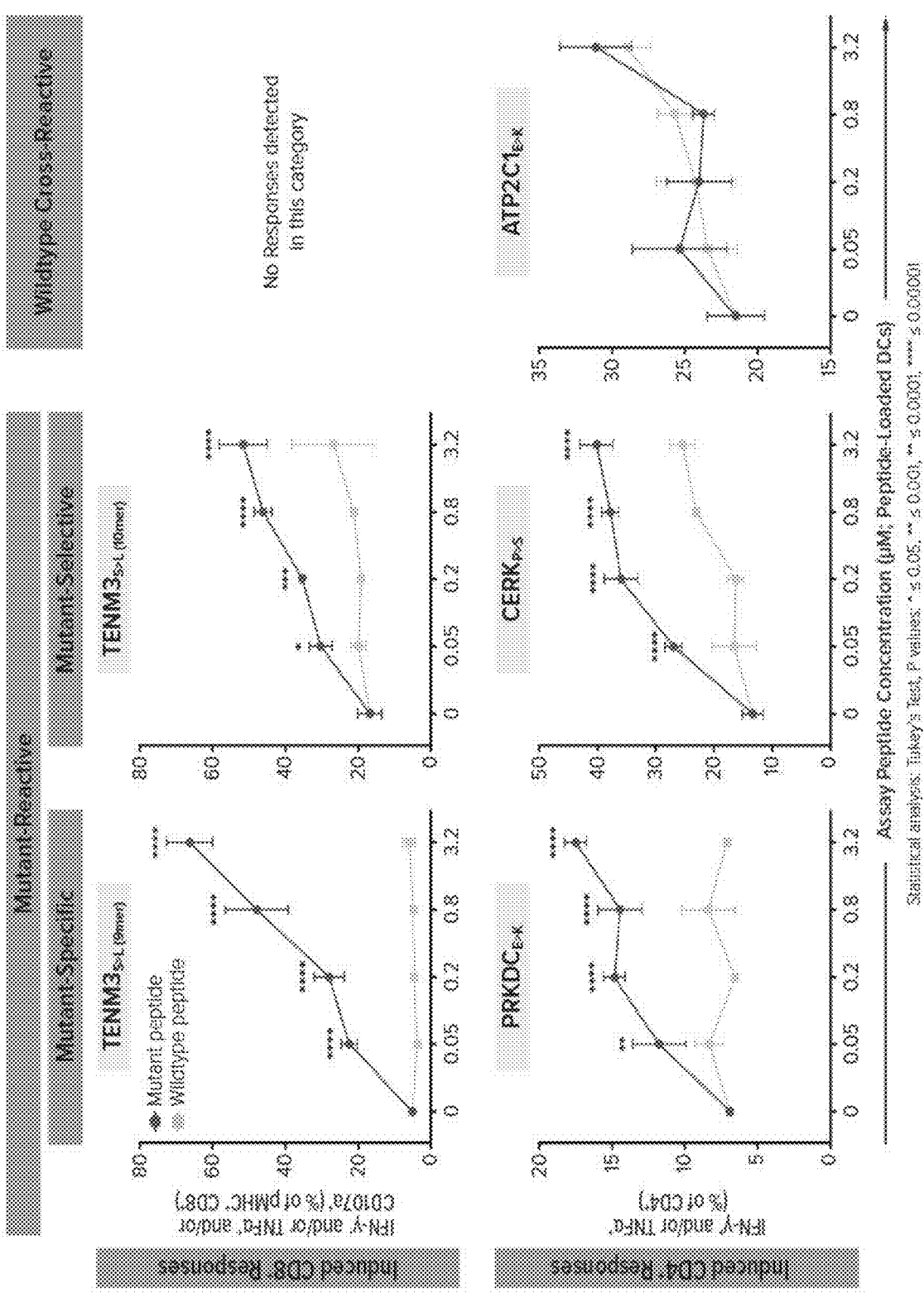
FIG. 72 depicts exemplary graphical representations of data from multimer assays showing the percentage of IFN-γ$^+$ and/or TNFα$^+$ and/or CD107a$^+$ cells of total CD8$^+$ cells (upper panel) or total CD4$^+$ T cells (lower panel) measured upon challenge with various concentrations of the peptide-loaded DCs in the sample. The peptide used for each of the graphs is shown.

Nineteen CD8$^+$ and 25 CD4$^+$ T cell responses were induced from PBMCs (range 4-5 and 4-7 per patient for CD8$^+$ and CD4$^+$ T cells, respectively, Table 22, FIGS. 69A-69C). All the T cell responses induced in the PBMCs from the melanoma patients are presumed de novo T cell responses; no pre-existing responses were detected in the unmanipulated starting material. This was also the case for the PBMCs from the healthy donor; however, one of the responses that was identified was towards MART1, which is known to have a high precursor frequency in peripheral blood. As such, this process successfully induced T cell responses from the naïve compartment. Additionally, in the healthy donor a T cell response known to have a high precursor frequency was expanded, which resembles the expansion of a memory T cell response.

the induced CD8$^+$ and CD4$^+$ T cell responses were assessed and assigned to 2 categories (FIG. 72): (i) Mutant reactive and (ii) Wildtype cross-reactive. Mutant reactive categories are (a) Mutant-specific, which show a significant increase in IFN-γ and/or TNFα toward mutant, but not wildtype, epitope; and/or (b) Mutant-selective which show significant increase in IFN-γ and/or TNFα toward mutant and wildtype epitopes. However, the signal toward the mutant epitope is significantly higher compared to the wildtype epitope. Wildtype cross-reactive category shows a significant increase in IFN-γ and/or TNFα toward mutant and wildtype epitopes. There is no significant difference between the 2 signals. In summary: For the CD4$^+$ compartment, T cell responses were detected in both categories; 85% of CD4$^+$ T cells were mutant-reactive and 15% were cross-reactive to the wildtype epitope. For the CD8$^+$ T cell compartment, 100% of all T cells were mutant-reactive (Table 23).

TABLE 23

| Summary of all tested responses, significance assigned using Tukey's test, P < 0.05 Pilot run, ENG-01 & ENG-02 | | | |
|---|---|---|---|
| | Responses Tested | Mutant reactive | Cross reactive to wildtype |
| CD4 | 13 | 85% | 15% |
| CD8 | 3 | 100% | 0% |

Finally, the cytotoxic capacity of the NEO-STIM-induced T cells was assessed for a subset of the identified T cell

TABLE 22

| Design for induction of engineering runs | | |
|---|---|---|
| Run ID Material Source | Induced CD8$^+$ responses | Induced CD4$^+$ responses |
| Pilot Run Healthy donor | REL$_{G>R}$, ZDBF2$_{P>L}$, KXD1$_{S>F}$, MART1 & SNA70 | PRKDC$_{E>K}$, MERTK$_{E>K}$, CDK4$_{R>C}$, GAS7$_{H>Y}$, RQDC1$_{P>L}$, HIV1 & HIV2 |
| Melanoma patient 1 | ZNF226$_{H>Y}$, LRBA$_{S>L}$, DNM2$_{I>V}$, BBS4$_{L>F}$, & GTF2H3$_{V>A}$ | PRKDC$_{E>K}$, MARCH7$_{S>F}$, TRAK2$_{G>V}$, RANBP9$_{P>S}$, DNM2$_{I>V}$, MERTK$_{E>K}$, OSBPL8$_{L>S}$ |
| Melanoma patient 2 | TENM3$_{S>L}$ (10mer), CERK$_{P>S}$, ITPR3$_{E>K}$, TENM3$_{S>L}$ (9mer) & ATP2C1$_{E>K}$ | TENM3$_{S>L}$, ARID2$_{S>L}$, ATP2C1$_{E>K}$, CERK$_{P>S}$, ATP5G2$_{S>F}$,TNFRSF10B$_{P>L}$, & ALG13$_{G>R}$ |
| Melanoma patient 3 | REL$_{G>R}$, PDE8A$_{P>S}$, WWP2$_{P>S}$ & VANGL2$_{S>F}$ | ACACA$_{H>Y}$, MYCBP2$_{S>F}$, ALS2$_{A>T}$ & TOR1AIP1$_{T>I}$ |

Figure 70:
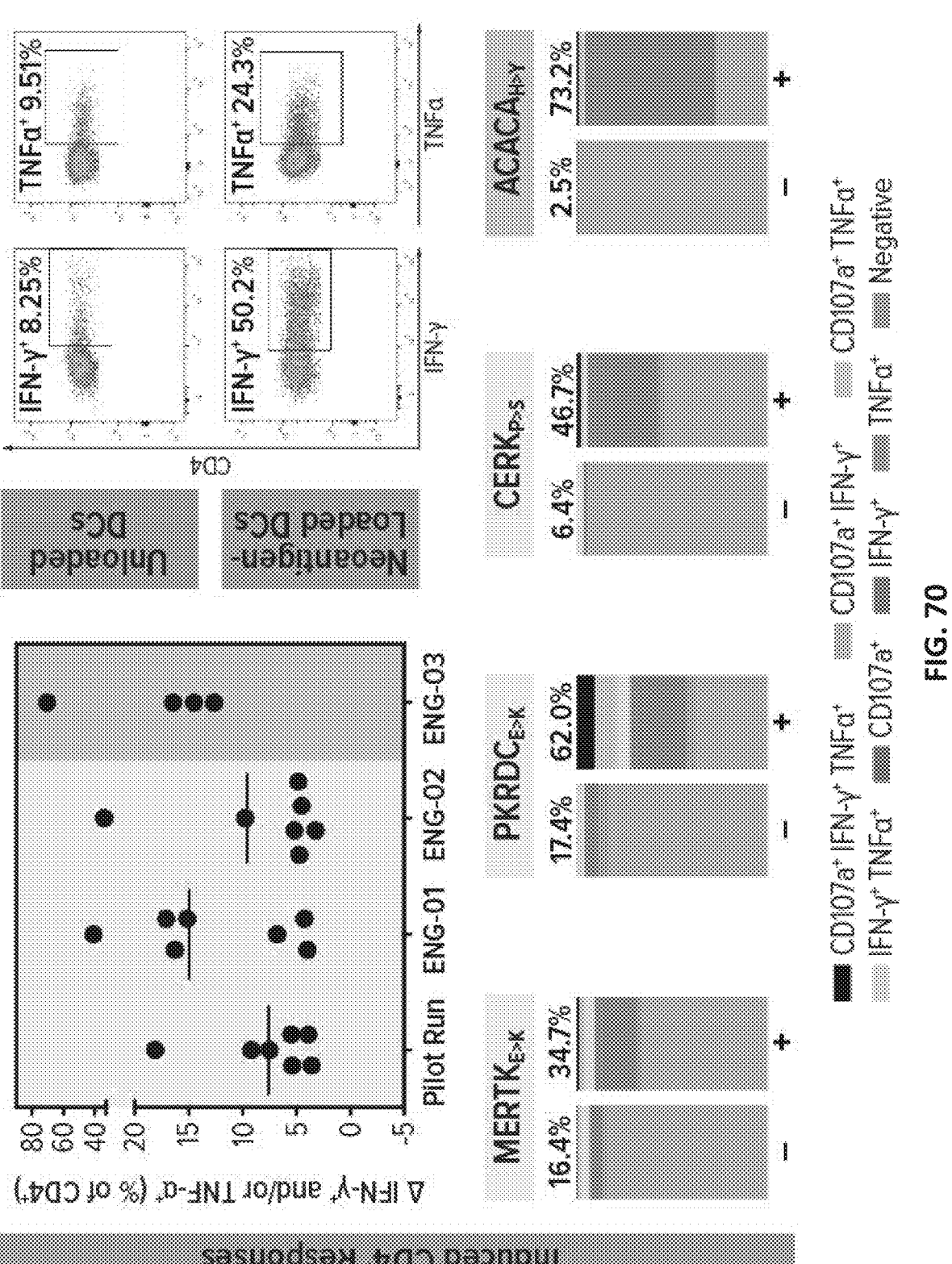
FIG. 70 depicts representative data indicating the change in production of IFNγ and/or TNFα by CD4$^+$ cells of a patient specific T cell product prepared by multiple engineering runs. Also depicted is exemplary representative data showing characterization of IFNγ$^+$ and/or TNFα$^+$ and/or CD107a$^+$ CD4$^+$ cells in patient specific T cell products prepared by multiple engineering runs.
Figure 71:
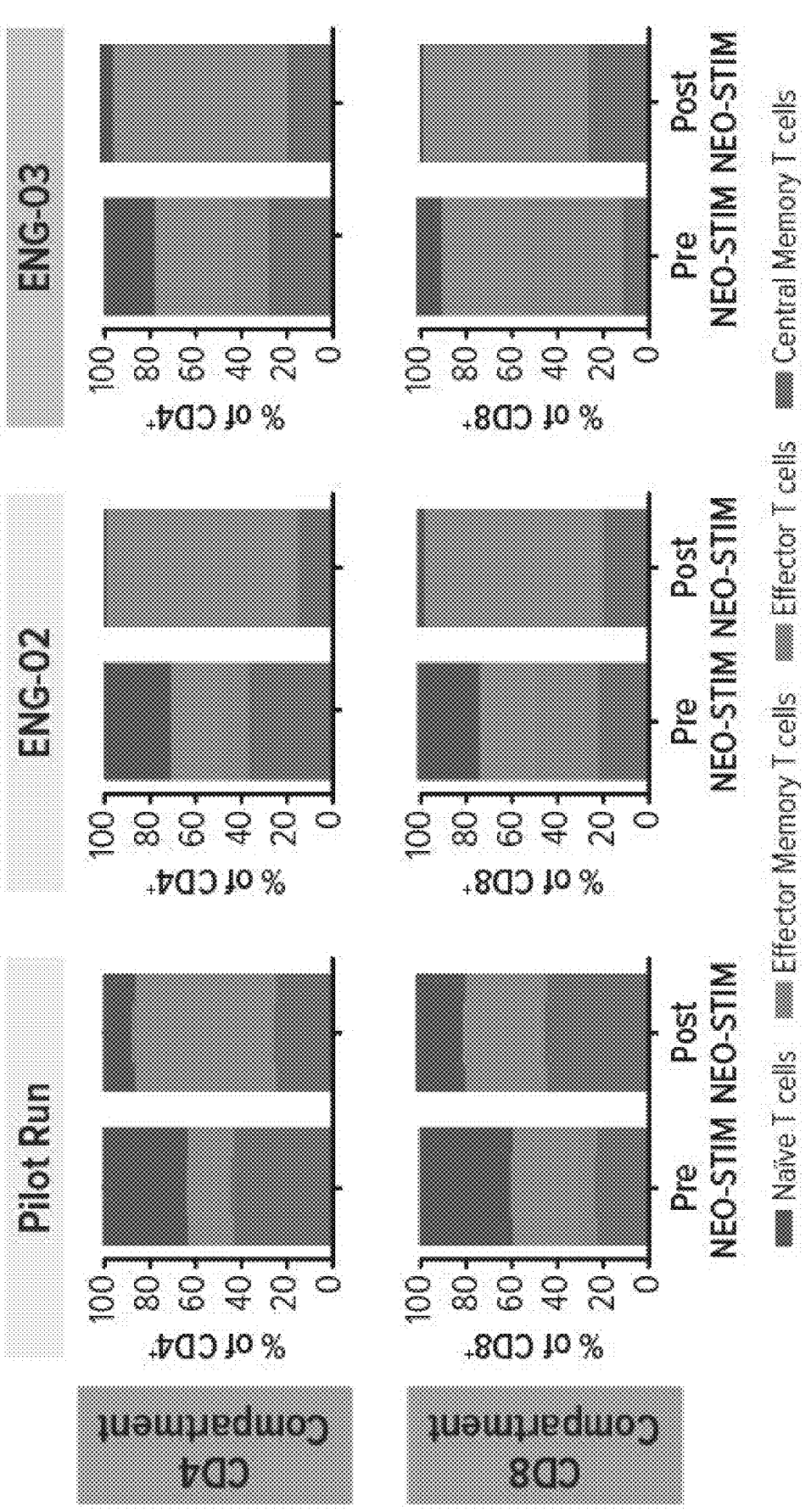
FIG. 71 depicts exemplary graphical representations showing the fraction of central memory T cells (T$_{cm}$), effector Memory T cells (T$_{em}$), effector T cells (T$_{eff}$) and naïve T cells (T$_{naive}$) in a patient specific T cell product prepared by multiple engineering runs. Central memory T cells (T$_{cm}$): CD62L$^+$ CD45RA$^-$, Effector Memory T cells (T$_{em}$): CD62L$^-$ CD45RA$^-$, Effector T cells (T$_{eff}$): CD62L$^-$ CD45RA$^+$, naïve T cells (T$_{naive}$): CD62L$^+$ CD45RA$^+$.

Further characterization was performed to assess the polyfunctionality profile and the differentiation status of the NEO-STIM-induced CD8$^+$ and CD4$^+$ T cells. Upon re-challenge with mutant peptide-loaded DCs, neoantigen-specific T cells exhibited 1, 2, and/or 3 functions (examples of the polyfunctionality profile of the CD8$^+$ and CD4$^+$ T cell responses are shown in FIG. 69C and FIG. 70 lower panel, respectively). FIG. 70 upper panel demonstrates representative data indicating fraction of CD4$^+$ cells expressing IFN-γ and/or TNF-α in a representative induced response. The upper right panel depicts representative data indicating exemplary flow cytometry plots of IFN-γ$^+$ CD4$^+$ T cells. Additionally, the differentiation status of the drug product was assessed. The majority of the NEO-STIM-induced T cells were of the effector memory and central memory phenotypes (FIG. 71).

Figure 73:
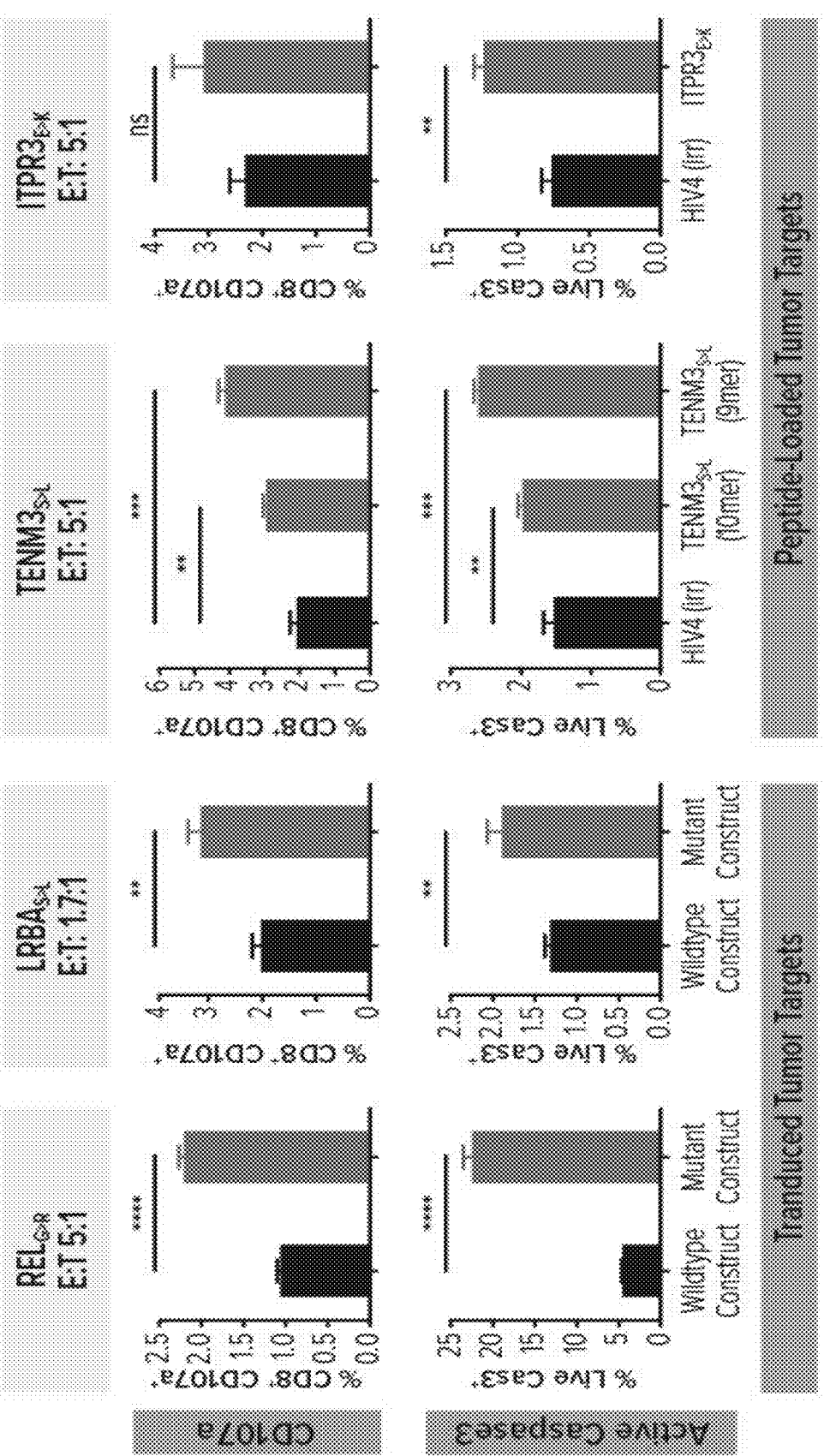
FIG. 73 depicts exemplary graphical representations of data indicating upregulation of CD107a (top row) on CD8$^+$ T cells and active Caspase3 on tumor cells (bottom row). Measurements were obtained after co-culture with un-transduced or transduced with a 200 amino acid construct in A375 tumor cell line or peptide-loaded or unloaded A375 tumor cell lines.

The NEO-STIM-induced T cell responses were shown to be highly specific for the mutant epitope. The specificities of responses. Transduced tumor cell lines were generated for the Pilot run and ENG-01, expressing the donor-specific HLA allele as well as the mutation studied. For ENG-02, peptide-loaded tumor cells were used expressing the donor-specific HLA allele (FIG. 73):

i. CD8$^+$ T cell responses directed toward REL$_{G>R}$ (Pilot) and LRBA$_{S>L}$ (ENG-01) showed a significant upregulation of CD107a on the CD8$^+$ T cells and active Caspase3 on the tumor cells transduced with the mutant construct after co-culture.

ii. CD8$^+$ T cell responses directed toward TENM3$_{S>L}$ and ITPR3$_{E>K}$ (ENG-02) showed a significant upregulation of active Caspase3 on the tumor cells and, in the case of TENM3$_{S>L}$, upregulation of CD107a on the CD8$^+$ T cells, after co-culture with peptide-loaded tumor targets.

Figure 74:
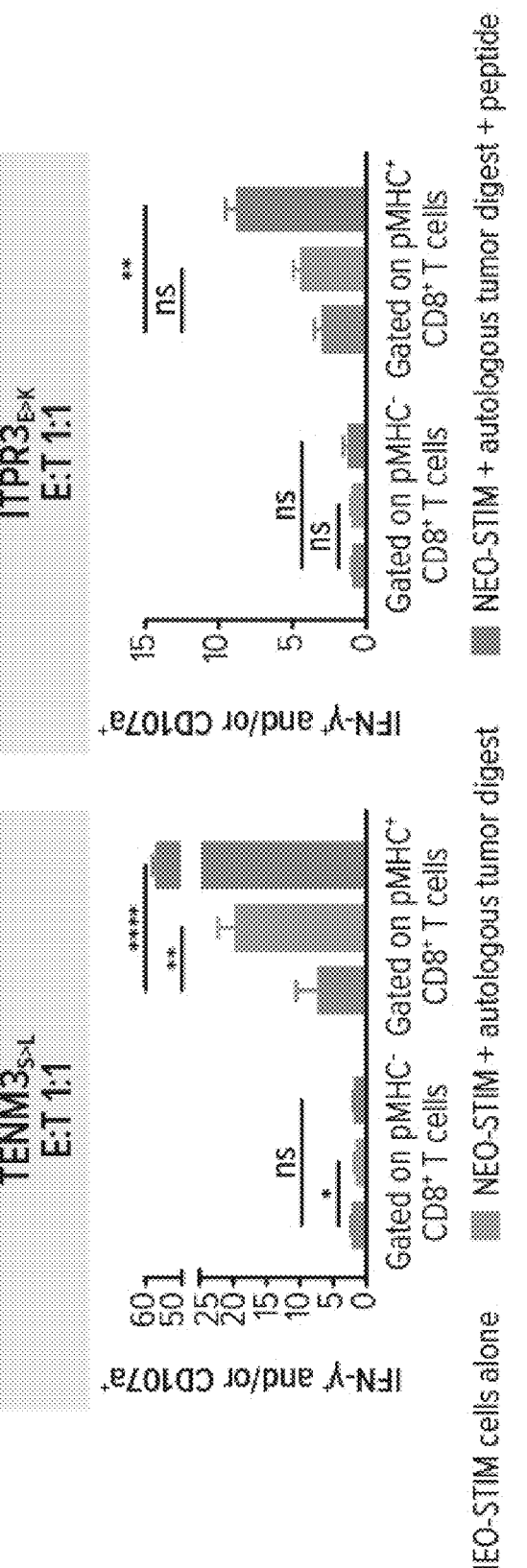
FIG. 74 depicts exemplary graphical representations of data indicating that induced T cells can kill antigen expressing cells. Neoantigen-specific T cells were tested to recognize autologous tumor or peptide-loaded autologous tumor through a recall response assay. Readout: IFN-$\gamma^+$ and/or TNF$\alpha^+$ and/or CD107a$^+$ of pMHC$^+$ (% of CD8$^+$) and pMHC$^-$ (% of CD8$^+$) T cells (Y axis). Significance was assigned using a 1-way ANOVA, P<0.05.

Importantly, co-culturing T cells generated from ENG-01 and ENG-02 with available autologous tumor digest proved that the induced T cells were capable of directly recognizing autologous tumor cells, based on upregulation of IFN-γf and CD107a on the neoantigen-specific T cells (FIG. 74).

Using this exemplary induction process, a potent T cell product can be reproducibly generated from PBMCs of melanoma patients at a therapeutic scale. The induction process induces multiple CD8+ and CD4+ T cell responses. The induced T cell responses are mutant-reactive, show a polyfunctional profile, and have central and effector memory phenotypes. The induced T cell responses have cytotoxic capability, shown by the upregulation of cytotoxic function upon recognition of antigen-expressing tumor cell lines. Importantly, the induced T cell cultures can directly recognize autologous tumor.

Clinical Application

An exemplary clinical application of the scaled manufactured T cell can any of the clinical applications disclosed in the application, including, but not limited to treatment for melanoma, lung cancer, pancreatic cancer, glioblastoma, ovarian cancer.

Figure 75:
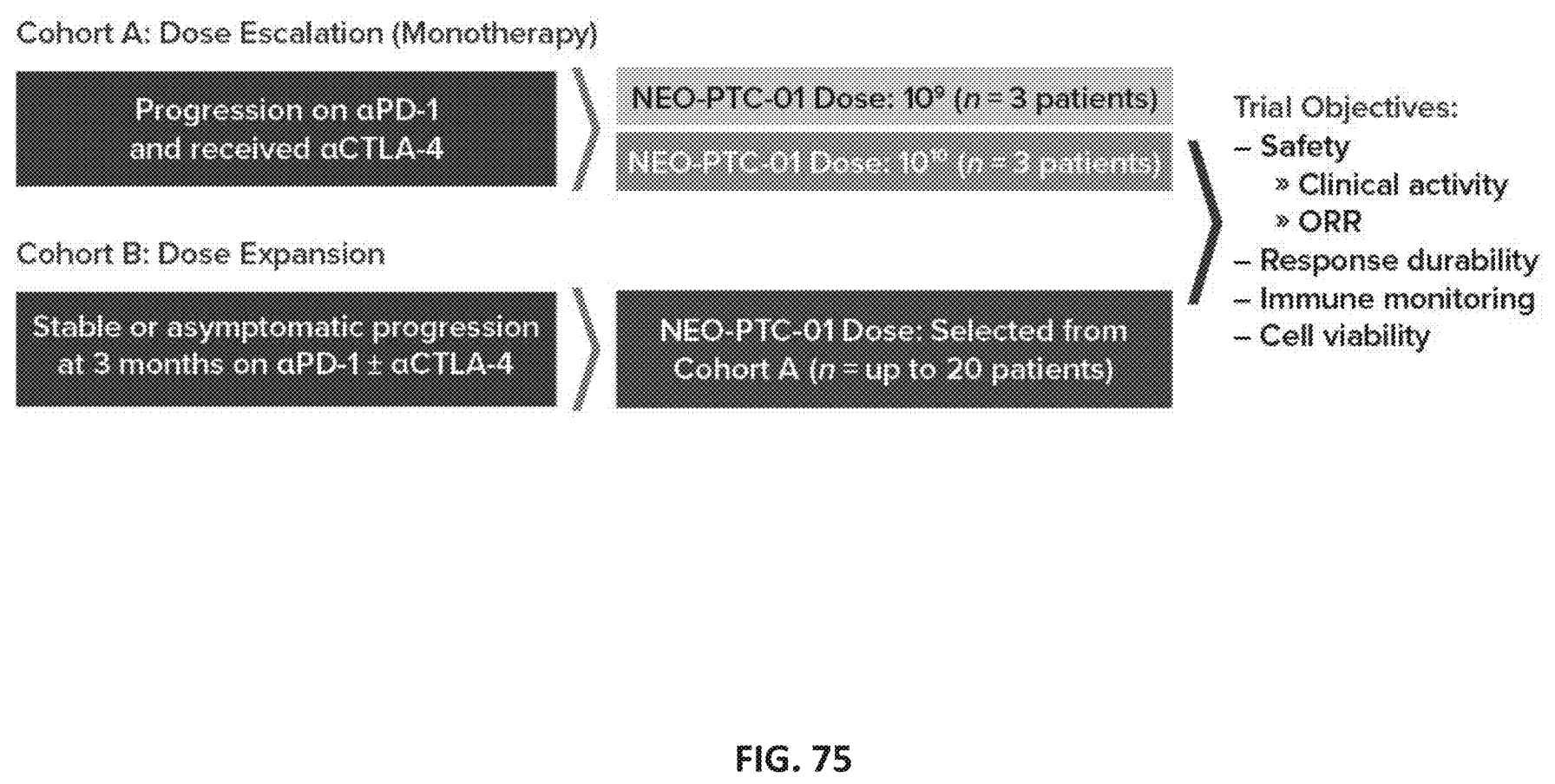

Yet another application in the program for commencing clinical trial is summarized in FIG. 75. In this application, patients are included in two cohorts. Cohort A: patients that are refractory to anti-PD1 treatment and received anti-CTLA-4 therapy. These patients are subjected to two doses of the drug product described above. (i) a small number of patients will be given $10^{8}$-$10^{9}$ cells monotherapy, and a small number of patients will be given $>10^{9}$-$10^{10}$ cells. Cohort B: inclusion of patients that are stable or asymptomatic progressor at 3 months on anti-PD1 with or without anti-CTLA4 with dose determined in cohort A.

Example 36: Open Label, Phase I Study of NEO-PTC-01 in Patients with Advanced or Metastatic Melanoma This study will investigate NEO-PTC-01, an autologous personalized T cell product for adoptive cell therapy that is manufactured ex vivo and targets neoantigens displayed on the tumour and the tumour microenvironment. Neoantigens are tumour-specific antigens derived of mutations in the DNA presented in the context of the patient's major histocompatibility complex (MHC) class I and class II alleles. Targeting neoantigens utilizes an individualized approach and offers an opportunity to tailor the composition of each cell product to generate a personalized T cell product for each patient. The cells derived from the product are expected to be from a central or effector memory phenotype, able to perform multiple functions (the anticipated mechanism of action includes cytokine production and degranulation upon recognition of the target cells) and are expected to be highly mutant specific when compared to the wild-type epitope. The addition of this neo-antigen specific adoptive T cell therapy may provide significant clinical benefit over checkpoint inhibitor SOC therapies, including a more durable anti-tumor response. symptom control, and prolonged freedom from tumor progression.

Objective of the Study

The primary objective of this study is to evaluate the safety and determine the highest tolerable dose of NEO-PTC-01 in patients with unresectable or metastatic melanoma. Secondary objectives of this study are 1) to determine anti-tumor activity as assessed by progression-free survival based on Response Criteria in Solid Tumors (RECIST) v1.1 (Eisenhauer, 2009) and 2) to determine anti-tumor activity as assessed by overall response rate (ORR), duration of response (DOR), and clinical benefit rate (CBR).

Study Design

Study NTC-001 is a Phase 1 investigation of the safety and activity of NEO-PTC-01 in patients with unresectable or metastatic melanoma. The study will be conducted in two parts, Part 1 (Dose-Finding) and Part 2 (Dose Expansion). The dose-finding part of the study will initiate NEO-PTC-01 therapy at a dose of $\geq 1\times10^{8}$ to $\leq 1\times10^{9}$ cells and will continue according to a 3+3 dose escalation design. Dose expansion Part 2 will test the highest tolerable Part 1 dose in an expanded patient cohort to further define the safety and tolerability.

Study Population

Adult males and females ages 18-75 years with unresectable or metastatic melanoma who have progressed while treated with both a PD-1/PD-L1 inhibitor and a CTLA-4 inhibitor (Part 1).

Intervention

Patients in study Part 1 will receive NEO-PTC-01 beginning at a dose of $\geq 1\times10^{8}$ to $\leq 1\times10^{9}$ cells. Patients in study Part 2 (expansion cohort) will receive NEO-PTC-01 at the highest tolerable dose from Part 1.

Primary Study Parameters/Outcome of the Study

The main study parameter is the assessment of safety of treatment with NEO-PTC-01 based on incidence of adverse events (AEs), serious adverse events (SAEs), and changes in safety laboratory values, physical examinations, and vital signs. Clinical response to treatment will be assessed according to serial radiographic evaluations (computed tomography [CT] or magnetic resonance imaging [MRI]) to determine response to treatment and progression of disease (RECIST v1.1).

Secondary Study Parameters/Outcome of the Study

Clinical response to treatment will be assessed according to serial radiographic evaluations (computed tomography [CT] or magnetic resonance imaging [MRI]) to determine response to treatment and progression of disease (RECIST v1.1). Overall response rate (ORR), defined as the proportion of patients who achieve a CR or partial response (PR), will be determined. PFS, defined as the time from the date of first dosing of NEO-PTC-01 to the date of first documented progressive disease (PD) or death. DOR, defined as the date of the first documentation of a confirmed response to the date of the first documented PD. Clinical benefit rate (CBR), defined as the proportion of patients who achieve CR, PR, or SD based on RECIST. Time to first subsequent therapy, defined as the time from the date of first dosing to the start date of first subsequent therapy. Nature and extent of the burden and risks associated with participation, benefit and group relatedness.

NTC-001 is a dose finding and safety First-in-Human (FIH) study of NEO-PTC-01 in patients with unresectable or metastatic melanoma. The dose-finding part of the study is structured according to a 3+3 dose escalation design, limiting exposure to study drug in the initial phase of safety evaluation. As an additional safety precaution, within dose cohorts, enrolment of the first 3 patients will be staggered at a minimum of 2-week intervals. Major areas of risk include infection during period of lymphodepletion, potential for cytokine release syndrome (CRS), and off-tumor, off-target toxicities. Additional potential risks are those associated with other study-specific procedures, of including tumor biopsies and leukaphereses. Patients will be hospitalized for inpatient monitoring during the initial treatment phase of lymphodepletion, T cell product infusion, and neutrophil recovery. Thereafter, weekly clinical exam and laboratory monitoring will occur in the outpatient setting from weeks 1-4 post discharge, followed by visits every 6 weeks for the remainder of study. Safety interventions will include fil-grastim growth factor support following the cyclophosph-amide+fludarabine lymphodepletion regimen, and cytokine release syndrome (CRS) monitoring and management. Previous studies with tumor infiltrating lymphocyte (TIL)-based therapies may be the most relevant comparative therapies. These studies are considered in devising a starting dose and dose range for this study. The lower starting dose is implemented as a core safety consideration for initial NEO-PTC-01 testing in patients. Assessments from tumor biopsies are critical to the rationale and design of this study. Wherever feasible, the study design allows for use of archival samples for the baseline tumor specimen. Postin-fusion tumor biopsy and leukapheresis samples are required to evaluate safety and pharmacodynamic effects, including correlations with toxicity and efficacy in this first-in-human study. These procedures will be performed according to protocol or institutional standards in a hospital-monitored setting. These risks are considered relative to potential NEO-PTC-01 clinical benefit in patients with unresectable or metastatic melanoma and disease progression or subop-timal response (Part 2) to prior therapies. NEO-PTC-01 represents a novel, individualized treatment approach; addi-tion of neoantigen-specific autologous T cell therapy may offer significant clinical benefit over checkpoint inhibitor regimens.

Main Inclusion Criteria

1. Adult (age 18 to 75) men and women willing and able to give written informed consent.
2. Histologically confirmed unresectable or metastatic melanoma.
3. Part 1:
   a. Have previously received a PD-1/PD-L1 inhibitor (either as single agent or in combination) and a CTLA-4 inhibitor containing regimen (single agent or combination).
   b. Have documented disease progression on their last treatment regimen.
4. Part 2:
   a. Have received/are currently receiving a PD-1/PD-L1 inhibitor (as a single agent or in combination with CTLA-4) for at least 3 months.
   b. Have documented stable disease by RECIST 1.1 or clinically asymptomatic progressive disease on the most recent imaging assessment, which must have occurred within 3 months of enrollment.
   c. Are medically fit to continue with PD-1/PD-L1 inhibitor therapy.
   d. In the opinion of the investigator would benefit from the addition of a T-cell based therapy.
5. For BRAF mutant patients: patients must have also previously received targeted therapy (B-raf inhibitor or B-raf/MEK combination therapy).
6. Patient must be clinically asymptomatic and expected to stay without symptoms that require antineoplastic treatment for at least 16 weeks.
7. Have at least one site of measurable disease by RECIST v1.1.
8. At least one site of disease must be accessible to biopsy for tumor tissue. For the pretreatment biopsy, an archi-val specimen may be used if the biopsy was taken within 6 months of enrollment.
9. Have ECOG performance status of 0 or 1.
10. Recovered from all toxicities associated with prior treatment to acceptable baseline status (for laboratory toxicities see below limits for inclusion) or a National Cancer Institute Common Terminology Criteria for Adverse Events (NCI CTCAE) version 5.0, Grade of 0 or 1, except for toxicities not considered a safety risk (e.g., alopecia).

11. Screening laboratory values must meet the following criteria and should be obtained within 28 days prior to study treatment:
    a. White blood cell (WBC) count $\geq 3 \times 10^{\wedge}3/\mu L$
    b. Absolute neutrophil count (ANC) $\geq 1.5 \times 10^{\wedge}3/\mu L$
    c. Platelet count $\geq 100 \times 10^{\wedge}3/\mu L$
    d. Hemoglobin >9 g/dL or 6 mmol/L
    e. Serum creatinine $\leq 1.5 \times$ upper limit of normal (ULN) or creatinine clearance (CrCl) $\geq 50$ mL/min by Cock-croft-Gault
    f. Aspartate aminotransferase (AST) and alanine ami-notransferase (ALT)$\leq 3 \times$ULN
    g. Total bilirubin $\leq 1.5 \times$ULN (except in patients with Gilbert Syndrome in which case total bilirubin <3.0 mg/dL is acceptable
    h. International Normalized Ratio (IN R), Prothrombin Time (PT), or Activated Partial Thromboplastin Time (aPTT) $\leq 1.5 \times$ULN unless the patient is receiv-ing anticoagulant therapy as long as PT or aPTT is within therapeutic range of intended use of antico-agulants Main Exclusion Criteria 1. Age greater than 75 years.
2. Received more than three prior therapies for metastatic disease.
3. Have an active or history of autoimmune disease (known or suspected). Exceptions are permitted for vitiligo, type I diabetes mellitus, residual hypothyroid-ism due to autoimmune condition requiring only hor-mone replacement, psoriasis not requiring systemic treatment, or conditions not expected to recur in the absence of an external trigger.
4. Have known active central nervous system (CNS) metastases and/or carcinomatous meningitis. Patients with previously treated brain metastases may partici-pate provided they are stable, have no evidence of new or enlarging brain metastases, and are not using steroids for at least 7 days prior to enrolment. This exception does not include carcinomatous meningitis, which is excluded regardless of clinical stability.
5. Active systemic infections requiring intravenous anti-microbial therapy, coagulation disorders or other active major medical illnesses of the cardiovascular, respira-tory or immune system, as evidenced by a positive stress thallium or comparable test, myocardial infarc-tion, clinically significant cardiac arrhythmias such as uncontrolled atrial fibrillation, ventricular tachycardia, or second or third degree heart block, and obstructive or restrictive pulmonary disease.
6. Have a condition requiring systemic treatment with either corticosteroids (>10 mg daily prednisone equiva-lents) or other immunosuppressive medications within 14 days prior to NEO-PTC-01 infusion. Inhaled or topical steroids and adrenal replacement doses (5 10 mg daily prednisone equivalents) are permitted in the absence of active autoimmune disease.
7. Known human immunodeficiency virus (HIV) infec-tion, active chronic hepatitis B or C, and/or life-threatening illnesses unrelated to cancer that could, in the investigator's opinion, interfere with participation in this study.
8. Have any underlying medical condition, psychiatric condition, or social situation that, in the investigator's opinion, would interfere with participation in the study.

9. Have a planned major surgery that is expected to interfere with study participation or confound the ability to analyse study data.

10. Are pregnant or breastfeeding, or expecting to conceive or father children within the projected duration of the trial, starting with the screening visit through 120 days after the end of the trial (E01") visit. Nursing women are excluded from this study because there is an unknown but potential risk of AEs in nursing infants secondary to treatment of the mother with treatments to be administered in this study.

11. Have a history of another invasive malignancy aside from melanoma, except for the following circumstances: a. Patient has been disease-free for at least 2 years and is deemed by the investigator to be at low risk for recurrence of that malignancy. b. Patient was not treated with systemic chemotherapy for carcinoma in situ of the breast, oral cavity or cervix, basal cell or squamous cell carcinoma of the skin Patients for dose escalation Part 1 have disease progression following standard regimens, there is no deferment or deviation of standard treatment. For Part 2 patients, NEO-PTC-01 is given with continued CPI therapy.

What is claimed is:

1. A method of treating a cancer in a human subject in need thereof, comprising:
   (a) depleting CD14+ cells and/or CD25+ cells from a washed and/or cryopreserved peripheral blood mononuclear cell (PBMC) sample from the human subject comprising antigen presenting cells (APCs) and T cells, thereby forming a CD14 and/or CD25 depleted PBMCs comprising a first population of APCs and T cells;
   (b) incubating the first population of APCs and T cells from step (a) for a first time period in the presence of:
      (i) FMS-like tyrosine kinase 3 receptor ligand (FLT3L), and
      (ii) (A) a polypeptide comprising at least two different tumor antigen epitope sequences expressed by cancer cells of a human subject with cancer, or (B) a polynucleotide encoding the polypeptide comprising the at least two different tumor antigen epitope sequences expressed by cancer cells of the human subject with cancer, and wherein the at least two different tumor antigen epitope sequences are not expressed in non-cancer cells of the human subject; thereby forming a population of cells comprising stimulated T cells;
   (c) expanding the stimulated T cells from step (b), thereby forming an expanded population of cells comprising tumor antigen-specific T cells,
      wherein the tumor antigen-specific T cells comprise T cells that are specific to a complex comprising (i) a tumor antigen epitope sequence of the at least two different tumor antigen epitope sequences from step (b)(ii), and (ii) an MHC protein expressed by the cancer cells or APCs of the human subject; and
   (d) administering the expanded population of cells from (c) to the human subject, wherein the human subject:
      (i) has unresectable melanoma,
      (ii) has previously received a PD-1 inhibitor or PD-L1 inhibitor and a CTLA-4 inhibitor containing regimen and has disease progression, or
      (iii) has received or is currently receiving a PD-1 inhibitor or PD-L1 inhibitor for at least 3 months and has stable disease or asymptomatic progressive disease.

2. The method of claim 1, wherein incubating in (b) comprises introducing an mRNA encoding the polypeptide into the APCs of the first population of APCs and T cells from step (a), wherein introducing comprises electroporating or nucleofecting, and wherein the electroporating or nucleofecting is carried out without separating the T cells from the APCs of the first population of APCs and T cells from step (a).

3. The method of claim 2, wherein the mRNA comprises a 5' CAP and a 3' polyA tail.

4. The method of claim 3, wherein the 5' CAP is CAP-1.

5. The method of claim 4, wherein the 5' CAP is operably linked to a tumor antigen epitope sequence of the at least two different tumor antigen epitope sequences via a linker sequence.

6. The method of claim 3, wherein the polyA tail is from 120 to 135 nucleotides in length.

7. The method of claim 1, wherein the at least two different tumor antigen epitope sequences are expressed as a single polypeptide chain, and wherein a first tumor antigen epitope sequence of the at least two different tumor antigen epitope sequences is connected to a second tumor antigen epitope sequence of the at least two different tumor antigen epitope sequences via a linker sequence.

8. The method of claim 1, wherein the polypeptide comprises at least 4 different tumor antigen epitope sequences expressed by cancer cells of a human subject with cancer.

9. The method of claim 1, wherein:
   (i) percentage of CD3+ cells in the expanded population of cells comprising tumor antigen-specific T cells is at least 40% of total cell population;
   (ii) percentage of CD107a+ cells in the expanded population of cells comprising tumor antigen-specific T cells is at least 10% of the tumor antigen-specific T cell population;
   (iii) percentage of TNFα+ cells in the expanded population of cells comprising tumor antigen-specific T cells is at least 5% of the tumor antigen-specific T cell population;
   (iv) percentage of IFNγ+ cells in the expanded population of cells comprising tumor antigen-specific T cells is at least 15% of the tumor antigen-specific T cell population;
   (v) percentage of TNFα+ and IFNγ+ cells in the expanded population of cells comprising tumor antigen-specific T cells is at least 2% of the tumor antigen-specific T cell population;

(vi) percentage of TNFα+ and CD107a+ cells in the expanded population of cells comprising tumor antigen-specific T cells is at least 0.5% of the tumor antigen-specific T cell population;

(vii) percentage of IFNγ+ and CD107a+ cells in the expanded population of cells comprising tumor antigen-specific T cells is at least 5% of the tumor antigen-specific T cell population; and/or (viii) percentage of TNFα+ and IFNγ+ and CD107a+ cells in the expanded population of cells comprising tumor antigen-specific T cells is at least 0.1% of the tumor antigen-specific T cell population.

10. The method of claim 1, wherein:

(i) percentage of CD4+ T cells in the expanded population of cells comprising tumor antigen-specific T cells that are naive T cells (CD62L+ and CD45RA+) is at most 15%;

(ii) percentage of CD4+ T cells in the expanded population of cells comprising tumor antigen-specific T cells that are effector memory T cells (CD62L− and CD45RA−) is at least 60%;

(iii) percentage of CD4+ T cells in the expanded population of cells comprising tumor antigen-specific T cells that are effector T cells (CD62L− and CD45RA+) is at most 5%; and/or (iv) percentage of CD4+ T cells in the expanded population of cells comprising tumor antigen-specific T cells that are central memory T cells (CD62L+ and CD45RA−) is at least 10%.

11. The method of claim 1, wherein:

(i) percentage of CD8+ T cells in the expanded population of cells comprising tumor antigen-specific T cells that are naive T cells (CD62L+ and CD45RA+) is at most 25%;

(ii) percentage of CD8+ T cells in the expanded population of cells comprising tumor antigen-specific T cells that are effector memory T cells (CD62L− and CD45RA−) is at least 60%;

(iii) percentage of CD8+ T cells in the expanded population of cells comprising tumor antigen-specific T cells that are effector T cells (CD62L− and CD45RA+) is at most 10%; and/or (iv) percentage of CD8+ T cells in the expanded population of cells comprising tumor antigen-specific T cells that are central memory T cells (CD62L+ and CD45RA−) is at least 15%.

12. The method of claim 1, wherein the expanded population of cells comprising tumor antigen-specific T cells produce cytokines and cause degranulation upon recognition of target cells.

13. The method of claim 1, wherein the human subject (i) is refractory to an anti-checkpoint inhibitor therapy;

(ii) is age 18 to 75 years old; and/or (iii) has a mutation in a BRAF gene and has previously received a B-raf inhibitor or a B-raf/MEK combination therapy.

14. The method of claim 1, wherein depleting comprises depleting CD14+ cells and CD25+ cells from a peripheral blood mononuclear cell (PBMC) sample from a human subject that has not been subject to a step of monocyte maturation into mature dendritic cells (DCs).

15. The method of claim 1, wherein depleting further comprises depleting CD11b+ cells from the peripheral blood mononuclear cell (PBMC) sample from the human subject that has not been subject to a step of monocyte maturation into mature dendritic cells (DCs).

16. The method of claim 1, wherein (i) at least 0.1% of the CD8+ T cells in the expanded population of cells comprising tumor antigen specific T cells are CD8+ tumor antigen-specific T cells derived from naïve CD8+ T cells; and/or (ii) at least 0.1% of the CD4+ T cells in the expanded population of cells comprising tumor antigen specific T cells are CD4+ tumor antigen-specific T cells derived from naïve CD4+ T cells.

17. The method of claim 1, wherein the expanded population of cells from step (c) administered to the human subject comprises from $1\times10^8$ to $1\times10^{11}$ total cells.

18. The method of claim 1, wherein depleting comprises contacting the washed and/or cryopreserved peripheral blood mononuclear cell (PBMC) sample from the human subject with anti-CD14 antibody and/or anti-CD25 antibody respectively.

* * * * *